United States Patent
Damha et al.

(10) Patent No.: US 11,014,948 B2
(45) Date of Patent: May 25, 2021

(54) IONIC TAGS FOR SYNTHESIS OF OLIGORIBONUCLEOTIDES

(71) Applicants: The Royal Institution for the Advancement of Learning/McGill University, Montreal (CA); Hong Kong Polytechnic University, Kowloon (HK)

(72) Inventors: Masad J. Damha, St-Hubert (CA); Matthew Hassler, Saskatoon (CA); Tak-Hang Chan, Toronto (CA); Mallikarjuna Reddy Nandyala, Montreal (CA); Robert Alexander Donga, Saint-Bruno (CA)

(73) Assignees: The Royal Institution for the Advancement of Learning/McGill University, Montreal (CA); Hong Kong Polytechnic University, Hong Kong (CN)

( * ) Notice: Subject to any disclaimer, the term of this patent is extended or adjusted under 35 U.S.C. 154(b) by 0 days.

(21) Appl. No.: 15/925,509

(22) Filed: Mar. 19, 2018

(65) Prior Publication Data

US 2019/0062355 A1    Feb. 28, 2019

Related U.S. Application Data

(63) Continuation of application No. 14/240,067, filed as application No. PCT/CA2012/000784 on Aug. 23, 2012, now Pat. No. 9,920,084, which is a continuation-in-part of application No. PCT/CA2011/000950, filed on Aug. 23, 2011.

(60) Provisional application No. 61/602,373, filed on Feb. 23, 2012.

(51) Int. Cl.
| | |
|---|---|
| *C07D 233/60* | (2006.01) |
| *C07F 9/54* | (2006.01) |
| *C07F 9/655* | (2006.01) |
| *C07F 9/6558* | (2006.01) |
| *C07H 19/02* | (2006.01) |
| *C07H 21/00* | (2006.01) |
| *C07H 21/02* | (2006.01) |
| *C40B 50/16* | (2006.01) |
| *C40B 80/00* | (2006.01) |

(52) U.S. Cl.
CPC .............. *C07F 9/54* (2013.01); *C07D 233/60* (2013.01); *C07F 9/5407* (2013.01); *C07F 9/5442* (2013.01); *C07F 9/5456* (2013.01); *C07F 9/65515* (2013.01); *C07F 9/65586* (2013.01); *C07H 19/02* (2013.01); *C07H 21/00* (2013.01); *C07H 21/02* (2013.01); *C40B 50/16* (2013.01); *C40B 80/00* (2013.01)

(58) Field of Classification Search
CPC combination set(s) only.
See application file for complete search history.

(56) References Cited

U.S. PATENT DOCUMENTS

| | | | |
|---|---|---|---|
| 6,770,754 B2 | 8/2004 | Azhayev et al. | |
| 7,759,513 B2 | 7/2010 | Buehler et al. | |
| 2004/0175741 A1* | 9/2004 | Buhler | C07H 19/06 435/5 |
| 2010/0041869 A1* | 2/2010 | Chan | C07H 21/00 530/333 |

FOREIGN PATENT DOCUMENTS

| | | |
|---|---|---|
| EP | 1404695 A2 | 4/2004 |
| WO | 02/44398 A2 | 6/2002 |
| WO | 2004/089529 A1 | 10/2004 |
| WO | 2006/096963 A1 | 9/2006 |
| WO | 2009/064115 A1 | 5/2009 |

(Continued)

OTHER PUBLICATIONS

Hodgson et al. J. Org. Chem. 2003, 68, 581-586. (Year: 2003).*

(Continued)

*Primary Examiner* — Amanda L. Aguirre

(74) *Attorney, Agent, or Firm* — DLA Piper LLP (US)

(57) ABSTRACT

The invention relates to the chemical synthesis of oligonucleotides, e.g., oligoribonucleotides. In another aspect, the invention relates to compounds of formula (II):

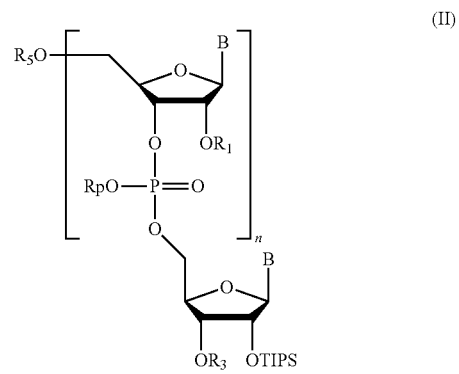

(II)

processes for making these compounds, and the use thereof in the chemical synthesis of oligonucleotides, e.g., oligoribonucleotides. The invention also relates to methods of synthesis of oligomers, including but not limited to oligopeptides, oligosaccharides and oligonucleotides, particularly oligoribonucleotides and also oligodeoxyribonucleotides, in solution systems, and ionic tag linkers for use in methods provided herein.

4 Claims, 1 Drawing Sheet

(56) References Cited

FOREIGN PATENT DOCUMENTS

| WO | 2010/012096 A1 | 2/2010 | | |
|---|---|---|---|---|
| WO | 2012/024776 A1 | 3/2012 | | |
| WO | WO-2012024776 A1 | * | 3/2012 | ............ C07H 21/00 |

OTHER PUBLICATIONS

Donga et al. Nucleos. Nucleot. Nucl. 2007, 26, 1287-1293. (Year: 2007).*
CAS STN Database Registry No. (RN) 90998-58-6 [Entered STN: Nov. 16, 1984]. (Year: 1984).*
Eritja et al. "A Synthetic Procedure for the Preparation of Oligonucleotides Without Using Ammonia and its Application for the Synthesis of Oligonucleotides Containing O-4-Alkyl Thymidines." Tetrahedron 1992, 48, 4171-4182. (Year: 1992).*
Johnsson et al. "New light labile linker for solid phase synthesis of 2'-O-acetalester oligonucleotides and applications to siRNA prodrug development" Bioorg. Med. Chem. Lett 2011, 21, 3721-3725. (Year: 2011).*
Donga et al. "A Novel Approach to Oligonucleotide Synthesis Using an Imidazolium Ion Tag as a Soluble Support" J. Org. Chem. 2006, 71, 7907-7910. (Year: 2006).*
Damha, et al, "Oligorbonucleotide synthesis: The silyl-phosphoramidite method", Methods in Molecular Biology, Edited by S. Agrawal, New Jersey: Humana Press Inc., vol. 20, Protocols for oligonucleotides and analogs, Chapter 5, 1993, pp. 81-114.
Chan, et al., J. Org. Chem., No. 70, 2005, pp. 3251-3255.
Chan, et al., Acc. Chem. Res., No. 39, 2006, pp. 897-908.
Caruthers, et al., Methods in Enzymology, No. 154, 1987, pp. 287-313.
Boehm, et al., J. Org. Chem., No. 61, 1996, pp. 6498-6499.
Beaucage,"Solid-Phase synthesis of siRNA oligonucleotides" Current Opinion in Drug Discovery and Development, vol. 11, No. 2, 2008, pp. 203-216.
Beaucage, et al., Curr. Protoc. Nucleic Acid Chem., vol. 47, No. 13, 2011, pp. 13.0-13.4.
Aoki, S. et al. "Synthesis of 4-keto pimelates by palladium-catalyzed carbonylativesymmetrical coupling of siloxycyclopropanes. "Tetrahedron Letters, 1988 (1988) vol. 29, pp. 1541-1542 ISSN:0040-4039.
Anderson, et al., Nucleosides, Nucleotides, and Nucleic Acids, No. 22, 2003, pp. 1403-1406.
Alvarado-Urbina, et al., Science, No. 214, 1981, pp. 270-274.
Wuts and Greene, Green's Protective Groups in Organic Synthesis, Wiley-Interscience, New York, NY, 2006, 27 pages.
Werstiuk, et, al., Can. J. Chem., No. 54, 1976, p. 2689.
Venkatesan et al., "Improved Utility of Photolabile Solid Phase Synthesis Supports for the Synthesis of Oligonucleotides Containing 3'-Hydroxyl Termini", J. Org. Chem., No. 61, 1996, pp. 525-529.
van Boom, et al., Tray. Chim. Pays-Bas, No. 97, 1978, p. 73.
Usman, et al. J. Am. Chem. Soc., No. 109, 1987, pp. 7845-7854.
Supplementary Partial European Search Report from related European Application No. EP12824951, dated Mar. 20, 2015, 4 pages.
Studer, et al., Science, No. 275, 1997, pp. 823-826.
STN Registry compounds and CAplus entry for: Donga et al. "Oligonucleotide Synthesis Using Ionic Liquids as Soluble Supports" Nucleos. Nucleot. Nucl. 2007, 26, 1287-1293.
Stetter, Angewandte Chemie, International Edition in English, No. 15, 1976, pp. 639-647.
Singapore Written Opinion dated Jul. 25, 2017, regarding SG 201301382-6.
Seela, et al., Helvetica Chimica Acta No. 76, 1993, pp. 1435-1449.
Scaringe, et al., Nucleic Acids Res., vol. 18, No. 18, 1990, pp. 5433-5441.
Ronald, et al., Journal of Organic Chemistry, No. 48, 1983, pp. 138-139.
Reese, Organic & Bimolecular Chemistry, No. 3, 2005, pp. 3851-3868.
Ramsay, Nature Biotechnology, No. 16, 1998, pp. 40-44.
Pon, et al., Nucleic Acids Research, No. 25, 1997, pp. 3629-3635.
Pirrung, et al., Org. Lett. No. 3, 2001, pp. 1105-1108.
Pfeiderer, et al., Nucleosides and Nucleotides, No. 17, 1998, pp. 1987-1996.
Pfeiderer, et al., Helvetica Chemimica Acta, No. 87, 2004, p. 620-659.
Ohtsuka, et al., J. Am. Chem. Soc., No. 100, 1978, p. 8210-8213.
Ogilvie, K. K. et al.: "The synthesis of oligoribonucleotides. II. The use of silyl protecting groups in nucleoside and nucleotide chemistry. VII"; Candadian Journal of Chemistry, 1978, vol. 56, pp. 2768-2780.
Ogilvie, et al., Tetrahedron Letters, No. 15, 1974, pp. 2861-2863.
Ogilvie, et al., Proc. Natl. Acad. Science (USA), No. 85, 1988, pp. 5764-5768.
Ogilvie, et al., J. of Carbohydrates, Nucleosides, Nucleotides, No. 3, 1976, pp. 197-227.
Ogilvie, et al., Carbohydrate Research, No. 89, 1981, pp. 203-210.
Ogilvie, et al., "Proceedings of the 5.sup.th International Round Table on Nucleosides, Nucleotides and their Biological Applications", 1983. (Rideout, et al., Academic London eds.), pp. 209-256.
Office Action received for European Patent Application No. 12824951. 3, dated Sep. 12, 2016, 6 pages.
Office Action received for European Patent Application No. 12824951. 3, dated Jul. 20, 2017, 4 pages.
Nemer, et al., Can J. Chem., No. 58, 1980, pp. 1389-1397.
Milecki, et al. Nucleosides and Nucleotides, No. 8, 1989, pp. 463-474.
Manoharan, Curr. Opin. Chem. Biol., No. 8., 2004, pp. 570-579.
Leisvuori et al., "4-Oxoheptanedioic acid: an orthogonal linker for solid-phase synthesis of base-sensitive oligonucleotides". Tetrahedron Letters, No. 49, 2008, pp. 4119-4121.
Lackey, et al. J. Am. Chem. Soc., No. 131, 2009, pp. 8496-8502.
Kumar, et al., J. Org. Chem., No. 49, 1984, pp. 4905-4912.
Kosuri, et al., Nature Biotechnology, No. 28, 2010, 1295-1299.
Johnsson, R. et al.: "New light labile linker for solid phase synthesis of 2'-O-acetalester oligonucleotides and applications to siRNA prodrug development." Bioorganic & Medicinal Chemistry Letters. Jun. 15, 2011 (Jun. 15, 2011) Epub Apr. 27, 2011, vol. 21, No. 12, pp. 3721-3725 ISSN:0960-894X.
International Search Report and Written Opinion received for PCT Patent Application No. PCT/CA2012/000784, dated Dec. 3, 2012, 15 pages.
International Preliminary Report on Patentability received for PCT Patent Application No. PCT/CA2012/000784, dated Mar. 6, 2014, 11 pages.
Horvath, et al., J. Science, No. 266, 1994, pp. 72-75.
Hodgson et al. "Catalytic Enantioselective [3+2]-Cycloadditions of Diazoketone-Derived Aryl-Substituted Carbonyl Ylides" J. Org. Chem. 2003, 68, 581-586.
Hassler, M. et al.: "RNA synthesis via dimer and trimer phosphoramidite block coupling."Tetrahedron Letters, Mar. 15, 2011 (Mar. 15, 2011) vol. 52, pp. 2575-2578 ISSN:0040-4039.
Guzaev, et al., J. Am. Chem. Soc., No. 125, 2003, pp. 2380-2381.
Gravert, et al., Chem. Rev., No. 97, 1997, pp. 489-509.
European Search Report and Search Opinion Received for EP Application No. 12824951.3, dated Aug. 19, 2015, 12 pages.
European Office Action dated Sep. 12, 2016, regarding EP 12 824 951.3.
Eckert, et al., J. Org. Process Res. Dev., No. 14, 2010, pp. 1501-1505.
Donga, et al., J. Org. Chem., No. 71, 2006, pp. 7907-7910.
Donga, et al., Can J. Chem., No. 85, 2007, pp. 274-282.
Donga et al. "Oligonucleotide Synthesis Using Ionic Liquids as Soluble Supports" Nucleos. Nucleot. Nucl. 2007,26, 1287-1293.
Damha, et al, Tetrahedron Letters, vol. 45, 1992, pp. 6739-6742.
Indian Examination Report dated Mar. 14, 2019, regarding in 813/KOLNP/2013.
Luvino, D. et al.: "Synthesis of a new internucleosidic linkage: the Borononucleotides"; Nucleic Acids Symposium Series, Dec. 2008, v. 52, No. 1, p. 403-404.

* cited by examiner

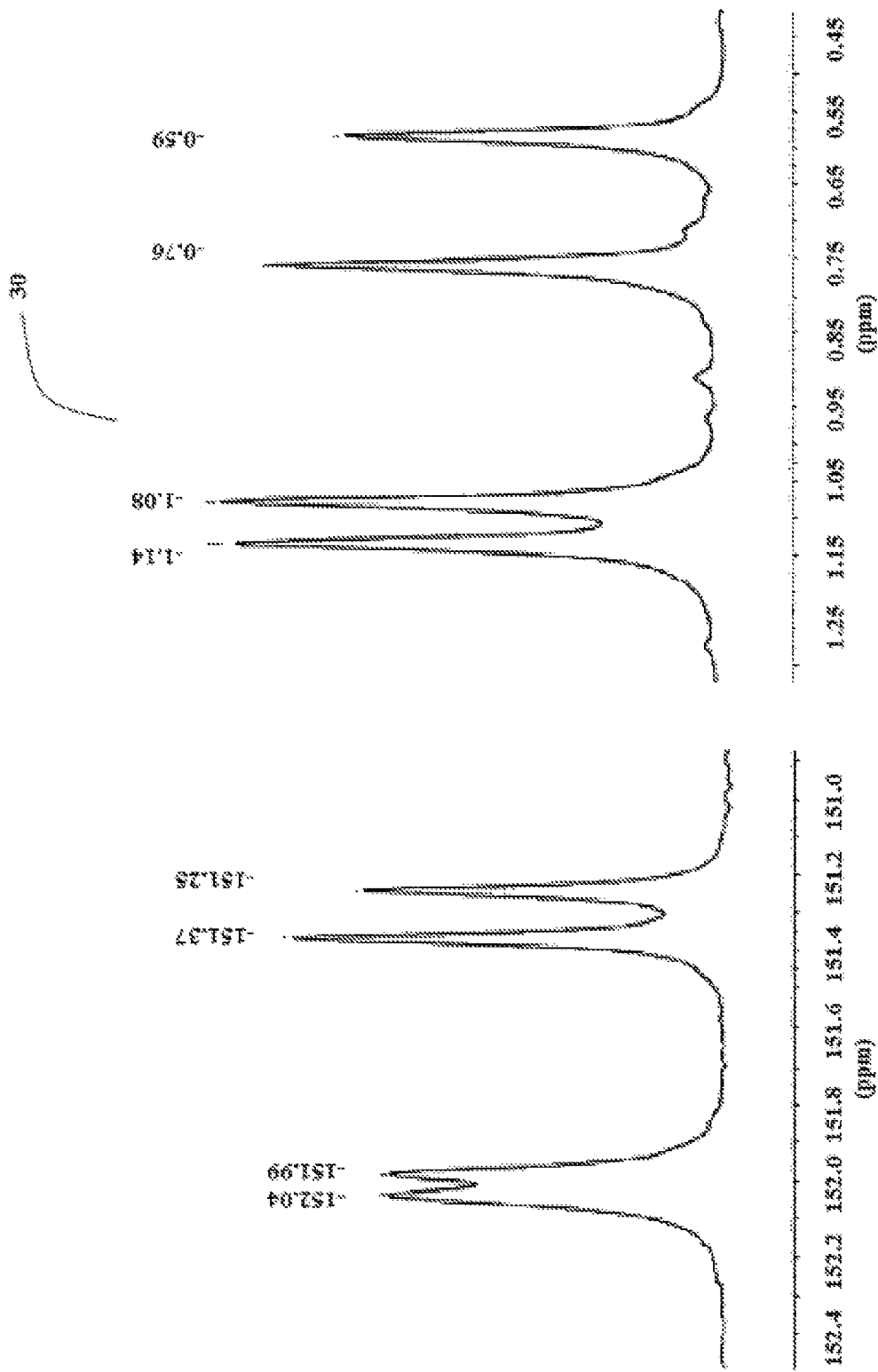

IONIC TAGS FOR SYNTHESIS OF OLIGORIBONUCLEOTIDES

RELATED APPLICATIONS

This application is a Continuation of application Ser. No. 14/240,067 filed May 29, 2014, which is a 371 application of International PCT Application No. PCT/CA2012/000784 filed Aug. 23, 2012, which claims priority to U.S. Provisional Application No. 61/602,373 filed Feb. 23, 2012 and International PCT Application No. PCT/CA2011/000950 filed Aug. 23, 2011, all of which are hereby incorporated by reference in their entirety.

FIELD OF THE INVENTION

The invention relates to the chemical synthesis of oligonucleotides, in particular oligoribonucleotides, in particular solution phase synthesis.

BACKGROUND OF THE INVENTION

The demand for synthetic oligonucleotides has grown exponentially as genome sequencing, functional genomics, and PCR-based detection methods consume enormous quantities of DNA oligonucleotides. In addition, the potential success of new DNA- and RNA-based therapeutic platforms (such as antisense and siRNA gene silencing strategies) currently undergoing clinical trials could result in an unprecedented demand for short synthetic DNA and RNA molecules.

RNA interference (RNAi) as potential therapeutics represents a fundamentally new way to treat human diseases [Manoharan, *Curr. Opin. Chem. Biol.* 8, 570-579 (2004)]. However, achieving targeted tissue and cellular delivery, stabilization in vivo, and cost effective large scale synthesis of RNA are significant bottlenecks in the development of RNAi technology. The reality of mainstream RNAi based therapeutics is rapidly approaching and the demand for these compounds on large scale may soon exceed the capability of manufacturers. Therefore, there is a need to develop synthetic strategies enabling RNA oligomers to be synthesized rapidly, in high purity and/or in a cost efficient, large scale synthesis.

Current methods for DNA and RNA synthesis rely on stepwise addition of monomeric phosphoramidite units on solid supports [Caruthers, M. H. et al. *Methods in Enzymology* 154, 287-313 (1987); Alvarado-Urbina, G. et al. Science 214, 270-274 (1981)]. Chain elongation from 3'- to 5'-end is preferred, which is achieved by coupling of a nucleoside unit having a 3'-phosphorus (III) group (in its activated form) to a free 5'-hydroxyl group of another nucleoside unit. As solid support, 500 to 1000 Å controlled pore glass (CPG) support or an organic polymer support, such as primer polystyrene support PS200, can be used.

Chain elongation begins by cleavage of the 5'-O-dimethoxytrityl group with an organic acid, thus liberating a nucleophilic 5'-hydroxyl group. This terminal nucleophile is then allowed to couple to a protected nucleoside 3'-O-phosphoramidite monomer in the presence of an activator. In the case of RNA synthesis suitable protection of the 2'-hydroxyl group is required. Any unreacted 5'-hydroxyl groups are acetylated in a process referred to as 'capping'. The most commonly used group used for this purpose is an acetyl ester. Thus, 'capping' with acetic anhydride esterifies any unreacted 5'-hydroxyl groups and halts the accumulation of by-products. The newly created phosphite triester 3',5'-linkage is then oxidized to provide the desired and more stable phosphate triester. This process is repeated until an oligomer of the desired length and sequence is obtained. Cleavage of the oligomer from the solid support and removal of the protecting groups from the sugars, phosphates and nucleobases provides the desired target oligomer, which is then separated from shorter failure sequences by ion exchange high pressure liquid chromatography (HPLC), ion-pair reverse phase HPLC, or polyacrylamide gel electrophoresis (PAGE). The full length oligomer is then characterized by mass spectrometry. Meanwhile a large number of DNA oligomers can be synthesized in parallel on DNA microarrays or "gene chips" [Ramsay G., *Nature Biotechnology* 16, 40-44 (1998)].

The same iterative method may be applied toward the synthesis of DNA and RNA oligonucleotides in solution, for example as described recently by Donga et al. using ionic soluble supports [e.g. Donga, R. A. et al., *J. Org. Chem.* 71, 7907-7910 (2006); Donga, R. A. et al., *Can. J. Chem.* 85, 274-282 (2007)]. The use of ionic soluble supports allows for selective precipitations of the growing oligonucleotide over all other reagents used in the oligonucleotide synthesis cycle.

To date, there have been many attempts to design protecting groups and methods that embody the conditions required for the construction of high quality oligoribonucleotides [for reviews, see Beaucage, S. L. *Curr. Opin. Drug Discov. Devel.* 11, 203-16 (2008); Reese, C. B. *Organic & Biomolecular Chemistry* 3, 3851-3868 (2005)]. In fact, for many years, RNA synthesis has been regarded as far more complicated than DNA synthesis because of the difficulty in finding a compatible 2'-protecting group that (a) affords high step-wise coupling yields, (b) is stable throughout chain assembly, and (c) can be removed selectively at the end of synthesis without phosphodiester bond isomerization or degradation.

The most widely used 2'-protecting group is the 2'-O-t-butyldimethylsilyl (TBDMS) group [Ogilvie, K. K. et al. *Tetrahedron Letters* 15, 2861-2867 (1974)]. This protecting group is removed at the end of RNA chain assembly in the presence of fluoride ions. Other silyl ether based protecting groups described for the protection of nucleosides are triisopropylsilyl (TIPS), methyldiisopropylsilyl (MDIPS), cyclic alkylsilyl and other silyl groups [Ogilvie, K. K. et al. *J. of Carbohydrates, Nucleosides, Nucleotides* 3, 197-227 (1976); Damha M. J, Ogilvie K. K. (1993), Oligoribonucleotide synthesis: the silyl-phosphoramidite method. In: Protocols for Oligonucleotides and Analogs: Synthesis and Properties, Methods in Molecular Biology (Agrawal S, ed.) Vol. 20. Totowa, N.J.: The Humana Press Inc. pp. 81-114]. Among these, TIPS protection has been described primarily for 5'-O-monomethoxytrityl N2-isobutyrylguanosine derivatives as the 2' and 3'-O-TIPS isomers are more readily separated from each other by silica gel chromatography [Damha M. J, Ogilvie K. K. (1993), Oligoribonucleotide synthesis: the silyl-phosphoramidite method. In: Protocols for Oligonucleotides and Analogs: Synthesis and Properties, Methods in Molecular Biology (Agrawal S, ed.) Vol. 20. Totowa, N.J.: The Humana Press Inc. pp. 81-114; Damha, M. J. et al. *Tetrahedron Letters* 45, 6739-6742 (1992)]. The smaller steric bulk of the TBDMS group relative to TIPS, TBDPS and other bulkier silyl ethers would favor the TBDMS protecting group, which has been used the most compared to other protecting group for RNA synthesis. Coupled with the phosphoramidite condensation-procedure, 2'-O-TBDMS monomers have allowed a highly efficient synthesis of oligoribonucleotides [Ogilvie, K. K. et al. *Proc.*

Natl. Acad. Science (USA), 85, 5764-5768 (1988); Usman, N. et al. *J. Am. Chem. Soc.* 109, 7845-7854 (1987)].

A potential drawback of silyl ethers for the protection of the 2'-hydroxyl group lies in their widely recognized ability to undergo 2'-to-3' isomerization under the influence of protic solvents, nucleophilic catalysts, or basic conditions. For example, the TBDMS group migrates from the O2' to O3' position (and vice versa) in the presence of either methanol, imidazole, pyridine/water, or aqueous ammonia, thereby generating a mixture of nucleoside O2' and O3' silyl regioisomers [Ogilvie, K. K. and Entwistle, D. W. *Carbohydrate Res.* 89, 203-210 (1981); Ogilvie, K. K. (1983) *Proceedings of the 5th International Round Table on Nucleosides, Nucleotides and Their Biological Applications*, (Rideout, J. L. et al. eds.), Academic, London, pp. 209-256); Damha M. J, Ogilvie K. K. (1993), Oligoribonucleotide synthesis: the silyl-phosphoramidite method. In: Protocols for Oligonucleotides and Analogs: Synthesis and Properties, Methods in Molecular Biology (Agrawal S, ed.) Vol. 20. Totowa, N.J.: The Humana Press Inc. pp. 81-114].

Silyl isomerization is characteristic of other O-silyl ether protecting groups. O-TIPS derivatives of uridine and 7-deazaguanosine also undergo isomerization in methanol, albeit more slowly than their O-TBDMS counterparts [Ogilvie, K. K. et al. *J. or Carbohydrates, Nucleosides, Nucleotides* 3, 197-227 (1976); Seela, F. and Mersmann, K., *Helvetica Chimica Acta,* 76, 1435-1449 (1993)]. 5'-O-Monomethoxytrityl-N2-isobutyryl-2'-O-TIPS guanosine undergoes isomerization under ethanolic aq. ammonia conditions to give a mixture of 2'/3'-TIPS regioisomers which can be separated by chromatography. This provides a method to convert (recycle) more of the unwanted 3'-isomer into the more useful 2'-isomer [Damha M. J, Ogilvie K. K. (1993), Oligoribonucleotide synthesis: the silyl-phosphoramidite method. In: Protocols for Oligonucleotides and Analogs: Synthesis and Properties, Methods in Molecular Biology (Agrawal S, ed.) Vol. 20. Totowa, N.J.: The Humana Press Inc. pp. 81-114].

2'-O-Silyl groups do not normally migrate to O3' in dry aprotic solvent. When these conditions are strictly adhered to it is possible to prepare 2'-O-silylated ribonucleoside-3'-O-phosphoramidite derivatives in regiosomerically pure form [Milecki, J. et al. *Nucleosides & Nucleotides,* 8, 463-474 (1989); Scaringe, S. A. et al. *Nucleic Acids Res.,* 18, 5433-5341 (1990)]. This is clearly an important requirement as the presence of even traces of the 3'-O-silyl regioisomer will impact on the quality and biological activity of the desired RNA sequence.

Many other protecting groups for the 2'-hydroxyl position have been used in the synthesis of RNA [reviewed in Beaucage, S. L. *Curr. Opin. Drug Discov. Devel.* 11, 203-16 (2008); Reese, C. B. *Organic & Biomolecular Chemistry* 3, 3851-3868 (2005)]. RNA synthesis using monomers containing the 2'-triisopropylsilyloxymethyl (TOM) group, the 2'-acetal-levulinyl group, and the 2'-O-bis(2-acetoxyethoxy) methyl (ACE) group, have been reported to yield higher coupling efficiency, because these protecting groups exhibit lower steric hindrance than the 2'-TBDMS group [for a comparative study, see Lackey, J. G. et al. *J. Am. Chem. Soc.* 131, 8496-8502 (2009)]. Like the TBDMS group, the TOM protecting group is removed using fluoride.

In all cases the synthesis of oligoribonucleotides is an elaborate multistep process, which entails assembly of the oligonucleotide chain typically from monomeric phosphoramidite building blocks (e.g., 5'-O-dimethoxytrityl-N-protected-2'-O-tert-butyldimethylsilyl-nucleoside-3'-O-phosphoramidites), deprotection of the base labile nucleobase protecting groups (e.g., benzoyl, isobutyryl, acetyl, phenoxyacetyl, levulinyl, etc), cleavage from the support (e.g., glass beads or polystyrene), followed by removal of the 2'-hydroxyl protecting group.

The generation of oligoribonucleotide blocks is more difficult due to the presence of the 2'-hydroxyl group and the protection it requires, thus this line of research has also lagged far behind that of DNA blocks. Nevertheless, there have been several reports describing the synthesis of RNA through block coupling condensation reactions. Ikehara and co-workers coupled RNA trimer and tetramers using the phosphotriester method to give 30% yield after several days [Ohtsuka, E. et al. *J. Am. Chem. Soc.* 100, 8210 (1978)]. Werstiuk and Nielson reported the coupling of an RNA tetramer and an RNA pentamer affording the desired nonanucleotide RNA sequence in 50% yield after 16 days [Werstiuk, E. S., Neilson, T. *Can. J. Chem.* 54, 2689 (1976)]. Van Boom and co-workers condensed an RNA tetramer and an RNA decamer in 58% yield in a 3.5 days reaction [van Boom, J. H. et al. *Trav. Chim. Pays-Bas,* 97, 73 (1978)]. Ogilvie and co-workers described the synthesis of 5'-O-monomethoxytrityl-2'-O-tert-butyldimethylsilyl-3'-O-levulinyl ribonucleoside monomers and their use in the assembly of a hexadecauridylic acid via the phosphodichloridite procedure [Nemer, M. J, and Ogilvie, K. K., *Can. J. Chem.* 58, 1389-1397 (1980)].

Solid-phase RNA synthesis is carried out almost exclusively using monomeric phosphoramidite synthons. Given the efficiency of the phosphoramidite chemistry, it is highly desirable to have access to block (dimer and trimer) phosphoramidites for RNA synthesis, as these would permit longer chain extensions at each step during chain assembly, significantly shortening the time required for synthesis.

However, while solid-supported synthesis overcomes the limitation of purification by allowing excess reagents to be washed away, it can be quite restricting in terms of scale. While it is true that current large scale methods of producing oligonucleotides in the kilogram scale utilize solid phase approaches, the mechanical requirements for this type of manufacturing are very specialized and costly. Therefore, an ideal method of large scale synthesis is in solution. In attempts to overcome this limitation, a variety of soluble polymer-based supports have been developed [Gravert, D. J., Janda, K. D. *Chem. Rev.* 97, 489-509 (1997)]. These however suffer from their own limitations such as poor loading, unfavorable atom economy, and the reliance on temperature cycling to solvate/precipitate the soluble support.

Some unique perfluorinated "supports" have been reported that are covalently attached to a desired molecule and hence adhere to long chain fluorocarbon derivatized silica. They can be selectively removed by perfluorinated solvents. This is a very efficient process, but requires many specialized and expensive materials [Horvath, I. T., Rabai, *J. Science,* 266, 72-75. (1994); Studer, A. et al., *Science,* 275, 823-826, (1997)].

It is also desirable therefore to have improved methods for solution phase RNA synthesis.

SUMMARY OF THE INVENTION

Methods for the synthesis of blockmer (dimer, trimer, tetramer, etc.) ribonucleotides that have applications in the synthesis of RNA through block coupling reactions are described herein. These building blocks allow longer chain extensions at each coupling stage of RNA synthesis, significantly reducing the total number of steps required in the synthesis of a target RNA oligomer. Additionally, the block coupling strategy disclosed herein produces crude RNA oligomers that are more readily separated from shorter failure sequences. The procedure is illustrated by the synthesis of UpU, ApA, and UpUpU blocks and their use in the assembly of oligoribonucleotide chains via a phosphoramidite coupling method. The disclosed compounds and processes benefit two critical aspects of siRNA manufacturing: speed, and purity of a target oligomer.

In another aspect, methods for the synthesis of blockmer (dimer, trimer, tetramer, etc.) deoxyribonucleotides that have applications in the synthesis of DNA through block coupling reactions are described herein. These building blocks allow longer chain extensions at each coupling stage of DNA synthesis, significantly reducing the total number of steps required in the synthesis of a target DNA oligomer. Additionally, the block coupling strategy disclosed herein produces crude DNA oligomers that are more readily separated from shorter failure sequences.

There are provided herein methods for the synthesis of ionically tagged linkers for, but not limited to, the synthesis of oligoribonucleotides, oligodeoxyribonucleotides, oligopeptides and oligosaccharides, which can be orthogonally cleaved in the presence of all other standard protecting groups. Tag-linker combinations provided herein make it possible to grow oligonucleotides in solution using stepwise iterative couplings, utilizing the ionic properties of the tags to selectively precipitate a growing oligonucleotide at each step, in order to remove coupling reagents and reactants. Tag-linkers enable removal of a synthesized oligonucleotide from solution at any point in the synthesis, to produce a free 3'-O-hydroxyl, 2'-TIPS protected oligomer, without any isomerisation of the 2'-O-silyl protecting group. This can be utilized for, but not limited to, converting an oligomer (dimer, trimer, tetramer, etc.) into block-phosphoramidites. These building blocks enable longer chain extensions at each coupling stage of RNA or DNA synthesis, significantly reducing the total number of steps required in the synthesis of a target RNA or DNA oligomer. Additionally, the block coupling strategy produces crude RNA or DNA oligomers that are readily separable from shorter, undesired sequences that arise during synthesis. It is also envisioned that, in some embodiments, tag linkers can be used in place of standard ester protecting groups, to provide both a mild cleavage alternative as well as a means to selectively precipitate a desired molecule and circumvent the use of costly and time consuming chromatography.

In one aspect, there is provided a compound of formula (II):

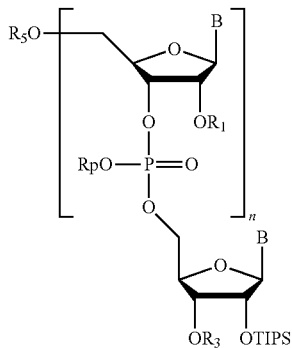

wherein
n is an integer from 1 to 19;
$R_1$ is a protecting group;
$R_3$ is selected from H, a protecting group, or

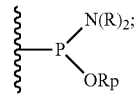

$R_5$ is selected from H, or a protecting group;
$R_p$ is a protecting group;
R is lower alkyl, or the $N(R)_2$ moiety is a cyclic alkylamine, or a substituted cyclic alkylamine, preferably morpholine;
B is a nitrogen-containing base;
wherein each B, $R_1$ and $R_p$ may be the same or different from any other B, $R_1$ and $R_p$, respectively.

In another aspect, there is provided a process for preparing a compound of formula (II):

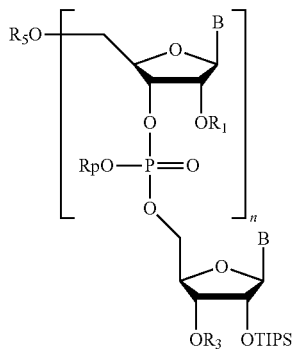

wherein
n is selected from 1, 2, or 3;
$R_1$ is a protecting group;
$R_3$ is selected from H or a protecting group;
$R_5$ is a protecting group;
$R_p$ is a protecting group;
B is a nitrogen-containing base;
wherein each B, $R_1$ and $R_p$ may be the same or different from any other B, $R_1$ and $R_p$, respectively;
the process comprising the steps of:
a) condensing a phosphoramidite of formula (III):

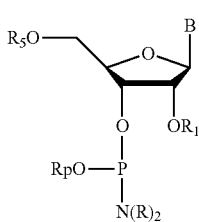

wherein B, $R_1$, $R_5$, and $R_p$ are as defined above; and
R is lower alkyl, or the $N(R)_2$ moiety is a cyclic alkylamine, or a substituted cyclic alkylamine, preferably morpholine;

with a nucleoside of formula (IV):

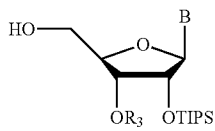

wherein B and $R_3$ are as defined above; and b) oxidizing the product of step (a) to produce the compound of formula (II) where n is 1, and B, $R_1$, $R_3$, $R_5$, and $R_p$ are as defined above; and c) where n>1, the process further comprising:
  (i) deprotecting the terminal —$OR_5$ group of the product of the previous step to form a free 5'-OH group;
  (ii) condensing the product of step (i) with a phosphoramidite of formula (III), wherein B, $R_1$, $R_5$, $R_p$ and R are as defined above, and each B, $R_1$, $R_5$, $R_p$ and R may be the same or different from any other B, $R_1$, $R_5$, $R_p$ and R, respectively;
  (iii) oxidizing the product of step (ii);
  (iv) repeating steps (i)-(iii) n-2 times;
to form the compound of formula (II)

In an aspect, there is provided herein an ionic tag linker comprising a gamma ketoester moiety, an ionic moiety and a linker. In one embodiment, the ionic tag linker has the structure of formula (K):

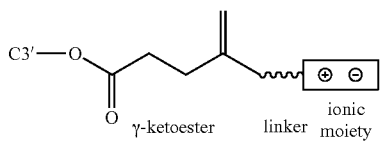

The linker may be, for example, alkyl, glycol or functionalized alkyl. In some embodiments, alkyl is C1 to C6 alkyl. The ionic moiety may be, for example, an imidazolium or phosphonium group. In some embodiments, an ionic moiety comprises a halide, for example an ionic moiety may comprise Br⁻, Cl⁻ or I⁻.

It should be understood that an ionic moiety in an ionic tag linker of the invention may comprise any salt, such as but not limited to a phosphonium salt, an imidazolium salt, etc. Many salts are known in the art and are within the capacity of a skilled technician. Further non-limiting examples include organic salts comprising a heterocyclic or substituted heterocyclic quaternary nitrogen-containing organic cation, a heterocyclic or substituted heterocyclic quaternary phosphonium containing organic cation, or a heterocyclic or substituted heterocyclic trivalent sulfonium containing organic cation; and an anion balancing the charge on the organic cation. In a more particular embodiment an organic cation is selected from the group consisting of N-substituted pyridine and 1,3-disubstituted imidazole. An anion balancing the charge on the organic cation may be selected from the group consisting of Cl'', Br', BF4'', PF6'', SbF6'', CuCl2'', I and AlCl4''. Other suitable anions could also be used and are well within the capacity of a skilled technician.

In an embodiment, an ionic moiety in an ionic tag linker of the invention is a zwitterionic phosphonium salt of Formula I:

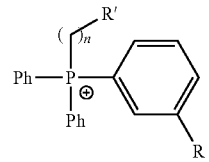

wherein: n is 0 or 1; R is H or $SO_3^-$; R' is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, phenyl, substituted phenyl, benzyl and $C_1$-$C_{10}$ alkoxycarbonyl; R' is $CX_3$ when n is 0; and X is selected from the group consisting of F, Cl, Br and I. For example, the zwitterionic phosphonium salt may have the following structure:

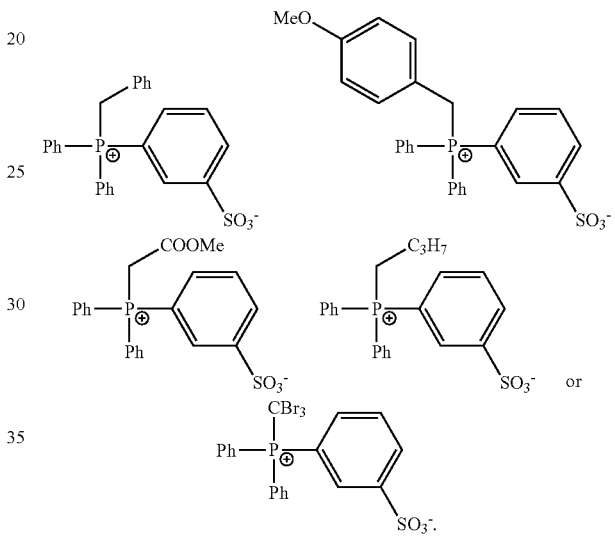

In an embodiment, a gamma ketoester moiety is cleavable with hydrazine.

In another aspect, there is provided herein an ionic tag linker comprising a photolabile moiety, an ionic moiety and a linker. The photolabile moiety may be, for example, a nitrobenzyl derivative. In an embodiment, the ionic tag linker has the structure of formula (P):

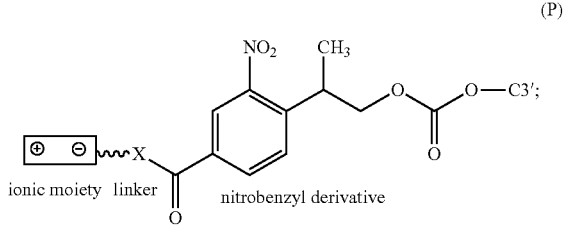

wherein X is N or O.

The linker may be alkyl, glycol or functionalized alkyl. In some embodiments, alkyl is C1 to C6 alkyl. The ionic moiety may be an imidazolium or phosphonium group. In one embodiment, the photolabile moiety is cleavable by photolysis.

In some embodiments, ionic tag linkers provided herein are orthogonally cleavable. In further embodiments, ionic tag linkers are attached to the terminal 3'-hydroxyl of an oligoribonucleotide or oligodeoxyribonucleotide. Ionic tag linkers may be selectively cleavable under conditions which do not cleave other oligoribonucleotide or oligodeoxyribonucleotide protecting groups. Ionic tag linkers may also be cleavable under conditions which do not cause isomerisation of, e.g., terminal oligoribonucleotide 2'-O-silyl protecting groups.

In an embodiment, an ionic tag linker is selected from:

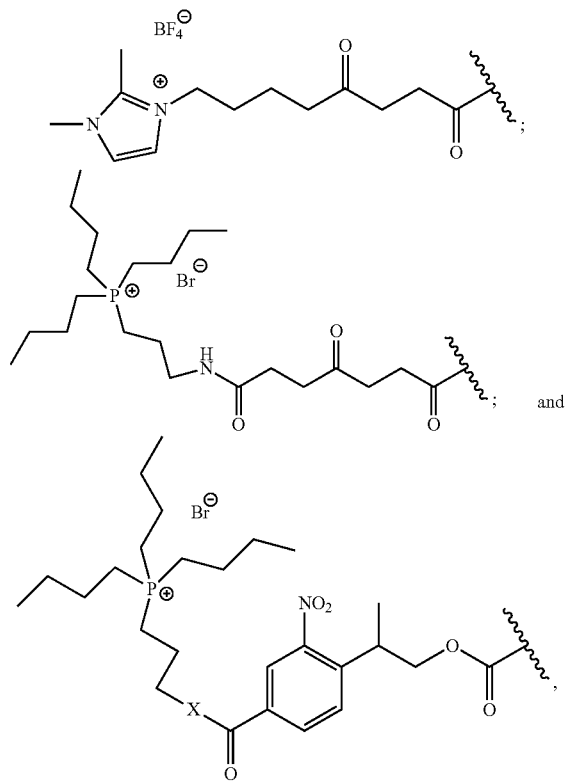

wherein X is selected from NH and O.

In another embodiment, an ionic tag linker is selected from:

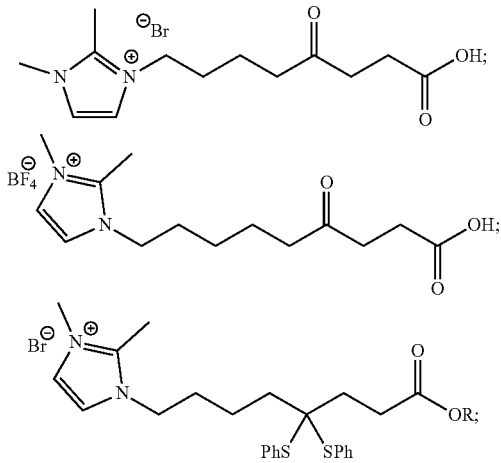

compound (17); compound (25); compound (32); compound (43); compound (55); compound (57); compound (23); compound (56); compound (54); compound (76); compound (7); compound (8); compound (9); compound (15); compound (16); compound (19); compound (70); compound (80); compound (82); and compound (10).

In an embodiment, an ionic tag linker comprises a diethoxy group or a dithiophenyl group. In a particular embodiment, an ionic tag linker comprises a dithiophenyl group and a phosphonium salt. In another embodiment, an ionic tag linker comprises a dithiophenyl group and an imidazolium salt. In yet another embodiment, an ionic tag linker comprises a diethoxy group and a phosphonium salt. In a further embodiment, an ionic tag linker comprises a diethoxy group and an imidazolium salt.

In another aspect, there are provided herein compounds of formula (II):

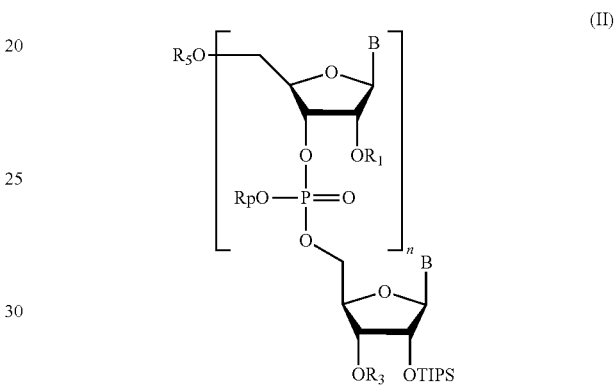

(II)

wherein:

n is an integer from 1 to 19;

$R_1$ is a protecting group;

$R_3$ is selected from H, a protecting group,

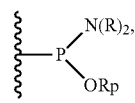

and an ionic tag linker provided herein;

$R_5$ is selected from H, and a protecting group;

$R_p$ is a protecting group;

R is lower alkyl, or the $N(R)_2$ moiety is a cyclic alkylamine or a substituted cyclic alkylamine, preferably morpholine; and B is a nitrogen-containing base;

wherein each B, $R_1$ and $R_p$ may be the same or different from any other B, $R_1$ and $R_p$, respectively.

In an embodiment, n is 1, 2, or 3. In another embodiment, $R_3$ is

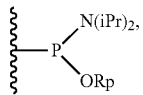

and $R_5$ is a protecting group. In yet another embodiment, $R_3$ is

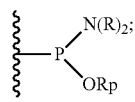

$R_5$ is selected from DMTr or MMTr; $R_p$ is selected from methyl (Me), 2-cyanoethyl (CNEt), ortho-chlorophenyl (o-ClPh), and para-chlorophenyl (p-ClPh); R is selected from isopropyl, methyl, and ethyl; and B is a nucleobase protected on at least one nitrogen by a suitable N-protecting group. In a still further embodiment, R is isopropyl. In another embodiment, a N-protecting group is selected from levulinyl, acetyl, difluoroacetyl, trifluoroacetyl, isobutyryl, benzoyl, 9-fluorenylmethoxycarbonyl, phenoxyacetyl, dimethylformamidine, and N,N-diphenyl carbamate.

In some embodiments, $R_3$ is substituted with an ionic tag linker provided herein. In embodiments, $R_3$ is

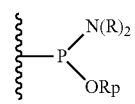

or a protecting group, and may or may not be substituted with an ionic tag linker provided herein. In another embodiment, the protecting group is a levulinyl group (Lev), or is an ionic tag linker provided herein, e.g., an ionic tag linker comprising a gamma ketoester moiety or an ionic tag linker comprising a photolabile moiety.

In another aspect, there are provided herein processes for preparing compounds disclosed herein. In an embodiment, a compound has the structure:

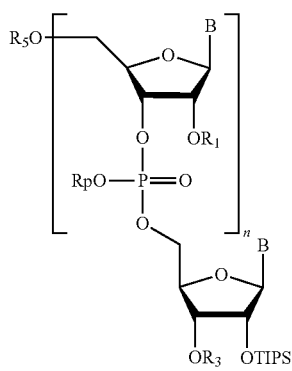

(II)

wherein:

n is selected from 1, 2, and 3;

$R_1$ is a protecting group;

$R_3$ is selected from H, a protecting group and an ionic tag linker provided herein;

$R_5$ is a protecting group; $R_p$ is a protecting group; and

B is a nitrogen-containing base;

wherein each B, $R_1$ and $R_p$ may be the same or different from any other B, $R_1$ and $R_p$, respectively;

and a process comprises the steps of:

a) condensing a phosphoramidite of formula (III):

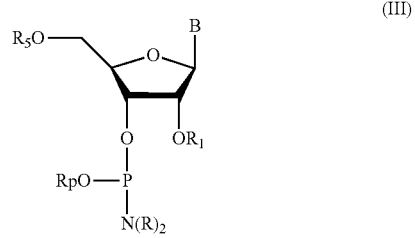

(III)

wherein B, $R_1$, $R_5$, and $R_p$ are as defined above; and

R is lower alkyl, or the $N(R)_2$ moiety is a cyclic alkylamine, or a substituted cyclic alkylamine, preferably morpholine;

with a nucleoside of formula (IV):

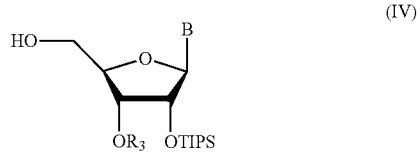

(IV)

wherein B and $R_3$ are as defined above; and b) oxidizing the product of step (a) to produce the compound of formula (II) where n is 1, and B, $R_1$, $R_3$, $R_5$, and $R_p$ are as defined above; and c) where n>1, the process further comprising:

(i) deprotecting the terminal —$OR_5$ group of the product of the previous step to form a free 5'-OH group;

(ii) condensing the product of step (i) with a phosphoramidite of formula (III), wherein B, $R_1$, $R_5$, $R_p$ and R are as defined above, and each B, $R_1$, $R_5$, $R_p$ and R may be the same or different from any other B, $R_1$, $R_5$, $R_p$ and R, respectively;

(iii) oxidizing the product of step (ii); and (iv) repeating steps (i)-(iii) n–2 times;

to form the compound of formula (II).

In an embodiment, $R_3$ is H. In another embodiment, $R_3$ is a protecting group, and the process further comprises: d) removal of the $R_3$ protecting group. In an embodiment, the protecting group is a levulinyl (Lev) group. In another embodiment, the protecting group is an ionic tag linker provided herein.

In other embodiments, processes of the invention further comprise phosphitylation of the product of step (b) or (c) to form a compound of formula (IIa):

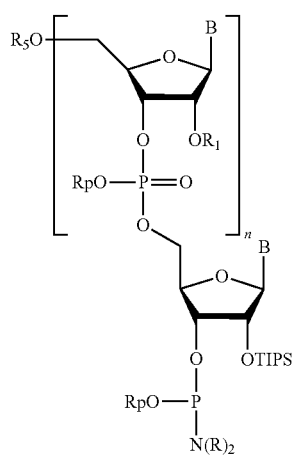

(IIa)

wherein n, B, $R_1$, $R_5$, $R_p$ and R are as previously defined.

Processes may also comprise phosphitylation of the product of step (d) to form a compound of formula (IIa):

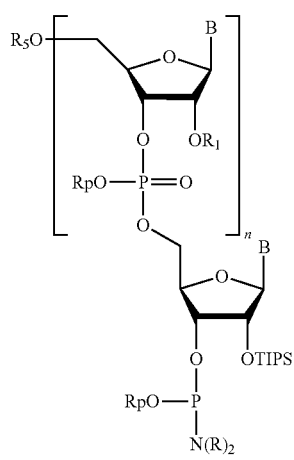

(IIa)

wherein n, B, $R_1$, $R_5$, $R_p$ and R are as previously defined.

In an embodiment, $R_1$ is TBDMS; $R_5$ is selected from DMTr and MMTr; $R_p$ is selected from methyl (Me), 2-cyanoethyl (CNEt), ortho-chlorophenyl (o-ClPh), and para-chlorophenyl (p-ClPh); R is selected from isopropyl, methyl, and ethyl; and B is a nucleobase protected on at least one nitrogen by a suitable N-protecting group, wherein the N-protecting group is selected from levulinyl, acetyl, difluoroacetyl, trifluoroacetyl, isobutyryl, benzoyl, 9-fluorenylmethoxycarbonyl, phenoxyacetyl, dimethylformamidine, and N,N-diphenyl carbamate.

In further aspects, there are provided herein methods for synthesizing an oligomer, the methods comprising: (a) attaching an ionic tag linker provided herein to a first monomer unit; (b) contacting the first monomer unit with at least one further monomer unit at reaction conditions to provide an oligomer comprising from 2 to 30 monomer units; and (c) cleaving the ionic tag linker from the oligomer to provide the free oligomer. In an embodiment, the oligomer is an oligopeptide, an oligosaccharide or an oligonucleotide. In a particular embodiment, the oligonucleotide is an oligoribonucleotide. In another embodiment, the oligonucleotide is an oligodeoxyribonucleotide.

In one embodiment, there is provided a method for synthesizing an oligoribonucleotide, the method comprising: (a) attaching an ionic tag linker provided herein to a first ribonucleoside at the terminal 3'-hydroxyl; (b) contacting the first ribonucleoside with at least one further ribonucleoside at reaction conditions to provide an oligoribonucleotide comprising from 2 to 30 ribonucleosides; and (c) cleaving the ionic tag linker from the oligoribonucleotide to provide the free oligoribonucleotide.

In some embodiments, methods provided herein further comprise a step of isolating an oligomer, oligoribonucleotide or oligodeoxyribonucleotide before cleaving an ionic tag linker from the oligomer, oligoribonucleotide or oligodeoxyribonucleotide. For example, an oligomer, oligoribonucleotide or oligodeoxyribonucleotide may be isolated by precipitation, based on ionic properties of an ionic tag linker.

In another aspect, there is provided herein a ribonucleoside having attached at its 3'-hydroxy an ionic tag linker provided herein.

In yet another aspect, there is provided herein a deoxyribonucleoside having attached at its 3'-hydroxy an ionic tag linker provided herein.

BRIEF DESCRIPTION OF THE DRAWINGS

FIGURE shows a $^{31}$P-NMR spectrum of compound (30) (4 P-diastereomers) in $CD_3CN$.

DETAILED DESCRIPTION

The present disclosure relates generally to the field of oligonucleotide synthesis, and provides compositions and methods for the synthesis of RNA and DNA. In some embodiments, novel dimer and trimer blocks are provided for the synthesis of RNA or DNA oligonucleotides on solid supports. In another embodiment, a tetramer block is provided. In yet another embodiment, larger blockmers are provided (e.g. 5-, 6-, 7-, 8-, 9-, 10-, 11-, 12-, 13-, 14-, 15-, 16-, 17-, 18-, 19-, or 20-mers). In further aspects, ionic tags for liquid phase synthesis and methods for liquid or solution phase synthesis of oligomers, e.g., oligopeptides, oligosaccharides, oligonucleotides, particularly RNA oligonucleotides and also DNA oligonucleotides, are provided.

In a standard oligonucleotide synthesis cycle, chain elongation begins with the selective cleavage of the 5'-O-dimethoxytrityl (DMTr) group by an organic acid (e.g. TFA), liberating a free 5'-hydroxyl group. This terminal nucleophile is then allowed to couple to a protected nucleoside 3'-O-phosphoramidite monomer in the presence of an activator. In the case of RNA synthesis, suitable protection of the 2'-hydroxyl group is required to prevent side reactions. Any unreacted 5'-hydroxyl groups are acetylated in a process referred to as 'capping', in order to prevent elongation of short-mers. The most common capping strategy utilizes acetic anhydride to produce an acetyl ester "cap". Thus, 'capping' esterifies any unreacted 5'-hydroxyl groups, and prevents the accumulation of by-products. The newly created phosphite triester 3',5'-linkage is then oxidized to produce the more stable phosphate triester. This process is repeated until an oligomer of a desired length and sequence is obtained. Cleavage of the oligomer from a solid support, and removal of all protecting groups from the sugars, phosphates and nucleobases, provides the desired target oligomer, which is then purified from shorter undesired sequences by ion exchange high performance liquid chromatography (HPLC), ion-pair reverse phase HPLC, or polyacrylamide gel electrophoresis (PAGE). A full length oligomer is then characterized by mass spectrometry. For high throughput synthesis applications, a very large number of DNA or RNA oligomers can be synthesized in parallel on DNA and RNA microarrays or "gene chips" [Ramsay G., Nature Biotechnology 16, 40-44 (1998)], although these methods are currently limited to the picomolar scale [Sriram Kosuri et al. Nature Biotechnology, 28, 1295-1299 (2010)].

Unlike a TBDMS group, ACE and TOM protecting groups are not shown to migrate to vicinal hydroxyl groups in the presence of mild base or aqueous polar protic solvents. While both overcome the isomerisation problem possessed by TBDMS groups, only ACE protecting groups are orthogonal (with respect to cleavage) to all other protecting groups used in standard ribonucleoside protection. This is a property that is highly desirable in RNA synthesis. A TOM protecting group, like most silyl protecting groups, is fluoride labile, whereas hydrazine hydrate buffered in pyridine acetic acid will selectively remove the gamma-keto ester of the acetal levulinyl ester (ALE) protecting group, without cleaving the dimethoxytrityl, N-benzoyl, methoxy-phosphate or silyl protecting groups used in standard oligoribonucleotide synthesis.

More recently, we have shown 2'-O-TIPS protecting groups can be used as an alternative to 2'-O-TBDMS. This allowed for cleavage of the 3'-hydroxyl protecting group, levulinyl, or ALE using buffered hydrazine hydrate, without isomerisation of the 2'-TIPS. This was previously determined to be prohibitive with the TBDMS group when cleaving 3'-hydroxyl protecting groups on ribonucleotide dimer and trimer blocks, as isomerisation was found to occur and separation of one regio-isomer over the other was not possible. The same effect could be achieved with TOM protecting groups, but the cost and availability of TIPS-chloride makes it a superior choice. This led to the production of isomerically pure "block" ribonucleotide phosphoramidites and their utility during solid supported oligo synthesis, resulting in higher overall yields, fewer coupling steps, and simplified purification protocols, as described herein.

Solid-supported synthesis overcomes the limitation of purification by allowing excess reagents to be washed away. Unfortunately, it can be quite restricting in terms of scale. While it is true that current large scale methods of producing oligonucleotides in the kilogram scale utilize solid phase approaches, the mechanical requirements for this type of manufacturing are very specialized and costly. Therefore, an ideal method of large scale synthesis is in solution. An improvement over the polymer based soluble supports was accomplished with use of ionic soluble supports, first described by Tak-Hang Chan for synthesis of carbohydrates and peptides [Chan, T-H. et al. J. Org. Chem., 70, 3251-3255 (2005); Chan, T-H. et al. Acc. Chem. Res. 39: 897-908 (2006)]. Soluble ionic tags, in contrast to polymer based alternatives, can be precipitated at room temperature in standard, commercially available solvents. These involve simple, inert, readily available ionic species, and they do not suffer from low loading and poor atom economy as seen with traditional soluble supports. This method of product isolation is therefore beneficial with respect to both cost and time when purifying compounds, as it can circumvent the use of chromatography traditionally used to purify organic compounds. Ionically-tagged molecules could open up synthetic routes once thought to be prohibitively expensive due to purification costs.

Using an ionic tag in place of traditional solid support, a similar iterative method of DNA and RNA oligonucleotides synthesis on solid support, has been applied recently in solution [Donga, R. A. et al., J. Org. Chem. 71, 7907-7910 (2006); Donga, R. A. et al., Can. J. Chem. 85, 274-282 (2007)]. Use of ionic soluble supports allows for selective precipitation of growing oligonucleotide over all other reagents used in the oligonucleotide synthesis cycle, significantly simplifying intermediate purification steps. This selective precipitation of products over reagents can be used in a variety of reactions, and has been shown to be effective as an alternative to chromatography. This can be advantageous, particularly in the context of a large scale industrial process where chromatography can be prohibitively expensive [Chan, T-H. et al. J. Org. Chem., 70, 3251-3255 (2005); Chan, T-H. et al. Acc. Chem. Res. 39: 897-908 (2006)].

Thus, we sought to combine a process of solution phase oligonucleotide synthesis using a soluble ionic-tag approach to produce block nucleotide, e.g., ribonucleotide, phosphoramidites, in particular to overcome at least some or all of the limitations of solid phase synthesis, which can be long and tedious.

Traditionally, the free 3'-hydroxyl group has been protected/linked to a solid support by an ester bond through a succinyl linker to a long chain alkyl amine derivatised to a solid support. This would remain covalently bound during the iterative stepwise synthesis of DNA, RNA, peptides or oligosaccharides. This covalent bond is cleaved at the end of the synthesis by amminolysis, which simultaneously cleaves other protecting groups (cyanoethyl and exocyclic amine base protecting groups for DNA and RNA) throughout the molecule. A fully deprotected molecule is released in the case of DNA and peptide synthesis, or a partially deprotected molecule in the case of RNA and some oligosaccharides [Beaucage, S. L.; Herdewijn, P. Curr. Protoc. Nucleic Acid Chem. 47:13.0-13.4 (2011)]. This multi-cleavage event is of great utility when the full deprotection of the final molecule is desired, but can be troublesome when the desired molecule must retain its protecting groups for further modifications or transformations post-oligomerization.

A variety of different linkers have now been developed for attaching nucleosides to their solid supports. A particularly versatile linker, Uny-Linker™, is widely used because it does not require derivatization of a nucleoside to the support prior to automated oligonucleotide synthesis. Other alternatives include the Q-linker developed by Pon and co-workers [Pon, R. T., Yu, S. Nucleic Acids Research 25, 3629-3635 (1997)] and silicon-based linkers, which are cleaved by a fluoride source via pyridine-HF [Boehm T. L., Showalter, H. D. H., J. Org. Chem., 61 6498-6499 (1996)]. Additionally, a variety of photolabile linkers based on the nitrophenyl group have been reported and used for many sensitive applications [Anderson, E., et al. Nucleosides, Nucleotides and Nucleic Acids, 22, 1403-1406 (2003); Pirrung, M. C. et al. Org Lett, 3, 1105-1108 (2001); Pfeiderer, W. et al. Nucleosides and Nucleotides, 17, 1987-1996 (1998)].

A levulinyl group in the place of traditional esters at the 3'-hydroxyl can be removed in conjunction with a 2'-TIPS protecting group without isomerisation allowing for chemical modifications following-chain elongation [Hassler, M. H. et al. Tett Lett, 52, 2575-2578 (2011); Nemer, M. J, and Ogilvie, K. K., Can. J. Chem. 58, 1389-1397 (1980)]. The levulinyl group possesses the same stability as traditional esters, but can be cleaved by mild treatment with buffered hydrazine. This method is compatible with all protecting groups used in DNA and RNA synthesis, as well as many protecting groups used in classical synthetic organic chemistry. Exceptions are any molecules bearing an unprotected ketone functional group, as hydrazine will readily react to form a hydrazone. This is fundamental in the cleavage mechanism of the levulinyl protecting group. Unfortunately, a problem with replacing the 3'-O-succinyl linker with a levulinyl group is that it is no longer attachable to a solid support. To overcome this issue a levulinyl-like linker would have to be chemically modified to install functional groups that allow for coupling to the ionic tag.

Among all previously developed linkers, a photolabile linker seems to offer the mildest of conditions. However no photolabile linker was previously developed and used to release an oligoribonucleotide from the 3'-terminal position, and shown to retain regio-isomeric purity. Such a linker is highly desirable and is provided herein. A NPPOC type photolabile linker that could be coupled to solid support provided partially esterified oligoribonucleotides Johnsson, R. et al., *Bioorganic & Medicinal Chemistry Letters,* 21, 3721-3725, (2011)].

The options of using linkers which are cleaved under mild conditions would be of particular interest to those attempting post synthesis modifications of oligonucleotides. To our knowledge, no photolabile or levulinyl-like linkers have been previously developed and used for DNA and RNA synthesis, which are cleavable in the presence of traditional oligoribonucleotide protecting groups, which also do not cause isomerisation of the terminal 2'-O-silyl protecting group when the linker is cleaved from the terminal 3'-hydroxyl.

There are provided herein methods which combine a process of solution phase oligonucleotide synthesis using a soluble ionic-tag approach to produce block ribonucleotide phosphoramidites. Methods provided herein are also applicable to oligodeoxyribonucleotide (oligo DNA) synthesis. For example, there are provided herein methods which combine a process of solution phase oligonucleotide synthesis using a soluble ionic-tag approach to produce block deoxyribonucleotide phosphoramidites.

Accordingly, we report herein novel linkers that can attach to an ionic-tag and the 3'-hydroxyl of a nucleoside with the ability to cleave without simultaneous deprotection of any other protecting groups, nor cause isomerization of the 2'-silyl group to the 3'-position. In an embodiment, ionic tag linkers are provided herein.

In one embodiment there is provided a compound of formula (II):

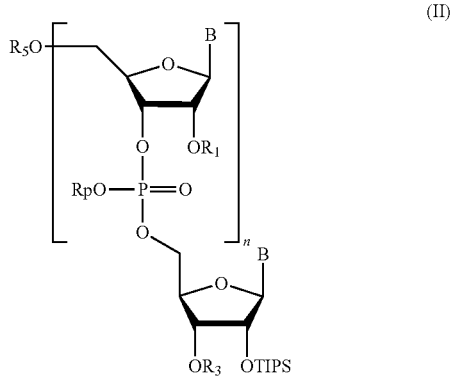

wherein
n is an integer from 1 to 19;
$R_1$ is a protecting group;
$R_3$ is selected from H, a protecting group, and

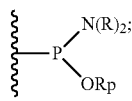

$R_5$ is selected from H, and a protecting group;
$R_p$ is a protecting group;
R is lower alkyl, or the $N(R)_2$ moiety is a cyclic alkylamine, or a substituted cyclic alkylamine, preferably morpholine;
B is a nitrogen-containing base;
wherein each B, $R_1$ and $R_p$ may be the same or different from any other B, $R_1$ and $R_p$, respectively.

In another embodiment, n is selected from 1, 2, and 3.

In another embodiment, $R_3$ is

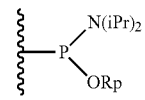

and $R_5$ is a protecting group.

In another embodiment:

$R_3$ is

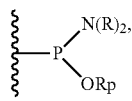

$R_p$ is selected from methyl (Me), 2-cyanoethyl (CNEt), ortho-chlorophenyl (o-ClPh), and para-chlorophenyl (p-ClPh), preferably methyl, and R is selected from isopropyl, methyl, and ethyl, preferably isopropyl.

In another embodiment:

$R_1$ is TBDMS;

$R_5$ is selected from DMTr and MMTr, preferably DMTr; and

B is a nucleobase protected on at least one nitrogen by a suitable N-protecting group.

In another embodiment, a suitable N-protecting group is selected from levulinyl, acetyl, difluoroacetyl, trifluoroacetyl, isobutyryl, benzoyl, 9-fluorenylmethoxycarbonyl, phenoxyacetyl, dimethylformamidine, and N,N-diphenyl carbamate.

In another embodiment, $R_3$ is a protecting group. In yet another embodiment, a protecting group is a levulinyl group (Lev). In still yet another embodiment, a protecting group is an ionic tag linker. In another embodiment, an ionic tag linker is selected from:

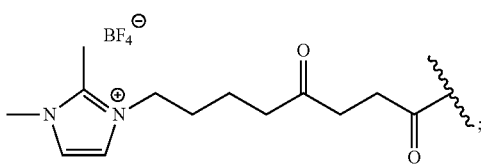

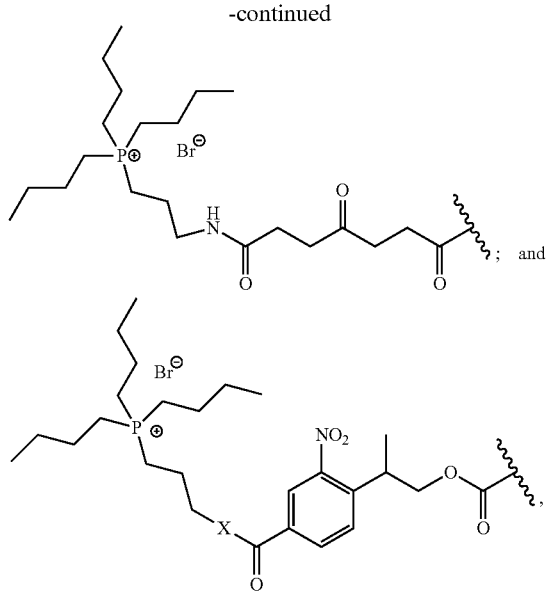

wherein X is selected from NH and O.

The term "lower alkyl" as used herein refers to acyclic, straight or branched chain alkyl groups containing from one to six carbons. Preferred lower alkyl groups include, for example, isopropyl, methyl, and ethyl.

Functional groups of compounds disclosed herein may be protected by a variety of protecting groups known to those of skill in the art. A "protecting group" is used in the conventional chemical sense to reference a group which reversibly renders unreactive a functional group under specified conditions of a desired reaction. Some protecting groups are well known to one skilled in the art. Examples of the protection/deprotection process as well as various protecting groups are described in Wuts and Greene, 2006, *Greene's Protective Groups in Organic Synthesis*, Wiley-Interscience, New York, N.Y. Any suitable protecting group known to one skilled in the art may be used. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

For instance, possible protecting groups for $R_1$ for the compounds of formula (II) above and the various compounds below include:

1. Fluoride labile protecting groups including: t-butyldimethylsilyl (TBDMS), triisopropylsilyl (TIPS); triisopropyloxymethyl (TOM); cyanoethylmethyl (CEM); 2-(4-tolylsulfonyl)ethoxymethyl (TEM).
2. Acid labile groups including acetal groups: 2'-O-bis(2-acetoxyethoxy)methyl (ACE) orthoester; 1-(2-fluorophenyl)-4-methoxypiperidin-4-yl (Fpmp); 1-(4-chlorophenyl)-4-ethoxypiperidin-4-yl (Cpep); 4-(N-dichloroacetyl-N-methylamino) benzyloxymethyl (4-MABOM); trityl ether groups including dimethoxytrityl (DMTr) and monomethoxytrityl (MMTr).
3. Reduction labile groups including: 2-tert-butyldithiomethyl (DTM); allyl.
4. Base labile groups including: levulinyl (Lev) and acetal levulinyl (ALE).
5. Photolabile groups including: photolabile groups including nitrobenzyl groups (including 2'-nitrobenzyl groups such as 2-(2-nitrophenyl)propoxycarbonyl (NP-POC), α-methylnitorpiperonyloxycarbonyl (MeN-POC) and derivatives therein (including thioxanthone-nitrobenzyl group conjugates) and 5'-O-dimethoxybenzoincarbonate group (DMBOC).

Possible protecting groups for $R_5$ for the compounds of formula (II) above and in the various compounds below include 9-phenylxanthyl (pixyl or Px) and its derivatives, MMTr, and DMTr. Preferably, these protecting groups are used for $R_5$ when options 1, 3, 4, and 5 are used as protecting groups for $R_1$ as noted above.

The $R_p$ group as shown for the compounds of formula (II) above and in the various compounds below may be methyl (Me), 2-cyanoethyl (CNEt), p-nitro-phenylethyl (NPE), and para- and ortho-chlorophenyl (p- or o-ClPh).

Possible protecting groups for the 3'-hydroxyl position ($R_3$ for the compounds of formula (II) and for the various compounds described below) include levulinyl, and ionic protecting groups, also referred to as ionic tag linkers. Suitable ionic tags are known to those of skill in the art. These may include those described in PCT Application Publication No. WO 2006/096963 of Chan, T.-H. et al., the contents of which are incorporated herein by reference in its entirety. Suitable ionic tags may include, for example, imidazolium and phosphonium ionic moieties having linkers selected from alkyl linkers, glycol linkers, etc.

In an embodiment, an ionic tag is a phosphonium ionic tag comprising a zwitterionic phosphonium salt of Formula I:

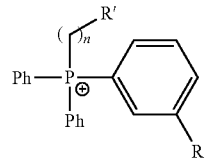

Formula I wherein: n is 0 or 1; R is H or $SO_3^-$; R' is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, phenyl, substituted phenyl, benzyl and $C_1$-$C_{10}$ alkoxycarbonyl; R' is $CX_3$ when n is 0; and X is selected from the group consisting of F, Cl, Br and I. In another embodiment, the zwitterionic phosphonium salt of Formula I is:

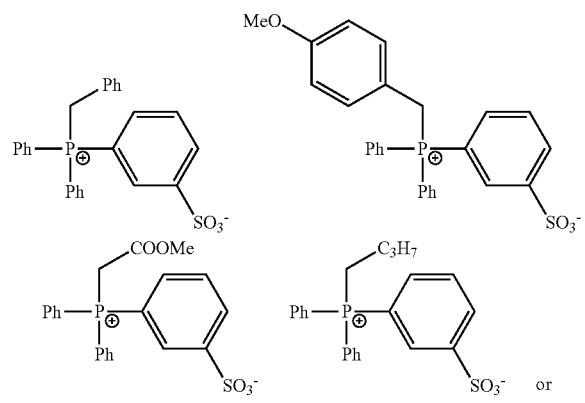

or

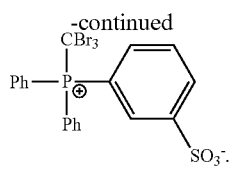

These and other zwitterionic phosphonium salts which may be included in ionic tags of the invention are described in, for example, International PCT Application Publication No. WO2010/012096, the entire contents of which are hereby incorporated by reference.

In one embodiment, a protecting group is an orthogonally cleavable ionic tag linker. For example, a protecting group can be in one embodiment an orthogonally cleavable ionic tag linker (K) comprising a gamma ketoester moiety, an ionic moiety and a linker:

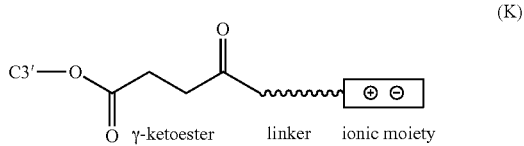

In another embodiment, a protecting group is an orthogonally cleavable ionic tag linker (P) comprising a photolabile moiety, e.g., a nitrobenzyl derivative, and an ionic moiety and a linker:

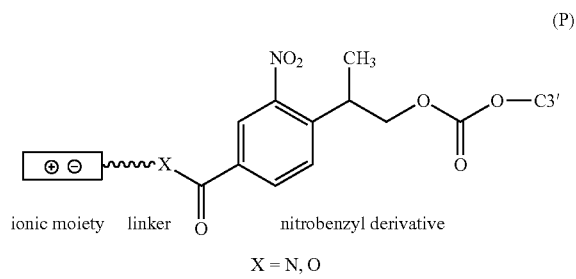

Both (K) and (P) contain an ionic moiety for use in a precipitation-based purification as described in described in PCT Application Publication No. WO 2006/096963 of Chan, T.-H. et al., the contents of which are incorporated herein by reference in its entirety. The ionic moiety in (K) and (P) is attached to a gamma-keto ester or photolabile moiety, respectively, through a linker, most simply a short alkyl chain or a functionalized alkyl chain of one or more carbons. A gamma-keto moiety is cleaved selectively with hydrazine, whereas (P), a nitrobenzyl derivative, is cleaved by photolysis, releasing the 3'OH group for further functionalization. The present invention provides a method for cleavage of (K) and (P), as well as phosphitylation of the unblocked 3'OH to afford amidite blocks for use in oligonucleotide synthesis.

The entity B in the compounds of formula (II) above and in the compounds described below is a nitrogen-containing base, preferably a base or a protected-base (also referred to herein as a "nucleobase"). The base is preferably a purine or pyrimidine base or analog thereof. Analogs include diaminopurine and its derivatives, inosine and its derivatives, alkylated purines or pyrimidines, acylated purines or pyrimidines, and thiolated purines or pyrimidines. More specific analogs include, for example, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, and the like. A "protected base" is protected on at least one nitrogen by any suitable N-protecting group including levulinyl, acetyl, difluoroacetyl, trifluoroacetyl, isobutyryl, benzoyl, 9-fluorenylmethoxycarbonyl, phenoxyacetyl, dimethylformamidine, N,N-diphenyl carbamate, and the like. Preferably, the base is selected such that the compound of formula (II) is a derivative of adenine (A), cytosine (C), guanine (G), or uracil (U). In an embodiment, where the compound is a deoxyribonucleotide, the base is selected such that the compound of formula (II) is a derivatice of adenine (A), cytosine (C), guanine (G), or thymine (T).

Various aspects related to the practice of the present invention are disclosed in PCT International Application Publication No. WO 2009/064115 to Samchully Pharm. Co., Ltd.; Kumar, G. and Poonian, M. S. *J. Org. Chem.*, 49, 4905-4912 (1984); Nemer, M. J, and Ogilvie, K. K., *Can. J. Chem.* 58, 1389-1397 (1980). Recent advances in RNA synthesis have been summarized in a review by S. Beaucage, *Curr. Opin. Drug Discov. Devel.* 11, 203-261 (2008)].

The use of previously reported dimer and trimer phosphoramidite synthons were directed at the synthesis of RNA oligomers, involving the use of such dimer or trimer units only in the first coupling reaction on solid supports (WO 2009/064115). Following coupling of one such dimer unit, the ensuing steps involved the exclusive coupling of monomeric phosphoramidite units until the desired length was produced (WO 2009/064115). This discourages the use of "various kinds of dimers" for the purpose of RNA synthesis, as this would require "long-term periods of synthesis and high production costs." The disclosure further emphasizes that it "employs just one dimer or trimer species only in the first coupling step and then common inexpensive monomer units in the subsequent steps, which enable the low-cost, high purity production of the nucleotide oligomers".

In contrast to the above disclosure, the RNA dimers and trimers presently described can be used exclusively or in combination with monomeric units. In addition to applications in solution-phase RNA synthesis, their use can also be extended to routine synthesis of RNA on conventional solid supports such as controlled pore glass and polystyrene. In this case, the RNA strand is assembled by several block couplings, cleaved and released from the support after synthesis and the resulting synthetic RNA utilized in physicochemical or biological studies. There are several derivatives that may be included for such block coupling reactions [see structures (30), (47) and (50) below].

The 2'-TIPS protecting group at the 3'-termini of such structures provides unique 5'-DMTr 3'-phosphoramidite dimer and trimer synthons for RNA synthesis. In some embodiments, the methods provided herein are adapted for use in solution-phase DNA synthesis as well as routine synthesis of DNA on conventional solid supports.

Furthermore, the 2'-TIPS protected dimer and trimer synthons described herein provide several distinct advantages over previously reported 2'-TBDMS 3'-phosphoramidite dimer synthons (WO 2009/064115). The inventors have discovered that the use of TIPS completely eliminates 2' to 3'-isomerization that occurs with 2'-TBDMS protecting groups present in previously reported synthons (WO 2009/064115); in fact, the present disclosure teaches that when synthetic procedures are followed as described in WO 2009/064115, that 2'-TBDMS dimer synthons are not isolated in pure form, but rather as mixtures of 2'+3'-TBDMS regioisomers that are difficult (if not impossible) to separate under the specifications provided.

In an embodiment, methods described herein provide isomerically pure dimer and trimer synthons in high yields. In another embodiment, methods provided herein lead to high fidelity RNA synthesis. Such dimer and trimer synthons when coupled in solution or solid phase, allow longer chain extensions at each coupling stage of RNA synthesis, significantly reducing the total number of steps required in the synthesis of target RNA oligomers, and reducing their exposure to acidic environment. Additionally, dimer and trimer synthetic routes produce crude RNA oligomers that are generally more readily separated from the products of failure couplings. Thus the dimer and trimer block approaches potentially benefit critical aspects of siRNA manufacturing: speed and purification of synthesis, and the integrity of the desired full length RNA chain.

In another embodiment, there is provided a process for preparing a compound of formula (II):

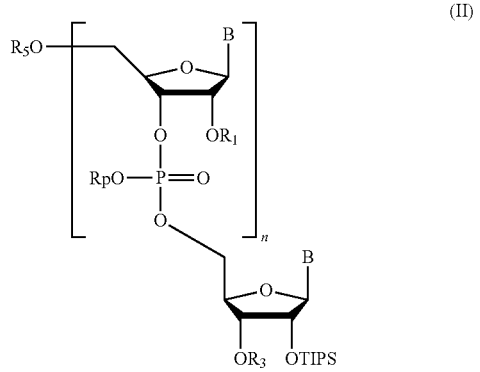

wherein
n is selected from 1, 2, or 3;
$R_1$ is a protecting group;
$R_3$ is selected from H, a protecting group and an ionic tag linker;
$R_5$ is a protecting group;
$R_p$ is a protecting group;
B is a nitrogen-containing base;
wherein each B, $R_1$ and $R_p$ may be the same or different from any other B, $R_1$ and $R_p$, respectively;
the process comprising the steps of:
a) condensing a phosphoramidite of formula (III):

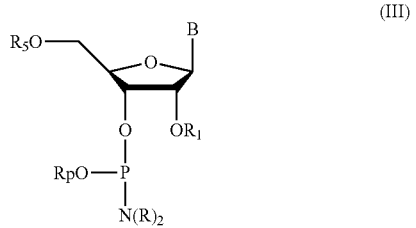

wherein B, $R_1$, $R_5$, and $R_p$ are as defined above; and
R is lower alkyl, or the $N(R)_2$ moiety is a cyclic alkylamine, or a substituted cyclic alkylamine, preferably morpholine;
with a nucleoside of formula (IV):

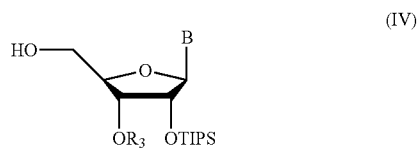

wherein B and $R_3$ are as defined above; and
b) oxidizing the product of step (a) to produce the compound of formula (II) where n is 1, and B, $R_1$, $R_3$, $R_5$, and $R_p$ are as defined above; and
c) where n>1, the process further comprising:
   (i) deprotecting the terminal —$OR_5$ group of the product of the previous step to form a free 5'-OH group;
   (ii) condensing the product of step (i) with a phosphoramidite of formula (III), wherein B, $R_1$, $R_5$, $R_p$ and R are as defined above, and each B, $R_1$, $R_5$, $R_p$ and R may be the same or different from any other B, $R_1$, $R_5$, $R_p$ and R, respectively;
   (iii) oxidizing the product of step (ii); and
   (iv) repeating steps (i)-(iii) n−2 times;
to form the compound of formula (II).

In one embodiment, $R_3$ is H.

In another embodiment, $R_3$ is a protecting group, and the process further comprises removal of the $R_3$ protecting group.

In another embodiment of the above processes, the $R_3$ protecting group is a levulinyl (Lev) group. In yet another embodiment of the above processes, the $R_3$ protecting group is an ionic tag linker. In still yet another embodiment of the above processes, the ionic tag linker is selected from:

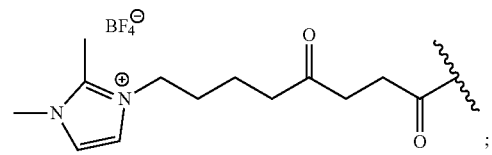

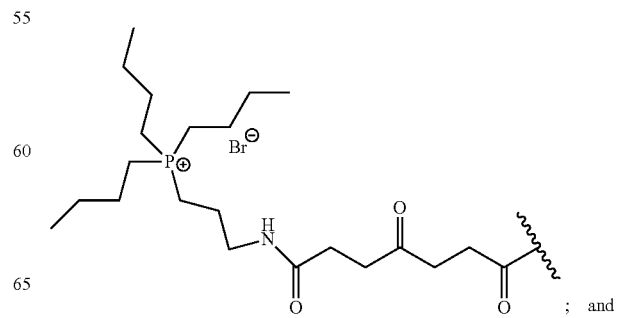

; and

-continued

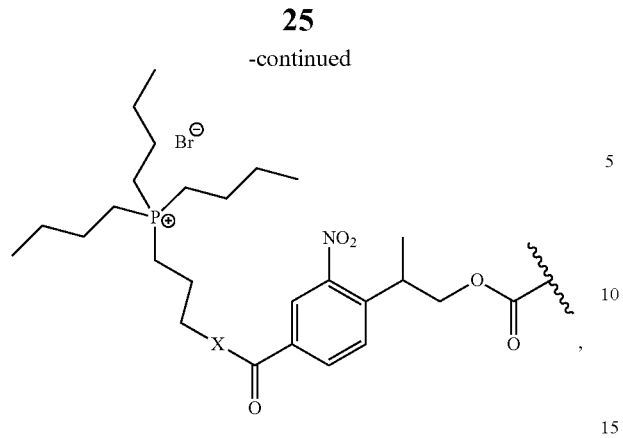

wherein X is selected from NH and O.

In another embodiment, when $R_3$ is

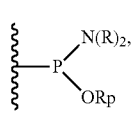

R is selected from lower alkyl, or the $N(R)_2$ moiety is a cyclic alkylamine, or a substituted cyclic alkylamine, preferably morpholine.

In another embodiment of the above processes:

$R_1$ is TBDMS;

$R_5$ is selected from DMTr and MMTr;

$R_p$ is selected from methyl (Me), 2-cyanoethyl (CNEt), ortho-chlorophenyl (o-ClPh), and para-chlorophenyl (p-ClPh);

R is selected from isopropyl, methyl, and ethyl; and

B is a nucleobase protected on at least one nitrogen by a suitable N-protecting group, wherein the N-protecting group is selected from levulinyl, acetyl, difluoroacetyl, trifluoroacetyl, isobutyryl, benzoyl, 9-fluorenylmethoxycarbonyl, phenoxyacetyl, dimethylformamidine, and N,N-diphenyl carbamate.

In another embodiment of the above processes, $R_5$ is DMTr, $R_p$ is methyl, and R is iPr.

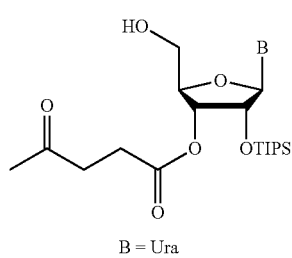

B = Ura

-continued

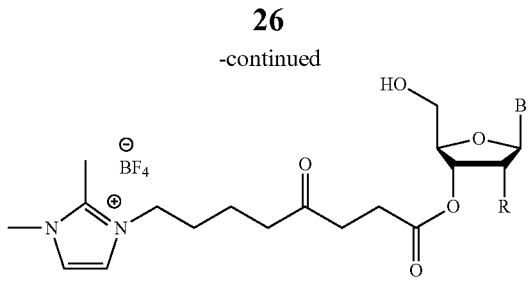

K1, R = H, B = Thy
K2, R = OTIPS, B = Ura

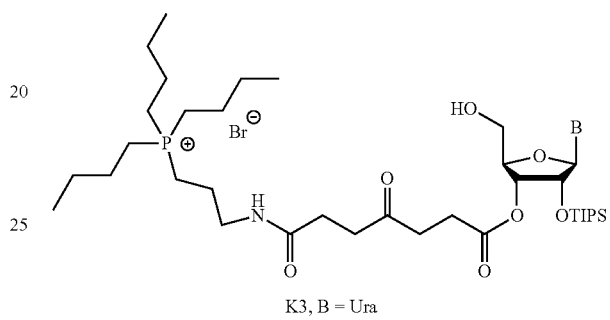

K3, B = Ura

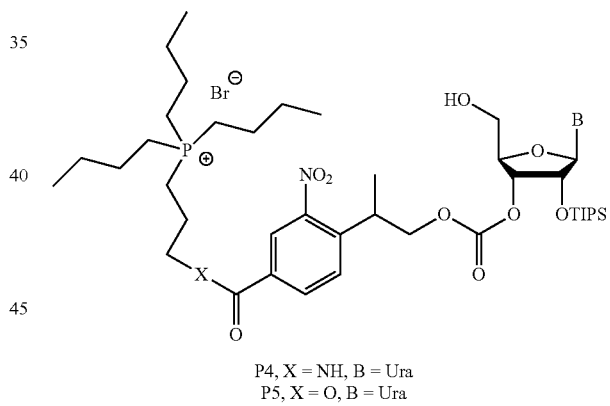

P4, X = NH, B = Ura
P5, X = O, B = Ura

Non limiting examples of the synthesis of the ionic tag linkers and their esterification with nucleosides are shown in Schemes 8 and 9. The ionic tag linkers of nucleosides K1, K2 and K3, like the levulinyl group, require one of the mildest sets of cleavage conditions for selective removal from the other protecting groups used in RNA synthesis, i.e., a simple treatment with hydrazine hydrate in a pyridine and acetic acid solution. Furthermore, their ionic nature permits precipitation based purification of the nucleoside (e.g. compounds (61) or (62), Schemes 8-9), or if desired, di- and tri-nucleotides derived from such ion tagged nucleoside. Scheme 8 depicts a methodology to synthesize a 2'-deoxynucleoside with a hydrazine cleavable gamma ketoester tag, which facilitates isolation via precipitation step.

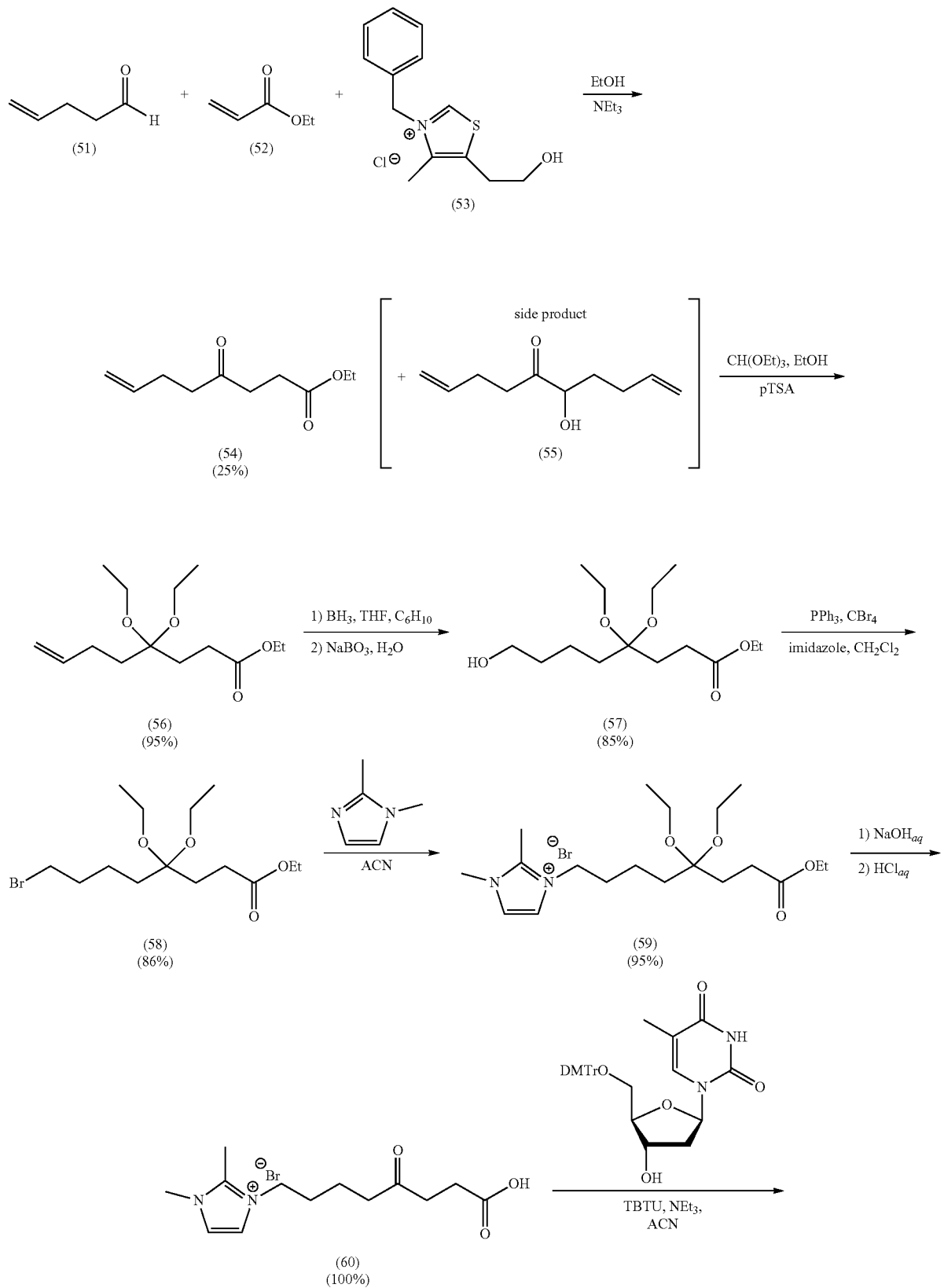
Scheme 8. Synthesis of orthogonal gamma-keto acid tag (60) and its derivatization with a protected 2'-deoxynucleoside.

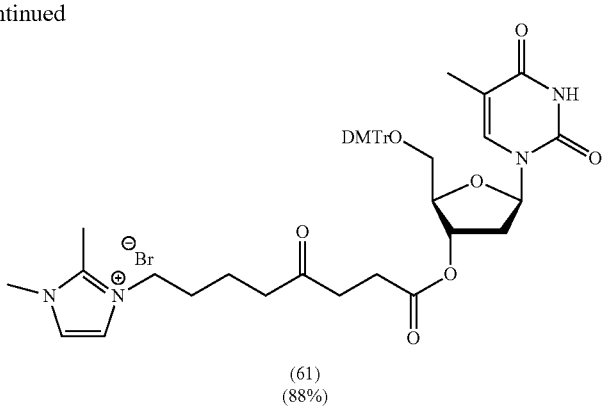

(61)
(88%)

Upon selective removal of the tag, the nucleoside (or dimer or trimer block) can be converted into 3'-phosphoramidite derivatives, by protocols described herein, that may be used in block condensations.

Several approaches can be applied to obtain the required gamma-ketoacid (60). For example, Scheme 8 employs a Stetter reaction as the first step [(51)+(52) (54)], a reaction that transforms aldehydes into nucleophiles using catalytic amounts of a thiazolium salt, e.g. (53), in the presence of a mild base (Stetter, H. *Angewandte Chemie, International Edition* in English 15: 639-47 (1976)). Thus 4-pentenal (51), an aldehyde attached to an aliphatic chain terminating in an alkene, was activated as a nucleophile and allowed to undergo a Michael addition using ethyl acrylate (52) as the electrophile. The substrates were mixed with thiazolium salt (53) and dissolved in ethanol. The reaction mixture was heated and once it was refluxing gently, the reaction was initiated by the addition of triethylamine. After 18 hours the solvent was removed and the material obtained was subjected to a dichloromethane/brine extraction followed by flash chromatography. The desired product, (54), co-eluted with an acyloin side-product, (55), in all the solvent systems investigated for the purification. The yield was approximately 25% (as estimated by 1H-NMR analysis of the mixture), however, enough material can readily be obtained to continue with the synthesis, with the impurity (55) becoming easily separable after the subsequent step. The next step in the synthetic route was to protect ketone (54) as an acetal [i.e., (56)]. Refluxing for 4 hours was found to be adequate for this reaction to reach completion and the desired product (56) was obtained in 90-95% yield. The product (56) was easily separable from the acyloin side-product (55) generated in the earlier step, which did not appear to undergo any transformation in the acetal formation reaction. The identity and purity of (56) were confirmed by TLC, LR-MS and NMR.

With the gamma-acetal-ester, (56), in hand, the next step (Scheme 8) was the hydroboration of the terminal alkene. This was achieved using an in situ generated dicyclohexyl borohydride reagent. An appropriate amount of cyclohexene was added to borane-THF at 0° C. and allowed to react for one hour, then (56) was added to the resultant slurry and the reaction was allowed to proceed for 2 hours at room temperature. The oxidation of the intermediate borane was achieved by the addition of aqueous sodium perborate, a mild oxidant that left the ester intact, and the reaction was continued for another 2 hours. The reaction mixture was then extracted with ethyl acetate and the product, (57), was purified by flash column chromatography, providing a colourless liquid in 80-85% yield, with 15-20% of (56) also being recovered. This reaction never proceeded further than 85% conversion, even with longer reaction times or an increase in the amount of the borohydride reagent generated relative to substrate.

The primary alcohol, (57), was then mixed with triphenylphosphine and tetrabromomethane in DCM in order to generate the terminal bromide (58). The reaction proceeded cleanly but upon aqueous workup, acetal cleavage occurred, likely due to the formation of hydrobromic acid from the hydrolysis of the excess reagents. The reaction was performed again in the presence of imidazole, which neutralized any hydrobromic acid generated, and the desired product, (58), was obtained in 79-86% yield after flash chromatography. Subsequent condensation with 1,2-dimethylimidazole in acetonitrile resulted in the ionic tag linker, (59), in 95% or greater yield.

The final steps in the synthesis (Scheme 8) involved the cleavage of the acetal and ester as well as anion metathesis of the ionic moiety and finally derivatization to a nucleoside. Initially aqueous acid was used to effectuate the deprotection, followed by anion metathesis but the material thus derived decomposed rapidly. Subsequently deprotection was performed via a two step process, the first a base mediated cleavage of the ester (59) followed by a limited acidification to protonate the carboxylic acid and cleave the acetal. The protected material, (59), was thus dissolved in aqueous sodium hydroxide and allowed to react for 16-18 hours followed by the addition of aqueous concentrated HCl to bring the solution to approximately pH 1 and finally drying under reduced pressure. The excess salt was removed by suspending the resulting solid in acetonitrile/dichloromethane and filtering off the insoluble material. The product obtained, (60), appeared pure by TLC, LR-MS and NMR but likely still contained a small amount of sodium chloride, which could not be detected with these techniques. Anion metathesis at this point also led to significant decomposition of the resulting product, as in the acid mediated deprotection. The bromide salt, (60), was stable upon long term storage, however, and was found to couple in the expected manner with a nucleoside. In fact, using O-(benzotriazol-1-yl)-N,N,N',N'-tetramethyluronium tetrafluoroborate (TBTU) as the coupling agent achieved both the coupling and anion exchange simultaneously, with the coupling proceeding quantitatively and the anion exchange confirmed by LR-MS as an absence of bromide ions and the presence of tetrafluoroborate in the negative mode. This product (61) was also stable upon long term storage.

With a derivatized nucleoside (61) in hand, the cleavage characteristics of the orthogonal gamma-ketoester ionic tag linker from the nucleoside were studied and compared to those of the levulinyl ester protecting group, which has been used as described above to generate oligomeric building blocks and is known to be easily removed without affecting any other protecting groups in the molecule. The rate of levulinyl ester cleavage under the conditions studied was faster than that of the ionic tag linker, with half lives of approximately 0.76 and 2.82 minutes respectively, corresponding to complete cleavage of the levulinyl ester in just over 5 minutes while the tag required almost 20 minutes for full cleavage. However, even though the tag cleaves more slowly than the levulinyl ester under the conditions studied, the normal reaction time employed for the cleavage of the 3'-hydroxyl protected levulinyl ester by hydrazine is 20 minutes and no degradation is observed in any of the other protecting groups in that time. This indicated that the ionic tag linker is suitable to the required task, and it is therefore a viable route to generating oligomeric building blocks as well.

The tag was also condensed with a 5'-O-DMTr-2'-O-TIPS Uridine nucleoside (12) (Scheme 9) using the same conditions employed for the derivatization of 5'-O-DMTr-Thymidine. The $^1$H-NMR of the coupled ribonucleoside did not appear to show any 2'-3' silyl isomerisation.

Scheme 9.
Derivatization of gamma keto-acid ionic tag linker (60) with ribonucleoside (12).

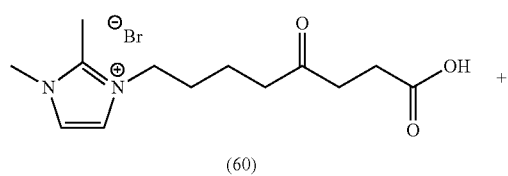

(60)

-continued

[Structure of compound (12): DMTrO-, OH, OTIPS uridine nucleoside]

TBTU, NEt$_3$,
ACN
→

[Structure of compound (62): DMTrO-, uridine with OTIPS and ionic tag linker]

(62)

(62%)

As an alternative to the gamma-ketoester linker 60, a novel linker derived from ketopemilic acid was developed (Scheme 10).

Scheme 10
Synthesis of orthogonal gamma-keto acid tag (70) and its derivatization with a protected ribonucleoside.

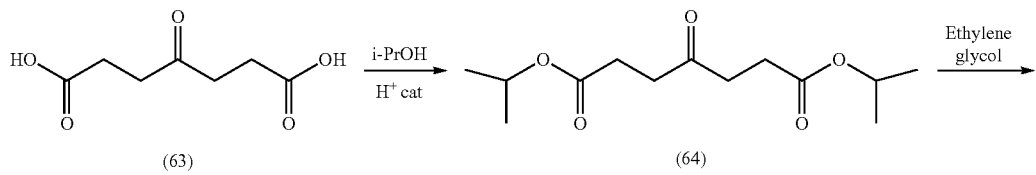

(63) → i-PrOH, H$^+$ cat → (64) → Ethylene glycol →

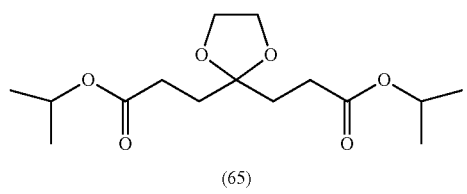

(65)

65% (2 steps)

↓ LiOH (5eq)
  MeOH/H$_2$O

-continued
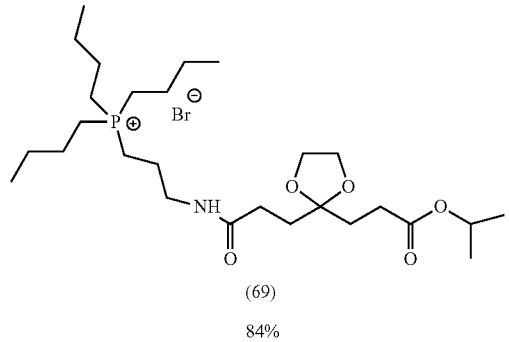
(69) 84%
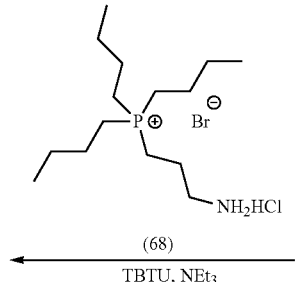
(68)
TBTU, NEt₃
ACN
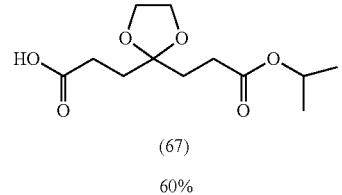
(67) 60%
+
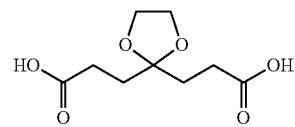
(66) 40%
LiOH (15eq)
MeOH/H₂O
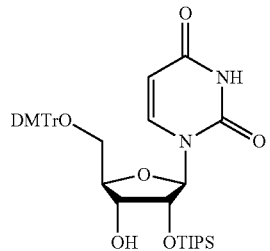
(70) 95% +
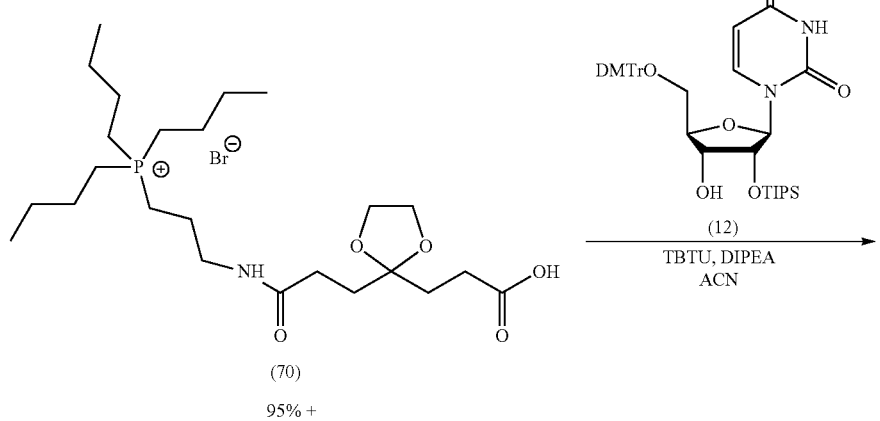
(12)
TBTU, DIPEA
ACN
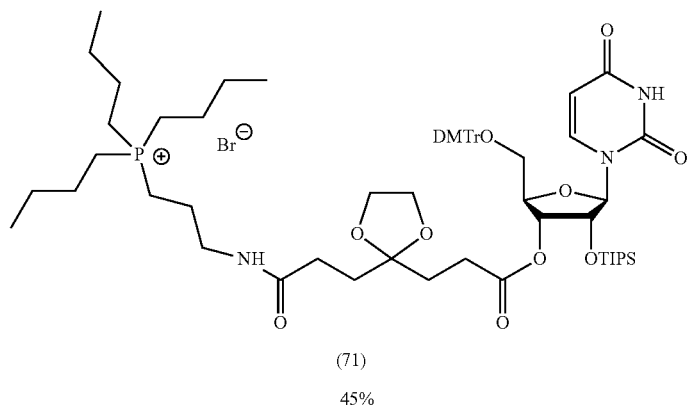
(71) 45%

Its synthesis started by treating ketopemilic acid (63) with iso-propanol and catalytic para-toluenesulfonic acid using a Dean-Stark trap to esterify both terminal carboxylic acid moieties, affording (64). The use of methanol and ethanol (instead of isopropanol) in this reaction resulted in lactone formation as the major product, instead of the desired diester (64).

Scheme 11
Esterification pathway (63) depends on the bulkiness of the alcohol's alkyl group.

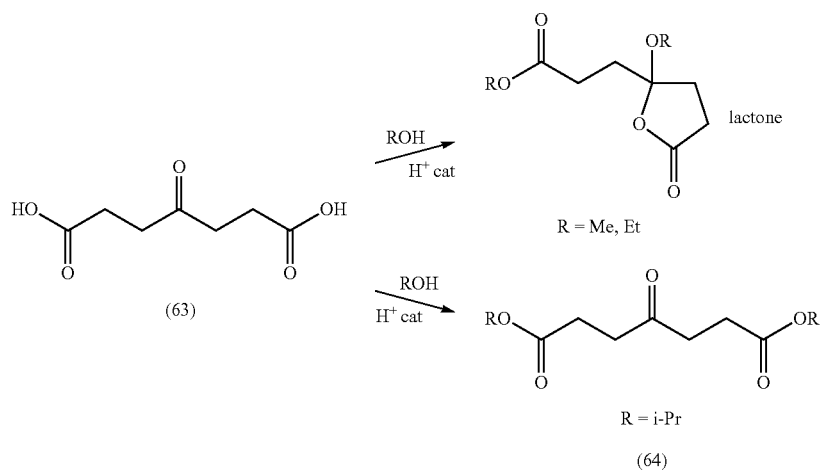

The diisopropyl ester (64) was isolated and then reacted with ethylene glycol and catalytic pyridinium para-toluenesulfonate by refluxing in a Dean Stark trap overnight to form the cyclic ketal (65) in 65% yield over two steps. Attempts to use ethylene glycol directly to form both the cyclic ketal and glycol ester resulted in the undesired lactone derivative (Scheme 11), necessitating that esterification and acetal formation be carried out in two separate steps.

Cyclic ketal diester (65) was taken up in methanol and 5 equivalents of aqueous lithium hydroxide were added to the reaction to preferentially hydrolyze one ester over both, producing a mixture of compounds (66) and (67), which were separated in yields of 40 and 60%, respectively. Coupling to the phosphonium ionic tag (68) to the cyclic ketal monoester (67) was accomplished using TBTU and DIPEA in acetonitrile at room temperature for 6 h affording compound (69) in 84% yield. After isolation the isopropyl ester was hydrolyzed by LiOH in MeOH/Water to afford compound (70) in nearly quantitative yield. If in an alternative method, the diisopropyl ester (64) and (65) were not isolated after each step, it can be imagined that the conversion of (63) to (66) or (67) could be achieved in one pot.

Also, an alternative approach could be to selectively hydrolyze compound (65) to the di-acid (66), and then couple this material with one equivalent of the phosphonium tag (68), potentially increasing overall yield and reducing the process by one step.

The ionic tag linker (70) was then conjugated to the 3'-hydroxy of ribonucleoside (12) using standard coupling conditions with TBTU and DIPEA to afford compound (71) in 4 h in a moderate yield of 45%. It is envisioned that mild acid hydrolysis of (71) would afford K3 (Scheme 12).

Scheme 12. Mild acid hydrolysis of (71).

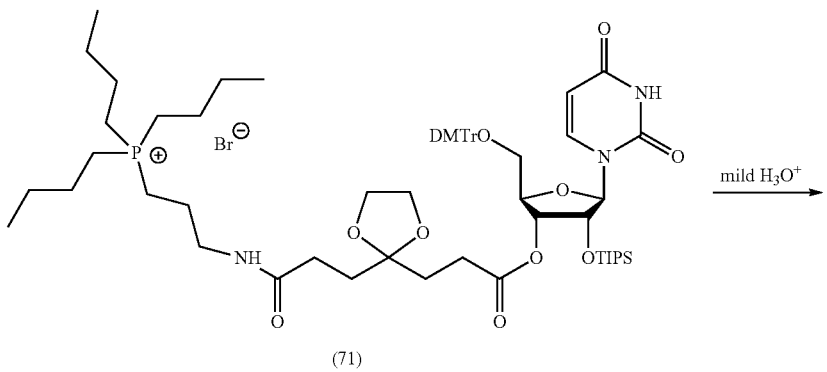

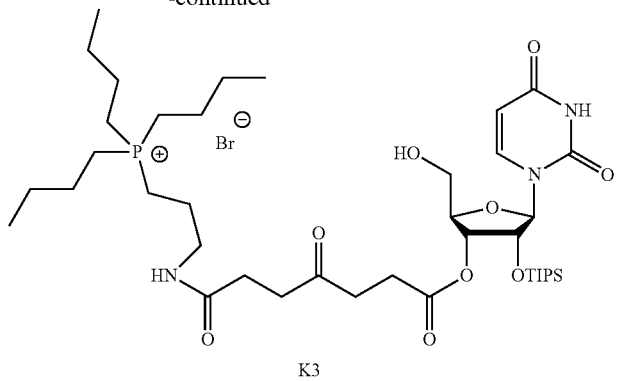

K3

The ionic tag linker of nucleoside K3 requires mild cleavage conditions for removal, that is, treatment with hydrazine hydrate in a pyridine and acetic acid solution. These conditions have been shown to be compatible with the protecting groups employed in RNA synthesis. Furthermore, the ionic nature of the tag permits precipitation based purification of the nucleoside as carried out for compound (71), or if desired, of di- and tri-nucleotides derived from (71).

Alternatively, given that a tag containing gamma-keto ester is orthogonally cleavable, several other routes to analogous molecules are also possible. One approach to a similar molecule is shown in Scheme 13, and exploits the 5-bromolevulinyl derived ylid to attach the linker to the gamma-keto ester moiety as shown in Scheme 13 [Ronald, R. C.; Wheeler, C. J. *Journal of Organic Chemistry* 48: 138-9 (1983)]. This would also utilize many of the transformations already demonstrated for the Stetter approach depicted in Scheme 8. Indeed it may even be possible to link the tag in a single step with this approach, since compounds containing the ionic moiety and an aldehyde can be easily prepared.

Scheme 13
5-Bromolevulinyl derived phosphonium ylid approach to the synthesis of ion-tagged gamma-ketoacids.

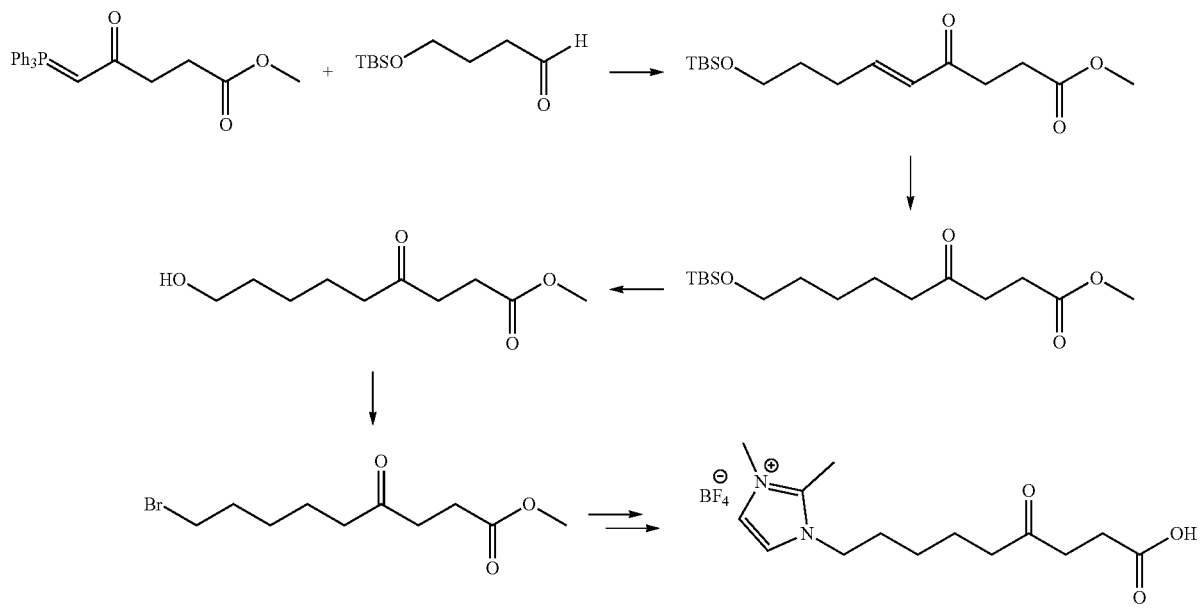

The hydrogenation of the resulting alkene would likely be necessary since it would be conjugated to the ketone and this conjugated system would likely react more slowly with hydrazine during the cleavage of the tag. It is understood that other ionic tags may replace the dimethylimidazolium tag shown, such as those described in PCT Application Publication No. WO 2006/096963 to Chan, T.-H. et al., the contents of which are incorporated herein by reference in their entirety. Suitable ionic tags may include, for example, phosphonium ionic tags.

Another possible approach to the same substrate would be to use a more traditional Umpolung reaction than the Stetter approach, employing a dithiane derived from the same aldehydes as the nucleophile (Scheme 14).

Scheme 14
Dithiane Umpolung approach.

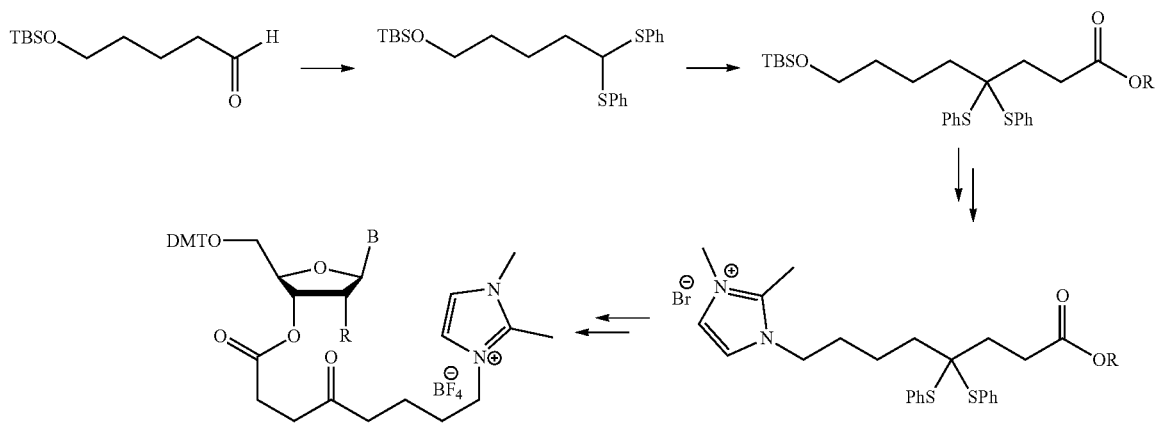

The same Michael acceptor could be used and this approach would eliminate the competing self-condensation reaction observed in the Stetter reaction [Scheme 8, product (55)]. The dithiane would also serve as the ketone protecting group for the bulk of the reaction and would likely be stable to the fluoride treatment employed for removal of the silyl ether (TBMS). This approach would also use many of the transformations described herein, though the timing of the dithiane cleavage to liberate the ketone might be required prior to the installation of the ionic moiety, if the reagents used for this cleavage prove difficult to separate from the desired product. In that case, the dithiane could be cleaved immediately after the carbon-carbon bond formation and an acetal could then be installed.

An alternative to the orthogonal levulinyl linker described above is a light cleavable linker which can be removed in the presence of all standard ribonucleotide protecting groups. This allows for the use of extremely mild conditions to expose the 3'-hydroxyl group at anytime during the synthesis of blockers. In combination with the 2'-TIPS protecting group there is no risk of silyl migration, allowing for the production of regioisomerically pure blockmers which can be readily converted into phosphoramidies. The synthesis of the NPPOC like derivative (80) begins with a few short and elegant steps reported by Pfleiderer [Pfleiderer, W. et al. *Helvetica Chemimica Acta*, 87: 620 (2004)].

Scheme 15
Synthesis of photolabile ionic tag linker (80)

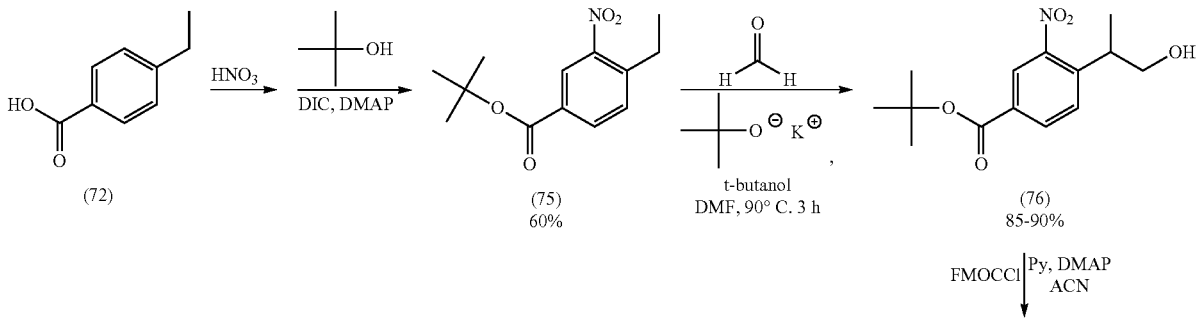

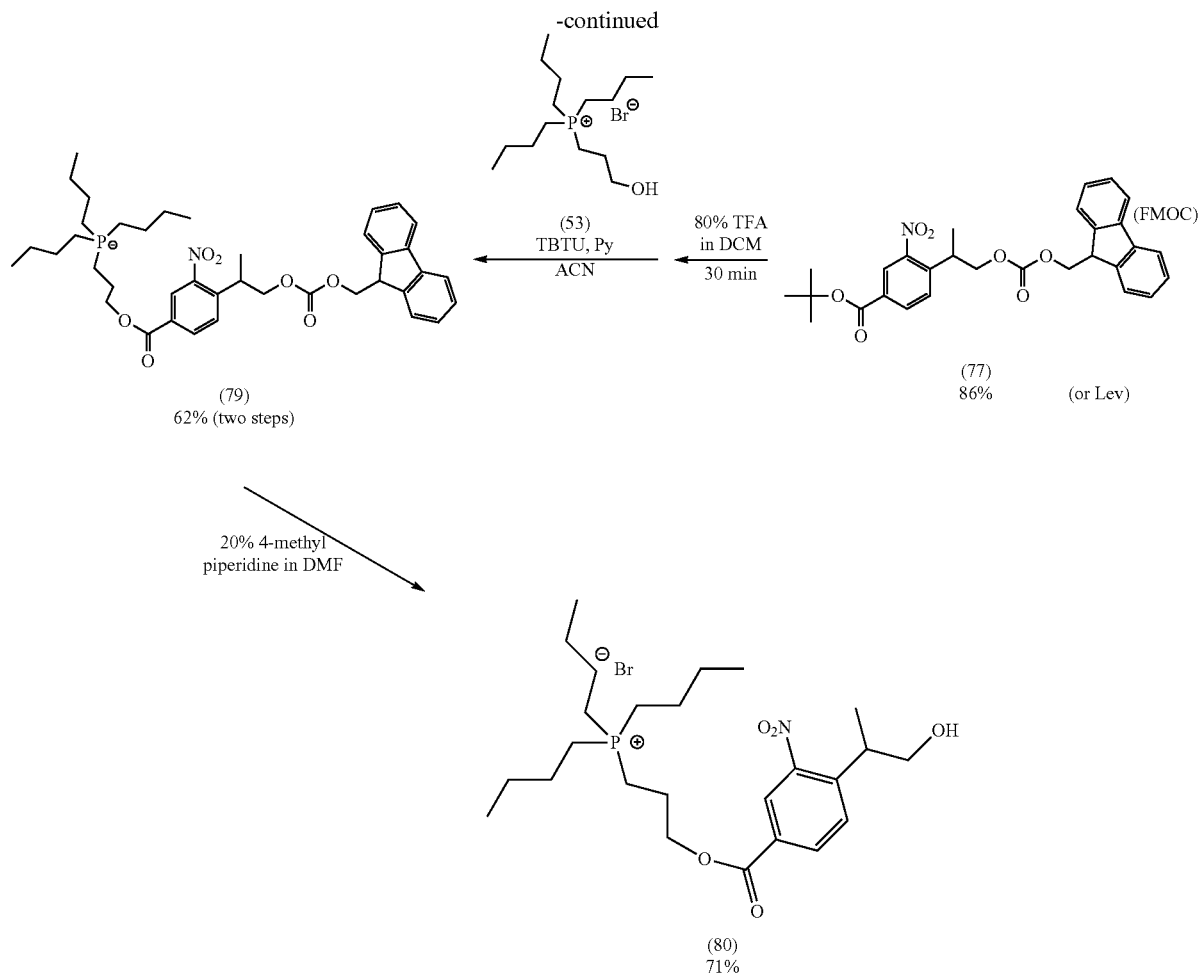

Fuming nitric acid was cooled to −10° C. and 4-ethyl-benzoic acid (72) was added over 30 min to the sitting solution, then allowed to stir for 30 min. The mixture was quenched over crushed ice and the solid precipitate of 3-nitro-4-ethyl-benzoic acid (73) was collected and crystallised with ethyl acetate and hexanes in good yield (95%). The tert-butyl ester was formed using DCC and DMAP with tert-butanol under standard conditions.

The formation of the 2-substituted propan-1-ol derivative was achieved as described by Pfleiderer by treating the tert-butyl ester with para-formaldehyde and a catalytic amount of potassium tert-butoxide in an aprotic dipolar solvent, such as DMF or DMSO, at 90° C. for 3 h [Pfleiderer, W. et al. Helvetica Chemimica Acta, 87: 620 (2004)]. The reaction is then quenched and neutralized to pH 7 with 1 M HCl, yielding 85-90% of the desired product (76). The newly formed primary hydroxyl is then protected with Fmoc-Cl (77), an acid stable protecting group. This allows cleavage of the t-butyl ester with 80% TFA in DCM without deprotection of the primary hydroxyl group. Without Fmoc protection, dehydration of the newly formed hydroxyl will occur, forming the propene derivative. As well, after the installation of the Fmoc it is imperative that the compound is not exposed to sunlight or tungsten light for long periods of time, as this compound will undergo photolytic cleavage, as per the design of the molecule.

The newly formed free acid was then coupled with phosphonium ionic tag (53) with TBTU in ACN and wrapped in aluminum foil for 8 h which afforded the tagged species (79) in a moderate yield of 65%, which can be easily separated from any starting material by column chromatography. Next, the Fmoc group was removed under standard conditions by treatment with 20% 4-methylpiperidine in DMF for 2 h, yielding compound (80) in good yields. Although no protecting group can be removed at the primary alcohol, this compound should be kept in the dark at all times. This is due to the fact that it was observed that some degradation does occur over time, albeit much more slowly than when the Fmoc was present.

The previous synthesis of the light labile linker is somewhat long and requires the use of an expensive transient protecting group, Fmoc. In an attempt to shorten the synthesis we were able to avoid protection, deprotection, and re-protection of the carboxylic acid moiety, while increasing overall yields. This was accomplished by directly conjugating a modified phosphonium ionic tag (68) containing a primary amine in place of the hydroxyl group, creating an amide bond in compound (81) (Scheme 16). This was achieved as described for the synthesis of (80) (Scheme 15) using TBTU and triethylamine as coupling reagents, producing (82) in 35% yield (unoptimized).

Scheme 16
Short synthesis of photolabile ionic tag linker (82)
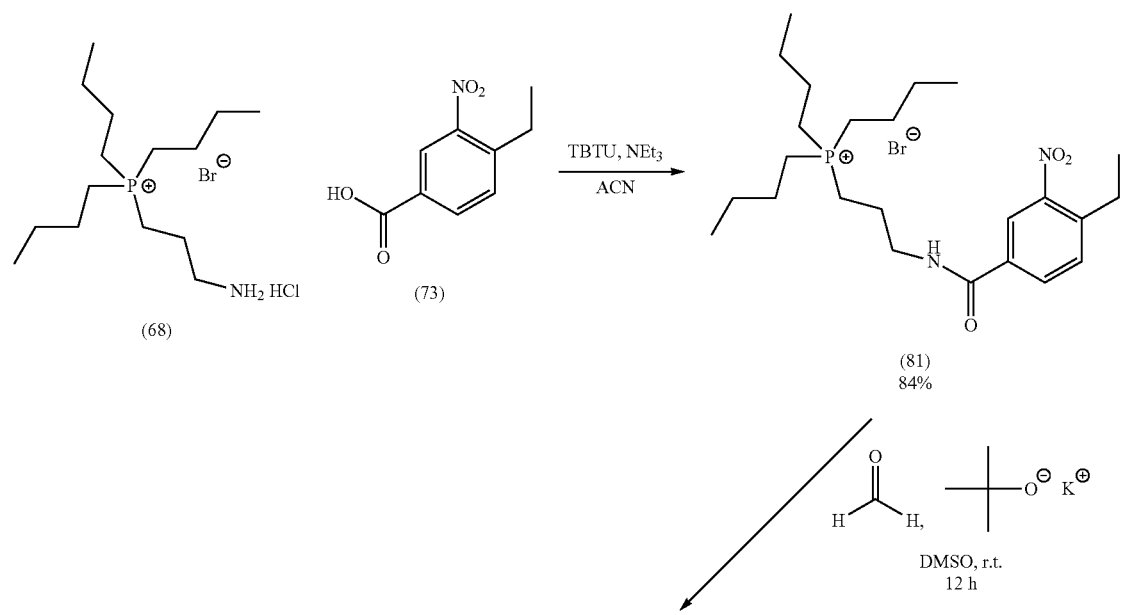
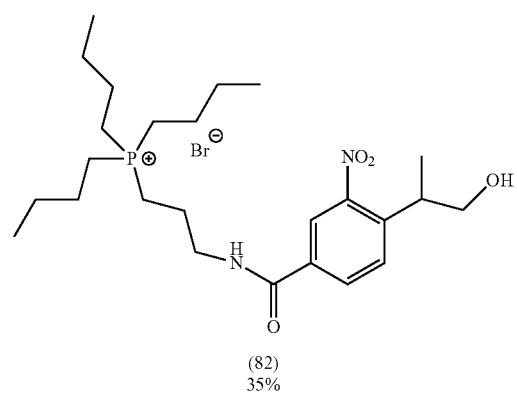

In another embodiment, there is provided a process for attaching an ionic tag linker (82) to a ribonucleoside, affording a building block, (85) or (86), for further elaboration into oligonucleotides. The general method for carrying out the conjugation is shown in Scheme 16, and involves phosgenation of an ionic tag linker followed by its attachment to the 3'-hydroxyl group of a nucleoside.

Thus, phosgenation of (80) or (82) was carried out by a modified procedure from Eckert, H. Auerweck, *J. Org. Process Res. Dev.* 14: 1501-1505, (2010), and is outlined in Scheme 17. Detailed experimental procedures for generating phosgene from triphosgene and phenanthridine are described in the Experimental section (Examples).

Scheme 17
Conjugation of nucleoside (12) to photolabile ionic tag linker.

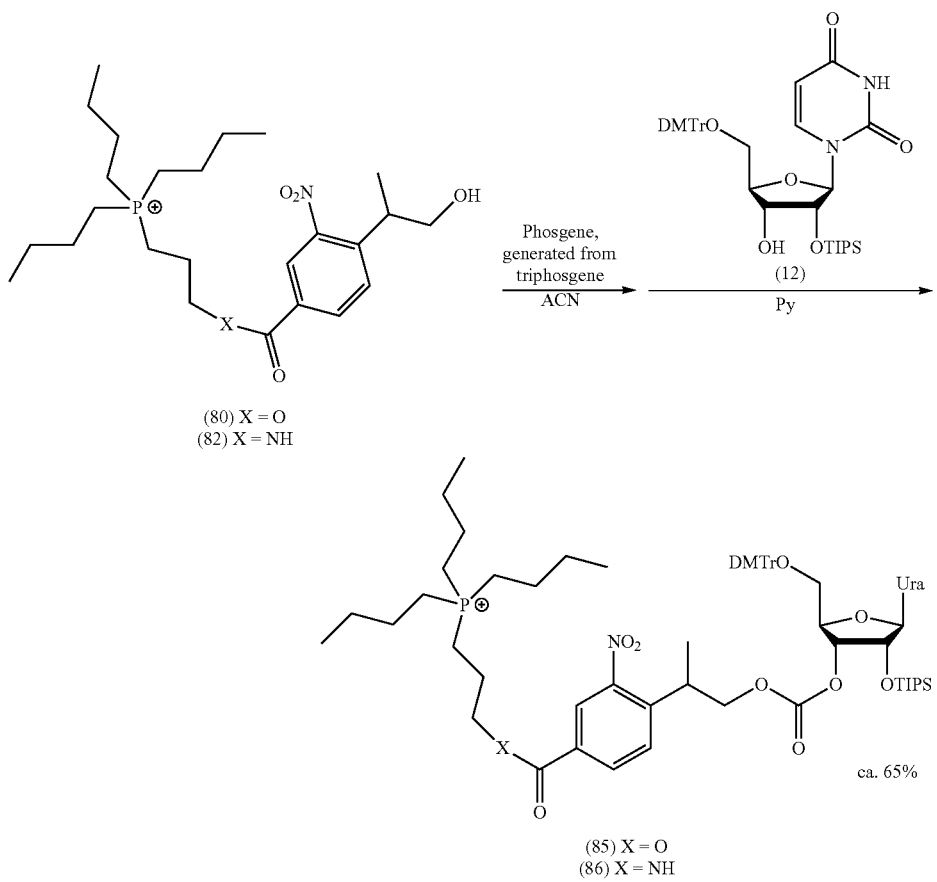

A solution of nucleoside (12) in acetonitrile was added directly to mixture of DIPEA and the phosgene generated above, and allowed to stir for 8 h at room temperature. After addition of ethyl acetate, the mixture was washed with sat. NaHCO₃ and brine, and precipitated in MTBE to remove excess (unreacted) nucleoside and DIPEA. The resulting precipitate was further purified by column chromatography in DCM:MeOH.

Nucleosides such as (86) have a number of applications. They can serve as starting materials for the synthesis of dimer or trimers or larger oligonucleotides requiring only a precipitation step for isolation by virtue of the polar ionic tag linker at the 3'-termini. Once the desired length has been synthesized, the 3'-tag and all protecting groups can be cleaved yielding the free (unprotected) oligonucleotide. Alternatively, because the 3'-ion tag can be selectively cleaved without deblocking all other protecting group on the heterocylic bases or sugar-phosphate backbone, it provides a novel means for preparing protected oligonucleotide blocks containing a 3'-hydroxyl group that can be further elaborated to a 3'-phosphoramidite derivative.

These processes are exemplified in the synthesis of the tetranucleotide rAGCU starting from nucleoside (86) (Schemes 18 and 19). Reactions were carried out in the dark by wrapping the reactions flasks with aluminum foil, to avoid premature cleavage of its ionic photolabile tag.

Scheme 18
Synthesis of ion-tagged rCpU (90) from nucleoside (86).
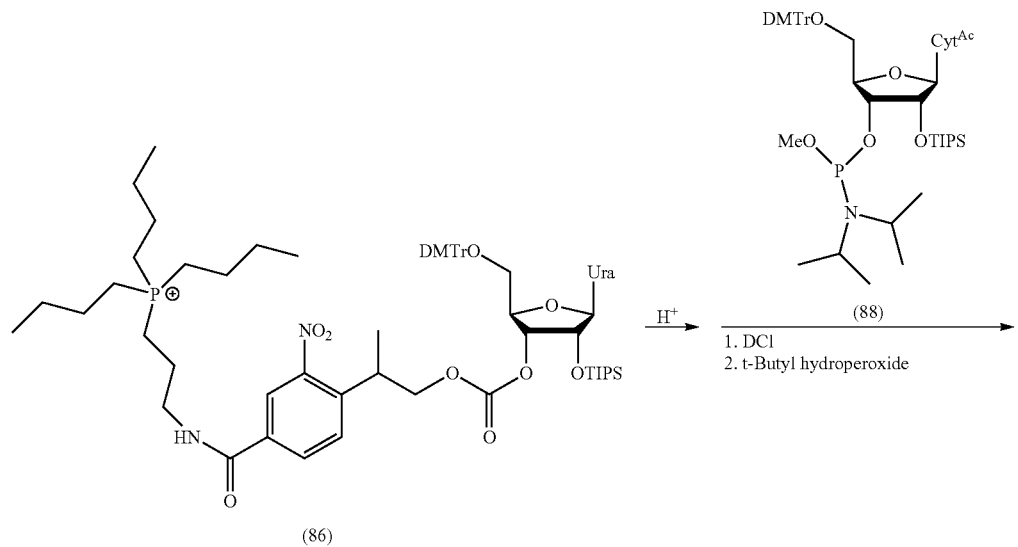
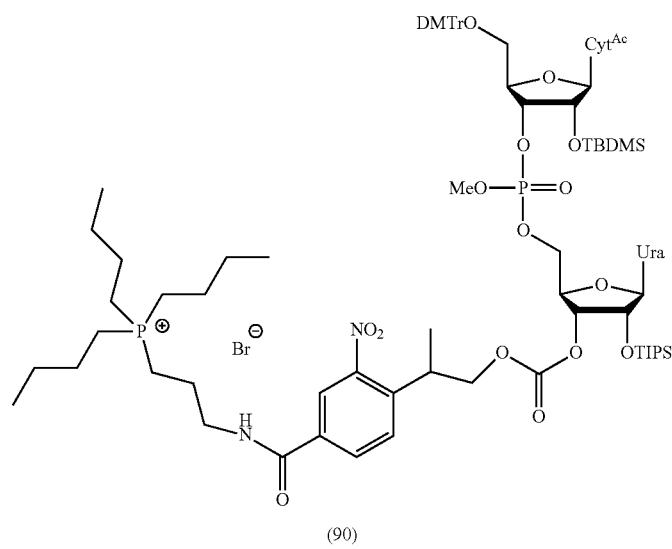

3′-Tagged-uridine (86) was detritylated by adding 3% trifluoroacetic acid in DCM and allowing the mixture to stir for 5 min. Addition of methanol ensured quenching of the trityl cation, preventing the re-tritylation of the 5′-hydroxyl group. The crude product was then precipitated in MTBE to remove DMTrOMe, and/or DMTrOH. The compound was then filtered over celite, collected in DCM and re-purified by column chromatography affording P4 in 95% yield. The synthesis of dimer rCpU (90) from P4 was carried out by coupling with rC phosphoramidite monomer (88) in the presence of 4,5-dicyanoimidazole (DCI), and the resulting solution was allowed to stir at room temperature for 3 h. Ten equivalents of tert-butanol was added to quench excess phosphoramidite, followed by 10 eq of tert-butyl hydroperoxide (1 mL of a 6 M solution in decane) to oxidize the internucleotide phosphite triester to the more stable phosphate triester. The reaction was then concentrated to an oil, taken up in minimal amounts of dichloromethane (DCM), and precipitated in MTBE to remove all excess reagents. The precipitation process was repeated if the presence of any quenched phosphoramidite was detected by TLC. Tagged rCU dimer (90) was isolated in 95% yield (0.63 g). The above process was repeated as described above, using the appropriate phosphoramidites until tetramer (92) was obtained. Full experimental procedures and characterization are provided in the Experimental section (Examples).

Scheme 19
Selective photocleavage of orthogonal phosphonium tag
from tetramer (91), affording protected DMTr-rGACU-3′OH (92).

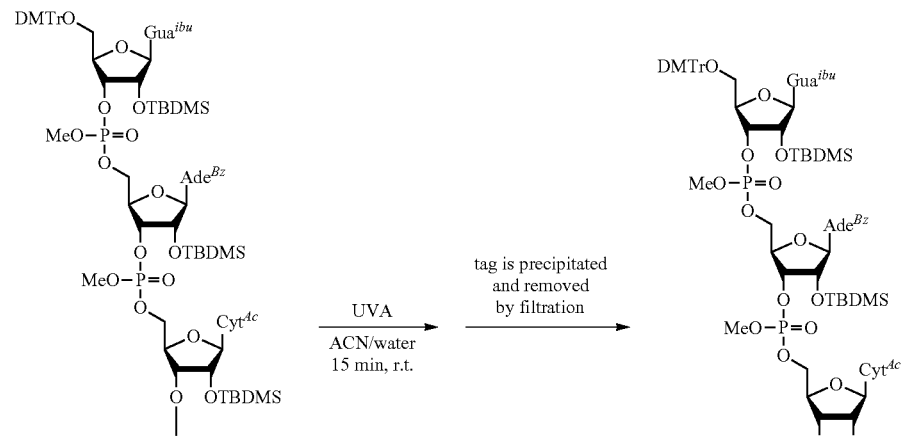

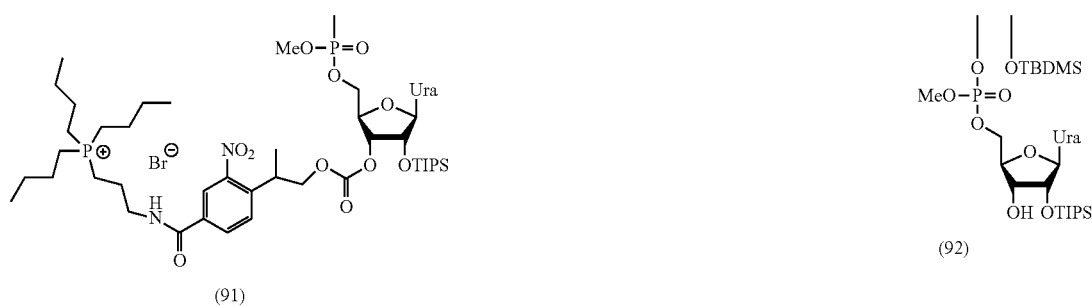

Tetramer (91) was dissolved in 1 mL of wet ACN (1200 ppm of H₂O), and transferred into a quartz cuvette. The cuvette was placed inside a photoreactor with stirring. The reaction was completed within 15 min (TLC analysis). The mixture was concentrated to about half volume and the cleaved tag removed by precipitation with methyl t-butyl ether (MTBE). The desired tetramer was found in the MTBE solution, which was collected after concentrating the solution to dryness. Isolated yield was 95% (92 mg). Phosphitylation of (92), as described previously, can provide the 3'-phosphoramidite derivative (93) that is suitable for RNA synthesis via block coupling.

Scheme 20
Synthesis of a tetrameric phosphoramidite derivative.

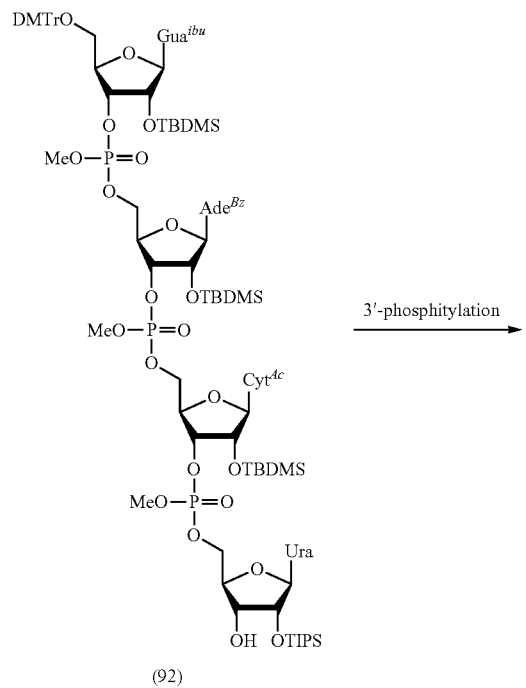

3'-phosphitylation

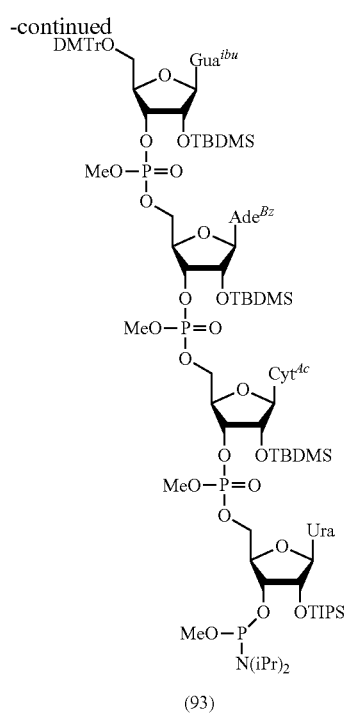

Oligonucleotide Synthesis.

In another embodiment, there is provided a process for preparing an N-mer oligonucleotide, said process comprising:

a) condensing a phosphoramidite of formula (IIa):

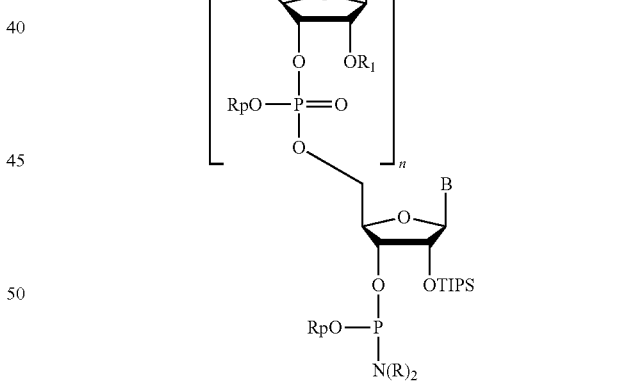

wherein n is an integer from 0 to 19;

$R_1$ is a protecting group;

$R_5$ is a protecting group;

$R_p$ is a protecting group;

R is lower alkyl, or the $N(R)_2$ moiety is a cyclic alkylamine, or a substituted cyclic alkylamine, preferably morpholine;

B is a nitrogen-containing base;

wherein each B, $R_1$ and $R_p$ may be the same or different from any other B, $R_1$ and $R_p$, respectively;

with
(a') a functionalized linker L bound to a support

, wherein

is selected from a solid support or an ionic support, or
(b') a compound of formula

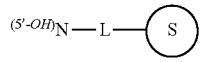

wherein $^{(5'-H)}N$ is a nucleoside/oligonucleotide chain bound to the solid support or the ionic support via the functionalized linker L and having a free 5'-OH group;
b) oxidizing the product of step (a) to form a compound of formula (VIII):

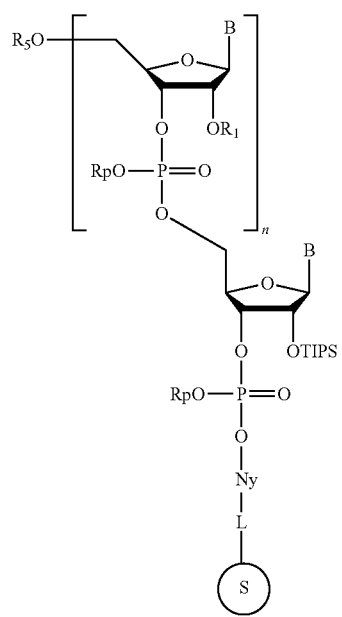

wherein
y is 0 or 1;
n, B, $R_1$, $R_5$ $R_p$,

,

L, and N are as defined above; and
c) optionally,
(i) deprotecting the terminal 5'-$OR_5$ group of the product of the previous step to form a free 5'-OH group;

(ii) condensing the product of step (i) with a phosphoramidite of formula (IIa)

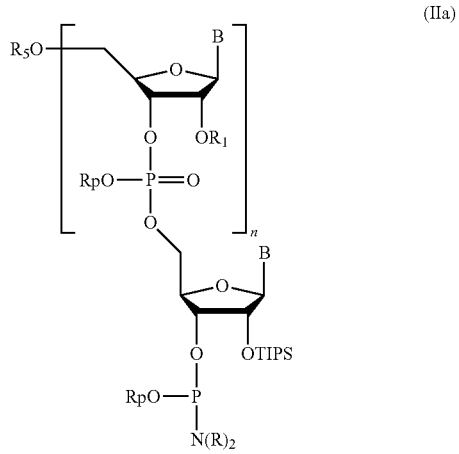

wherein n, B, $R_1$, $R_5$, $R_p$ and R are as defined above, and each n, B, $R_1$, $R_5$, $R_p$ and R may be the same or different from any other n, B, $R_1$, $R_5$, $R_p$ and R, respectively;
(iii) oxidizing the product of step (ii); and
(iv) optionally repeating steps (i)-(iii);
with the proviso that if y is 0, step (c) is not optional;
to form a bound N-mer oligonucleotide.
In another embodiment, y is 1 and N is a nucleoside.
In yet another embodiment,

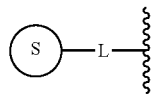

is

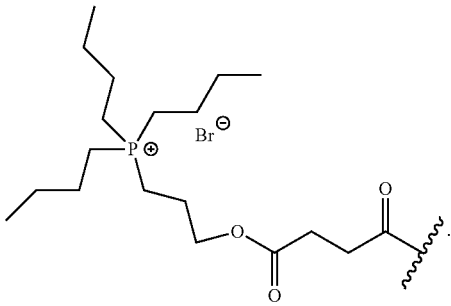 [SMILES: *C(=O)CCC(=O)OCCC[P+](CCCC)(CCCC)CCCC ; [Br-]]

In still yet another embodiment, there is provided a process for preparing an N-mer oligonucleotide, said process comprising:

a) condensing a compound of formula (IIb):

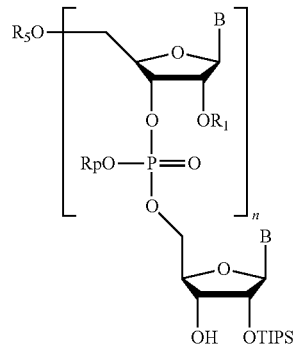

(IIb)

wherein n is an integer from 0 to 19;

$R_1$ is a protecting group;

$R_5$ is a protecting group;

$R_p$ is a protecting group;

B is a nitrogen-containing base;

wherein each B, $R_1$ and $R_p$ may be the same or different from any other B, $R_1$ and $R_p$, respectively;

with a functionalized linker L bound to an ionic support

b) oxidizing the product of step (a) to form a compound of formula (IX):

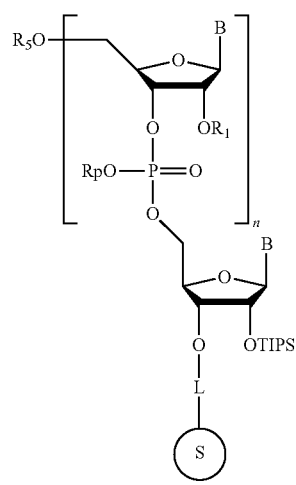

(IX)

wherein n, B, $R_1$, $R_5$ $R_p$,

and L, are as defined above; and c) (i) deprotecting the terminal 5'-$OR_5$ group of the product of the previous step to form a free 5'-OH group;

(ii) condensing the product of step (i) with a phosphoramidite of formula (IIa)

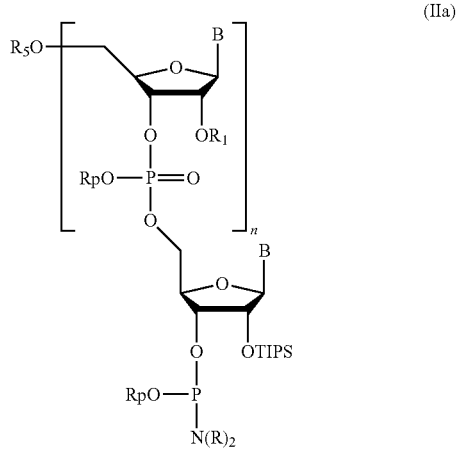

(IIa)

wherein n, B, $R_1$, $R_5$, and $R_p$ are as defined above, and R is lower alkyl, or the $N(R)_2$ moiety is a cyclic alkylamine, or a substituted cyclic alkylamine, preferably morpholine; wherein each n, B, $R_1$, $R_5$, and $R_p$ may be the same or different from any other n, B, $R_1$, $R_5$, and $R_p$, respectively;

(iii) oxidizing the product of step (ii); and (iv) optionally repeating steps (i)-(iii);

to form a bound N-mer oligonucleotide.

In another embodiment of the above processes, n is selected from 0, 1, 2, or 3.

In yet another embodiment of the above processes:

$R_1$ is TBDMS;

$R_5$ is selected from DMTr and MMTr;

$R_p$ is selected from methyl (Me), 2-cyanoethyl (CNEt), ortho-chlorophenyl (o-ClPh), and para-chlorophenyl (p-ClPh);

R is selected from isopropyl, methyl, and ethyl; and

B is a nucleobase protected on at least one nitrogen by a suitable N-protecting group, wherein the N-protecting group is selected from levulinyl, acetyl, difluoroacetyl, trifluoroacetyl, isobutyryl, benzoyl, 9-fluorenylmethoxycarbonyl, phenoxyacetyl, dimethylformamidine, and N,N-diphenyl carbamate.

In still yet another embodiment of the above processes:

$R_5$ is DMTr;

$R_p$ is methyl; and

R is iPr.

In another embodiment of the above processes, the processes further comprise fully deprotecting the bound N-mer oligonucleotide to yield a free N-mer oligonucleotide. In another embodiment of the above processes, the N-mer oligonucleotide has a length from 4-100 ribonucleotides. In yet another embodiment of the above processes, the N-mer oligonucleotide has a length from 4-100 deoxyribonucleotides.

In another embodiment of the above processes,

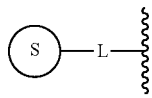

is selected from:

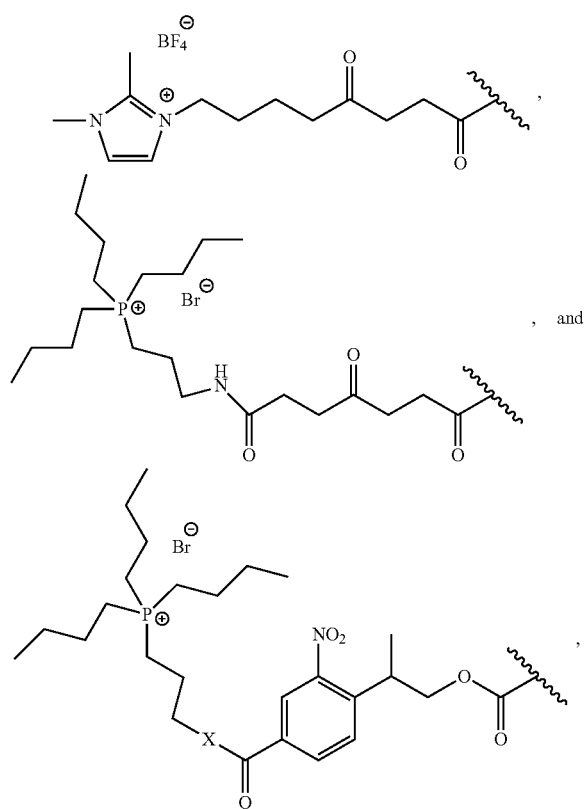

wherein X is selected from NH and O.

In yet another embodiment, there is provided an oligonucleotide prepared by the above processes. In one embodiment, the oligonucleotide prepared by the above processes is an oligoribonucleotide. In another embodiment, the oligonucleotide prepared by the above processes is an oligodeoxyribonucleotide.

Suitable solid supports for use in the above-mentioned processes are known to those of skill in the art and may include controlled pore glass (CPG) or long chain alkylamine CPG (LCAA-CPG); polystyrene, polyvinyl, and the like.

Suitable ionic supports are also known to those of skill in the art. These may include those described in PCT Application Publication No. WO 2006/096963 to Chan, T.-H. et al., the contents of which are incorporated herein by reference in its entirety. Suitable ionic supports may include, for example, imidazolium and phosphonium ionic salts.

Functionalized linkers ("L" in formulae (VIII) and (IX)) are usually attached to solid/ionic supports to space out the oligomer from the surface of the support, and suitable linkers are known to those of skill in the art. The most common ones used with CPG (controlled-pore glass) and highly cross-linked polystyrene (PS) solid supports are long-chain alkylamines that are further functionalized with a succinyl, oxalyl, hydroquinone-O,O'-diacetic acid ('Q-linker'), or universal linkers like those described in U.S. Pat. No. 6,770,754; European Patent No.: 1404695; Guzaev, A. P. et al. *J. Am. Chem. Soc.*, 125, 2380-2381 (2003). Other options for linkers are disclosed in Pon, R. T. et al. *Nucleic Acids Research*, 25, 3629-3635 (1997), the contents of which are incorporated herein by reference in its entirety.

As noted above, the moiety

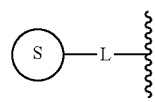

may be selected from

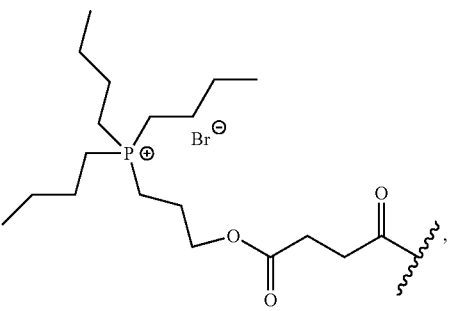 [SMILES: *C(=O)CCC(=O)OCCC[P+](CCCC)(CCCC)CCCC ; [Br-]]

and orthogonally cleavable ionic tag linkers such as

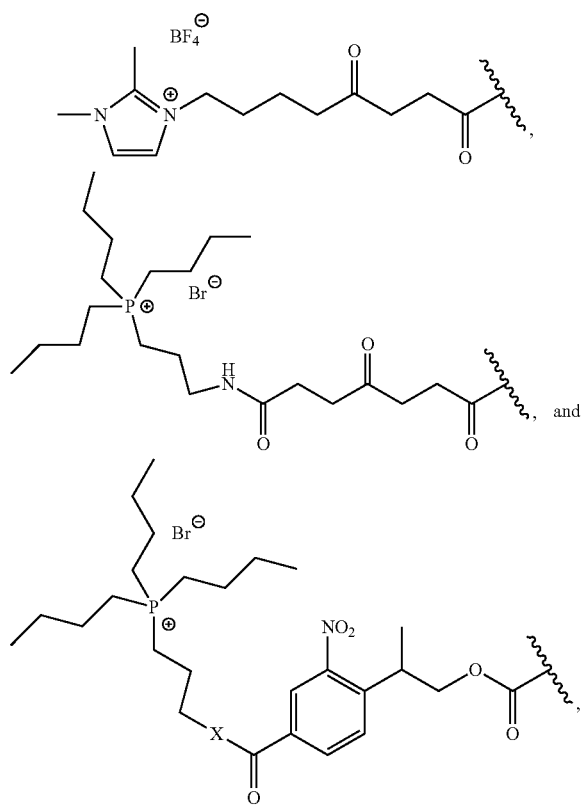

wherein X is selected from NH and O.

The utility of the dimer and trimer synthons described herein was tested through the solution phase synthesis of a decanucleotide, 5'-rUUAAUUAA-dTT-3', and the solid phase synthesis of oligonucleotides of uridine and mixed uridine/adenosine composition. The decamer was constructed by coupling of the previously synthesized dimer amidite blocks UpU (30) and ApA (47) (shown in Schemes 1 and 6) with a dTpdT dimer attached to a novel tetraalkylphosphonium ion tag (Scheme 21).

In an embodiment, the present invention relates to methods for synthesis of oligomers, including but not limited to oligopeptides, oligosaccharides and oligonucleotides (e.g., oligoribonucleotides, oligodeoxyribonucleotides), in solution using cleavable ionic tag linkers provided herein. In a further embodiment, the present invention relates to ionic tag linkers for use in chemical synthesis of oligomers, including but not limited to oligopeptides, oligosaccharides and oligonucleotides, the ionic tag linkers being capable of being cleavable under conditions which do not cleave other oligomer protecting groups. In an embodiment, the ionic tag linkers are orthogonally cleavable. Ionic tag linkers of the invention are compatible with the various synthetic methodologies generally applied in organic synthesis. More specifically, ionic tag linkers are compatible with the various synthetic methodologies generally applied in the synthesis of oligomers, including but not limited to oligopeptides, oligosaccharides and oligonucleotides (e.g., oligoribonucleotides, oligodeoxyribonucleotides). Furthermore, particularly but not exclusively in the case of oligoribonucleotide synthesis, ionic tag linkers must not induce isomerization of other protecting groups when cleaved. Moreover, solubility of ionic tag linkers is, in an embodiment, not influenced by a growing oligopeptide, oligosaccharide or oligonucleotide chain, such that separation and purification procedures become unduly complex. In an embodiment, separation and purification procedures are simplified using ionic tag linkers of the invention, and may involve washing steps with aqueous and/or organic solvents.

In an embodiment of the present invention, the ionic moiety in an ionic tag linker of the invention is an organic salt comprising a heterocyclic or substituted heterocyclic quaternary nitrogen-containing organic cation and an anion balancing the charge on the organic cation. In another embodiment an organic cation is selected from the group consisting of N-substituted pyridine and 1,3-disubstituted imidazole and the anion is selected from the group consisting of Cl, Br, BF4, PF6, SbF6, CuCl2, and AlCl4. Other ionic moieties are known in the art, and are within the capacity of a skilled technician. Furthermore, it is within the capacity of a skilled technician that an anion may also be an organic anion, non-limiting examples of which include $CH_3CO_2$, $CF_3CO_2$, $CH_3SO_4$, and $CF_3SO_2$.

In an embodiment, a substrate (reactant) attached to an ionic tag linker is soluble in polar organic solvents and can undergo liquid-phase reaction. After completion of the reaction and evaporation of the solvent, excess reagents can be removed by a less polar organic solvent in which an ionic tag linker is not soluble. Inorganic reagents and/or side products can be removed by precipitation or by washing with aqueous solution. A sequence of reactions can be repeated to give more complex structures. Finally, a product can be detached and then separated from an ionic tag linker by organic solvent extraction. Substrates attached to an ionic tag linker are expected to largely retain their reactivity analogously to traditional solution based reactions. Progress of reactions is readily monitored and analyzed by standard spectroscopic techniques.

In some embodiments, purification of products is achieved simply by precipitation of an attached ionic tag linker.

In summary, the present invention describes a viable route for the synthesis of regioisomerically pure dimer and trimer RNA phosphoramidites that couple with similar efficiency as monomeric phosphoramidite units. The method increases the overall yield of the target oligoribonucleotide sequence by decreasing the number of coupling steps required for chain assembly and has the potential of significantly simplifying the final purification of RNA sequences. The present invention also demonstrates that dimer and trimer synthons can be utilized either in solution or solid-phase in conjunction with monomer synthons in the final stages of chain assembly, affording n−2 or n−3 failure sequences that are more readily resolved. Dimer and trimer amidite blocks will likely find use in the large scale solution (or solid)-phase synthesis of siRNA drugs. It should be understood that methods provided herein are also applicable to DNA synthesis.

In addition, novel solution phase approaches to synthesis of oligopeptides, oligosaccharides and oligonucleotides, supported by ionic tag linkers, are described herein. Ionic tag linkers and methods for large scale solution-phase synthesis are provided.

EXAMPLES

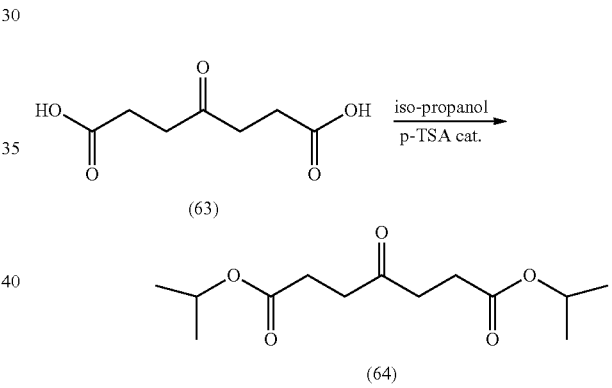

Diisopropyl 4-oxoheptanedioate (64)

4-ketopemilic acid (63) (10 g, 57.4 mmol; purchased from Sigma-Aldrich) was suspended in 50 mL of isopropanol and 50 mL of benzene. Catalytic amount of p-toluene solfonic acid was added to the mixture and brought to reflux using a Dean Stark trap to remove the water produced. Once the volume had decreased to approximately 50 mL in the flask, another 50 mL of 50:50 Benzene:iso-propanol was added and further reduced to approximately 30 ml. The mixture was then taken up in ethyl acetate and extracted with $NaHCO_3$ (×3) and once with brine. The organic layer was dried with $MgSO_4$ and condensed to dryness yielding pure (64): 14.2 g (95%).

$^1$H NMR (300 MHz, CHLOROFORM-d) δ ppm 1.06 (d, J=6.45 Hz, 12H) 2.39 (t, J=7.00 Hz, 1H) 2.60 (t, J=6.70 Hz, 4H) 4.72-4.89 (m, 2H) $^{13}$C NMR (75 MHz, CHLOROFORM-d) δ ppm 21.57 (s, 1C) 28.13 (s, 3C) 28.13 (s, 3C) 36.92 (s, 3C) 67.66 (s, 1C) 171.90 (s, 2C) 206.82 (s, 1C) $C_{13}H_{22}O_5Na^{1+}$ low resolution ESI-MS calculated: 258.14, found: 281.21.

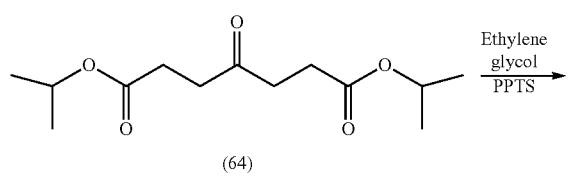

(64)

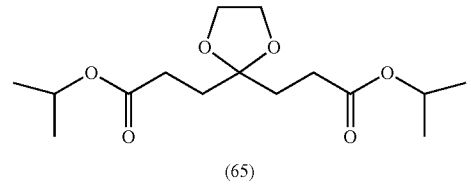

(65)

Diisopropyl 3,3'-(1,3-dioxolane-2,2-diyl)dipropanoate (65)

Compound (64) (0.55 g, 2.1 mmol) was solvated with 5 eq of ethylene glycol (0.58 mL, 10.5 mmol), 90 mL of dry toluene and catalytic amount of pyridinium para-toluene sulfonate. This mixture was refluxed at 140° C. replacing the toluene 3 times and finally allowing the reaction to reflux overnight. The mixture was then distilled to approximately 30 mL, removed from heat and diluted with DCM and extracted with sat. NaHCO$_3$ (×2) then water (×3) to remove any excess ethylene glycol. The product was purified by column chromatography (DCM:MeOH, 100:0→95:5). Isolated yield: 0.41 g (65%).

$^1$H NMR (500 MHz, CHLOROFORM-d) δ ppm 1.05 (d, J=6.36 Hz, 12H) 1.78 (t, J=7.58 Hz, 15H) 2.16 (t, J=7.58 Hz, 15H) 3.76 (s, 15H) 4.82 (dt, J=12.53, 6.33 Hz, 8H) $^{13}$C NMR (126 MHz, CHLOROFORM-d) δ ppm 21.59 (s, 1C) 29.02 (s, 1C) 32.07 (s, 1C) 64.94 (s, 1C) 67.23 (s, 1C) 67.26 (s, 1C) 109.84 (s, 1C) 172.56 (s, 1C) C$_{15}$H$_{26}$O$_6$Na$^{1+}$ low resolution ESI-MS calculated: 302.17, found: 325.0.

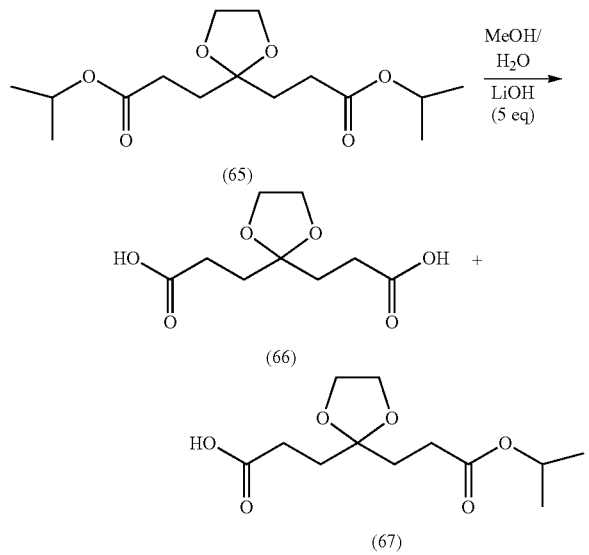

3-(2-(3-hydroxy-3-oxopropyl)-1,3-dioxolan-2-yl) propanoic acid (66) and 3-(2-(3-isopropoxy-3-oxopropyl)-1,3-dioxolan-2-yl)propanoic acid (67)

Compound (65) (1.3 g, 4.3 vmmol) was solvated in 2.5 mL of MeOH to which was added 5 eq of LiOH (0.51 g, 21.5 mmol) in 2.5 mL of water. This mixture was allowed to stir for 6 h until all starting material was consumed. The solution was brought to neutrality by the addition of 1 M HCl in MeOH.

This mixture was purified by column chromatography (DCM:MeOH, 100:0→90:10). Isolated yield of (66): 0.35 g (40%). Yield of (67): 0.68 g (60%).

(66)

$^1$H NMR (300 MHz, METHANOL-d$_4$) δ ppm 1.94 (t, J=8.20 Hz, 4H) 2.33 (t, J=7.30 Hz, 15H) 3.94 (s, 26H) $^{13}$C NMR (75 MHz, METHANOL-d$_4$) δ ppm 28.19 (s, 1C) 31.82 (s, 1C) 64.77 (s, 1C) 109.81 (s, 1C) 175.90 (s, 1C) C$_9$H$_{14}$O$_6$Li$^{1-}$ low resolution ESI-MS calculated: 218.07, found: 224.12.

(67)

$^1$H NMR (500 MHz, METHANOL-d$_4$) δ ppm 1.22 (d, J=6.36 Hz, 6H) 1.87-2.03 (m, 4H) 2.23-2.34 (m, 4H) 3.55 (m, J=5.14 Hz, 3H) 3.67 (m, J=5.14 Hz, 3H) 4.89-5.00 (m, 2H) $^{13}$C NMR (126 MHz, METHANOL-d$_4$) δ ppm 7.75 (s, 1C) 20.72 (s, 1C) 28.80 (s, 1C) 31.81 (s, 1C) 60.87 (s, 1C) 62.94 (s, 1C) 67.60 (s, 1C) 72.13 (s, 1C) 109.92 (s, 1C) 173.40 (s, 1C) 176.73 (s, 1C) C$_{12}$H$_{20}$O$_6$$^{1-}$ low resolution ESI-MS calculated: 260.12, found: 259.03.

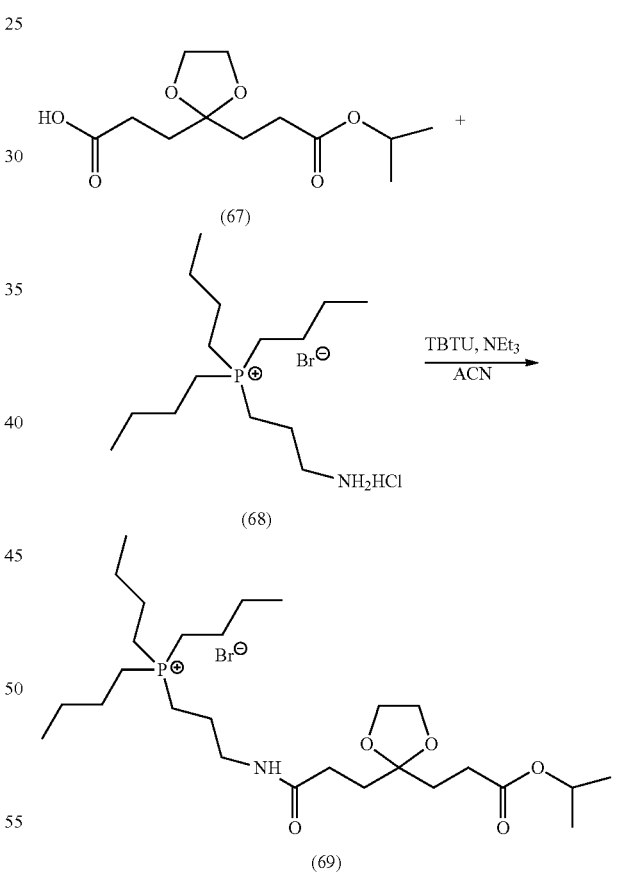

Tributyl (3-(3-(2-(3-isopropoxy-3-oxopropyl)-1,3-dioxolan-2-yl) propanamido)propyl) phosphonium bromide (69)

Compound (67) (0.3 g, 1.1 mmol) was solvated in 1.5 mL of ACN followed by TBTU (0.39 g, 1.2 mmol), 2.5 eq of triethylamine (0.38 ml) and phosphonium ionic tag (68) (0.45 g, 1.2 mmol). This mixture was allowed to stir for 4 h until the starting material (67) was completely consumed. The reaction mixture was diluted with ethyl acetate and extracted with 5% NaHCO$_3$×2 and once with brine. The organic layer was dried and concentrated and purified by column chromatography. DCM:MeOH 100:0→95:5. Isolated yield: 0.54 g (84%).

$^1$H NMR (300 MHz, CHLOROFORM-d) δ ppm 0.91 (t, J=6.74 Hz, 9H) 1.06 (d, J=6.45 Hz, 6H) 1.25 (s, 6H) 1.38-1.59 (m, 11H) 1.80-1.95 (m, 7H) 2.15-2.30 (m, 9H) 2.18 (t, J=7.03 Hz, 8H) 3.28-3.44 (m, 2H) 3.84 (br. s., 5H) 3.94 (s, 6H) 4.72-4.89 (m, 1H) C$_{27}$H$_{53}$NO$_6$P$^{1+}$ low resolution ESI-MS calculated: 502.36, found: 502.36.

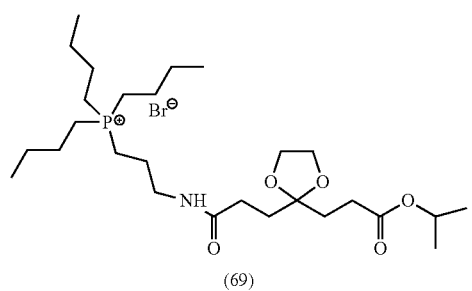

(69)

MeOH/H$_2$O
LiOH (15 eq)
→

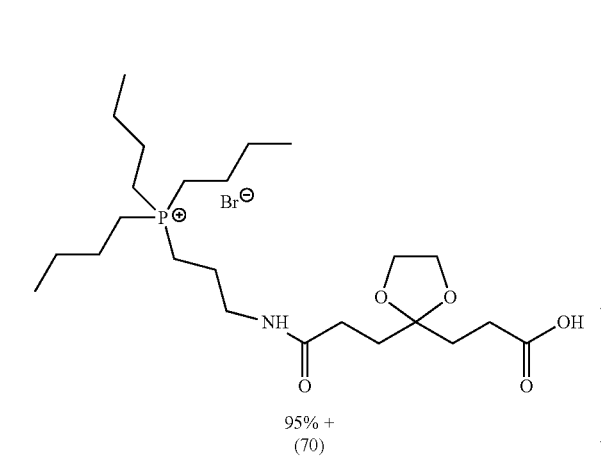

95% +
(70)

Tributyl (3-(3-(2-(3-hydroxy-3-oxopropyl)-1,3-dioxolan-2-yl)propanamido) propyl)phosphonium bromide (70)

Compound (69) (0.25 g, 0.4 mmol) was solvated in 2.5 mL of MeOH to which was added 10 eq of LiOH (0.1 g, 4 mmol) in mL of water.

This mixture was allowed to stir for 3 h until all starting material was consumed. The solution was brought to neutrality by the addition of 1M HCl in MeOH. This mixture was purified by column chromatography (DCM:MeOH, 100:0→90:10). Isolated yield of (70): 0.20 g (95%).

$^1$H NMR (300 MHz, CHLOROFORM-d) δ ppm 0.91 (t, J=6.74 Hz, 9H) 1.25 (s, 6H) 1.38-1.59 (m, 11H) 1.96-2.05 (m, 7H) 2.15-2.30 (m, 9H) 2.40 (t, J=7.03 Hz, 8H) 3.28-3.44 (m, 2H) 3.84 (br. s., 5H) 3.94 (s, 6H) C$_{24}$H$_{47}$NO$_5$P$^{1+}$ low resolution ESI-MS calculated: 460.31, found: 460.30.

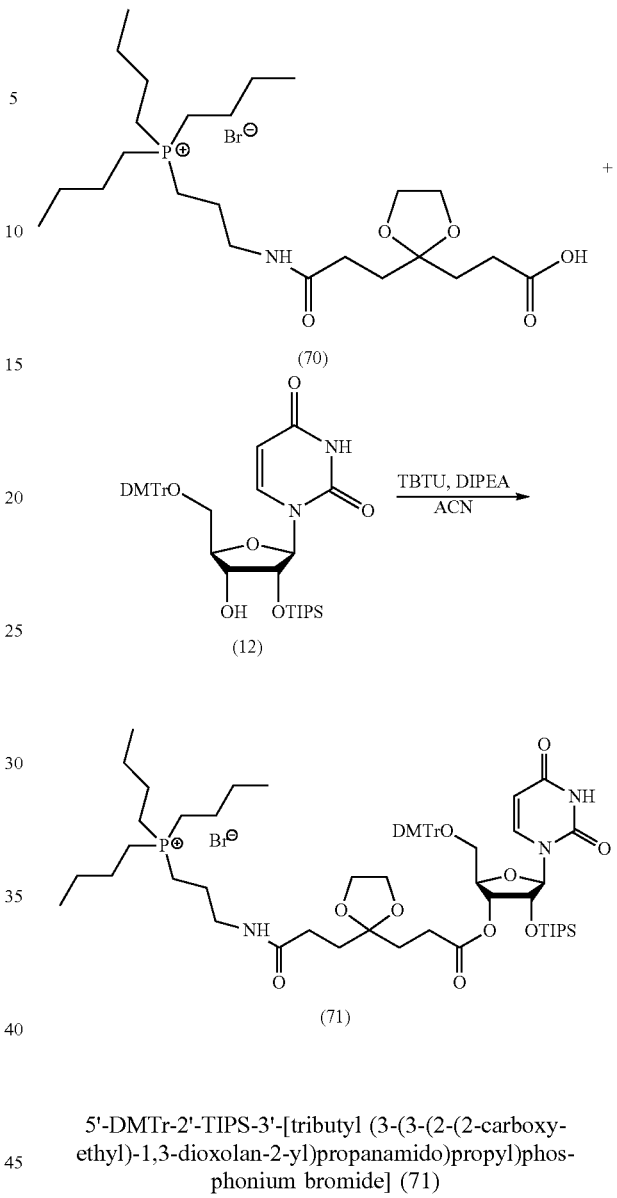

(70)

+

(12)

TBTU, DIPEA
ACN
→

(71)

5'-DMTr-2'-TIPS-3'-[tributyl (3-(3-(2-(2-carboxyethyl)-1,3-dioxolan-2-yl)propanamido)propyl)phosphonium bromide] (71)

To a solution of compound (70) (0.2 g, 0.37 mmol) in ACN (1 mL) was added TBTU (0.19 g, 0.6 mmol), triethylamine (0.5 mL) and compound (12) (0.42 g, 0.6 mmol). The resulting mixture was allowed to stir for 12 h until the starting material (70) was completely consumed. The reaction mixture was diluted with ethyl acetate and extracted with 5% NaHCO$_3$×2 and once with brine. The organic layer was dried and concentrated, taken up in minimal amounts of DCM at precipitated in 100 ml of MTBE, filtered over Celite©. Isolated yield of (71): 0.20 g (45%).

$^1$H NMR (300 MHz, CHLOROFORM-d) δ ppm 0.91 (t, J=6.74 Hz, 9H) 1.02-1.59 (m, 38H) 1.96-2.05 (m, 7H) 2.15-2.30 (m, 9H) 2.40 (t, J=7.03 Hz, 8H) 3.37-3.40 (m, 4H) 3.78-3.94 (br. m, 17H) 4.15 (d, J=2.77 Hz, 1H) 4.63-4.67 (m, 1H) 5.31 (dd, J=5.14, 2.96 Hz, 1H) 5.40-5.46 (m, 1H) 5.42 (s, 1H) 5.99 (d, J=6.32 Hz, 1H) 6.87-6.93 (m, 4H) 7.27-7.37 (m, 7H) 7.41-7.45 (m, 2H) 7.75 (d, J=8.30 Hz, 1H) C$_{63}$H$_{95}$N$_3$O$_{12}$PSi$^{1+}$ low resolution ESI-MS calculated: 1144.64, found: 1144.7.

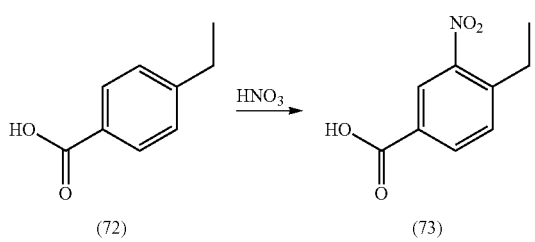

3-Nitro-4-ethyl-benzoic acid (73)

Fuming nitric acid (90%) (150 ml) was cooled with stirring to −10° C. and 4-ethyl benzoic acid (72) (30 g, 0.2 moles; Sigma-Aldrich) was added slowly over 30 min directly into the sitting solution (1.33 mmol/ml of (72) to fuming nitric acid). The mixture was then allowed to stir for 30 min after addition was complete. The mixture was then poured over approximately 600 g of crushed ice to quench the reaction. The product formed a white ppt which can be filtered over a sintered glass funnel. The excess ice melted by washing the product with water. The sample was then re-crystallized from ethyl acetate/hexanes. Two rounds of crystallization were preformed. Yield: 37.2 g (95%).

$^1$H NMR (500 MHz, CHLOROFORM-d) δ ppm 1.33 (t, J=7.58 Hz, 3H) 2.99 (q, J=7.58 Hz, 2H) 7.52 (d, J=8.07 Hz, 1H) 8.23 (dd, J=8.07, 1.71 Hz, 1H) 8.58 (d, J=1.71 Hz, 1H) $^{13}$C NMR (126 MHz, CHLOROFORM-d) δ ppm 14.62 (s, 1C) 26.38 (s, 1C) 126.37 (s, 1C) 128.29 (s, 1C) 131.67 (s, 1C) 133.87 (s, 1C) 144.85 (s, 1C) 149.36 (s, 1C) 170.40 (s, 1C) $C_9H_9NO_4Na^{1+}$ low resolution ESI-MS calculated: 195.05, found: 218.2.

tert-Butyl 3-nitro-4-ethyl-benzoate (75)

Compound (73) (19.65 g 0.10 moles) was solvated in 500 ml of THF (0.2 M) followed by 1.15 eq (10.14 g, 0.15 moles) of diisopropylcarbodimide. This mixture was allowed to stir for 5 min followed by 1.5 eq of tert-butanol (17.9 mL) and catalytic amounts of 4-(dimethylamino)-pyridine. The mixture was allowed to stir for 60 h before the reaction was complete. The reaction was diluted with diethyl ether and filtered to remove the diisopropylurea (DIU) and condensed to dryness. The mixture was solvated in ethyl acetate and extracted with 5% NaHCO$_3$. The product was separated from (74) by column chromatography (solvent system: hexanes:DCM 100:0→0:100). Yield of (75): 15.1 g (60%); yield of (74): 30%.

(74)
$^1$H NMR (300 MHz, CHLOROFORM-d) δ ppm 0.94 (d, J=6.45 Hz, 6H) 1.26 (t, J=7.47 Hz, 3H) 1.39 (d, J=6.74 Hz, 6H) 2.91 (q, J=7.33 Hz, 2H) 3.80 (dq, J=13.88, 6.70 Hz, 1H) 4.44 (quin, J=6.74 Hz, 1H) 6.49 (d, J=7.91 Hz, 1H) 7.40 (d, J=8.20 Hz, 1H) 7.67 (dd, J=7.91, 1.76 Hz, 1H) 8.02 (d, J=1.76 Hz, 1H) $^{13}$C NMR (75 MHz, CHLOROFORM-d) δ ppm 14.80 (s, 1C) 20.75 (s, 1C) 22.04 (s, 1C) 26.12 (s, 1C) 42.96 (s, 1C) 49.54 (s, 1C) 76.63 (s, 1C) 77.05 (s, 1C) 77.48 (s, 1C) 123.13 (s, 1C) 130.76 (s, 1C) 131.52 (s, 1C) 135.78 (s, 1C) 141.49 (s, 1C) 148.95 (s, 1C) 153.60 (s, 1C) 168.67 (s, 1C) $C_{16}H_{23}N_3O_4Na^{1+}$ low resolution ESI-MS calculated: 321.16, found: 344.23.

(75)
$^1$H NMR (300 MHz, CHLOROFORM-d) δ ppm 1.26 (t, J=7.47 Hz, 3H) 1.57 (s, 11H) 2.91 (q, J=7.33 Hz, 2H) 7.40 (d, J=7.91 Hz, 1H) 8.08 (dd, J=7.91, 1.47 Hz, 1H) 8.38 (d, J=1.47 Hz, 1H) $^{13}$C NMR (75 MHz, CHLOROFORM-d) δ ppm 14.70 (s, 1C) 26.18 (s, 1C) 28.05 (s, 1C) 76.64 (s, 1C) 77.06 (s, 1C) 77.49 (s, 1C) 82.13 (s, 1C) 125.42 (s, 1C) 131.12 (s, 1C) 131.18 (s, 1C) 133.23 (s, 1C) 143.00 (s, 1C) 149.12 (s, 1C) 163.56 (s, 1C) $C_{13}H_{17}NO_4Na^{1+}$ low resolution ESI-MS calculated: 251.11, found: 274.32.

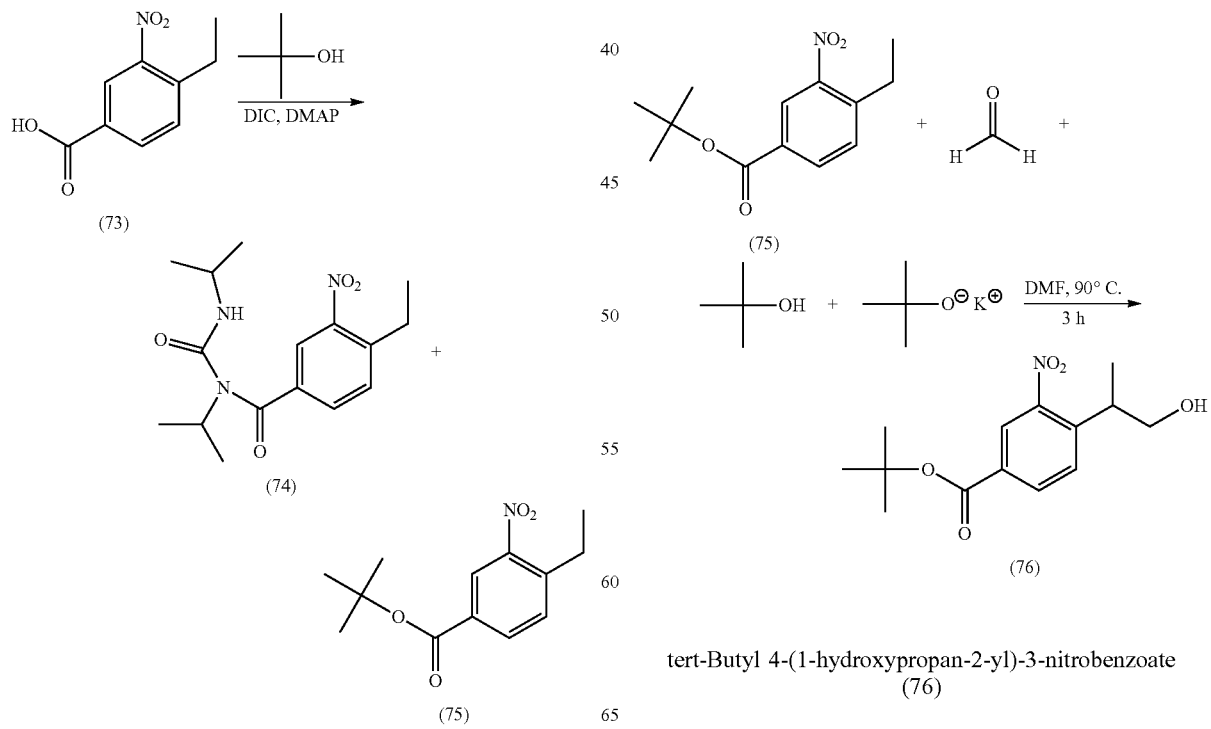

tert-Butyl 4-(1-hydroxypropan-2-yl)-3-nitrobenzoate (76)

Compound (75) (10.5 g, 41.7 mmol) was solvated in 19 mL of DMF (2.2M) to which 1.5 eq (1.88 g) of paraformaldehyde was added followed by a solution of potassium tert-butoxide (0.12 eq, 0.56 g) in tert-butanol (5.7 mL). This mixture was allowed to stir at room temperature for 10 min before being brought up 90° C. for 3 h.

The mixture was then acidified to neutrality by the addition of a 1M HCl monitored by a pH meter. This mixture was then diluted with sat. NaCl and ethyl acetate (×2). Compound (76) was purified by column chromatography in DCM:ethyl acetate 100:0→90:10. Yield: 9.4 g (85%).

$^1$H NMR (400 MHz, ACETONITRILE-$d_3$) δ ppm 1.41 (d, J=7.03 Hz, 3H) 3.80 (sxt, J=6.88 Hz, 1H) 4.49-4.67 (m, 2H) 7.40 (d, J=7.91 Hz, 1H) 8.08 (dd, J=7.91, 1.47 Hz, 1H) 8.38 (d, J=1.47 Hz, 1H) $^{13}$C NMR (75 MHz, CHLOROFORM-d) δ ppm 17.35 (s, 1C) 27.96 (s, 1C) 36.57 (s, 1C) 67.01 (s, 1C) 82.27 (s, 1C) 124.77 (s, 1C) 128.50 (s, 1C) 131.04 (s, 1C) 131.06 (s, 1C) 132.81 (s, 1C) 142.62 (s, 1C) 150.41 (s, 1C) 163.58 (s, 1C) $C_{14}H_{19}NO_5Na^{1+}$ low resolution ESI-MS calculated: 281.12, found: 304.02.

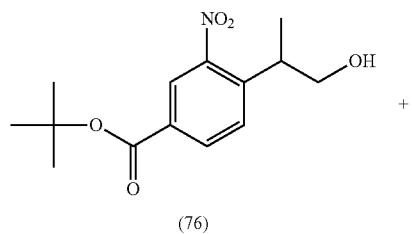

(76)

+

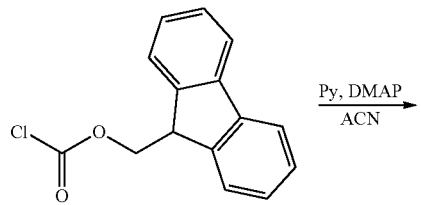

Py, DMAP / ACN →

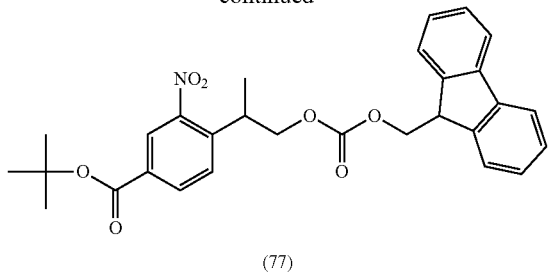

(77)

tert-Butyl 4-(1-(F-moc)propan-2-yl)-3-nitrobenzoate (77)

Compound (76) (5.38 g, 20.2 mmol) was co-evaporated with pyridine (×3) and solvated in 97 mL of ACN (0.2M) and 2 eq of pyridine (3.13 mL, 38.7 mmol). Fmoc-Cl (5.0 g, 19.33 mmol) was added directly to solution and was allowed to stir for 16 h in the dark, covered with aluminum foil. The reaction went to completion by TLC. The solution was extracted (×3) with 5% ammonium chloride and once with brine and purified by column chromatography Hex/EtAc 100:0→75:25. Isolated yield: 8.19 g (86%).

$^1$H NMR (500 MHz, ACETONITRILE-$d_3$) δ ppm 1.30 (d, J=7.09 Hz, 3H) 1.60 (s, 9H) 3.65 (sxt, J=6.94 Hz, 1H) 4.19 (t, J=6.24 Hz, 1H) 4.23-4.34 (m, 2H) 4.39-4.53 (m, 2H) 7.27-7.34 (m, 2H) 7.41 (t, J=7.46 Hz, 2H) 7.53 (d, J=7.34 Hz, 2H) 7.62 (d, J=8.31 Hz, 1H) 7.80 (d, J=7.58 Hz, 2H) 8.13 (dd, J=8.19, 1.59 Hz, 1H) 8.28 (d, J=1.71 Hz, 1H) $^{13}$C NMR (126 MHz, ACETONITRILE-$d_3$) δ ppm −0.10 (s, 1C) 0.06 (s, 1C) 0.23 (s, 1C) 0.40 (s, 1C) 0.56 (s, 1C) 0.73 (s, 1C) 0.89 (s, 1C) 16.83 (s, 1C) 27.30 (s, 1C) 27.32 (s, 1C) 33.47 (s, 1C) 46.64 (s, 1C) 68.89 (s, 1C) 70.90 (s, 1C) 82.13 (s, 1C) 117.34 (s, 1C) 120.06 (s, 1C) 124.56 (s, 1C) 124.87 (s, 1C) 124.90 (s, 1C) 127.17 (s, 1C) 127.18 (s, 1C) 127.81 (s, 1C) 127.83 (s, 1C) 128.87 (s, 1C) 131.72 (s, 1C) 132.75 (s, 1C) 141.03 (s, 1C) 141.17 (s, 1C) 143.50 (s, 1C) 143.55 (s, 1C) 150.42 (s, 1C) 154.54 (s, 1C) 163.26 (s, 1C) $C_{29}H_{29}NO_7Na^{1+}$ low resolution ESI-MS calculated: 503.19, found: 526.41.

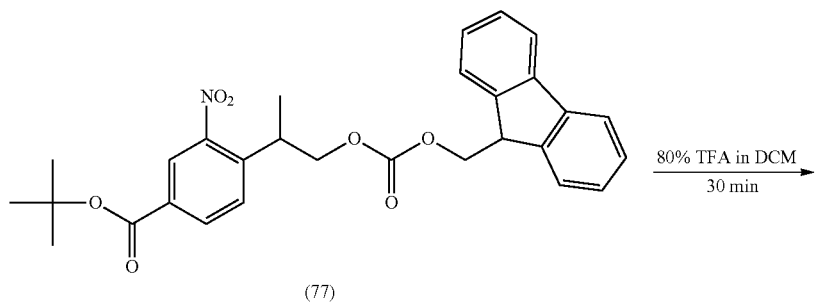

80% TFA in DCM / 30 min →

(77)

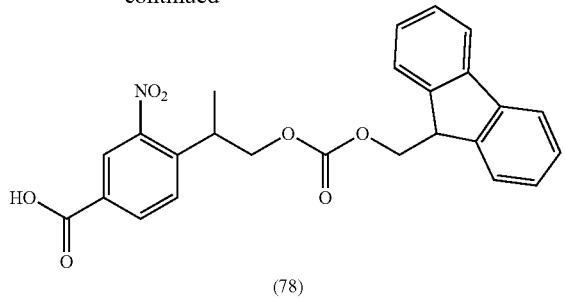

(78)

4-(1-(Fmoc) propan-2-yl)-3-nitrobenzoic acid (78)

Compound (77) (8.9 g, 17.7 mmol) was directly solvated in a solution of 80% TFA in DCM (50 mL) and allowed to stir for 30 min, until all starting material had been consumed. The sample was then evaporated to dryness on the rotovap and purified by column chromatography, Hex/EtAc 100:0→60:40. Isolated yield: 6.09 g (77%).

$^1$H NMR (500 MHz, CHLOROFORM-d) δ ppm 1.43 (d, J=6.85 Hz, 3H) 3.86 (sxt, J=6.80 Hz, 1H) 4.32-4.46 (m, 4H) 7.28-7.36 (m, 2H) 7.41 (t, J=7.58 Hz, 2H) 7.57 (dd, J=6.97, 4.52 Hz, 2H) 7.65 (d, J=8.07 Hz, 1H) 7.76 (d, J=7.34 Hz, 2H) 8.29 (dd, J=8.07, 1.71 Hz, 1H) 8.53 (d, J=1.71 Hz, 1H) 11.69 (br. s., 1H) $^{13}$C NMR (126 MHz, CHLOROFORM-d) δ ppm 17.58 (s, 1C) 33.71 (s, 1C) 46.62 (s, 1C) 70.08 (s, 1C) 71.14 (s, 1C) 76.80 (s, 1C) 77.05 (s, 1C) 77.31 (s, 1C) 120.06 (s, 1C) 125.10 (s, 1C) 125.11 (s, 1C) 126.16 (s, 1C) 127.16 (s, 1C) 127.17 (s, 1C) 127.91 (s, 1C) 127.93 (s, 1C) 128.87 (s, 1C) 129.00 (s, 1C) 133.71 (s, 1C) 141.26 (s, 1C) 141.27 (s, 1C) 142.82 (s, 1C) 143.14 (s, 1C) 143.20 (s, 1C) 150.39 (s, 1C) 155.00 (s, 1C) 169.79 (s, 1C) $C_{25}H_{20}NO_7^{1-}$ low resolution ESI-MS calculated: 447.13, found: 446.0.

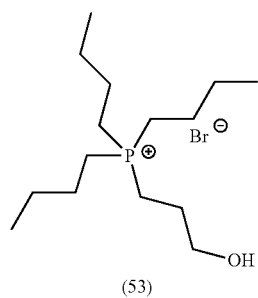

(53)

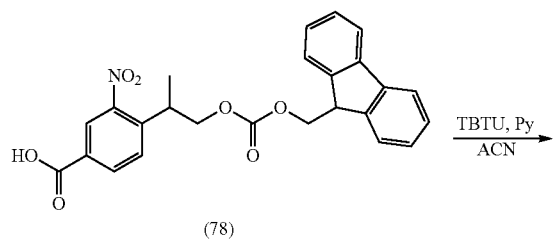

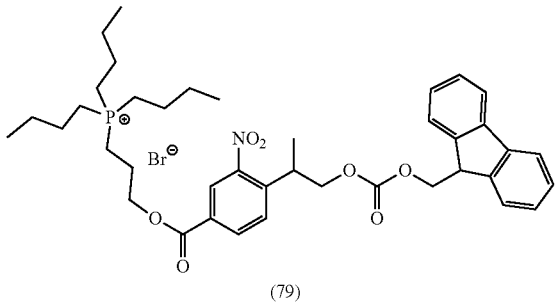

(79)

Phosphonium tag 4-(1-(Fmoc)propan-2-yl)-3-nitrobenzoate (79)

Compound (78) (3.726 g, 8.33 mmol) was solvated in half the solvent (ACN:Py, 28 mL:1.25 mL) to which was added a solution of the phosphonium tag (53) (3.86 g, 9.16 mmol) in the other half of the solvent, followed directly by TBTU (4.0 g, 12.5 mmol). The solution was allowed to stir overnight and by morning the reaction was complete (12 h), and was concentrated to half solvent volume then extracted with ethyl acetate and 5% NaHCO$_3$ (×3) and once with brine. The organic layer was dried with MgSO$_4$ and condensed to dryness. The compound was then precipitated in 500 mL of MTBE to remove the excess pyridine and TBTU byproduct.

The precipitated white goo was filtered and collected over Celite© then purified by column chromatography, DCM:MeOH 100:0→92:8. Isolated yield of (79): 5.52 g (86%).

$^1$H NMR (300 MHz, CHLOROFORM-d) δ ppm 0.81-0.99 (m, 8H) 1.35 (d, J=7.03 Hz, 3H) 1.38-1.61 (m, 11H) 1.99-2.38 (m, 8H) 2.66 (br. s., 2H) 3.54-3.83 (m, 3H) 4.10-4.41 (m, 5H) 7.21-7.44 (m, 4H) 7.57 (dd, J=10.11, 8.06 Hz, 3H) 7.72 (d, J=7.33 Hz, 2H) 8.55 (d, J=1.76 Hz, 1H) 8.70 (dd, J=8.20, 1.76 Hz, 1H) $^{13}$C NMR (75 MHz, CHLOROFORM-d) δ ppm 13.35 (s, 1C) 17.68 (s, 1C) 18.59 (s, 1C) 19.22 (s, 1C) 23.55 (s, 1C) 23.62 (s, 1C) 23.81 (s, 1C) 24.01 (s, 1C) 33.40 (s, 1C) 46.62 (s, 1C) 69.91 (s, 1C) 71.36 (s, 1C) 76.67 (s, 1C) 77.09 (s, 1C) 77.52 (s, 1C) 119.96 (s, 1C) 124.31 (s, 1C) 125.21 (s, 1C) 127.18 (s, 1C) 127.83 (s, 1C) 128.61 (s, 1C) 131.93 (s, 1C) 133.41 (s, 1C) 139.59 (s, 1C) 141.19 (s, 1C) 143.27 (s, 1C) 143.33 (s, 1C) 150.18 (s, 1C) 154.87 (s, 1C) 165.19 (s, 1C) 31P NMR (81 MHz, CHLOROFORM-d) δ ppm 35.07 (s, 1P) $C_{40}H_{53}NO_7P^{1+}$ low resolution ESI-MS calculated: 690.30, found: 690.35.

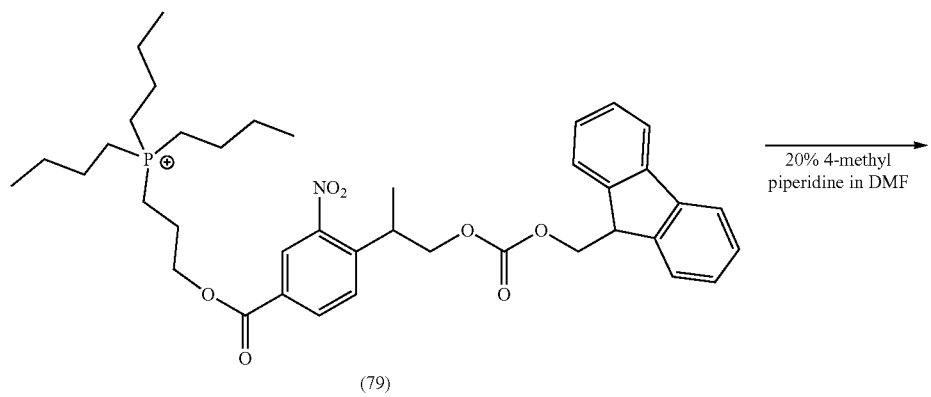

(79)

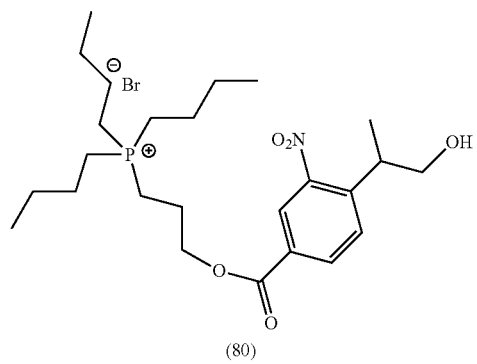

(80)

Phosphonium tag 4-(1-hydroxypropan-2-yl)-3-nitrobenzoate (80)

To compound (79) (6.408 g, 9.29 mmol) was added a 20% solution of 4-methylpiperidine in DMF (20 ml). After 2 h the reaction was complete by TLC and the solution was evaporated to dryness, then taken up in DCM and precipitated in 500 ml of MTBE to yield 3.09 g of (80) (71%).

$^1$H NMR (400 MHz, CHLOROFORM-d) δ ppm 0.91 (t, J=7.03 Hz, 11H) 1.26 (d, J=7.03 Hz, 3H) 1.38-1.59 (m, 13H) 1.98 (d, J=7.03 Hz, 2H) 2.11-2.28 (m, 7H) 2.36-2.51 (m, 2H) 3.40-3.59 (m, 3H) 3.64-3.82 (m, 2H) 7.51 (d, J=8.21 Hz, 1H) 8.22 (d, J=8.21 Hz, 1H) 8.26 (s, 1H) $C_{25}H_{43}NO_5P^{1+}$ low resolution ESI-MS calculated: 468.28, found: 468.28.

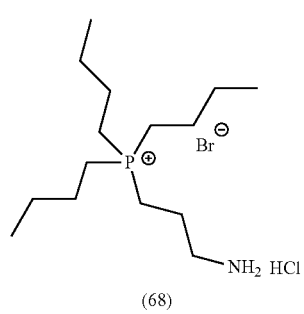

(68)

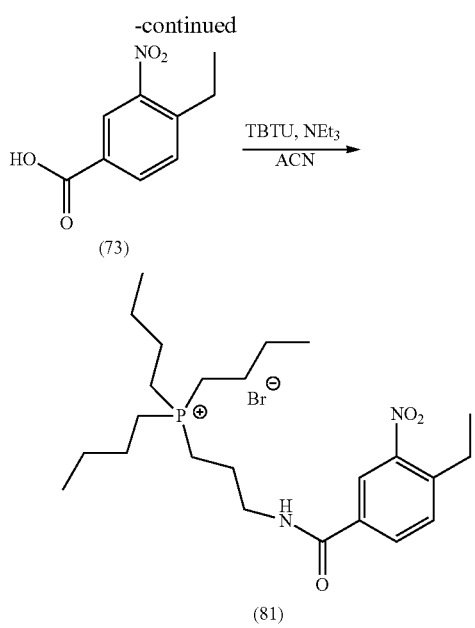

(81)

Tributyl(3-(4-ethyl-3-nitrobenzamido)propyl)phosphonium bromide (81)

To a solution of 3-nitro-4-ethyl-benzoic acid (73) (3.15 g, 16.1 mmol) and diisopropylethylamine (4 eq, 11.25 ml) in ACN (30 mL) was added compound (68) (1.3 eq, 20.9 mmol) and TBTU (1.3 eq, 6.74 g, 20.9 mmol). This mixture was allowed to stir for 12 h.

The dark brown solution was concentrated to a viscous oil, and taken up in DCM and precipitated in 500 ml of MTBE. The solid was collected and re-purified by silica gel column chromatography (DCM:MeOH, 100:0→85:15) eluting as very dark yellow oil. Isolated yield: 7.07 g (84%).

$^1$H NMR (500 MHz, CHLOROFORM-d) δ ppm 0.90 (t, J=6.97 Hz, 9H) 1.24 (t, J=7.46 Hz, 3H) 1.35-1.56 (m, 12H) 1.96 (d, J=8.07 Hz, 2H) 2.05-2.19 (m, 7H) 2.25-2.38 (m, 2H) 2.78 (s, 2H) 2.87 (q, J=7.34 Hz, 2H) 3.60 (q, J=5.79 Hz, 2H) 7.40 (d, J=8.07 Hz, 1H) 7.78 (t, J=5.50 Hz, 1H) 8.07 (d, J=8.07 Hz, 1H) 8.37 (s, 1H) $^{13}$C NMR (126 MHz, CHLOROFORM-d) δ ppm 13.21 (s, 1C) 14.61 (s, 1C) 18.17 (s, 1C) 18.56 (s, 1C) 23.33 (s, 1C) 23.37 (s, 1C) 23.76 (s, 1C) 23.88 (s, 1C) 25.97 (s, 1C) 38.57 (s, 1C) 76.77 (s, 1C) 77.02 (s, 1C) 77.28 (s, 1C) 123.82 (s, 1C) 131.09 (s, 1C) 131.47 (s, 1C) 132.89 (s, 1C) 141.77 (s, 1C) 149.21 (s, 1C) 165.48 (s, 1C) $C_{24}H_{42}N_2O_3P^{1+}$ low resolution ESI-MS calculated: 437.29, found: 437.30.

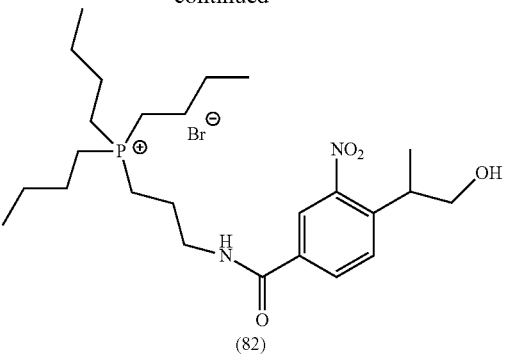

Tributyl(3-(4-(1-hydroxypropan-2-yl)-3-nitrobenzamido)propyl) phosphonium bromide (82)

To a solution of compound (81) (3.56 g, 6.89 mmol) dry DMSO (13.8 mL), was added para-formaldehyde (2.1 eq, 0.43 g, 14.4 mmol). This mixture was sonicated for 20 min till all of para-formaldehyde dissolved. The resulting mixture was treated with 1.5 eq of potassium tert-butoxide (1.16 g, 10.3 mmol). The reaction turned a dark purple immediately. The reaction was allowed to stir for 12 h at room temperature. The reaction was monitored by MS, showing the disappearance of the starting material. The reaction was treated with 1M HCl in MeOH to bring it to neutrality at which point the reaction was precipitated in diethyl ether, and then in DCM. This last precipitation step separated the product from unreacted para-formaldehyde. The product was purified by reverse phase chromatography, using 100 mM TEAA buffer in water (pH 7): ACN 80:20→20:80. Isolated yield: 1.3 g (35%).

$^1$H NMR (400 MHz, CHLOROFORM-d) δ ppm 0.84-0.98 (m, 9H) 1.26 (d, J=7.03 Hz, 3H) 1.38-1.59 (m, 11H) 1.98 (d, J=5.86 Hz, 2H) 2.09-2.27 (m, 6H) 2.34-2.50 (m, 2H) 3.39-3.49 (m, 1H) 3.53 (d, J=5.47 Hz, 2H) 3.64-3.81 (m, 2H) 7.51 (d, J=8.21 Hz, 1H) 8.22 (d, J=8.21 Hz, 1H) 8.26 (s, 1H) 8.45 (br. s., 1H) $^{13}$C NMR (75 MHz, CHLOROFORM-d) δ ppm 13.38 (s, 1C) 17.65 (s, 1C) 18.43 (s, 1C) 19.05 (s, 1C) 23.61 (s, 1C) 23.68 (s, 1C) 23.78 (s, 1C) 23.99 (s, 1C) 36.68 (s, 1C) 50.06 (s, 1C) 66.17 (s, 1C) 76.69 (s, 1C) 77.11 (s, 1C) 77.54 (s, 1C) 124.73 (s, 1C) 128.38 (s, 1C) 129.42 (s, 1C) 133.08 (s, 1C) 144.51 (s, 1C) 150.43 (s, 1C) 164.33 (s, 1C) $^{31}$P NMR (81 MHz, CHLOROFORM-d) δ ppm 35.07 (s, 1P) $C_{25}H_{44}N_2O_4P^{1+}$ low resolution ESI-MS calculated: 467.30, found: 467.31.

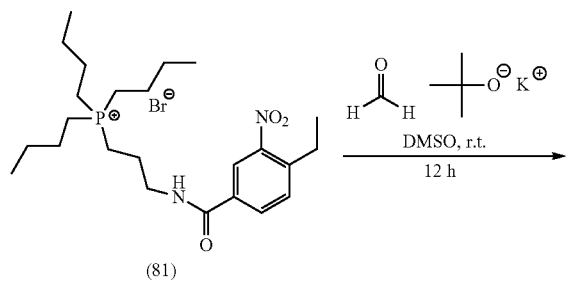

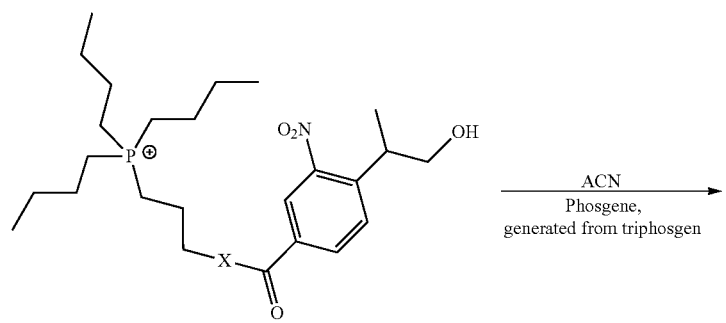

(80) X = O
(82) X = NH

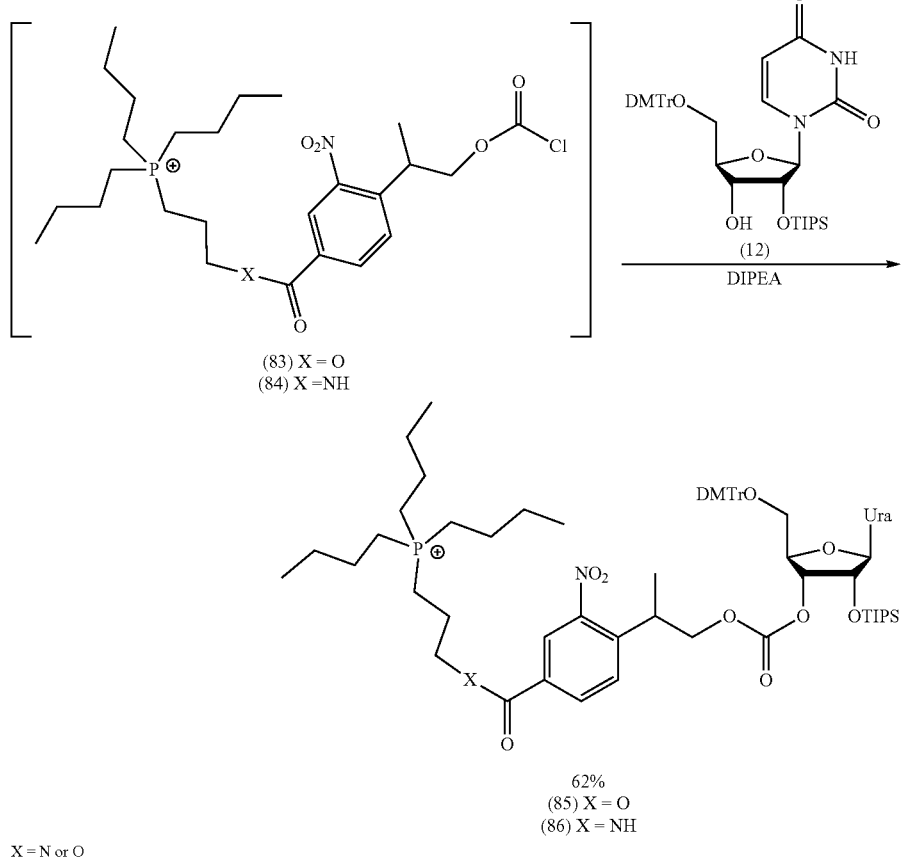

(83) X = O
(84) X = NH

62%
(85) X = O
(86) X = NH

X = N or O

5'-DMTr-2'-TIPS-3'-(tributyl(3-(4-(1-hydroxypropan-2-yl)-3-nitrobenzamido)propyl) phosphonium bromide)-uridine (86)

A two necked flask containing the triphosgene and phenanthridine was connected to a distillation head and condenser. The receiving end of the condenser was attached to an ammonia trap and cooled by a dry ice/acetone bath to condense the phosgene that was produced. The bottom of the ammonia trap was connected to a three necked round bottom flask with a stir bar which was also cooled by a dry ice/acetone bath. All open necks of round bottoms were sealed by fresh septa wrapped with Teflon tape. One neck of the three necked flask was punctured with a 20G needle attached to a tygon tube and two bubblers in series; the first was empty and the second contained mineral oil. Tygon tubing was used to connect the second bubbler to a 9-inch 20G needle that was fully inserted into a saturated solution of sodium hydroxide in methanol. A second needle and tube was inserted into the septa of the methanolic sodium hydroxide, which acted as a vent up into the fume hood. Triphosgene (1.87 g, 6.33 mmol) and cat. phenanthridine were heated to 90° C., at which point the triphosgene melted and solvated the phenanthridine catalyst, promoting the evolution of phosgene gas. After 30 min, all triphosgene was consumed and phosgene had begun condensing in the receiving flask. At this point a balloon of argon was punctured through the septa on the two necked flask, pushing any phosgene gas to the condenser and quenching solution. Once phosgene had stopped condensing, an acetonitrile solution of (80) (1.06 g, 1.9 mmol) was added dropwise to the stirring phosgene, then removed from the dry ice/acetone bath after 10 min. The reaction was stirred for 2 h at room temperature. Next, argon gas was passed over the whole apparatus and also bubbled through the reaction mixture into the methanolic sodium hydroxide to remove and quench the excess phosgene. NOTE: a very low flow from a balloon was used at first to ensure the phosgene was quenched. Once all phosgene was removed, DIPEA (4 mL) was added to the mixture to quench the HCl produced in the reaction with phosgene and compound (82).

A solution of nucleoside (12) (1 eq, 1.35 g, 1.9 mmol) in ACN (3 mL) was added directly to the above mixture, and the resulting solution allowed to stir for 8 h at room temperature. The solution was diluted with ethyl acetate and extracted with sat. NaHCO$_3$ (×3) and once with brine. The mixture was precipitated in 300 mL of MTBE to remove excess nucleoside and DIPEA. The resulting precipitate was then purified by column chromatography (DCM:MeOH 100:0→90:10) to afford 1.32 g of (86) (62% yield).

$^1$H NMR (300 MHz, CHLOROFORM-d) δ ppm 0.82-1.16 (m, 34H) 1.34 (dd, J=6.89, 2.20 Hz, 3H) 1.38-1.63 (m, 15H) 2.05 (br. s., 2H) 2.11-2.31 (m, 12H) 2.67 (br. s., 1H) 3.39-3.53 (m, 1H) 3.57-3.72 (m, 3H) 3.78 (s, 7H) 4.08-4.38 (m, 2H) 4.59-4.69 (m, 1H) 5.16-5.33 (m, 2H) 5.63-5.76 (m, 1H) 6.00 (dd, J=5.27, 2.05 Hz, 1H) 6.81 (dd, J=8.79, 1.47 Hz, 4H) 7.15 (d, J=8.79 Hz, 1H) 7.18-7.41 (m, 10H) 7.56 (d, J=7.91 Hz, 1H) 7.88 (dd, J=8.20, 1.76 Hz, 1H) 8.53 (d, J=7.91 Hz, 1H) 8.67 (t, J=8.94 Hz, 2H) 9.64 (br. s., 1H) $C_{65}H_{92}N_4O_{13}PSi^{1+}$ low resolution ESI-MS calculated: 1195.61, found: 1195.60.

Ion-Tagged Synthesis of Tetramer rGACU from Nucleoside (86)
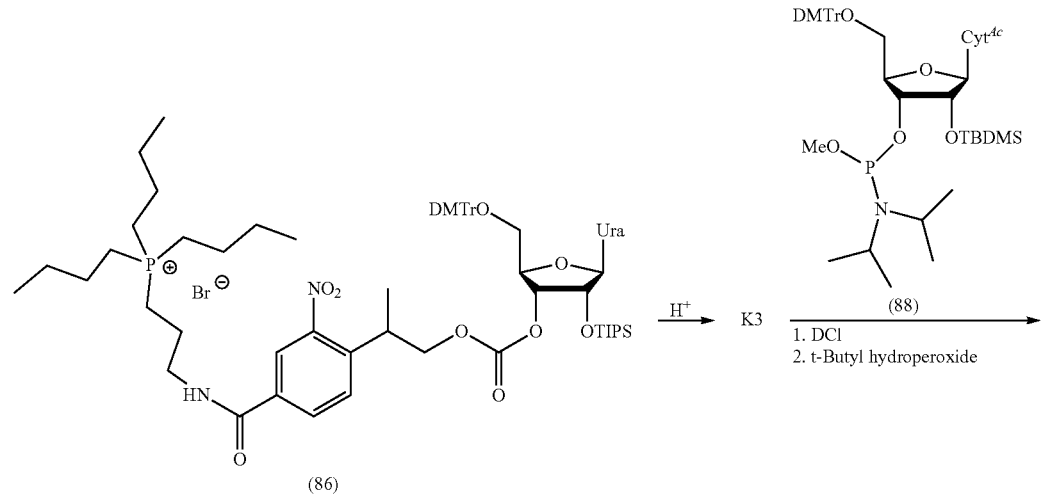
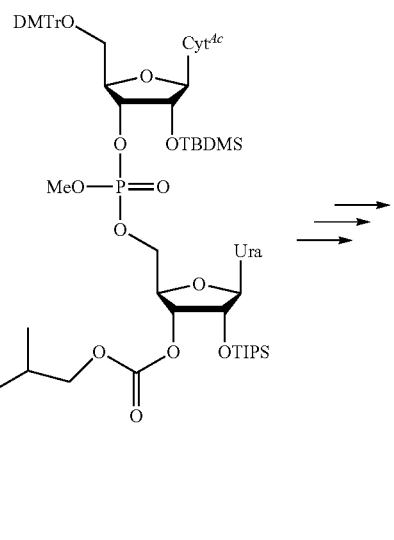

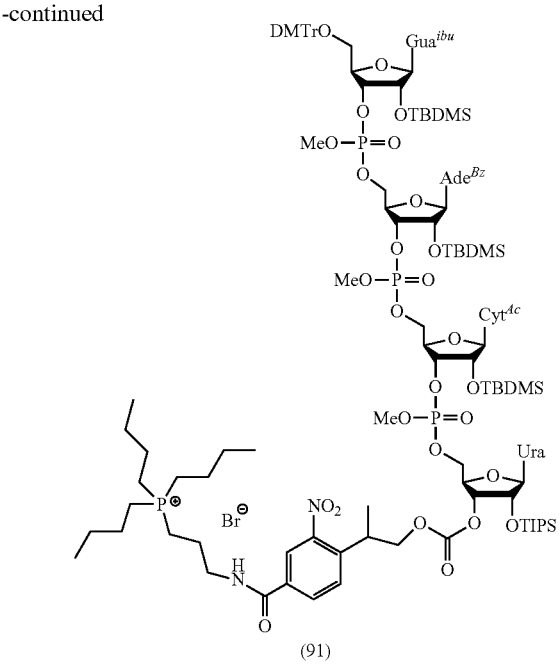

(91)

5'-OH-2'-TIPS-3'-(tributyl(3-(4-(1-hydroxypropan-2-yl)-3-nitrobenzamido)propyl)phosphonium bromide)-uridine (K3)

3'-Tagged-uridine (86) (0.49 g, 0.38 mmol) was dissolved in 3% TFA in DCM and allowed to stir for 5 min before adding methanol to quench the trityl cation. The reaction was then concentrated to an oil taken up in minimal amounts of DCM and precipitated in MTBE to remove dimethoxytritanol. The compound was filtered over celite, collected in DCM and purified by column chromatography (DCM: MeOH, 100:0→90:10%). Isolated yield of K3: 0.37 g (95%).

$^1$H NMR (500 MHz, ACETONITRILE-$d_3$) δ ppm 0.87-1.12 (m, 15H) 1.38 (dd, J=6.97, 3.55 Hz, 1H) 1.42-1.61 (m, 6H) 1.96 (dt, J=4.89, 2.45 Hz, 1H) 1.98-2.07 (m, 1H) 2.07-2.17 (m, 3H) 2.22-2.33 (m, 1H) 3.49 (br. s., 1H) 3.66-3.79 (m, 1H) 4.13 (dd, J=13.45, 1.96 Hz, 1H) 4.30-4.46 (m, 2H) 4.57-4.66 (m, 1H) 5.03 (ddd, J=10.82, 5.07, 1.71 Hz, 1H) 5.70 (d, J=8.07 Hz, 1H) 5.85 (dd, J=6.97, 4.28 Hz, 1H) 7.73-7.83 (m, 1H) 8.27 (d, J=8.31 Hz, 1H) 8.39 (t, J=1.71 Hz, 1H) 9.17 (br. s., 1H) $^{13}$C NMR (126 MHz, ACETONITRILE-$d_3$) δ ppm−0.16 (s, 1C) 0.17 (s, 1C) 0.34 (s, 1C) 0.36 (s, 1C) 0.50 (s, 1C) 0.52 (s, 1C) 0.54 (s, 1C) 0.67 (s, 1C) 0.83 (s, 1C) 11.91 (s, 1C) 11.93 (s, 1C) 12.57 (s, 1C) 15.13 (s, 1C) 15.52 (s, 1C) 16.93 (s, 1C) 16.99 (s, 1C) 17.00 (s, 1C) 17.01 (s, 1C) 17.11 (s, 1C) 17.69 (s, 1C) 18.07 (s, 1C) 20.64 (s, 1C) 20.67 (s, 1C) 22.84 (s, 1C) 22.88 (s, 1C) 23.45 (s, 1C) 23.57 (s, 1C) 33.49 (s, 1C) 33.64 (s, 1C) 61.34 (s, 1C) 61.37 (s, 1C) 64.62 (s, 1C) 64.76 (s, 1C) 71.11 (s, 1C) 71.31 (s, 1C) 73.49 (s, 1C) 76.99 (s, 1C) 77.10 (s, 1C) 82.99 (s, 1C) 87.73 (s, 1C) 87.76 (s, 1C) 102.64 (s, 1C) 102.66 (s, 1C) 117.32 (s, 1C) 124.83 (s, 1C) 124.86 (s, 1C) 129.10 (s, 1C) 129.32 (s, 1C) 129.84 (s, 1C) 129.85 (s, 1C) 133.06 (s, 1C) 133.08 (s, 1C) 140.43 (s, 1C) 140.46 (s, 1C) 141.68 (s, 1C) 141.82 (s, 1C) 150.41 (s, 1C) 150.53 (s, 1C) 150.81 (s, 1C) 150.83 (s, 1C) 154.10 (s, 1C) 154.15 (s, 1C) 162.65 (s, 1C) 164.03 (s, 1C) 164.04 (s, 1C) $C_{44}H_{74}N_4O_{11}PSi^{1+}$ low resolution ESI-MS calculated: 893.48, found: 893.50.

Synthesis of rCpU (90).

Compound K3 (0.37 g, 0.38 mmol) was dried by two co-evaporations of dry toluene:DCM on a rotovap before placed under high vacuum. K3 was dissolved in 15 ml of ACN containing 2 eq of DCI (0.982 g, 8.32 mmol). Immediately after, phoshoramidite (88) (0.51 g 0.57 mmol) was added, and the resulting solution was allowed to stir at room temperature for 3 h. MS analysis indicated that the reaction was complete (no starting material K3 present). Ten eq of tert-butanol was added to quench excess phosphoramidite, followed by 10 eq of tert-butyl hydroperoxide (1 mL of a 6 M solution in decane), and the resulting mixture allowed to stir for 20 min until all the phosphite triester was converted to the phosphate, as monitored by MS. The reaction was then concentrated to an oil, taken up in minimal amounts of DCM, and precipitated in MTBE to remove all excess reagents. The precipitation process was repeated if the presence of any quenched phosphoramidite was detected by TLC. Tagged dimer (90) was isolated in 95% yield (0.63 g). $C_{63}H_{122}N_7O_{21}P_2Si_2^{1+}$ low resolution ESI-MS calculated: 1670.77, found: 1670.73.

The above process was repeated as described above, using the appropriate phosphoramidites till tetramer (92) was obtained. Intermediates isolated were characterized (data shown in Table 7 below).

TABLE 7

Characterization of DMTr-rGACU-tag and intermediates

| Step | Compound 5'→3' | Mass cal. (m/z) | Mass found (m/z) |
|---|---|---|---|
| 1 | DMTr-rCU-tag (a) | 1654.77 | 1654.71 |
| 2 | DMTr-rCU-tag (b) (90) | 1670.77 | 1670.73 |
| 3 | HO-rCU-tag | 1368.63 | 1368.59 |
| 4 | DMTr-rACU-tag (a) | 2215.95 | 1119.46 (M$^+$ + Na$^+$)/2 |

TABLE 7-continued
Characterization of DMTr-rGACU-tag and intermediates
| Step | Compound 5'→3' | Mass cal. (m/z) | Mass found (m/z) |
|---|---|---|---|
| 5 | DMTr-rACU-tag (b) | 2231.95 | 1127.44 $(M^+ + Na^+)/2$ |
| 6 | HO-rACU-tag | 1929.82 | 1929.80 |
| 7 | DMTr-rGACU-tag (a) | 2645.06 | 1334.11 $(M^+ + Na^+)/2$ |
| 8 | DMTr-rGACU-tag (b) (91) | 2661.05 | 1341.94 $(M^+ + Na^+)/2$ |
Tag = light labile phosphonium tag.
(a) = phosphite triester;
(b) = phosphate triester.
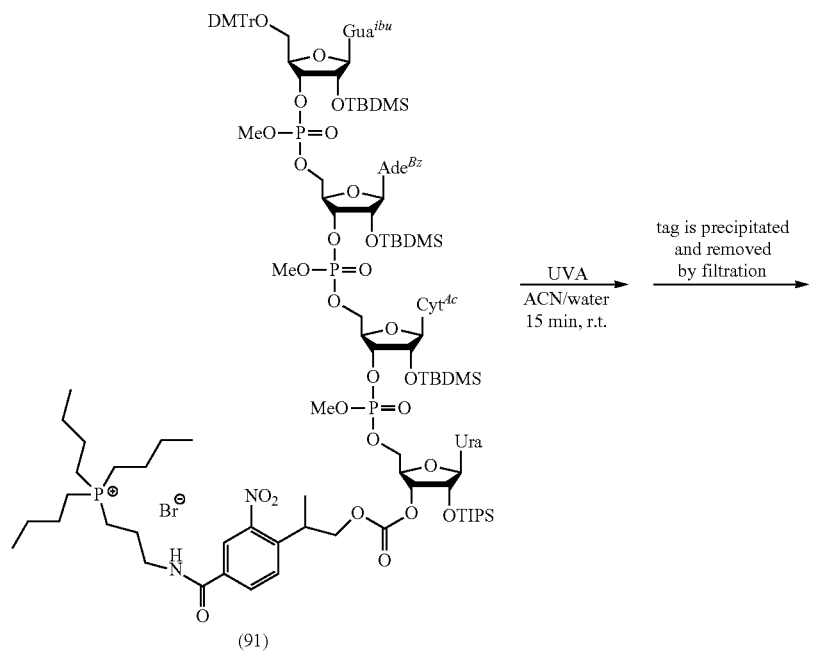
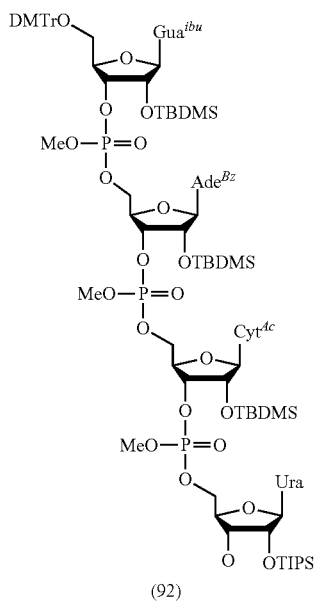

Photocleavage of Orthogonal Phosphonium Tag from Tetramer (91), Affording Protected DMTr-rGACU-3'OH (92)

Teramer (91) (0.120 g, 0.042 mmol) was dissolved in 1 mL of wet ACN (1200 ppm of H₂O), and transferred into a quartz cuvette (no frosted sides) containing a small stir bar. The cuvette was placed inside a photoreactor for 15 min with stirring. The reaction appeared complete (TLC analysis). The mixture was concentrated to about half volume and the cleaved tag precipitated in MTBE (25 mL) and filtered to afford a white powder. The desired tetramer was found in the MTBE solution, which was collected after concentrating the solution to dryness. Isolated yield: 0.092 g, 0.00403 mmol (95%).

FURTHER EXAMPLES

Syntheses of Ionic Tags, for Liquid Synthesis

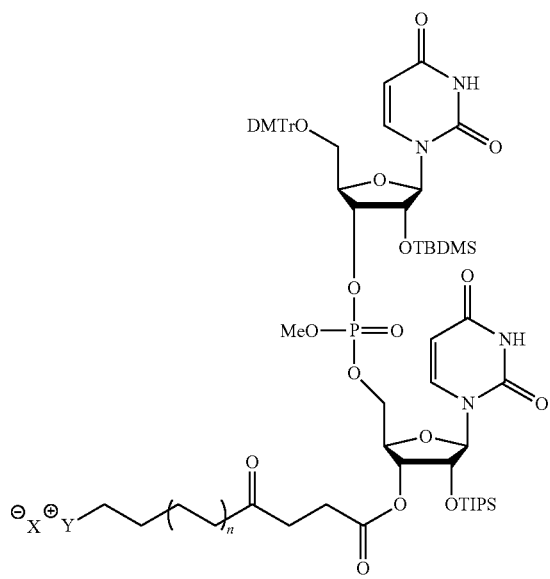

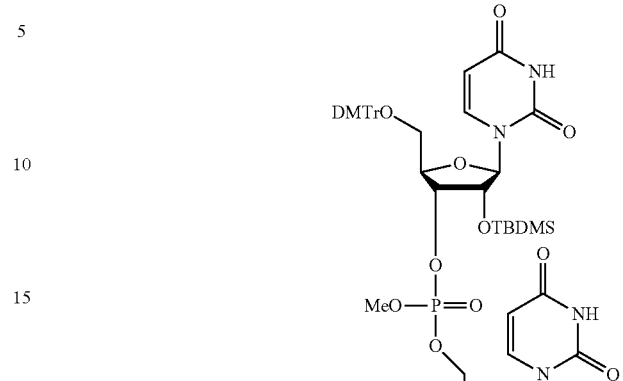

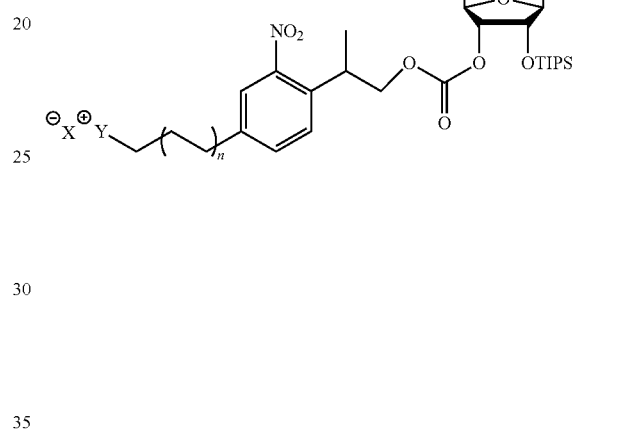

where:
Y is any cationic atom or organic molecule;
X is any anionic atom or organic molecule; and
n is any integer from 0 to 10.

Scheme 1

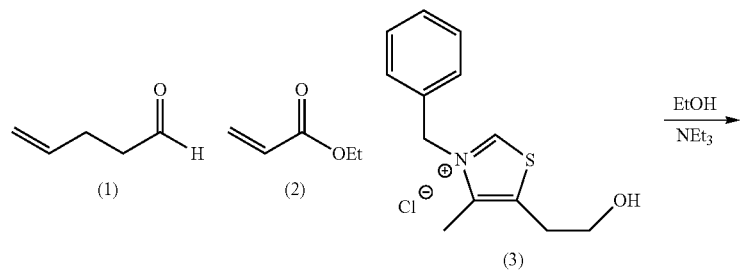

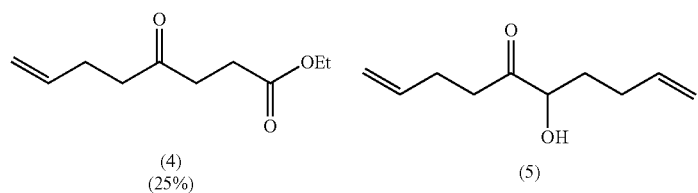

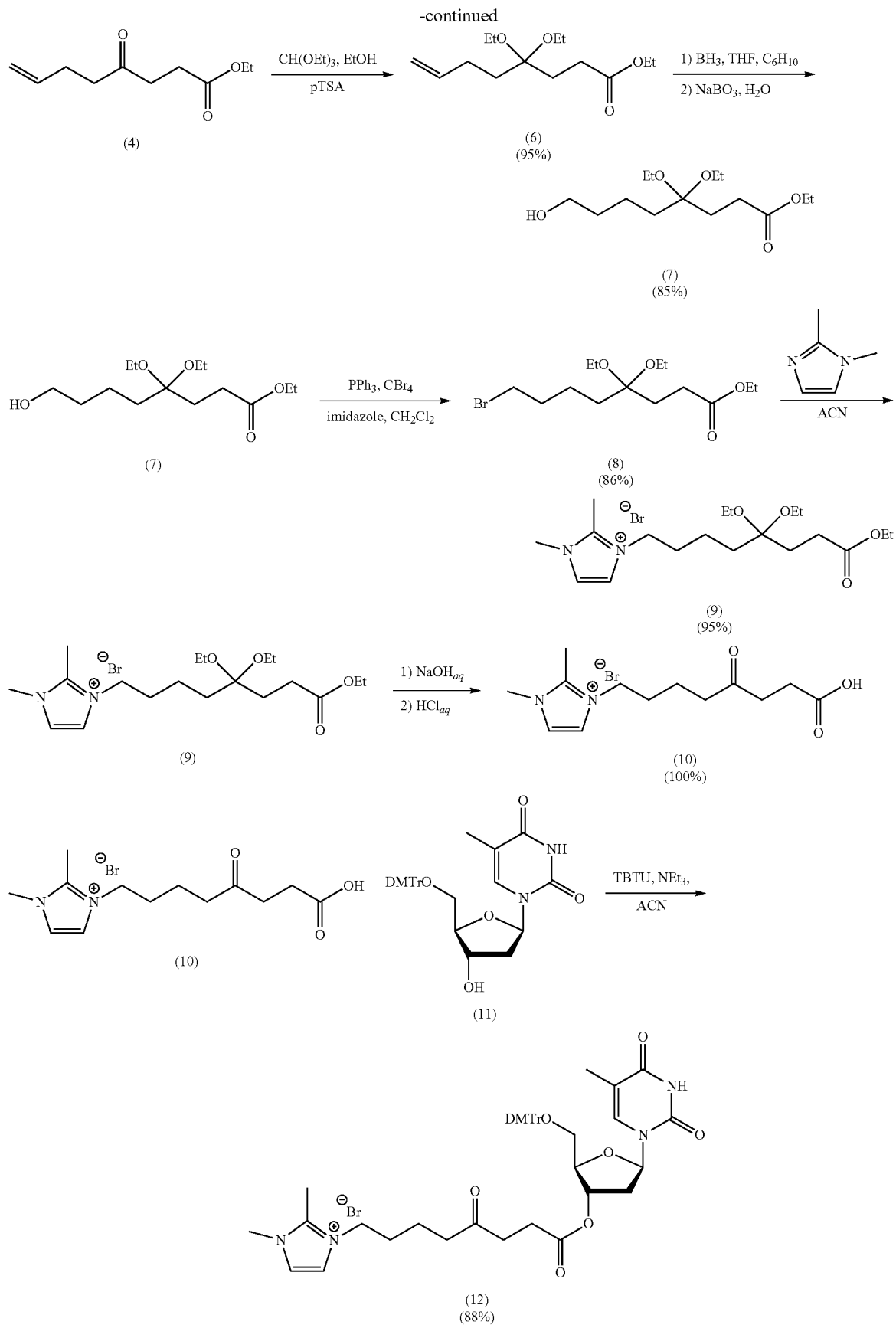

Several approaches can be applied to obtain the desired gamma-ketoacid (10). For example, Scheme 1 employs a Stetter reaction as the first step [(1)+(2)-(4)], a reaction that transforms aldehydes into nucleophiles using catalytic amounts of a thiazolium salt, e.g. (3), in the presence of a mild base (Stetter, H. *Angewandte Chemie, International Edition* in English 15: 639-47 (1976)). Thus 4-pentenal (1), an aldehyde attached to an aliphatic chain terminating in an alkene, was activated as a nucleophile and allowed to undergo a Michael addition using ethyl acrylate (2) as the electrophile. The substrates were mixed with thiazolium salt (3) and dissolved in ethanol. The reaction mixture was heated and once it was refluxing gently, the reaction was initiated by the addition of triethylamine. After 18 hours the solvent was removed and the material obtained was subjected to a dichloromethane/brine extraction followed by flash chromatography. The desired product, (4), co-eluted with an acyloin side-product, (5), in all the solvent systems investigated for the purification. The yield was approximately 25% (as estimated by 1H-NMR analysis of the mixture), however, enough material can readily be obtained to continue with the synthesis, with the impurity (5) becoming easily separable after the subsequent step. The next step in the synthetic route was to protect ketone (4) as an acetal [i.e., (6)]. Refluxing for 4 hours was found to be adequate for this reaction to reach completion and the desired product (6) was obtained at 90-95% yield. The product (6) was easily separable from the acyloin side-product (5) generated in the earlier step, which did not appear to undergo any transformation in the acetal formation reaction. The identity and purity of (6) were confirmed by TLC, LR-MS and NMR.

With the gamma-acetal-ester, (6), in hand, the next step (Scheme 22) was the hydroboration of the terminal alkene. This was achieved using an in situ generated dicyclohexyl borohydride reagent. An appropriate amount of cyclohexene was added to borane-THF at 0° C. and allowed to react for one hour, then (6) was added to the resultant slurry and the reaction was allowed to proceed for 2 hours at room temperature. The oxidation of the intermediate borane was achieved by the addition of aqueous sodium perborate, a mild oxidant that left the ester intact, and the reaction was continued for another 2 hours. The reaction mixture was then extracted with ethyl acetate and the product, (7), was purified by flash column chromatography, providing a colourless liquid at 80-85% yield, with 15-20% of (6) also being recovered. This reaction never proceeded further than 85% conversion, even with longer reaction times or an increase in the amount of the borohydride reagent generated relative to substrate.

The primary alcohol, (7), was then mixed with triphenylphosphine and tetrabromomethane in DCM in order to generate the terminal bromide (8). The reaction proceeded cleanly but upon aqueous workup, acetal cleavage occurred, likely due to the formation of hydrobromic acid from the hydrolysis of the excess reagents. The reaction was performed again in the presence of imidazole, which neutralized any hydrobromic acid generated, and the desired product, (8), was obtained at 79-86% yield after flash chromatography. Subsequent condensation with 1,2-dimethylimidazole in acetonitrile resulted in the ionic tag, (9), in 95% or greater yield.

The final steps in the synthesis (Scheme 1) involved the cleavage of the acetal and ester as well as anion metathesis of the ionic moiety and finally derivatization to a nucleoside. Initially aqueous acid was used to effect the deprotection, followed by anion metathesis, but the material thus derived decomposed rapidly. Subsequently the deprotection was performed via a two step process, the first a base mediated cleavage of the ester (9) followed by a limited acidification to protonate the carboxylic acid and cleave the acetal. The protected material, (9), was thus dissolved in aqueous sodium hydroxide and allowed to react for 16-18 hours followed by the addition of aqueous concentrated HCl to bring the solution to approximately pH 1 and finally drying under reduced pressure. The excess salt was removed by suspending the resulting solid in acetonitrile/dichloromethane and filtering off the insoluble material. The product obtained, (10), appeared pure by TLC, LR-MS and NMR but likely still contained a small amount of sodium chloride, which could not be detected with these techniques. Anion metathesis at this point also led to significant decomposition of the resulting product, as in the acid mediated deprotection. The bromide salt, (10), was stable upon long term storage, however, and was found to couple in the expected manner with a nucleoside. In fact, using O-(benzotriazol-1-yl)-N,N,N',N'-tetramethyluronium tetrafluoroborate (TBTU) as the coupling agent achieved both the coupling and anion exchange simultaneously, with the coupling proceeding quantitatively and the anion exchange confirmed by LR-MS as an absence of bromide ions and the presence of tetrafluoroborate in the negative mode. This product (12) was also stable upon long term storage.

With a derivatized nucleoside (12) in hand, the cleavage characteristics of the orthogonal gamma-ketoester ionic tag from the nucleoside were studied and compared to those of the levulinyl ester protecting group, which has been used as described above to generate oligomeric building blocks and is known to be easily removed without affecting any other protecting groups in the molecule. The rate of levulinyl ester cleavage under the conditions studied was faster than that of the ionic tag, with half lives of approximately 0.76 and 2.82 minutes respectively, corresponding to complete cleavage of the levulinyl ester in just over 5 minutes while the tag required almost 20 minutes for full cleavage. However, even though the tag cleaved more slowly than the levulinyl ester under the conditions studied, the normal reaction time employed for the cleavage of the 3'-hydroxyl protected levulinyl ester by hydrazine was 20 minutes and no degradation was observed in any of the other protecting groups in that time. This indicated that the ionic tag is suitable to the required task, and it is therefore a viable route to generating oligomeric building blocks as well.

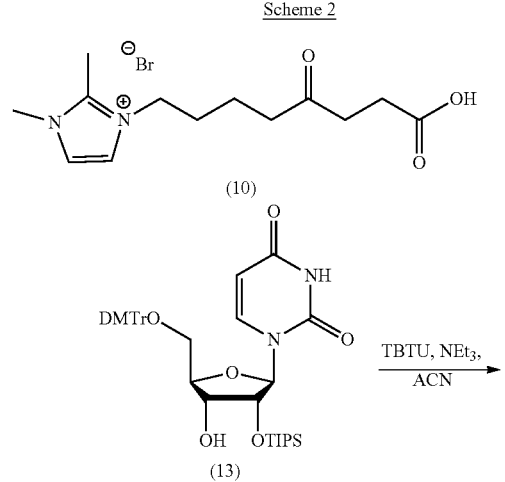

Scheme 2

-continued

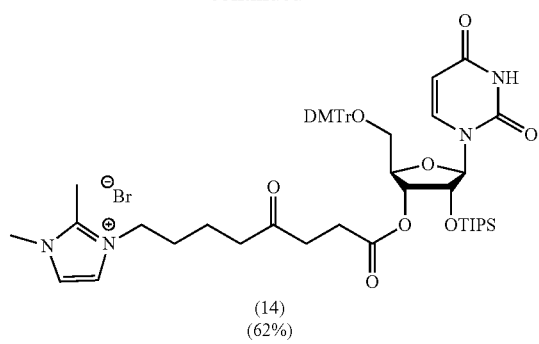

(14)
(62%)

The tag was also condensed with a 5'-O-DMTr-2'-O-TIPS Uridine nucleoside (13) (Scheme 2) using the same conditions employed for the derivatization of 5'-O-DMTr-Thymidine. The $^1$H-NMR of the coupled ribonucleoside did not appear to show any 2'-3' silyl isomerisation.

To install an alternative ionic tag in place of the imidazolium tag outlined in scheme 1, the alkyl bromide (8) was simply treated with 1.5 eq of tributyl phosphine at 65° C. for 6 h producing the phosphonium tagged compound (15) quantitatively, which was isolated by precipitation in methyl tert-butyl ether. Unfortunately, the same procedure of simultaneous ketal and ester hydrolysis, used in scheme 1, led to the undesired cyclic hemi-lactone (16), and if only the ester was removed and purified, compound (17) was isolated. In either case attempts of conjugation to a nucleoside (13) as described in scheme 2, using both TBTU and DCC proved to be difficult, yielding only 5-10% the desired nucleoside conjugate.

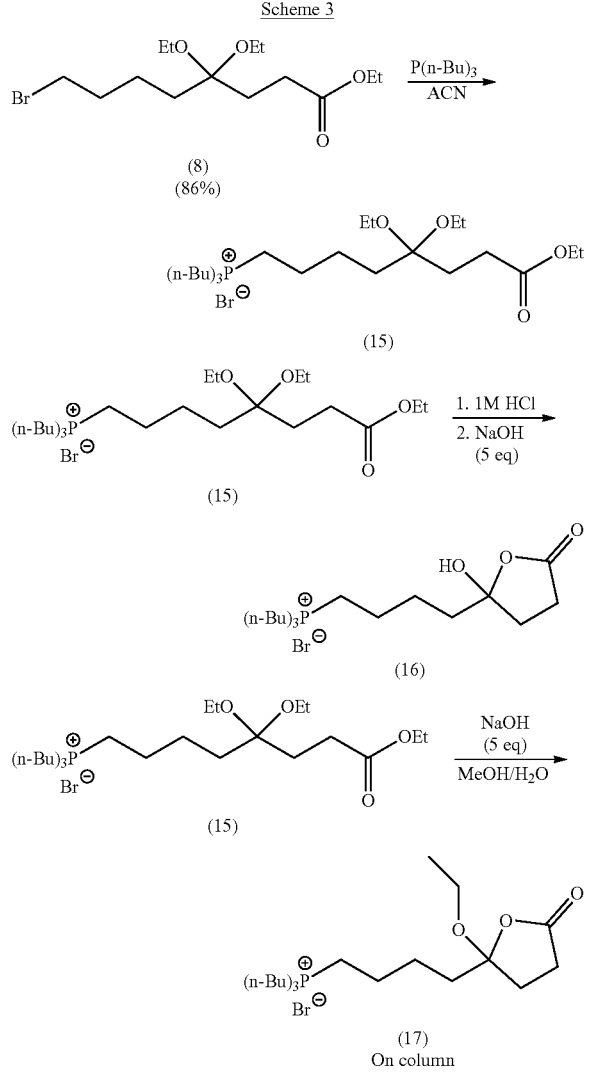

Scheme 3

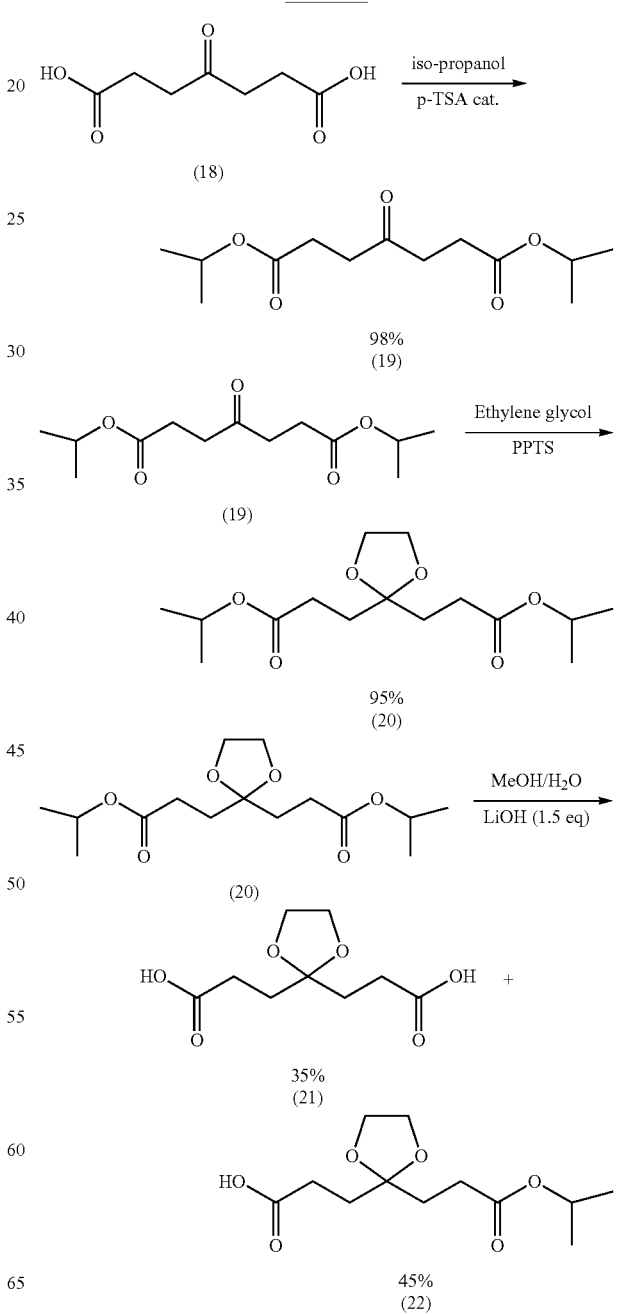

Scheme 23

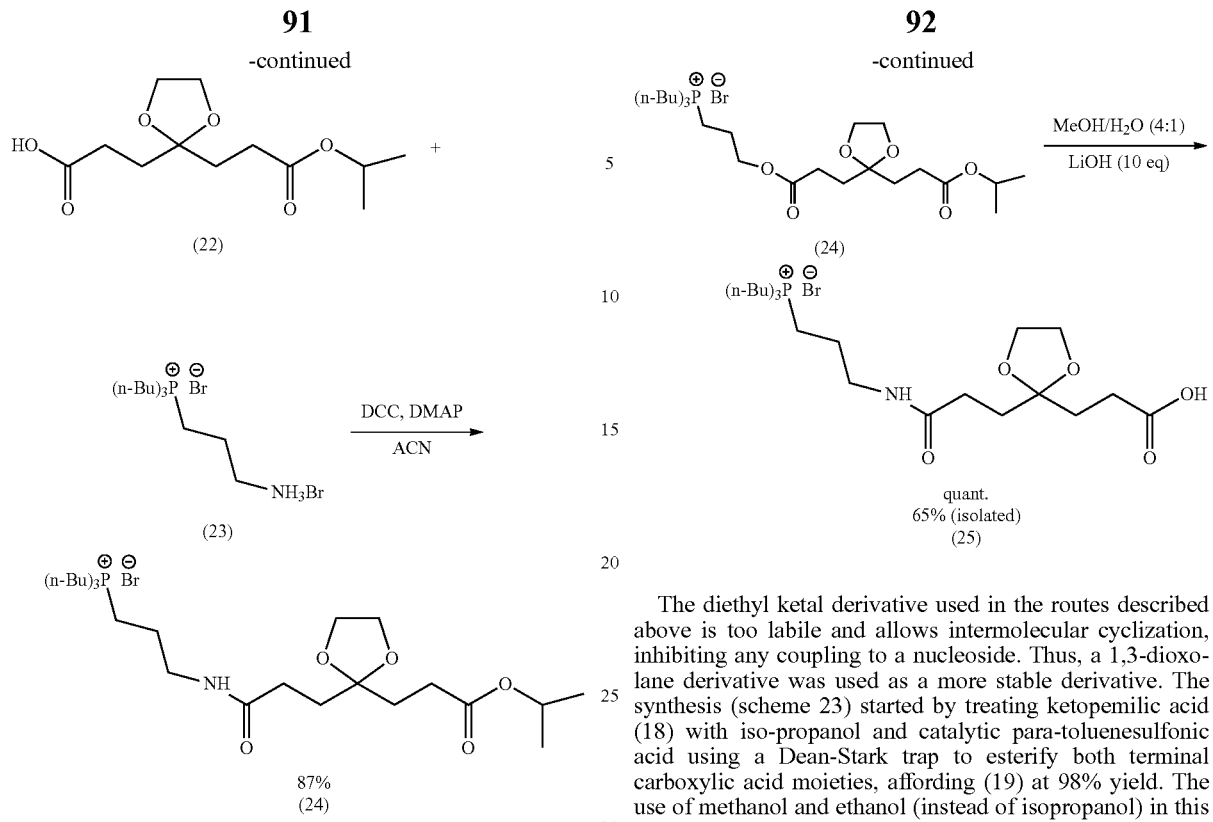

The diethyl ketal derivative used in the routes described above is too labile and allows intermolecular cyclization, inhibiting any coupling to a nucleoside. Thus, a 1,3-dioxolane derivative was used as a more stable derivative. The synthesis (scheme 23) started by treating ketopemilic acid (18) with iso-propanol and catalytic para-toluenesulfonic acid using a Dean-Stark trap to esterify both terminal carboxylic acid moieties, affording (19) at 98% yield. The use of methanol and ethanol (instead of isopropanol) in this reaction resulted in lactone formation as the major product, instead of the desired diester (19).

Scheme 4
Esterification pathway (19) depends on the bulkiness of the alcohol's alkyl group.

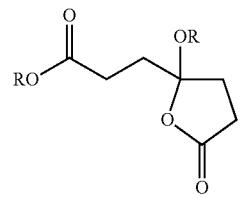

lactone
R = Me, Et

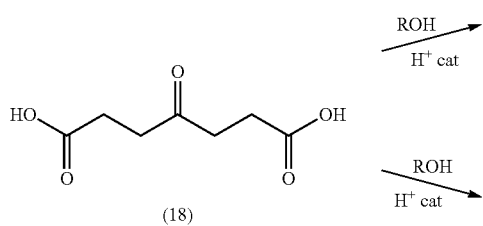

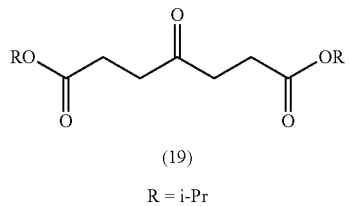

(19)

R = i-Pr

The diisopropyl ester (19) was isolated and then reacted with ethylene glycol and catalytic pyridinium para-toluenesulfonate by refluxing in a Dean-Stark trap overnight to form the cyclic ketal (20) in 65% yield over two steps. Attempts to use ethylene glycol directly to form both the cyclic ketal and glycol ester resulted in the undesired lactone derivative (Scheme 3), necessitating that esterification and acetal formation be carried out in two separate steps.

Cyclic ketal diester (20) was taken up in methanol and 4 equivalents of aqueous lithium hydroxide was added to the reaction to preferentially hydrolyze one ester over both, producing a mixture of compounds (21) and (22), which were separated in yields of 35% and 45%, respectively. Coupling the phosphonium ionic tag (23) to the cyclic ketal monoester (22) was accomplished using DCC and DMAP in a pyridine/acetonitrile mixture (50:50) at room temperature for 6 h affording the phosphonium tagged compound (24) in 84% yield. After isolation, the isopropyl ester was hydrolyzed by LiOH in MeOH/Water to afford compound (25) in nearly quantitative yield. After column chromatography (MeOH/DCM 0→10% in 1% AcOH) the yield was reduced to 65%, likely due to the phosphonium tag's affinity to the silica.

Scheme 5

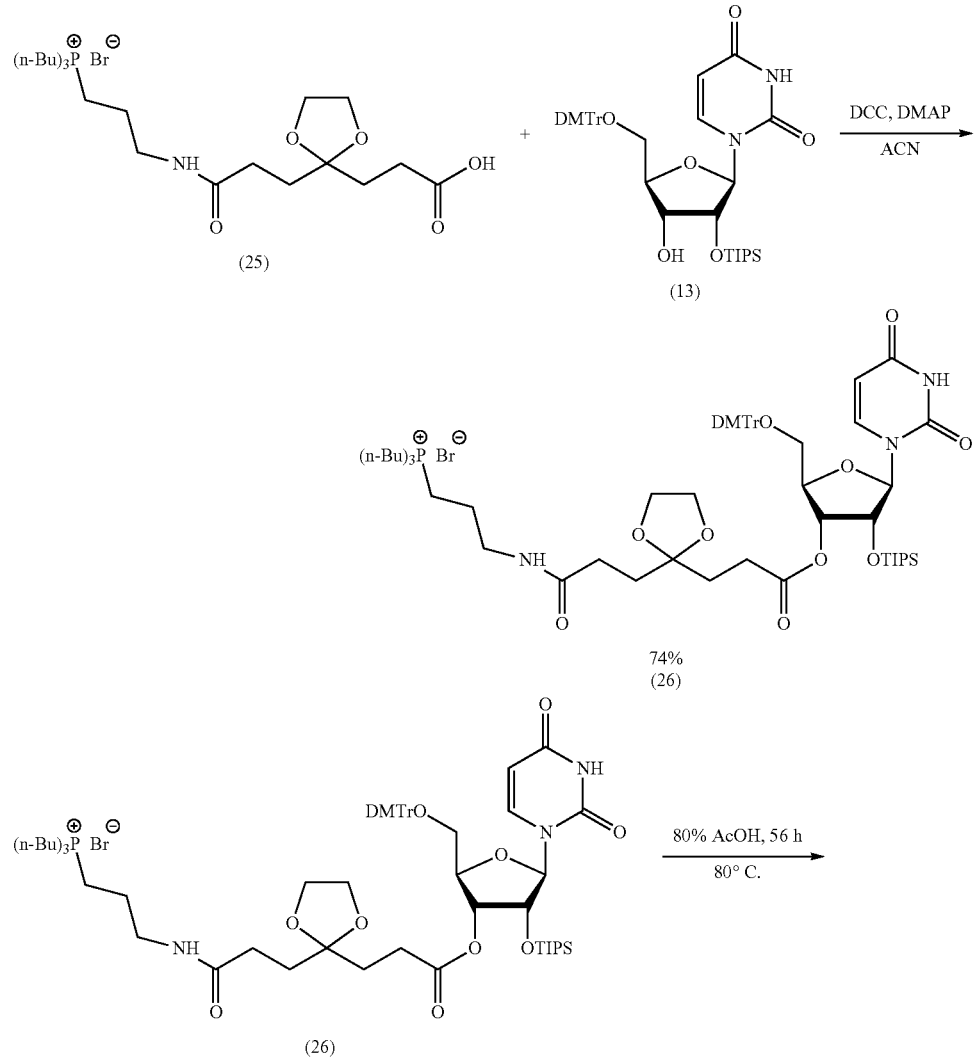

-continued

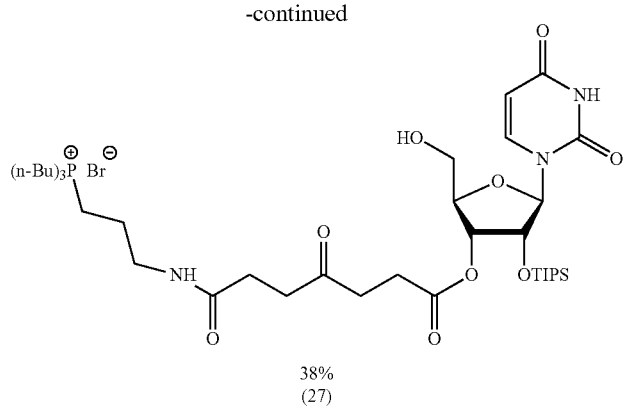

38%
(27)

The ionically tagged species (25) and NaBr were taken up in methanol to exchange any acetate ion that had exchanged previously during silica gel purification. If this step were skipped, a significant amount of acytelated nucleoside formed upon reaction with compound (13). The ionic tag (25) was then conjugated to the 3'-hydroxy of ribonucleoside (13) using standard coupling conditions with DCC and DMAP to afford compound (26) in 4 h in a moderate yield of 74%.

Removal of the cyclic ketal was achieved by treatment with either 80% AcOH in water or 5 eq of Pyridiniumn p-tolunesulfonate in 50:50 acetone:water at 80° C. over 4 days. The majority of the ketal was removed over this time; unfortunately, there was significant removal of the TIPS group under these conditions as well. The reaction mixture was neutralized with saturated sodium bicarbonate and extracted with a brine bicarbonate mixture then columned to yield 38% of the detritylated compound (27).

To overcome some of the limitations described above, a thioketal was used over the traditional cyclic dioxalane approach as shown in Scheme 6. Thiophenol and compound (19) were treated with boron trifluoride eitehrate to afford compound (28) in 92% yield. Next, mono hydrolysis of compound was achieved by treatment of (28) in MeOH/water (4:1) and with 0.2 eq of NaOH at 0° C. drop wise over 30 min. The reaction was allowed to stir at zero for 30 min then the ice bath was removed and the solution was allowed to warm up to room temperature. The reaction mixture was condensed to remove the methanol and a portion of the water. To the solution was added ethyl acetate and 1M HCl to isolate a significant amount of starting material and the desired product, compound (30) in 85% yield (in reference to the NaOH added). The ability to perform HCl workups in this synthetic route was a significant improvement over using the acyclic and cyclic ketals previously, as the thioketals are much more tolerant to acidic conditions. The phosphonium ionic tag was then conjugated to compound (30) under standard coupling conditions of DCC, DMAP in pyridine:acetonitrile (50:50) to afford compound (31) in good yield, 87%. Next, the ester of compound (31) was hydrolyzed with 5 eq of NaOH in methanol/water to afford compound (32) in near quantitative yield after an HCl extraction in ethyl acetate.

Scheme 6

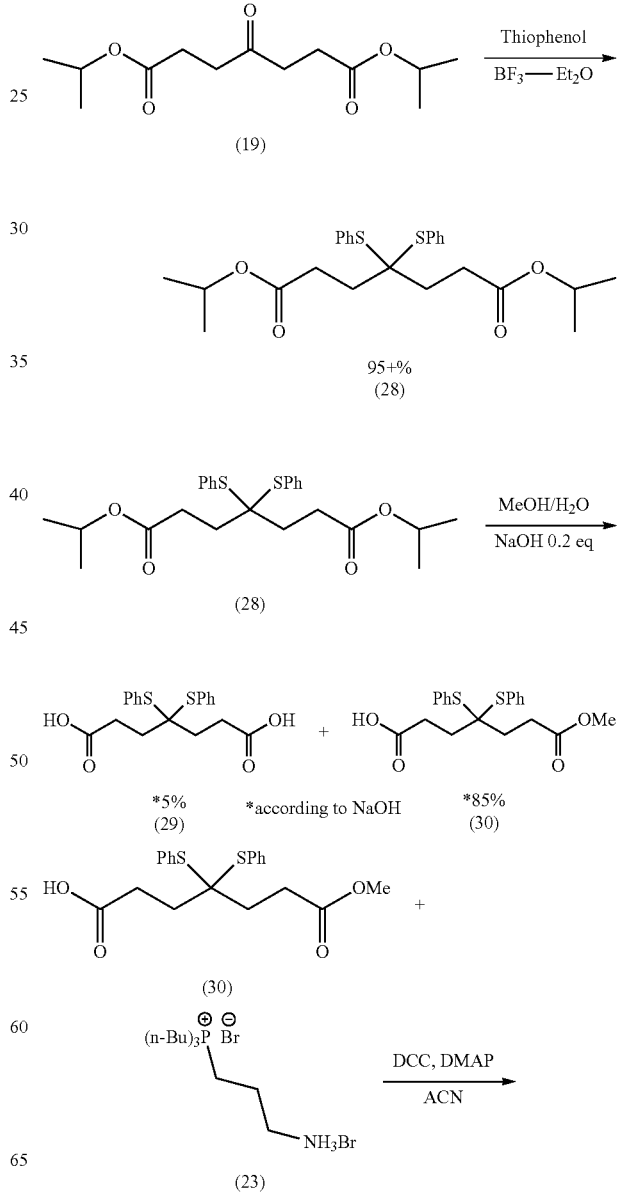

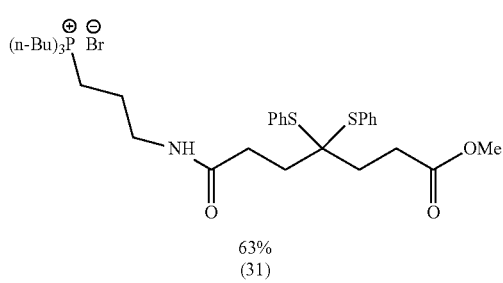

63%
(31)

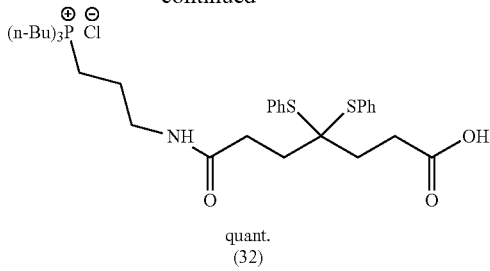

quant.
(32)

*in reference to NaOH

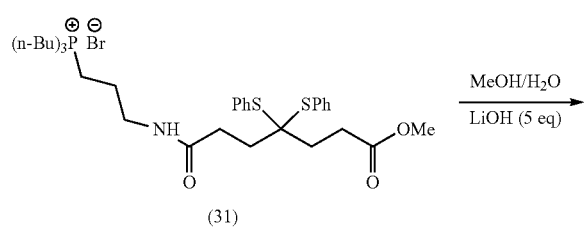

With compound (32) in hand the nucleoside conjugation was achieved, again with the use of DCC and DMAP to afford the nucleoside conjugate (34) in moderate yield. Unfortunately, there was significant byproduct formed (33) which could not be completely separated by silica gel column chromatography. Attempts to reduce the formation of this by the addition of more DMAP, and the use of other coupling reagents, such as TBTU, HATU and CMPI, proved unsuccessful. Conversion of the carboxyl to the acid chloride may be a useful alternative.

Scheme 7

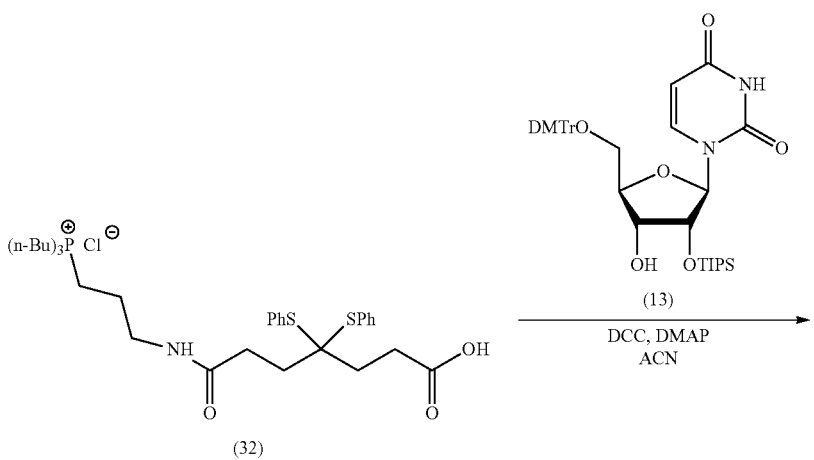

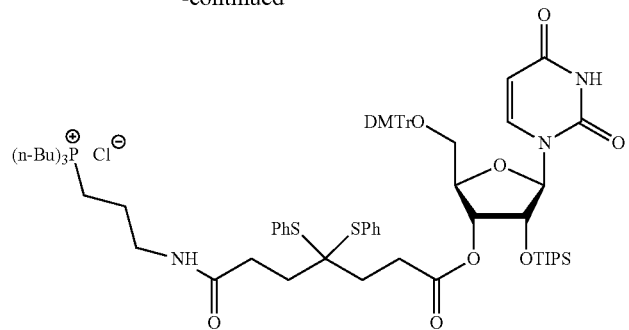
89%
(34)
+
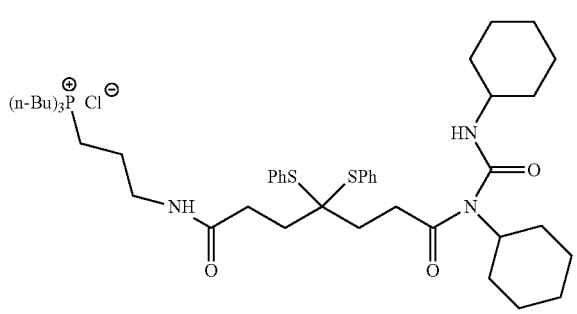
~8%
(33)
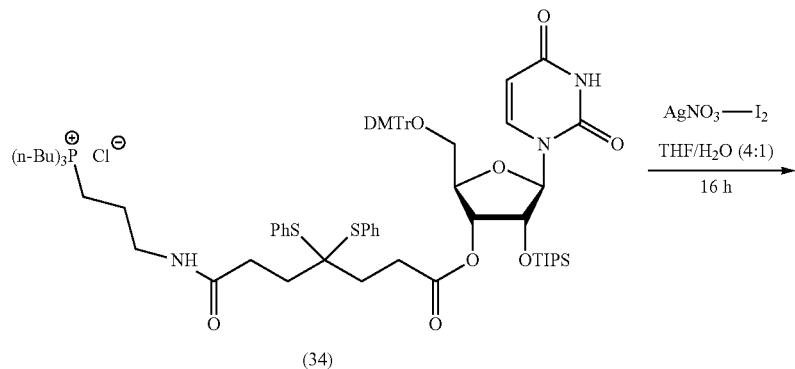
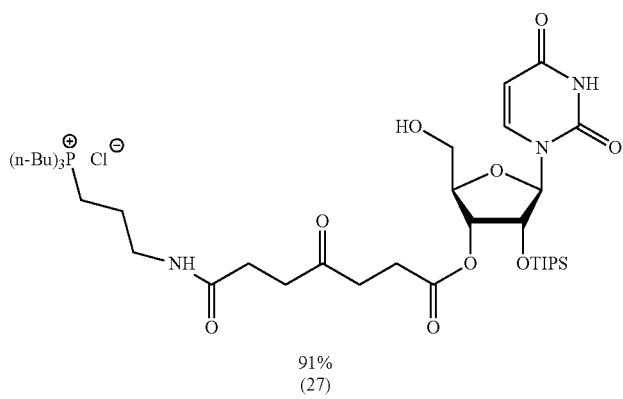
91%
(27)

The thioketal was then removed by treatment of compound (34) with silver nitrate and molecular iodine in 80% THF/water resulting in a mixture of tritylated and detritylated material. When the same reaction was attempted in the presence of sodium bicarbonate, a very different product was observed. In this case, the C-5 thiophenyl derivative (35) was formed in moderate yields via electrophilic addition of iodine to C-5 followed by substitution by thiophenol. In another deprotection strategy, NBS was used as a source of bromonium ion to cleave the thioketal. Instead, however, bromination of the C-5 position occurred to produce (36) as the major product. The use of collidine in place of sodium bicarbonate in the silver nitrate/iodine method reduced the formation of the C-5 thiophenyl derivative to almost nothing. Another effective approach that minimized modification at C-5 involved diluting the solution of (34) while increasing the amount of silver nitrate and iodine used. The absence of any base produced a mixture of tritylated and detritylated material, which underwent complete detritylation to afford (27) (Scheme 7).

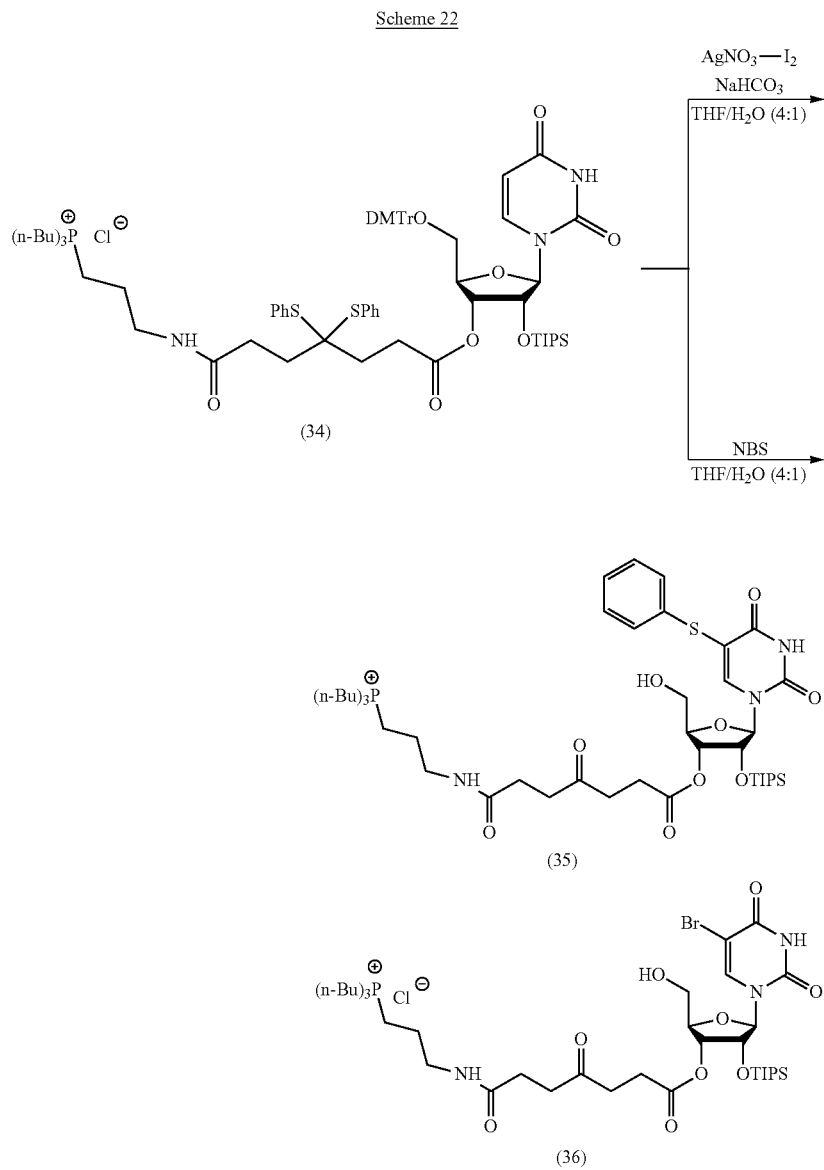

Scheme 22

The material from collidine treated silver nitrate-iodine hydrolysis of the thioacetal, compound (37) Scheme 24, was taken and treated with 3% TFA in DCM with 2.5 eq of triethylsilane to quench the trityl cation for 10 min, then 20 mL of toluene was added followed by concentration on rotovap. The sample was then taken up in acetone and precipitated from methyl tert-butyl ether (MTBE) producing an undesired compound (38) in 95% yield. This was likely due to the dehydrating conditions created by condensing the TFA and toluene together. The experiment was repeated without the toluene concentration, but rather a direct precipitation into MTBE. Similar results were obtained, 60% of compound (38), the rest being the desired product (27).

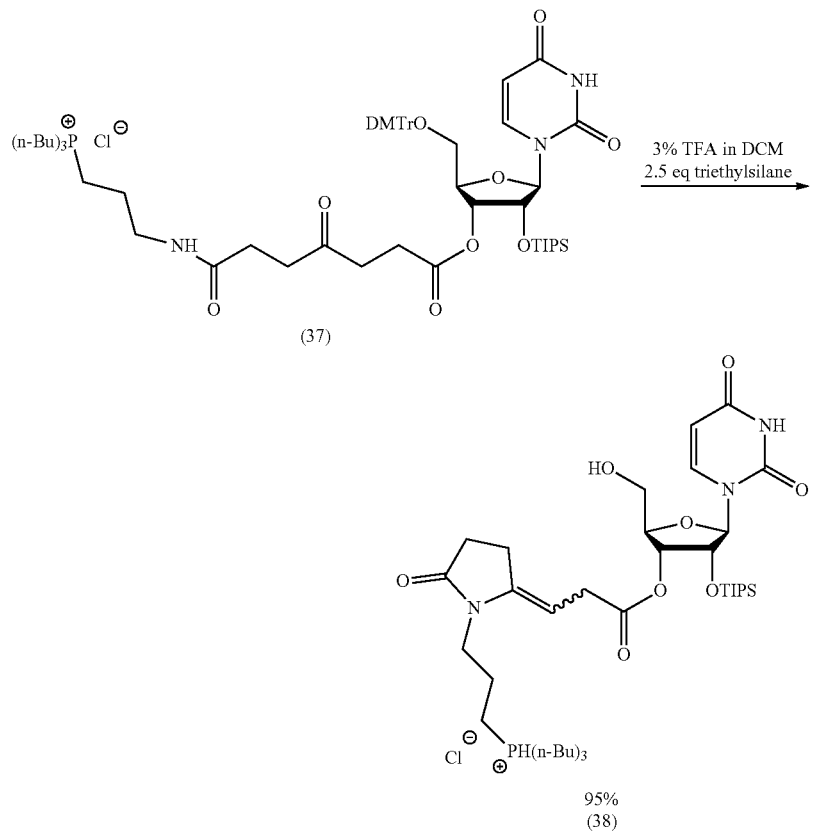

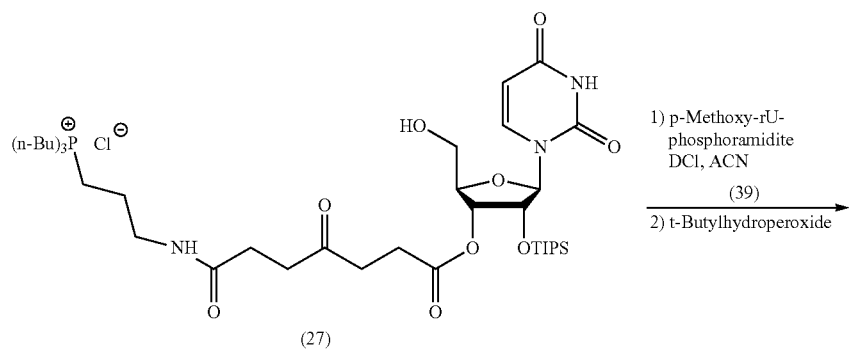

-continued
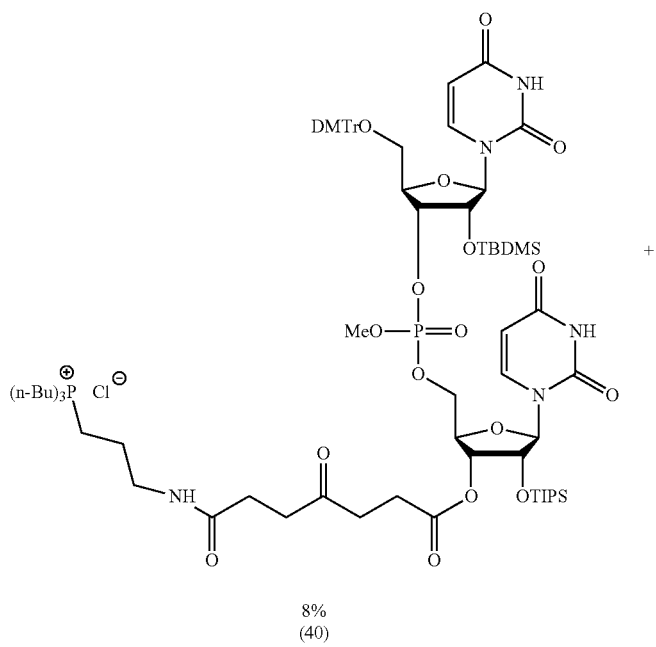
8%
(40)
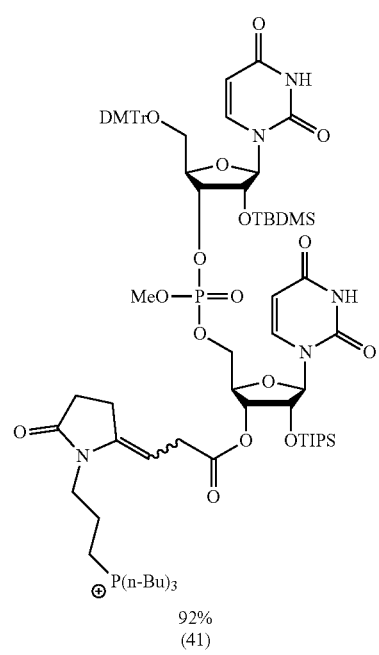
92%
(41)

Compound (27) derived from the hydrolysis of the thioketal in the absence of base, which also removed the trityl protecting group, was coupled with p-methoxy-rU-phosphoramidite (39), followed by oxidation to produce mainly the undesired dimer nucleotide (41), Scheme 25. The reaction was monitored by MS, and clearly throughout the reaction the formation of the undesired compound (41) was seen to increase over time. To further identify the reasons for the formation of the enamino ester seen in both compounds (38) and (41), compound (27) was treated with DCI in anhydrous ACN and monitored by MS over time. It was clear after 2 h that the acidity of DCI was enough to promote the formation of the undesired cyclic enamino product (38).

Scheme 26

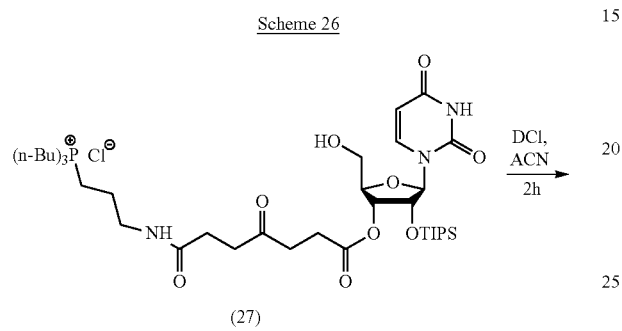

(27)

-continued

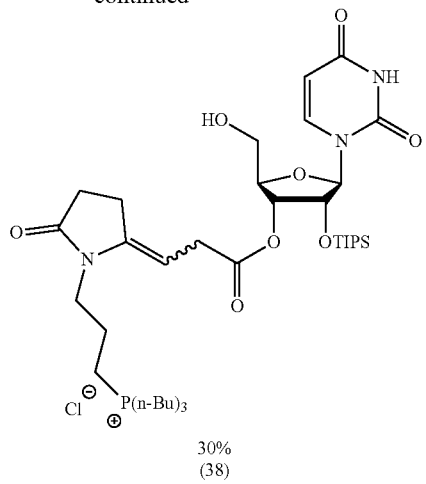

30%
(38)

The inseparable mixture of compound (40) and (41) in Scheme 25 was treated with 0.5M hydrazine hydrate buffered in pyridine acetic acid (3:2) releasing 8% of the desired UpU dimer (47) isomerically pure.

Scheme 27

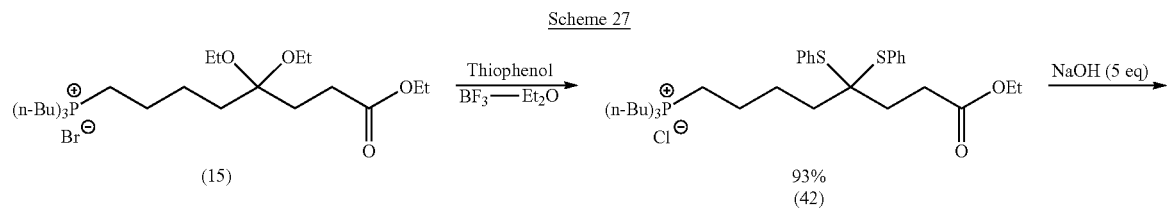

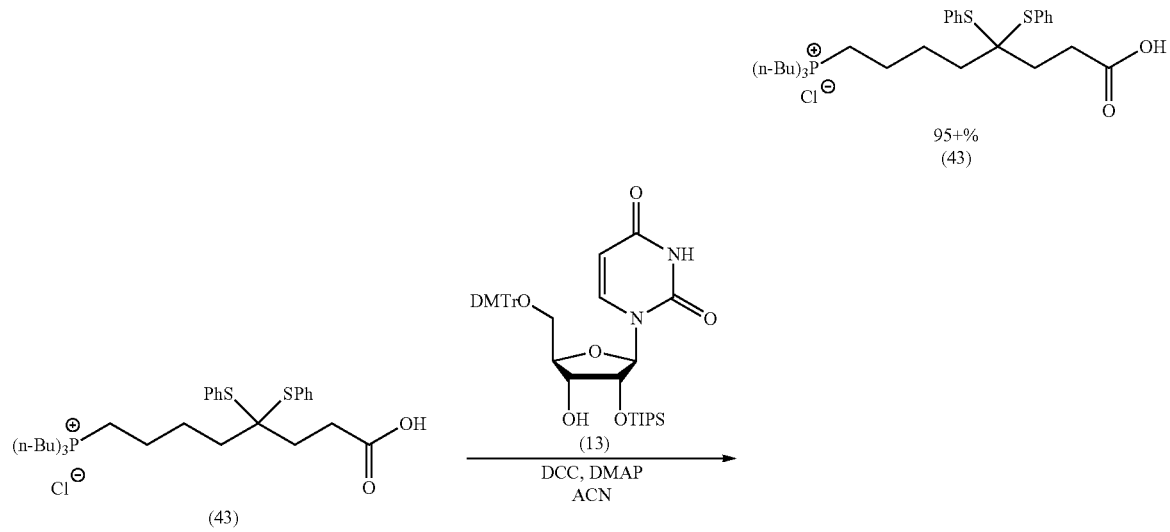

-continued
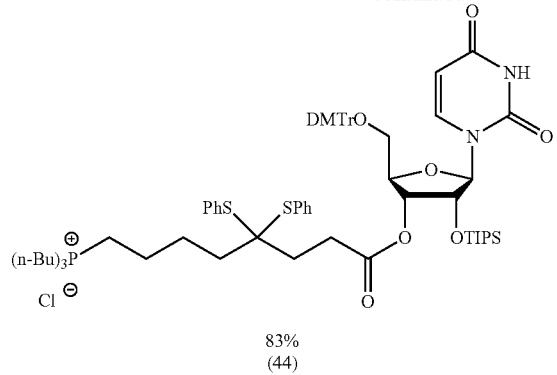
83%
(44)
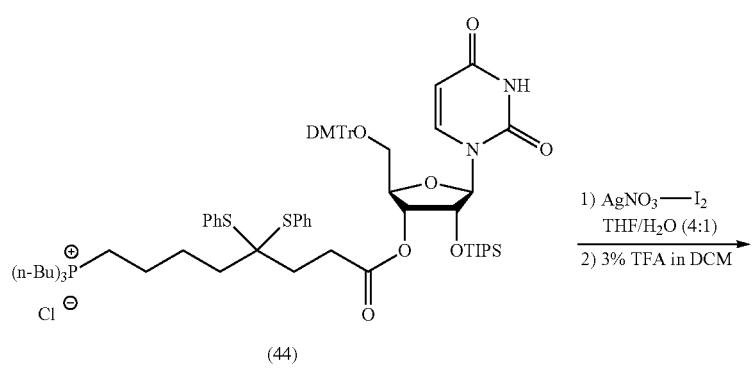
1) AgNO₃—I₂
  THF/H₂O (4:1)
2) 3% TFA in DCM
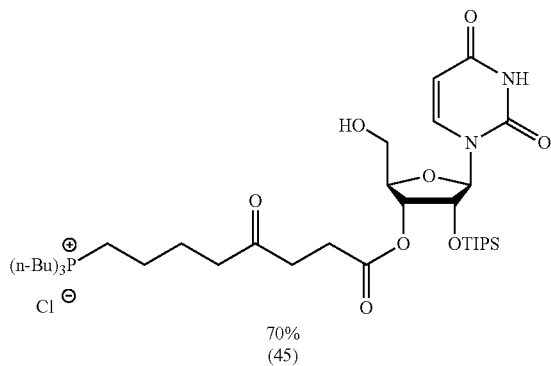
70%
(45)
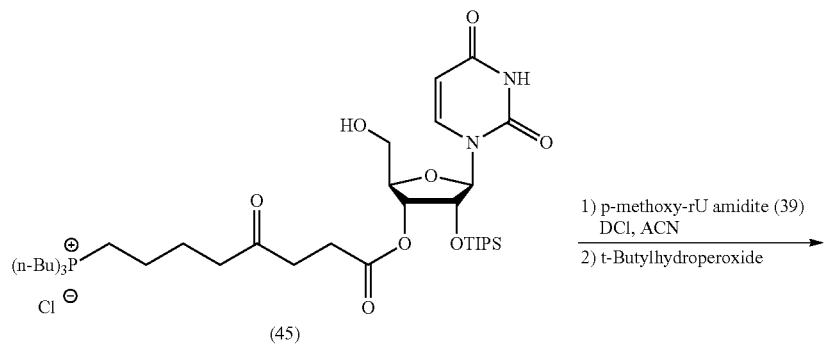
1) p-methoxy-rU amidite (39)
  DCl, ACN
2) t-Butylhydroperoxide

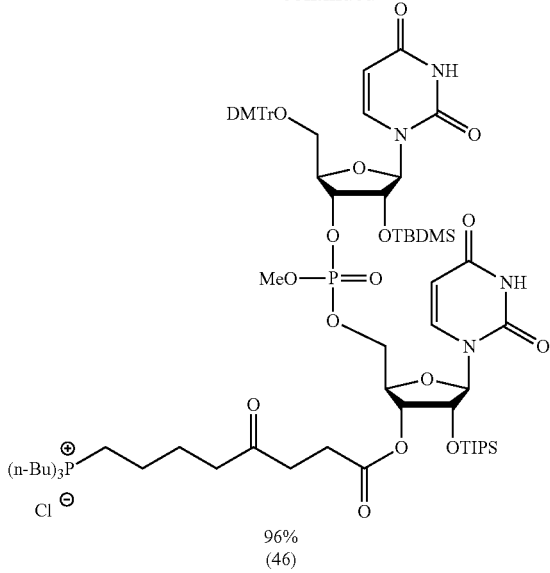

96%
(46)

With the knowledge that acyclic and cyclic acetals are a poor choice for a ketone protecting group on nucleoside conjugates and that keto-gamma amides are not compatible with standard phosphoramidite couplings, an alternative synthetic route, scheme 27, was attempted. Compound (15) originally from scheme 3 was taken and the ketal was replaced with the thioketal by treatment with thiophenol and boron trifluoride etherate, producing compound (42) in good yields, 94%. The ester was hydrolysed easily and quantitatively by sodium hydroxide, and compound (43) isolated by 1M HCl extraction. Unlike with previous attempts, the ketal remained in place and no cyclisation was observed. Coupling to the nucleoside (13) was achieved as previously described in scheme 7, accompanied with the same issue of significant DCC failure product. Despite this small limitation, the synthetic route was continued without optimisation. The thioacetal was removed by silver nitrate/iodine in 80% THF-water followed by detritylation to yield compound (45) in good yield. Phosphoramidite (39) was coupled to the free 5'-hydroxyl of (45) for 4 h and after the reaction was complete, as monitored by MS, the sample was treated with tert-butanol to couple any excess phosphoramidite and precipitated in MTBE. The sample was then solvated in DCM then oxidised to yield compound 46 in 96% yield.

An alternative method for producing ionically tagged monomers is shown below in Scheme 27B.

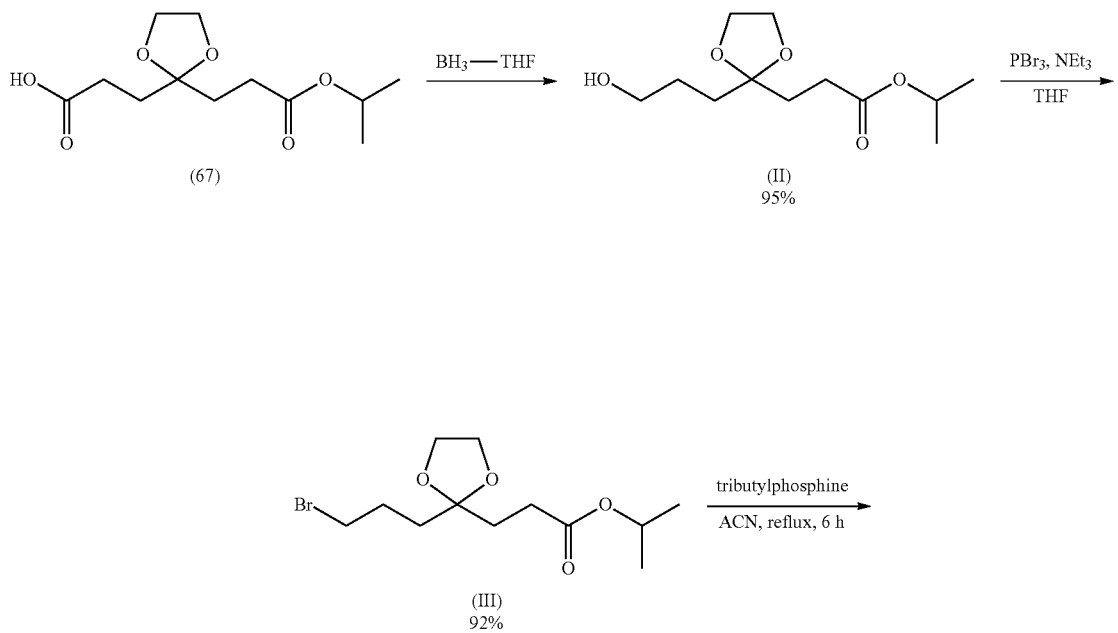

-continued
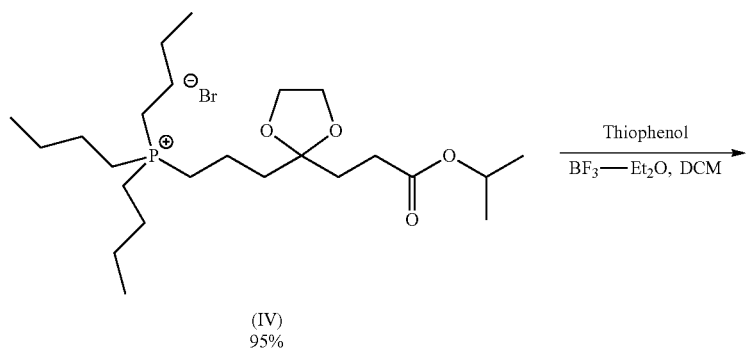
(IV)
95%
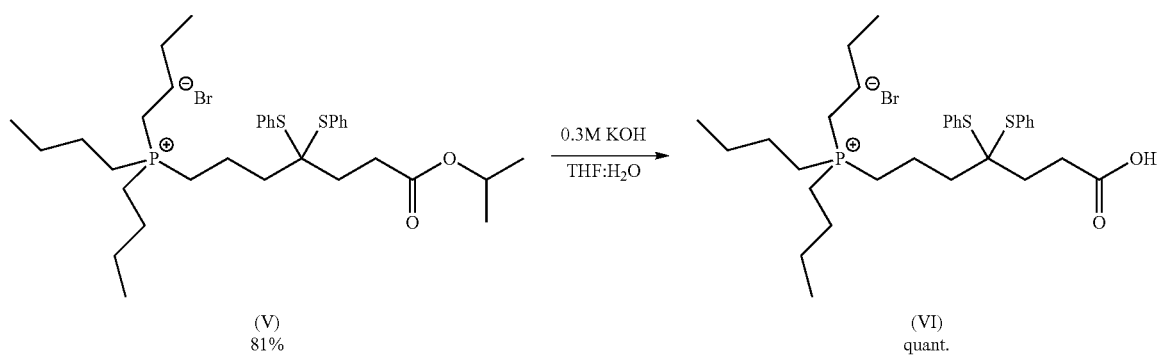
(V)
81%
(VI)
quant.
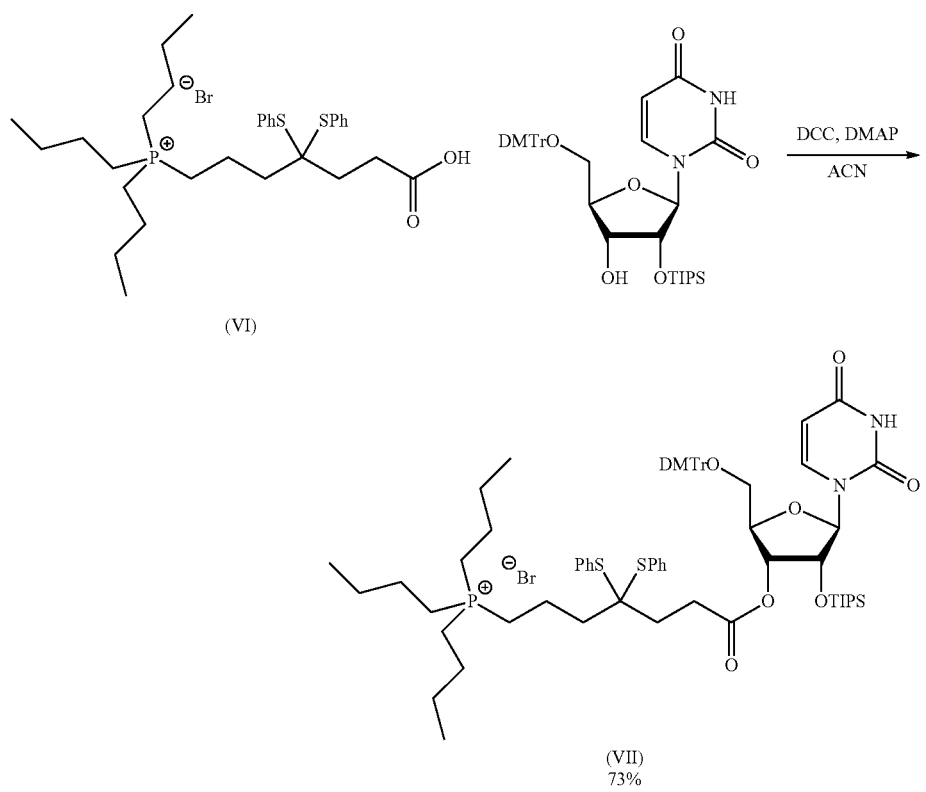
(VII)
73%

-continued

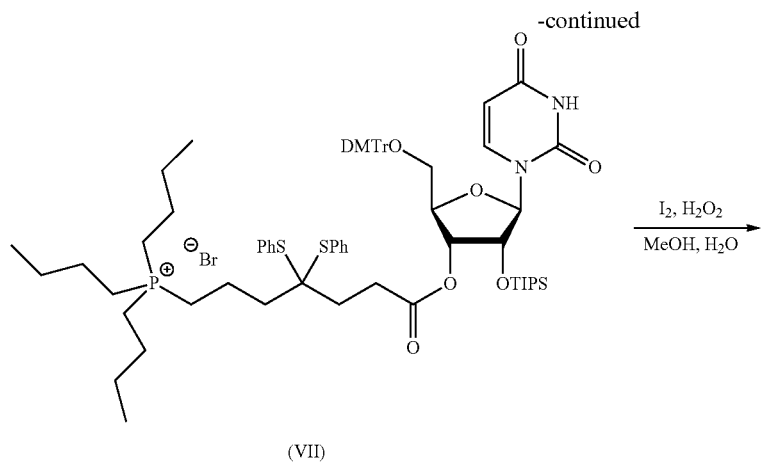

(VII)

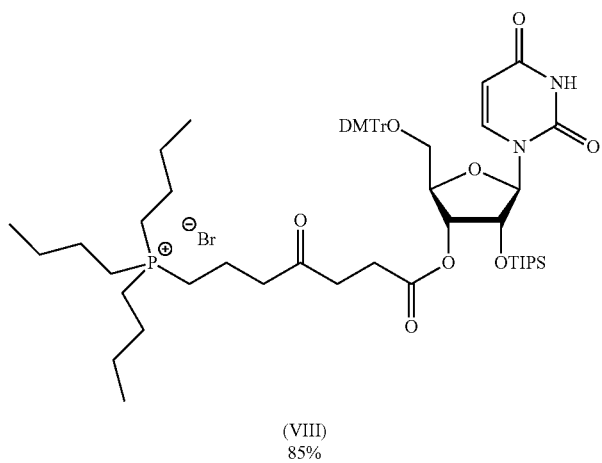

(VIII)
85%

Compound (67) was dissolved in dry THF and cooled to 0° C. in an ice bath with stirring. To this solution the borane-THF was added drop wise over 15 min at which point the ice bath was removed and the solution was stirred at room temperature over 2 h until the reaction was complete. The mixture was once again cooled to 0° C. and methanol was added to quench. The mixture was then concentrated to dryness and treated once more with methanol to ensure removal of all trimethyl borate. This mixture was purified by a column chromatography yielding 95+% of the desired primary hydroxyl ketal ester (II). Compound (II) was then dissolved in dry DCM and triethylamine, cooled to 0° C. and phosphorus tribromide was added drop wise over 10 min and allowed to stir for 1 h until the reaction was complete as determined by TLC. The mixture was diluted with ethyl acetate and extracted twice with saturated sodium bicarbonate and once with brine, followed by purification by column chromatography affording the alkyl bromide in good yield of 92%. Compound (III) was dissolved with minimal amounts of acetonitrile to which tributylphosphine was added drop wise over 10 min. This exothermic reaction was then refluxed for 6 h, concentrated, diluted with minimal acetone and triturated into vigorously stirring hexanes. The hexanes layer was passed through a Celite® filter and discarded; the remaining goo on the filter and in the flask was pure phosphonium tagged compound (IV) in quantitative yield. Next, the ketal was replaced with the more stable and more easily removed thioketal by treatment with thiophenol and borane trifluoride etherate in the presence of molecular sieves for 6 h at room temperature. This resulted in compound (V) after purification by column chromatography in 81% yield. Ester hydrolysis was performed with a 0.2M potassium hydroxide solution in a 50:50 water THF mixture. This reaction was quenched by the addition of 1M HCl and sodium chloride and extracted with ethyl acetate. The organic layer was then washed three times with brine to remove any excess HCl, dried and concentrated providing the pure acid, compound (VI). The nucleoside (13) was coupled to compound (VI) using standard DCC conditions affording the 3' tag-linker nucleoside (VII) in moderate yield of 73%. Lastly the thioketal was removed under very mild conditions by treatment with 20 mol % of molecular iodine and in a solution of methanol, water and hydrogen peroxide. This mixture was easily purified by quenching with a 10% solution of sodium thiosulfite, extraction with ethyl acetate and a short silica column, providing the deprotected monomer (VIII) in good yield of 85%.

Scheme 28

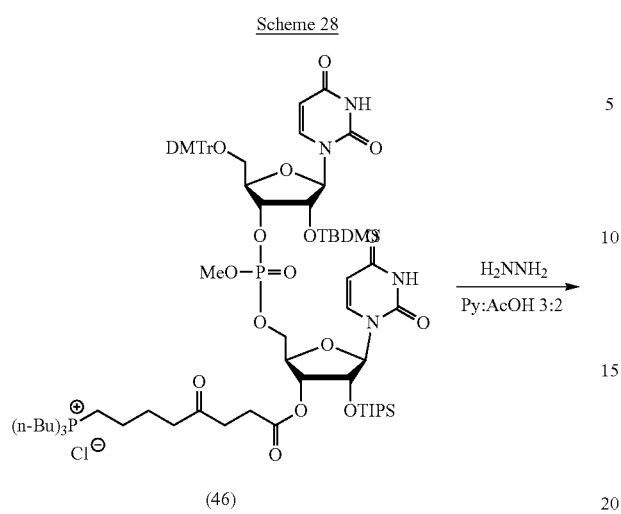

(46)

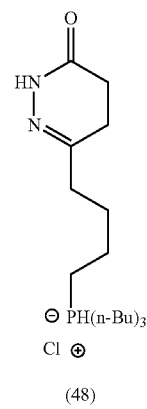

(48)

Lastly, the dimer nucleotide with the 3'-tag linker (46) was treated with hydrazine hydrate (0.5M in pyridine: acetic acid 3:2) producing the dimer nucleotide in near quantitative yield, and the expected linker cleavage product, observed by MS. The dimer nucleotide was isomerically pure as confirmed by phosphorus NMR.

An alternative to the orthogonal levulinyl linker described above is a light cleavable linker which can be removed in the presence of all standard ribonucleotide protecting groups. This allows for the use of extremely mild conditions to expose the 3'-hydroxyl group at anytime during the synthesis of blockers. In combination with the 2'-TIPS protecting group there is no risk of silyl migration, allowing for the production of regioisomerically pure blockmers which can be readily converted into phosphoramidies. The synthesis of the NPPOC like derivative (55) begins with a few short and elegant steps reported by Pfleiderer [Pfleiderer, W. et al. *Helvetica Chemimica Acta*, 87: 620 (2004)].

Scheme 29
Synthesis of photolabile ionic tag (55)

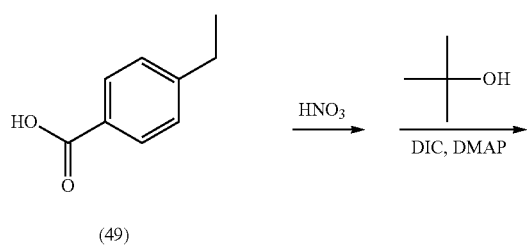

(49)

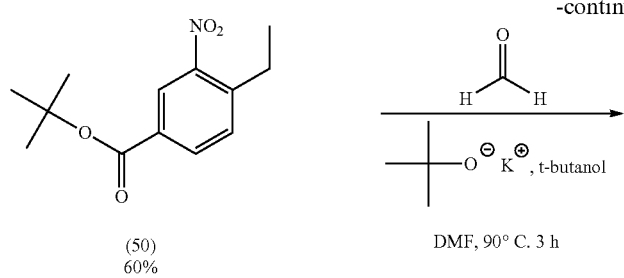

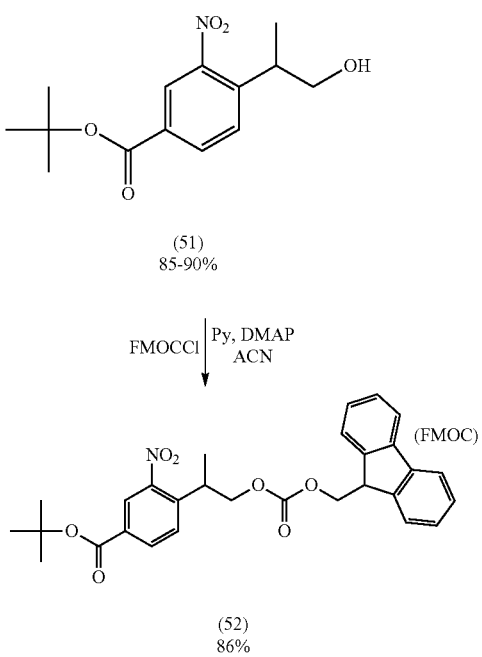

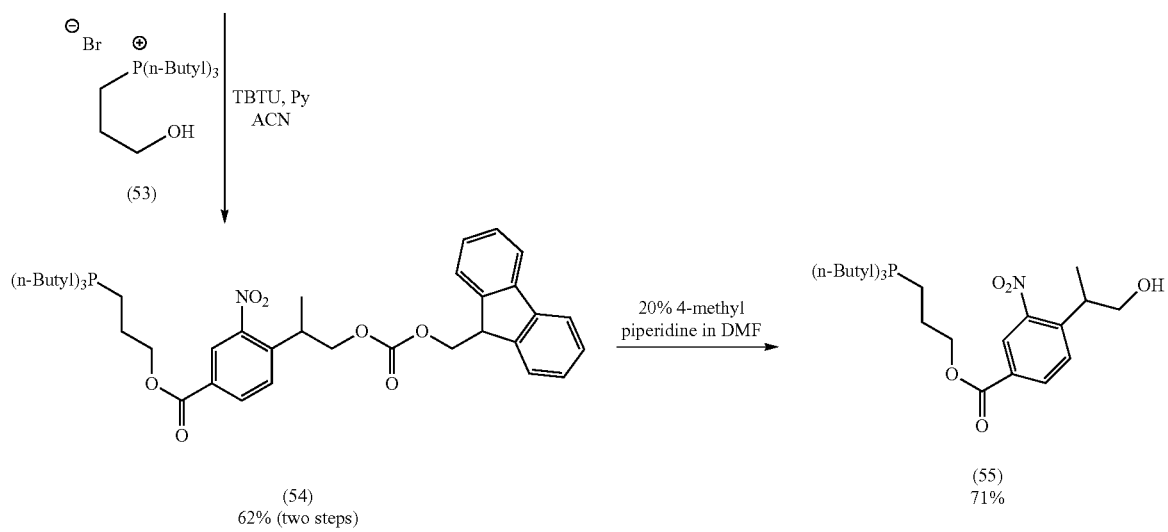

Fuming nitric acid was cooled to −10° C. and 4-ethyl-benzoic acid (49) was added over 30 min to the sitting solution, then allowed to stir for 30 min. The mixture was quenched over crushed ice and the solid precipitate of 3-nitro-4-ethyl-benzoic acid (50) was collected and crystallised with ethyl acetate and hexanes in good yield (95%). The tert-butyl ester was formed using DCC and DMAP with tert-butanol under standard conditions.

The formation of the 2-substituted propan-1-ol derivative was achieved as described by Pfleiderer by treating the tert-butyl ester with para-formaldehyde and a catalytic amount of potassium tert-butoxide in an aprotic dipolar solvent, such as DMF or DMSO, at 90° C. for 3 h [Pfleiderer, W. et al. Helvetica Chemimica Acta, 87: 620 (2004)]. The reaction was then quenched and neutralized to pH 7 with 1 M HCl, yielding 85-90% of the desired product (51). The newly formed primary hydroxyl was then protected with Fmoc-Cl (52), an acid stable protecting group. This allows cleavage of the t-butyl ester with 80% TFA in DCM without deprotection of the primary hydroxyl group. Without Fmoc protection, dehydration of the newly formed hydroxyl will occur, forming the propene derivative. As well, after the installation of the Fmoc it is imperative that the compound is not exposed to sunlight or tungsten light for long periods of time, as this compound will undergo photolytic cleavage, as per the design of the molecule.

The newly formed free acid was then coupled with phosphonium ionic tag (53) with TBTU in ACN and wrapped in aluminum foil for 8 h which affords the tagged species (54) in a moderate yield of 65%, which could be easily separated from any starting material by column chromatography. Next, the Fmoc group was removed under standard conditions by treatment with 20% 4-methylpiperidine in DMF for 2 h, yielding compound (55) in good yields. Although no protecting group can be removed at the primary alcohol, this compound should be kept in the dark at all times. This is due to the fact that it was observed that some degradation does occur over time, albeit much more slowly than when the Fmoc was present.

The previous synthesis of the light labile linker is somewhat long and requires the use of an expensive transient protecting group, Fmoc. In an attempt to shorten the synthesis, we were able to avoid protection, deprotection, and re-protection of the carboxylic acid moiety, while increasing overall yields. This was accomplished by directly conjugating a modified phosphonium ionic tag (23) containing a primary amine in place of the hydroxyl group, creating an amide bond in compound (56) (Scheme 30). This was achieved as described for the synthesis of (55) (Scheme 29) using TBTU and triethylamine as coupling reagents, producing (57) in 35% yield (unoptimized).

Scheme 30
Short synthesis of photolabile ionic tag (57)

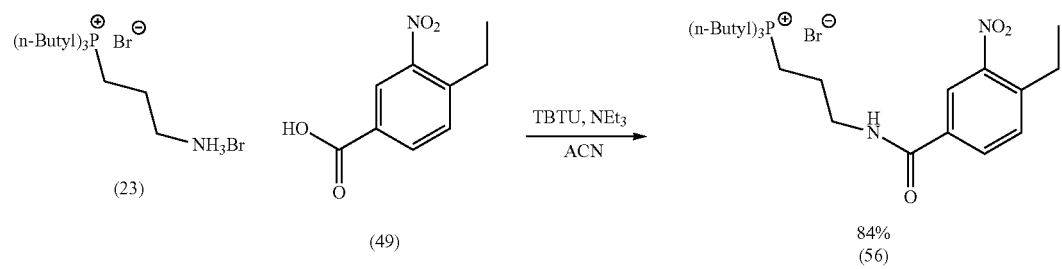

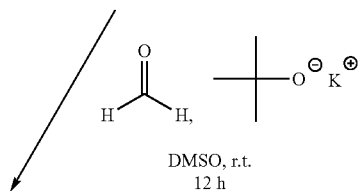

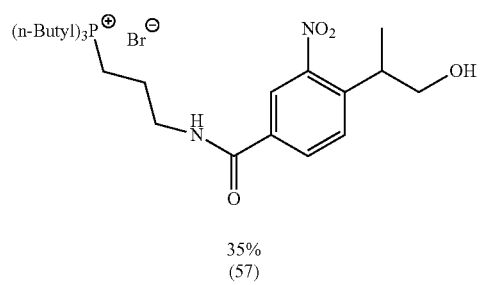

In another embodiment, there is provided a process for attaching ionic tag (57) to a ribonucleoside, affording a building block, (58) or (59), for further elaboration into oligonucleotides. The general method for carrying out the conjugation is shown in Scheme 31, and involves phosgenation of the ionic tag followed by its attachment to the 3'-hydroxyl group of the nucleoside.

Thus, phosgenation of (55) or (57) was carried out by a modified procedure from Eckert, H. Auerweck, *J. Org. Process Res. Dev.* 14: 1501-1505, (2010), and is outlined in Scheme 32. Detailed experimental procedures for generating phosgene from triphosgene and phenanthridine are described herein.

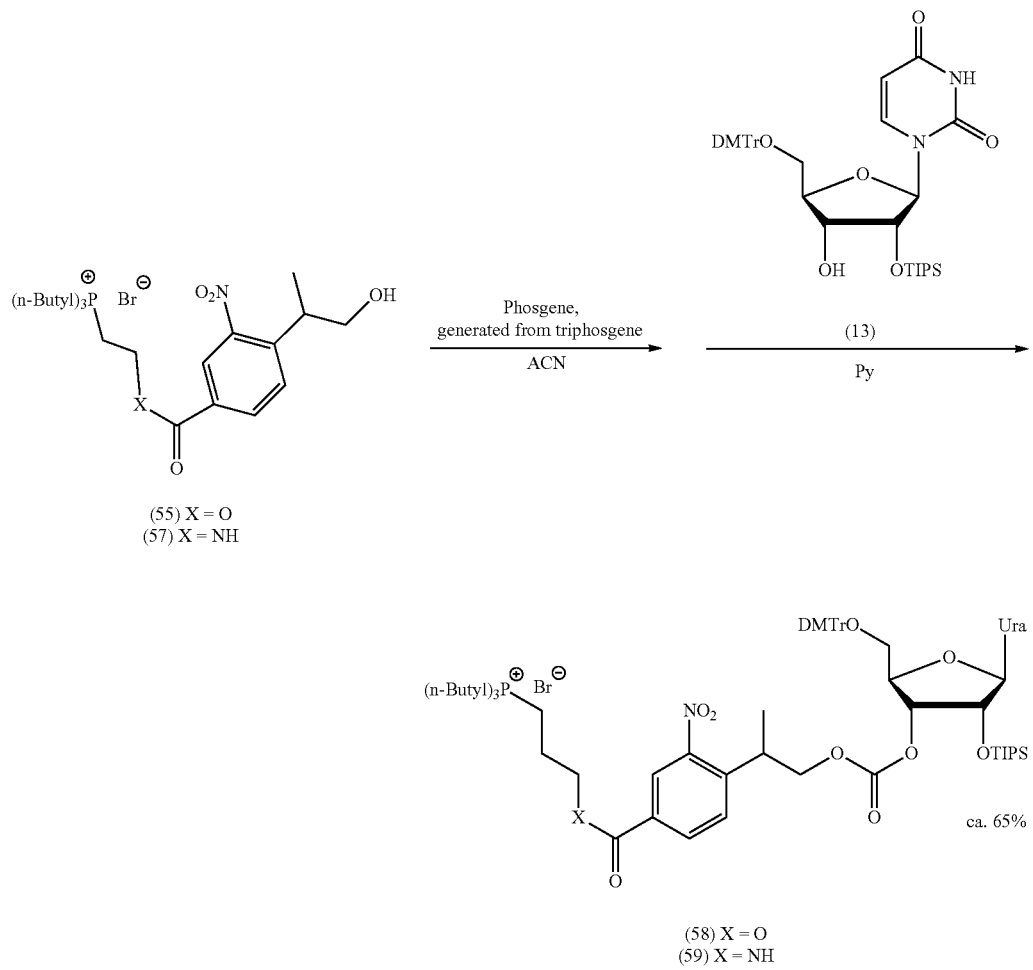

Scheme 31
Conjugation of nucleoside (13) to photolabile ionic tags.

A solution of nucleoside (13) in acetonitrile was added directly to mixture of DIPEA and chloro carbonate produced from the phosgene reaction generated above, and allowed to stir for 8 h at room temperature. After addition of ethyl acetate, the mixture was washed with sat. $NaHCO_3$ and brine, and precipitated in MTBE to remove excess (unreacted) nucleoside and DIPEA. The resulting precipitate was further purified by column chromatography in DCM:MeOH.

Nucleosides such as (59) have a number of applications. They can serve as starting materials for the synthesis of dimer or trimers or larger oligonucleotides requiring only a precipitation step for isolation by virtue of the polar ionic tag at the 3'-termini. Once the desired length has been synthesized, the 3'-tag and all protecting groups can be cleaved yielding the free (unprotected) oligonucleotide. Alternatively, because the 3'-ion tag can be selectively cleaved without deblocking all other protecting group on the heterocylic bases or sugar-phosphate backbone, it provides a novel means for preparing protected oligonucleotide blocks containing a 3'-hydroxyl group that can be further elaborated to a 3'-phosphoramidite derivative.

Scheme 32. Synthesis of ion-tagged rUpU (60) from nucleoside (59).

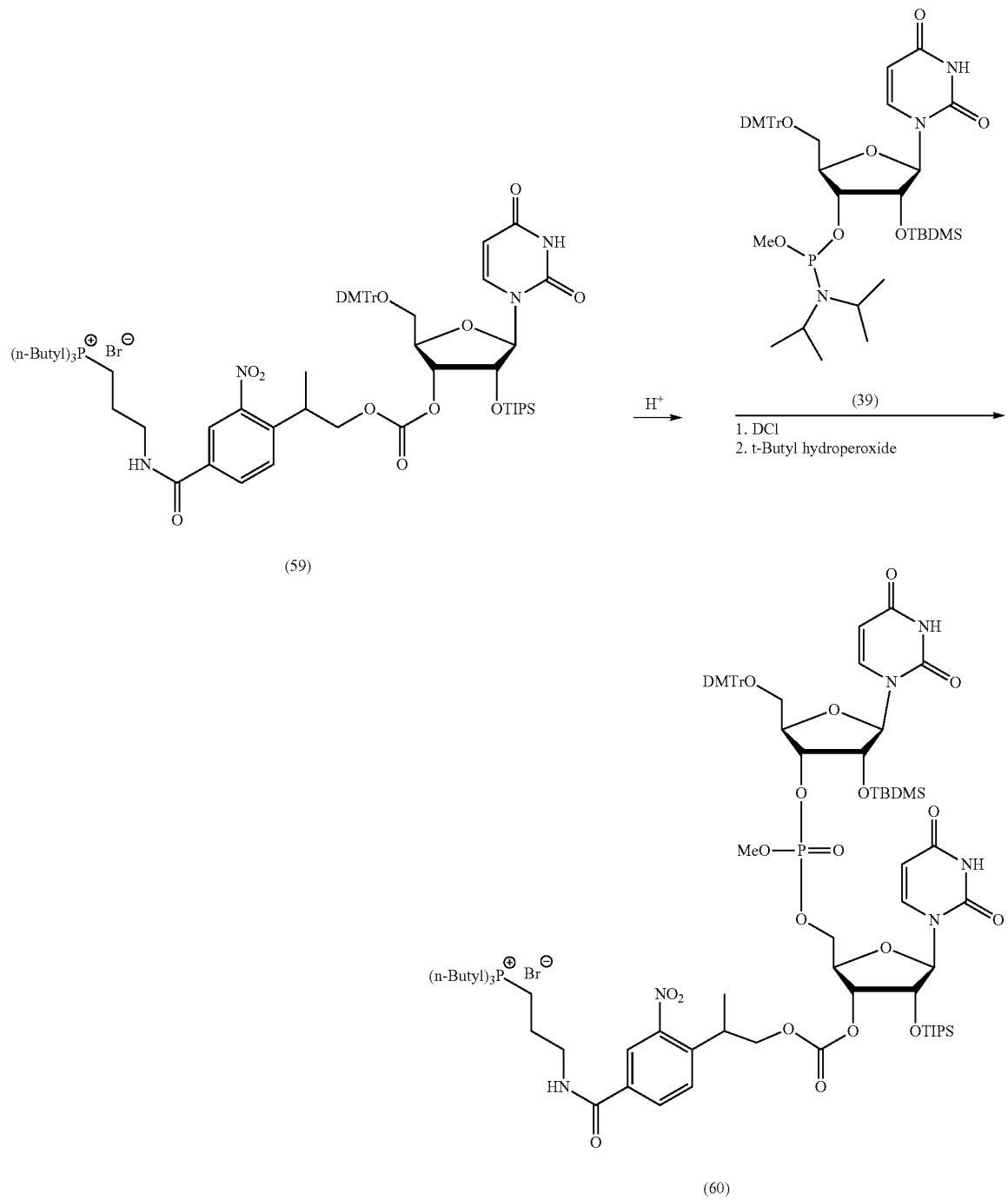

3'-NPPOC-tagged-uridine (86) was detritylated by adding 3% trifluoroacetic acid in DCM and triethylsilane, allowing the mixture to stir for 5 min. Addition of methanol ensured quenching of the trityl cation, preventing the re-tritylation of the 5'-hydroxyl group. The crude product was then precipitated in MTBE to remove DMTrOMe, and/or DMTrOH. The compound was then filtered over celite, collected in DCM and re-purified by column chromatography affording a 95% yield. The synthesis of dimer rUpU (60) was carried out by coupling with rU phosphoramidite monomer (39) in the presence of 4,5-dicyanoimidazole (DCI), and the resulting solution was allowed to stir at room temperature for 3 h. Ten equivalents of tert-butanol were added to quench excess phosphoramidite, followed by 10 eq of tert-butyl hydroperoxide (1 mL of a 6 M solution in decane) to oxidize the internucleotide phosphite triester to the more stable phosphate triester. The reaction was then concentrated to an oil, taken up in minimal amounts of dichloromethane (DCM), and precipitated in MTBE to remove all excess reagents. The precipitation process was repeated if the presence of any quenched phosphoramidite was detected by TLC. Tagged rUpU dimer (60) was isolated in 95% yield.

Scheme 33
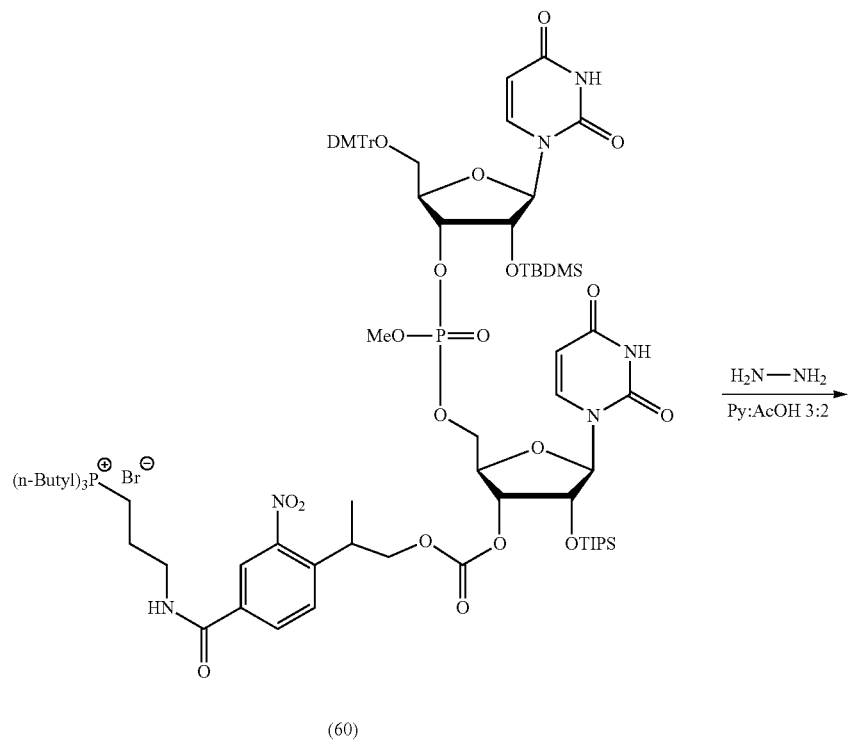
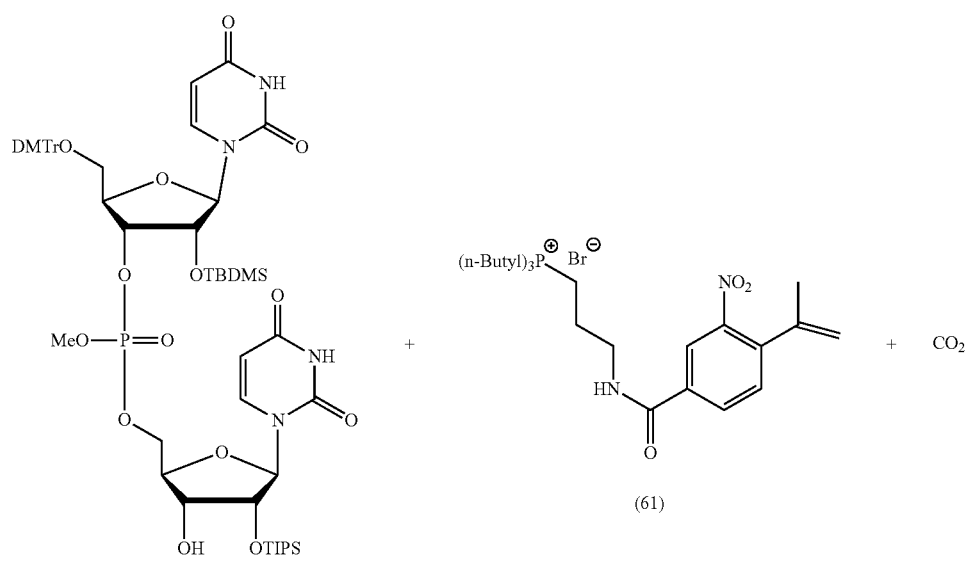

Dimer (60) was dissolved in wet ACN (3200 ppm of H$_2$O), in a 50 ml Pyrex round bottomed flask. The flask was placed inside a photoreactor equipped with UVB bulbs and reacted for 35 min with stirring at a concentration of 0.01M. The mixture was concentrated to about 3 ml and the cleaved tag removed by precipitation with methyl t-butyl ether (MTBE). The desired dimer was found in the MTBE solution, which was collected after concentrating the solution to dryness. Isolated yield was 95%.

Experimental Synthesis of Orthogonally Cleavable Tags

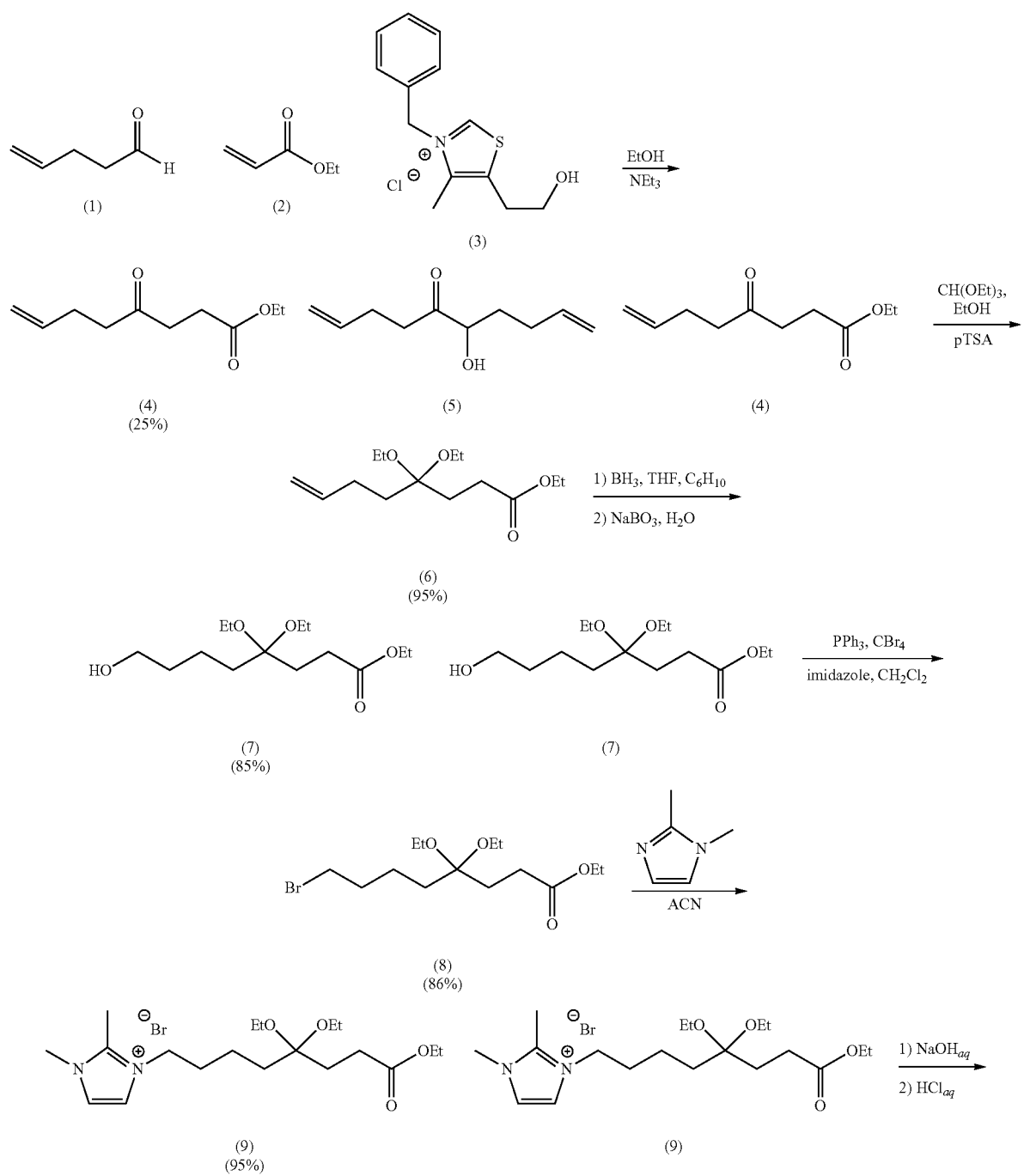

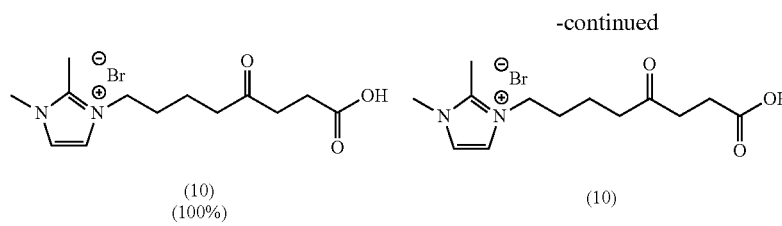

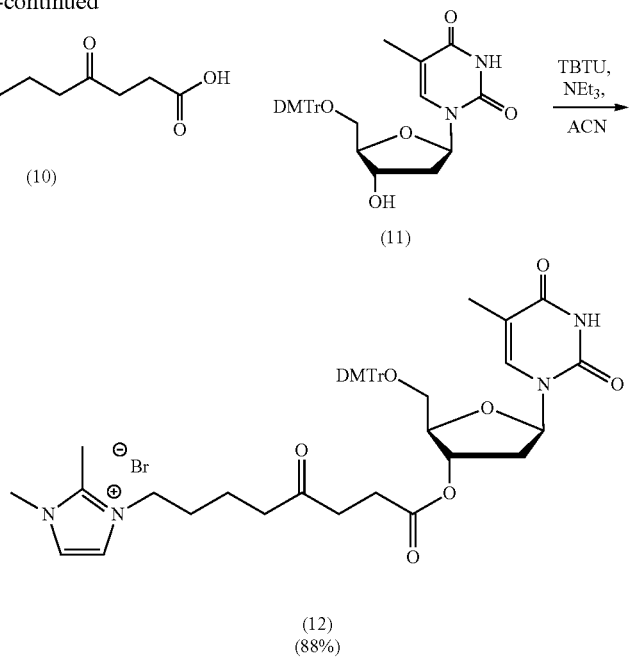

Ethyl 4-oxooct-7-enoate (54)

4-Pentenal (1) (3.8 g, 45 mmol) was mixed with 3-benzyl-5-(2-hydroxyethyl)-4-methylthiazolium chloride ((3), 2.45 g, 9.1 mmol) and ethyl acrylate ((2), 9.0 g, 90 mmol) and dissolved in 22 mL of anhydrous ethanol. The reaction mixture was heated to reflux and then triethylamine (7.6 mL) was added to begin the reaction.

The reaction mixture was refluxed for 18 hours and was then cooled to room temperature. The ethanol was removed under reduced pressure and the reaction mixture was then suspended in dichloromethane and extracted with brine. The organic layer was dried over magnesium sulphate and the solvent was removed under reduced pressure. The products were purified by flash column chromatography using a hexanes/ethyl acetate gradient elution system to give (4) (3.96 g, mixed with (5), app. 25% yield) as a pale yellow oil. $^1$H NMR (300 MHz, Acetonitrile-$d_3$) δ=5.99-5.73 (m, 1H, with acyloin impurity), 5.15-5.05 (m, 2H), 5.04-4.93 (acyloin impurity), 4.15-4.06 (q, J=7.0 Hz, 2H), 2.76-2.67 (m, 2H, with acyloin impurity), 2.67-2.60 (acyloin impurity), 2.55-2.48 (m, 2H, with acyloin impurity), 2.35-2.26 (m, 2H), 2.20-2.17 (acyloin impurity), 2.16-2.12 (m, 2H), 1.99-1.94 (acyloin impurity), 1.21 (t, J=7.0 Hz, 3H), $C_{10}H_6O_3Na^{1+}$ low resolution ESI-MS calculated: 207.10, found: 207.31.

Ethyl 4,4-diethoxyoct-7-enoate (56)

Compound (4) (2.0 g, as mixture with (5), approx. 5.7 mmol) was dissolved in a 1:1 v/v mixture of ethyl orthoformate and ethanol (6 mL) and mixed with a catalytic amount of pTSA (0.1 g). The reaction mixture was then refluxed for 4 hours and it was then cooled to 0° C. Saturated aqueous sodium bicarbonate (20 mL) was then added along with diethyl ether (20 mL). The aqueous phase was extracted several times with diethyl ether and then the combined organic layers were rinsed with aqueous brine and dried over magnesium sulphate. The solvent was removed under reduced pressure and the product was purified by flash column chromatography using a hexanes/ethyl acetate gradient system to give (6) (1.36 g, 92% yield) as a colourless oil. $^1$H NMR (500 MHz, DMSO-$d_6$) δ=5.85-5.73 (m, 1H), 5.05-4.88 (m, 2H), 4.03 (q, J=7.2 Hz, 2H), 3.32 (q, J=7.0 Hz, 4H), 2.20 (t, J=7.8 Hz, 2H), 1.97-1.88 (m, 2H), 1.79 (t, J=7.8 Hz, 2H), 1.53 (t, J=8.4 Hz, 2H), 1.16 (t, J=7.2 Hz, 3H), 1.06 (t, J=7.0 Hz, 6H), $^{13}$C NMR (75 MHz, Acetonitrile-$d_3$) δ=173.0, 138.5, 113.8, 102.0, 60.1, 55.0, 32.3, 28.7, 28.3, 27.8, 14.6, 13.6, $C_{14}H_{26}O_4Na^{1+}$ low resolution ESI-MS calculated: 281.17, found: 281.13.

Ethyl 4,4-diethoxy-8-hydroxyoctanoate (7)

A 1 M solution of borane in THF (2.4 mL, 2.4 mmol) was cooled to 0° C. and to it was added, dropwise, 0.47 mL of cyclohexene (4.6 mmol). The reaction was stirred for 1 hour at 0° C. and to the resultant white slurry was added compound (6) (0.51 g, 2.0 mmol). The reaction was allowed to warm to room temperature and was stirred for 2 hours. After this time, sodium perborate tetrahydrate (1.07 g, 7.0 mmol) and 2.4 mL of water were added. The reaction was stirred for a further 2 hours and then the reaction mixture was extracted with ethyl acetate several times. The combined organic layers were dried of magnesium sulphate and the solvent was removed under reduced pressure. The products were purified using a dichloromethane/methanol gradient elution system to give (7) (0.45 g, 81% yield) as a colourless oil. Starting material (6) was also recovered. $^1$H NMR (300 MHz, DMSO-$d_6$) δ=4.33 (t, J=5.2 Hz, 1H), 4.02 (q, J=7.1 Hz, 2H), 3.36 (m, 2H), 3.31 (q, J=7.3 Hz, 4H), 2.18 (t, J=7.7 Hz, 2H), 1.76 (t, J=7.7 Hz, 2H), 1.46-1.41 (m, 2H), 1.40-1.31 (m, 2H), 1.25-1.19 (m, 2H), 1.16 (t, J=7.1 Hz, 3H), 1.05 (t, J=7.3 Hz, 6H), $^{13}$C NMR (75 MHz, DMSO-$d_6$) δ=173.1, 102.4, 61.0, 60.3, 55.0, 33.2, 33.0, 29.0, 28.5, 20.2, 15.7, 14.5, $C_{14}H_{28}O_5Na^{1+}$ low resolution ESI-MS calculated: 299.18, found: 299.19.

Ethyl 8-bromo-4,4-diethoxyoctanoate (8)

Compound (7) (0.50 g, 1.8 mmol) was mixed with triphenylphosphine (0.80 g, 3.0 mmol) and imidazole (0.20 g, 2.9 mmol) and dissolved in 18 mL of dichloromethane. The solution was cooled to 0° C. and a solution of carbon tetrabromide (0.85 g, 2.6 mmol) in dichloromethane (1.5 mL) was added slowly. The reaction mixture was allowed to warm to room temperature and was stirred for 1 hour. The reaction was then quenched by the addition of saturated aqueous sodium sulphite and extracted with dichloromethane. The combined organic layers were dried over sodium sulphate and the solvent was removed under reduced pressure. The product was purified by flash column chromatography with a hexanes/ethyl acetate gradient elution system to yield (58) (0.49 g, 81% yield) as a colourless oil. 1H NMR (400 MHz, DMSO-$d_6$) δ=4.04 (q, J=7.1 Hz, 2H), 3.54 (t, J=6.5 Hz, 2H), 3.32 (q, J=6.9 Hz, 4H), 2.22 (t, J=7.8 Hz, 2 H), 1.83-1.74 (m, 4H), 1.47 (t, J=7.2 Hz, 2H), 1.35-1.25 (m, 2H), 1.18 (t, J=7.1 Hz, 3H), 1.07 (t, J=6.9 Hz), $^{13}$C NMR (126 MHz, Acetonitrile-$d_3$) δ=173.0, 102.1, 60.1, 55.0, 34.2, 32.5, 32.1, 28.8, 28.4, 22.0, 14.7, 13.5, $C_{14}H_{27}BrO_4Na^{1+}$ low resolution ESI-MS calculated: 361.10, found: 361.11.

Ethyl 4,4-diethoxy-8-(2,3-dimethyl-1H-imidazol-1-yl) octanoate bromide (9)

Compound 58) (0.31 g, 0.90 mmol) was dissolved in 5 mL of acetonitrile and mixed with 1,2-dimethylimidazole (0.13 g, 1.3 mmol). The reaction was warmed to 50° C. and stirred overnight. The reaction mixture was then cooled to room temperature and the solvent was then removed under reduced pressure. The resultant oil was rinsed several times with diethyl ether and then the compound was again subjected to reduced pressure. This gave (9) (0.38 g, 95% yield) as a colourless oil. $^1$H NMR (500 MHz, DMSO-$d_6$) δ=7.63 (d, J=2.2 Hz, 1H), 7.60 (d, J=2.2 Hz, 1H), 4.09 (t, J=7.2 Hz, 2H), 4.04 (q, J=7.2 Hz, 2H), 3.73 (s, 3H), 3.31 (q, J=6.9 Hz, 4H), 2.56 (s, 3H), 2.20 (t, J=8.1 Hz, 2H), 1.76 (t, J=8.1 Hz, 2H), 1.71-1.63 (m, 2H), 1.49 (t, J=7.6 Hz, 2H), 1.24-1.19 (m, 2H), 1.16 (t, J=7.2 Hz, 3H), 1.05 (t, J=6.9 Hz, 6H), $^{13}$C NMR (126 MHz, DMSO-$d_6$) δ=173.6, 122.8, 121.3, 102.5, 60.7, 55.6, 48.6, 35.3, 33.2, 29.9, 29.3, 28.8, 20.8, 15.2, 14.1, 9.7, $C_{19}H_{35}N_2O_4^{1+}$ low resolution ESI-MS calculated: 355.26, found: 355.28.

8-(2,3-dimethyl-1H-imidazol-1-yl)-4-oxooctanoic acid bromide (10)

Compound (9) (0.44 g, 1.0 mmol) was mixed with 1 M aqueous sodium hydroxide (5 mL) and stirred overnight. The solution was then acidified to pH 1 by addition of concentrated aqueous HCl. The aqueous solution was then rinsed with diethyl ether, followed by the removal of water under reduced pressure. The resulting solid was dissolved in a minimum of cold acetone and dichloromethane any undissolved material was removed by filtration. The solvent was then removed under reduced pressure to give (10) (0.34 g, >100% yield) as an off-white solid, likely mixed with a small amount of sodium chloride. $^1$H NMR (400 MHz, DMSO-$d_6$) δ=7.63 (d, J=2.1 Hz, 1H), 7.61 (d, J=2.1 Hz, 1H), 4.09 (t, J=7.3 Hz, 2H), 3.73 (s, 3H), 2.61 (t, J=6.3 Hz, 2H), 2.56 (s, 3H), 2.49 (t, J=7.3 Hz, 2H), 2.37 (t, J=6.3 Hz, 2H), 1.65 (m, 2H), 1.43 (m, 2H), $^{13}$C NMR (126 MHz, Acetonitrile-$d_3$) d=208.9, 173.4, 122.3, 120.9, 48.0, 41.0, 36.7, 34.8, 28.6, 27.7, 19.9, 9.2, $C_{13}H_{21}N_2O_3^{1+}$ high resolution ESI-MS required: 253.15467, found: 253.15459.

General Procedure for the Derivatization of (10) with Nucleosides.

Compound (10) (0.4 mmol) was dissolved in 15% v/v DMF/acetonitrile and mixed with DCC (0.6 mmol), DMAP (0.2 mmol), and the desired 5'-DMTr-dT or 5'-DMTr 2'-TIPS rU (13) (0.5 mmol). The reaction mixture was stirred overnight and was then precipitated from MTBE. The resultant solid was removed by filtration and recovered from the filter by dissolving it in acetonitrile. The solvent was removed under reduced pressure and the resulting solid was taken up in dichloromethane and washed with dilute aqueous sodium tetrafluoroborate to achieve ion metathesis. The organic phase was dried over magnesium sulphate and the solvent was removed under reduced pressure. The resultant solid was then dissolved in acetonitrile and the solution was precipitated from MTBE, followed by filtration and recovery in acetonitrile. The solvent was then removed under reduced pressure to yield the desired tagged nucleoside in 80-90% yield.

(12) $^1$H NMR (500 MHz, DMSO-$d_6$)=11.37 (s, 1H), 7.59 (d, J=2.1 Hz, 1H), 7.57 (d, J=2.1 Hz, 1H), 7.49 (s, 1H), 7.39-7.36 (m, 2H), 7.34-7.30 (m, 2H), 7.29 (t, J=7.1 Hz, 2H), 7.25-7.19 (m, 5H), 6.90-6.85 (m, 4H), 6.17 (dd, J=5.9 Hz, 1H), 5.25 (d, J=6.3 Hz, 1H), 4.08 (t, J=7.1 Hz, 2H), 4.01 (dd, J=3.5 Hz, 1H), 3.72 (s, 6H), 3.71 (s, 3H), 3.33-3.27 (m, 1H, and H$_2$O), 3.22-3.17 (dd, J=7.2, 3.3 Hz, 1H), 2.69 (t, J=6.1 Hz, 2H), 2.60 (s, 3H), 2.55-2.44 (m, 8H, and DMSO), 2.53 (dd, J=8.1, 5.4 Hz, 1H), 1.72-1.61 (m, 2H), 1.48-1.42 (m, 2H), $C_{44}H_{51}N_4O_9^{1+}$ high resolution ESI-MS required: 779.36506, found: 779.36526.

(14) $^1$H NMR (500 MHz, DMSO-$d_6$) δ=11.47 (s, 1H, H3), 8.22-8.16 (m, 1H, DMT), 7.72-7.70 (br. s, 1H, H6), 7.69-7.68 (m, 1H, tag CH=CH), 7.63-7.60 (m, 1H, tag CH=CH), 7.60-7.58 (m, 2H, DMTr), 7.58-7.56 (m, 2H, DMTr), 7.36-7.27 (m, 2H, DMT), 7.26-7.18 (m, 2H, DMT), 6.91-6.84 (m, 4H, DMTr), 5.87 (d, J=6.8 Hz, 1H, H1'), 5.49 (dd, J=2.0, 5.9 Hz, 1H, H5), 5.16 (t, J=2.3 Hz, 1H, H3'), 4.64 (t, J=6.2 Hz, 1H, H2'), 4.06 (t, J=7.4 Hz, 2H, NCH$_2$), 3.73 (s, 6H, DMT OCH$_3$), 3.70 (s, 3H, tag NCH$_3$), 3.29-3.15 (m, water and H5'&5"), 2.70 (t, J=6.7 Hz, 2H, tag CH$_2$CH$_2$COO), 2.63-2.58 (m, 3H, tag CH$_3$CN$_2$), 2.55 (m, DMSO and tag CH$_2$CH$_2$COO and tag NCH$_2$CH$_2$CH$_2$CH$_2$), 2.54-2.45 (m, 5H), 1.73-1.61 (m, tag NCH$_2$CH$_2$CH$_2$CH$_2$ and 10% impurity), 1.49-1.35 (m, tag, NCH$_2$CH$_2$CH$_2$CH$_2$ and 10% impurity), 1.28-1.13 (m, impurity), 0.99-0.90 (m, 9H), $C_{52}H_{69}N_4O_{10}Si^{1+}$ high resolution ESI-MS required: 937.47775, found: 937.47680.

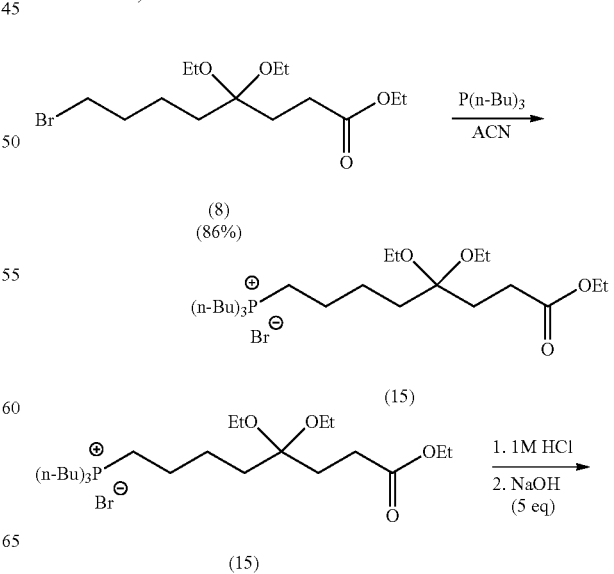

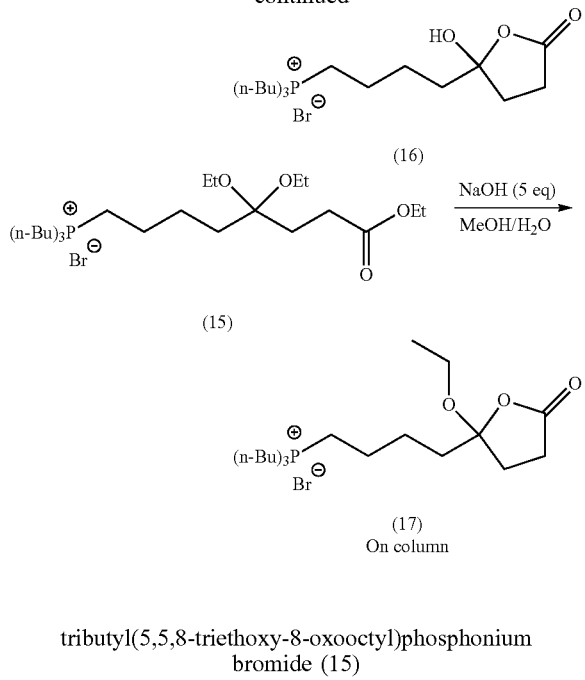

tributyl(5,5,8-triethoxy-8-oxooctyl)phosphonium bromide (15)

Alkyl-bromide (8) (3.8 g, 11.2 mmol) was solvated in 22.4 mL of dry ACN to which was added to 1.5 eq of tributylphosphine (3.4 g, 16.8 mmol) and was stirred at 50° C. for 8 h. The reaction mixture was then concentrated to dryness on rotovap then precipitated in hexanes to afford pure phosphonium tagged species (15) in 93% yield, 5.64 g.

$^1$H NMR (300 MHz, CHLOROFORM-d) δ ppm 0.76-0.91 (m, 16H) 0.95-1.07 (m, 10H) 1.08-1.19 (m, 6H) 1.27-1.58 (m, 33H) 1.71-1.89 (m, 3H) 2.07-2.21 (m, 4H) 2.22-2.49 (m, 15H) 3.18-3.39 (m, 8H) 3.88-4.08 (m, 2H)

$^{31}$P NMR (81 MHz, CHLOROFORM-d) δ ppm 49.63 (s, 1P)

tributyl(4-(2-hydroxy-5-oxotetrahydrofuran-2-yl)butyl)phosphonium bromide (16)

Compound (15) (0.2 g, 0.37 mmol) was solvated in minimal methanol approx 3 mL to which was added 3 mL of 5M HCl and was allowed to stir for 20 min, at which point the reaction was observed to be complete by TLC. The reaction was then neutralized by the addition of 3 mL of 5M NaOH, then approximately 5 eq (75 mg, 1.9 mmol) of extra NaOH was added and allowed to stir for an additional 30 min. The reaction was monitored by MS, showing complete consumption of starting material. The reaction was then neutralized with 1M HCl, taken up in ethylacetate and shaken acidified brine to remove all excess salts, and twice with brine to remove any excess HCl. The ethyl acetate was dried with magnesium sulfate and concentrated to dryness. Yielding compound (16) in 88% yield, 176 mg.

$^1$H NMR (300 MHz, CHLOROFORM-d) δ ppm 0.78-0.97 (m, 9H) 1.45 (br. s., 17H) 1.87 (br. s., 1H) 1.97-2.07 (m, 1H) 2.13 (m, J=9.38, 6.74 Hz, 1H) 2.28 (br. s., 8H) 2.38-2.72 (m, 2H) 3.40-3.57 (m, 1H)

tributyl(4-(2-ethoxy-5-oxotetrahydrofuran-2-yl)butyl)phosphonium bromide (17)

Compound (15) (0.25 g, 0.46 mmol) was solvated in minimal amount of methanol, 1.5 mL, and treated with approximately 5 eq (80 mg, 2.1 mmol) of NaOH and allowed to stir for 1 h at room temperature. The reaction mixture was neutralized to pH 8 then concentrated to dryness. The mixture was then passed through a silica column with 1% acetic acid and 10% MeOH— DCM to remove all salts and generate the acid form of the product. Yielding 74% of compound (17)

$^1$H NMR (300 MHz, CHLOROFORM-d) δ ppm 0.78-0.97 (m, 9H) 1.07 (t, J=7.00 Hz, 4H) 1.45 (br. s., 17H) 1.87 (br. s., 1H) 1.97-2.07 (m, 1H) 2.13 (m, J=9.38, 6.74 Hz, 1H) 2.28 (br. s., 8H) 2.38-2.72 (m, 2H) 3.23-3.39 (m, 2H) 3.40-3.57 (m, 1H)

$^{13}$C NMR (75 MHz, CHLOROFORM-d) δ ppm 13.41 (s, 1C) 15.28 (s, 1C) 18.38 (s, 1C) 19.02 (s, 1C) 23.55 (s, 1C) 23.61 (s, 1C) 23.69 (s, 1C) 23.77 (s, 1C) 23.97 (s, 1C) 28.70 (s, 1C) 31.54 (s, 1C) 32.59 (s, 1C) 35.21 (s, 1C) 42.36 (s, 1C) 55.17 (s, 1C) 57.98 (s, 1C) 102.33 (s, 1C) 110.85 (s, 1C) 176.42 (s, 1C) 177.15 (s, 1C)

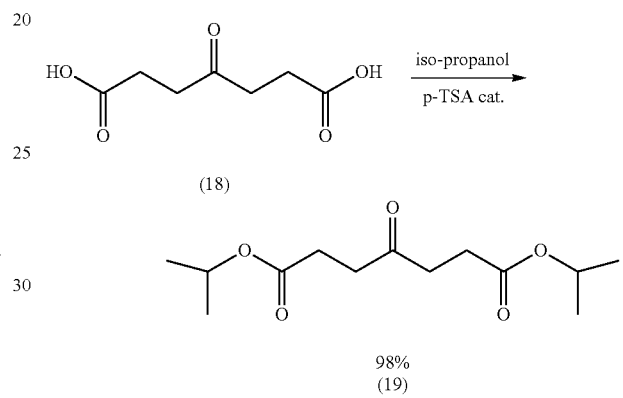

Diisopropyl 4-oxoheptanedioate (19)

4-ketopemilic acid (18) (10 g, 57.4 mmol; purchased from Sigma-Aldrich) was suspended in 50 mL of isopropanol and 50 mL of benzene. Catalytic amount of p-toluene solfonic acid was added to the mixture and brought to reflux using a Dean Stark trap to remove the water produced. Once the volume had decreased to approximately 50 mL in the flask, another 50 mL of 50:50 Benzene:iso-propanol was added and further reduced to approximately 30 ml. The mixture was then taken up in ethyl acetate and extracted with NaHCO$_3$ (×3) and once with brine. The organic layer was dried with MgSO$_4$ and condensed to dryness yielding pure (19): 14.2 g (95%).

$^1$H NMR (300 MHz, CHLOROFORM-d) δ ppm 1.06 (d, J=6.45 Hz, 12H) 2.39 (t, J=7.00 Hz, 1H) 2.60 (t, J=6.70 Hz, 4H) 4.72-4.89 (m, 2H) $^{13}$C NMR (75 MHz, CHLOROFORM-d) δ ppm 21.57 (s, 1C) 28.13 (s, 3C) 28.13 (s, 3C) 36.92 (s, 3C) 67.66 (s, 1C) 171.90 (s, 2C) 206.82 (s, 1C) C$_{13}$H$_{22}$O$_5$Na$^{1+}$ low resolution ESI-MS calculated: 258.14, found: 281.21.

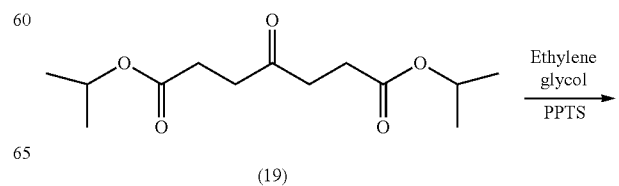

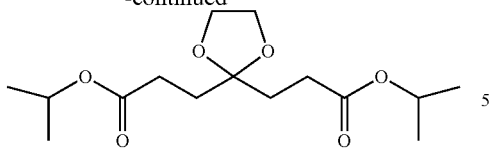

95%
(20)

Diisopropyl 3,3'-(1,3-dioxolane-2,2-diyl)dipropanoate (20)

Compound (19) (0.55 g, 2.1 mmol) was solvated with 5 eq of ethylene glycol (0.58 mL, 10.5 mmol), 90 mL of dry toluene and catalytic amount of pyridinium para-toluene sulfonate. This mixture was refluxed at 140° C. replacing the toluene 3 times and finally allowing the reaction to reflux overnight. The mixture was then distilled to approximately 30 mL, removed from heat and diluted with DCM and extracted with sat. NaHCO$_3$ (×2) then water (×3) to remove any excess ethylene glycol. The product was purified by column chromatography (DCM:MeOH, 100:0→95:5). Isolated yield: 0.41 g (65%).

$^1$H NMR (500 MHz, CHLOROFORM-d) δ ppm 1.05 (d, J=6.36 Hz, 12H) 1.78 (t, J=7.58 Hz, 15H) 2.16 (t, J=7.58 Hz, 15H) 3.76 (s, 15H) 4.82 (dt, J=12.53, 6.33 Hz, 8H) $^{13}$C NMR (126 MHz, CHLOROFORM-d) δ ppm 21.59 (s, 1C) 29.02 (s, 1C) 32.07 (s, 1C) 64.94 (s, 1C) 67.23 (s, 1C) 67.26 (s, 1C) 109.84 (s, 1C) 172.56 (s, 1C) C$_{15}$H$_{26}$O$_6$Na$^{1+}$ low resolution ESI-MS calculated: 302.17, found: 325.0.

35%
(21)

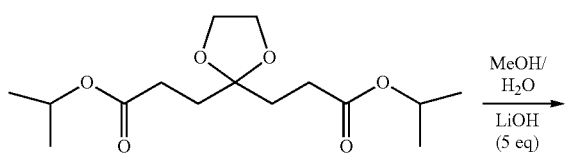

45%
(22)

3-(2-(3-hydroxy-3-oxopropyl)-1,3-dioxolan-2-yl) propanoic acid (21) and 3-(2-(3-isopropoxy-3-oxopropyl)-1,3-dioxolan-2-yl)propanoic acid (22)

Compound (20) (2.1 g, 6.9 mmol) was solvated in 20 mL of MeOH to which was added 1.5 eq of LiOH (0.51 g, 21.5 mmol) in 5 mL of water. This mixture was allowed to stir for 2 h until all starting material was consumed. The solution was brought to neutrality by the addition of 1 M HCl. This mixture was purified by column chromatography (DCM: MeOH with 1% AcOH, 100:0→90:10). Isolated yield of (21): 0.53 g (35%). Yield of (22): 0.81 g (45%).

(21)

$^1$H NMR (300 MHz, METHANOL-d$_4$) δ ppm 1.94 (t, J=8.20 Hz, 4H) 2.33 (t, J=7.30 Hz, 15H) 3.94 (s, 26H) $^{13}$C NMR (75 MHz, METHANOL-d$_4$) ppm 28.19 (s, 1C) 31.82 (s, 1C) 64.77 (s, 1C) 109.81 (s, 1C) 175.90 (s, 1C) C$_9$H$_{14}$O$_6$Li$^{1-}$ low resolution ESI-MS calculated: 218.07, found: 224.12.

(22)

$^1$H NMR (500 MHz, METHANOL-d$_4$) δ ppm 1.22 (d, J=6.36 Hz, 6H) 1.87-2.03 (m, 4H) 2.23-2.34 (m, 4H) 3.55 (m, J=5.14 Hz, 3H) 3.67 (m, J=5.14 Hz, 3H) 4.89-5.00 (m, 2H) $^{13}$C NMR (126 MHz, METHANOL-d$_4$) δ ppm 7.75 (s, 1C) 20.72 (s, 1C) 28.80 (s, 1C) 31.81 (s, 1C) 60.87 (s, 1C) 62.94 (s, 1C) 67.60 (s, 1C) 72.13 (s, 1C) 109.92 (s, 1C) 173.40 (s, 1C) 176.73 (s, 1C) C$_{12}$H$_2$O$_6^{1-}$ low resolution ESI-MS calculated: 260.12, found: 259.03.

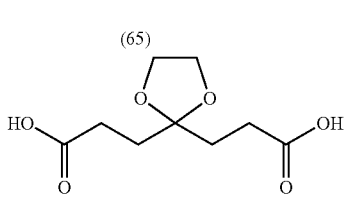

(65)

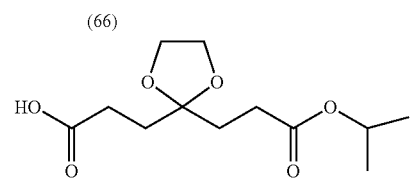

(66)

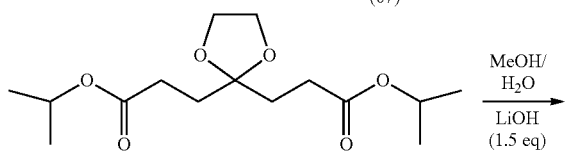

(67)

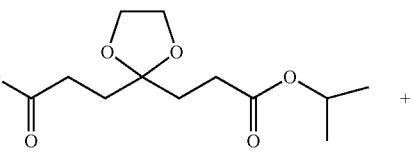

(22)

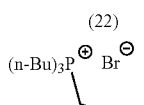

(23)

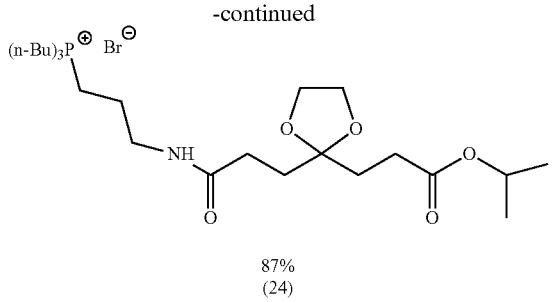

87%
(24)

Tributyl (3-(3-(2-(3-isopropoxy-3-oxopropyl)-1,3-dioxolan-2-yl)propanamido)propyl)phosphonium bromide (24)

Compound (22) (0.3 g, 1.1 mmol) was solvated in 1.5 mL of ACN followed by TBTU (0.39 g, 1.2 mmol), 2.5 eq of triethylamine (0.38 ml) and phosphonium ionic tag (23) (0.45 g, 1.2 mmol).

This mixture was allowed to stir for 4 h until the starting material (22) was completely consumed. The reaction mixture was diluted with ethyl acetate and extracted with 5% NaHCO$_3$×2 and once with brine. The organic layer was dried and concentrated and purified by column chromatography. DCM:MeOH 100:0→95:5. Isolated yield: 0.54 g (84%).

$^1$H NMR (300 MHz, CHLOROFORM-d) δ ppm 0.91 (t, J=6.74 Hz, 9H) 1.06 (d, J=6.45 Hz, 6H) 1.25 (s, 6H) 1.38-1.59 (m, 11H) 1.80-1.95 (m, 7H) 2.15-2.30 (m, 9H) 2.18 (t, J=7.03 Hz, 8H) 3.28-3.44 (m, 2H) 3.84 (br. s., 5H) 3.94 (s, 6H) 4.72-4.89 (m, 1H) C$_{27}$H$_{53}$NO$_6$P$^{1+}$ low resolution ESI-MS calculated: 502.36, found: 502.36.

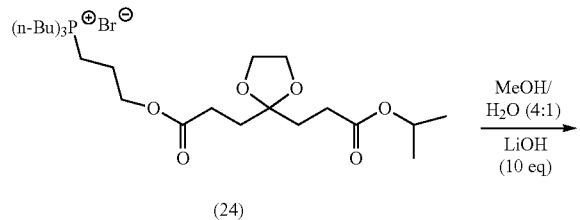

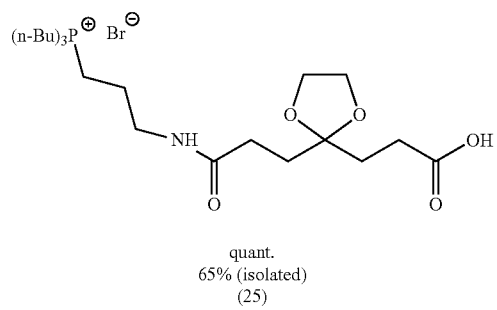

quant.
65% (isolated)
(25)

Tributyl(3-(3-(2-(3-hydroxy-3-oxopropyl)-1,3-dioxolan-2-yl)propanamido) propyl)phosphonium bromide (25)

Compound (24) (0.25 g, 0.4 mmol) was solvated in 2.5 mL of MeOH to which was added 10 eq of LiOH (0.1 g, 4 mmol) in mL of water.

This mixture was allowed to stir for 3 h until all starting material was consumed. The solution was brought to neutrality by the addition of 1M HCl in MeOH. This mixture was purified by column chromatography (DCM:MeOH with 1% AcOH, 100:0→90:10). Isolated yield of (25): 0.20 g (95%).

$^1$H NMR (300 MHz, CHLOROFORM-d) δ ppm 0.91 (t, J=6.74 Hz, 9H) 1.25 (s, 6H) 1.38-1.59 (m, 11H) 1.96-2.05 (m, 7H) 2.15-2.30 (m, 9H) 2.40 (t, J=7.03 Hz, 8H) 3.28-3.44 (m, 2H) 3.84 (br. s., 5H) 3.94 (s, 6H) C$_{24}$H$_{47}$NO$_5$P$^{1+}$ low resolution ESI-MS calculated: 460.31, found: 460.30.

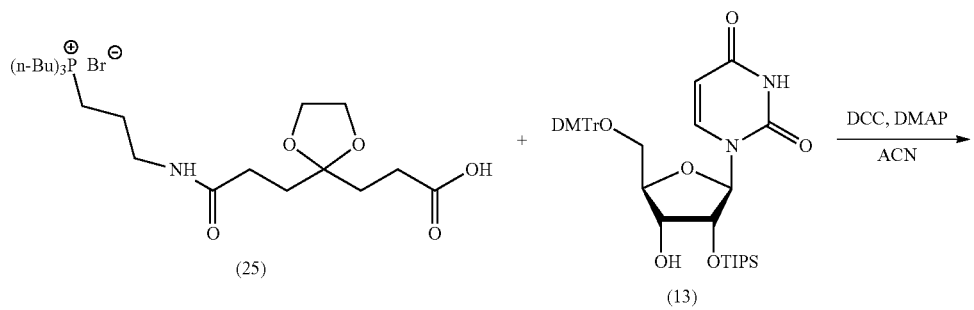

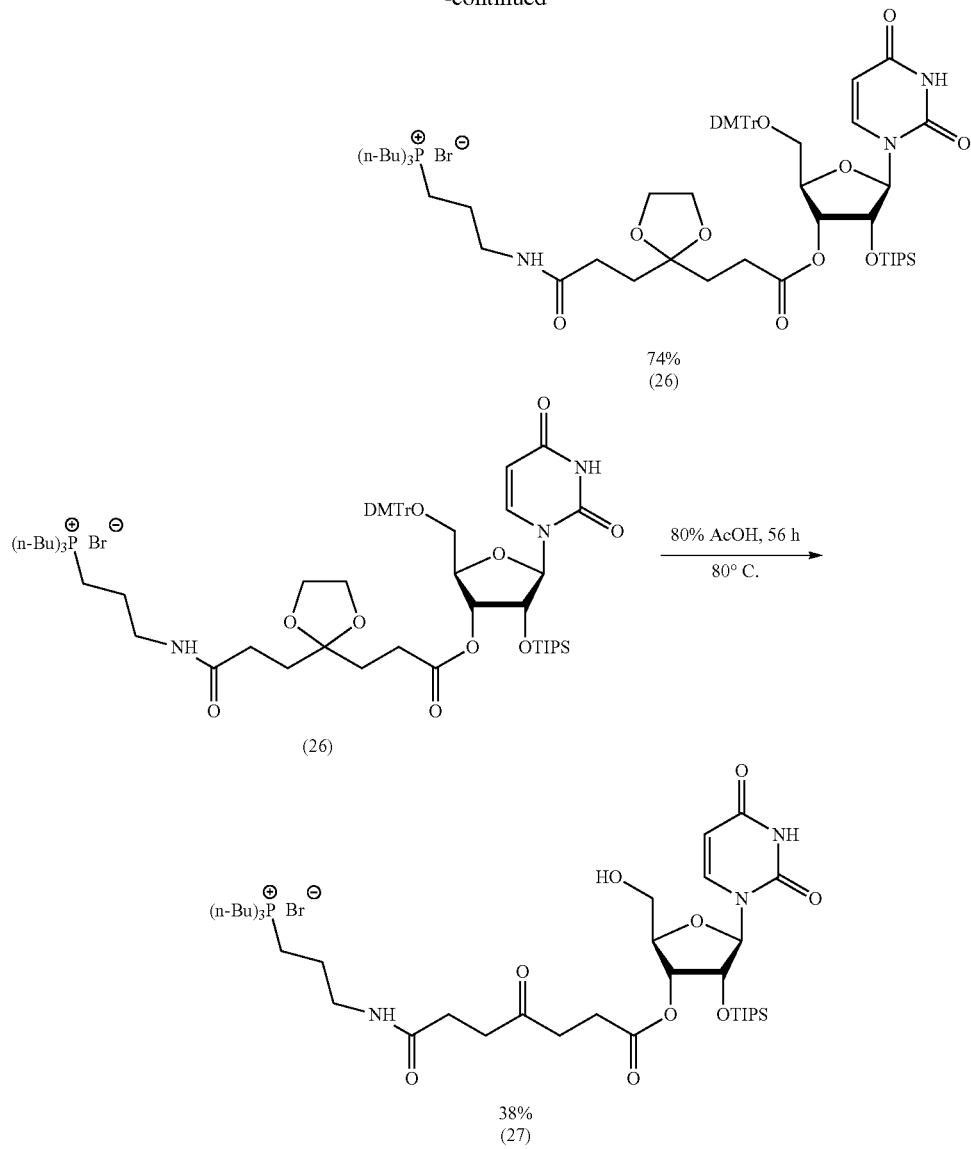

5'-DMTr-2'-TIPS-3'-[tributyl(3-(3-(2-(2-carboxyethyl)-1,3-dioxolan-2-yl)propanamido)propyl)phosphonium bromide] (26)

To a solution of compound (25) (0.2 g, 0.37 mmol) in ACN (1 mL) was added TBTU (0.19 g, 0.6 mmol), triethylamine (0.5 mL) and compound (13) (0.42 g, 0.6 mmol). The resulting mixture was allowed to stir for 12 h until the starting material (25) was completely consumed. The reaction mixture was diluted with ethyl acetate and extracted with 5% NaHCO$_3$×2 and once with brine. The organic layer was dried and concentrated, taken up in minimal amounts of DCM at precipitated in 100 ml of MTBE, filtered over Celite©. Isolated yield of (26): 0.20 g (45%).

$^1$H NMR (300 MHz, CHLOROFORM-d) δ ppm 0.91 (t, J=6.74 Hz, 9H) 1.02-1.59 (m, 38H) 1.96-2.05 (m, 7H) 2.15-2.30 (m, 9H) 2.40 (t, J=7.03 Hz, 8H) 3.37-3.40 (m, 4H) 3.78-3.94 (br. m, 17H) 4.15 (d, J=2.77 Hz, 1H) 4.63-4.67 (m, 1H) 5.31 (dd, J=5.14, 2.96 Hz, 1H) 5.40-5.46 (m, 1H) 5.42 (s, 1H) 5.99 (d, J=6.32 Hz, 1H) 6.87-6.93 (m, 4H) 7.27-7.37 (m, 7H) 7.41-7.45 (m, 2H) 7.75 (d, J=8.30 Hz, 1H) $C_{63}H_{95}N_3O_{12}PSi^{1+}$ low resolution ESI-MS calculated: 1144.64, found: 1144.7.

2'-TIPS-3'-[(tributyl(3-(7-oxy-4,7-dioxoheptanamido)propyl)phosphonium chloride] uridine (27)

Compound (26) (0.228 g, 0.199 mmol) was solvated with 15 ml of 80% acetic acid in water and first allowed to stir at room temperature for 6 h showing almost no loss of the ketal, but complete loss of the trityl group. The reaction was then heated to 50° C. for 12 h which then showed about a 25% loss of ketal. Then the reaction was placed at 80° C. for 40 h which then showed almost complete consumption of starting material. The mixture was diluted with DCM and extracted with 3 portions of saturated NaHCO$_3$. The organic layers were dried with MgSO$_4$ and concentrated to dryness. The crude mixture was then solvated in minimal amounts of DCM and precipitated in MTBE to remove trityl and some cleaved TIPS. The compound was then filtered over Celite© and collected with DCM. The resulting mixture then had to be purified by column chromatography (0-15% MeOH in DCM) affording compound 27 in moderate yield of 62%, 0.108 g.

$^1$H NMR (400 MHz, CHLOROFORM-d) δ ppm 0.90-1.13 (m, 37H) 1.39-1.52 (m, 17H) 1.78-1.87 (m, 2H) 1.90-1.95 (m, 1H) 2.00-2.03 (m, 1H) 2.06-2.25 (m, 11H) 2.27-2.34 (m, 5H) 2.44-2.60 (m, 4H) 2.73-2.80 (m, 2H) 3.37 (d, J=5.47 Hz, 1H) 3.68-3.92 (m, 3H) 4.16-4.22 (m, 1H) 4.64-4.72 (m, 1H) 5.01-5.13 (m, 1H) 5.62-5.72 (m, 1H) 5.78 (dd, J=7.62, 4.49 Hz, 1H) 8.07 (d, J=7.82 Hz, 1H) 8.23 (d, J=8.21 Hz, 1H) 8.70-9.11 (m, 1H)

$^{13}$C NMR (101 MHz, CHLOROFORM-d) δ ppm 12.05 (s, 1C) 12.16 (s, 1C) 13.37 (s, 1C) 17.66 (s, 1C) 17.67 (s, 1C) 17.75 (s, 1C) 17.77 (s, 1C) 17.79 (s, 1C) 17.85 (s, 1C) 18.25 (s, 1C) 18.73 (s, 1C) 21.25 (s, 1C) 23.44 (s, 1C) 23.50 (s, 1C) 23.55 (s, 1C) 23.80 (s, 1C) 23.94 (s, 1C) 125.81 (s, 1C) 128.58 (s, 1C) 139.39 (s, 1C) 143.40 (s, 1C) 183.06 (s, 1C) 207.78 (s, 1C)

$^{31}$P NMR (81 MHz, CHLOROFORM-d) δ ppm 33.29 (s, 1P) 33.36 (s, 1P) 33.42 (s, 1P) 33.51 (s, 1P) 33.72 (s, 1P) 33.78 (s, 1P) C$_4$OH$_{73}$N$_3$O$_9$PSi$^{+1}$ low resolution ESI-MS calculated: 798.48, found: 798.51.

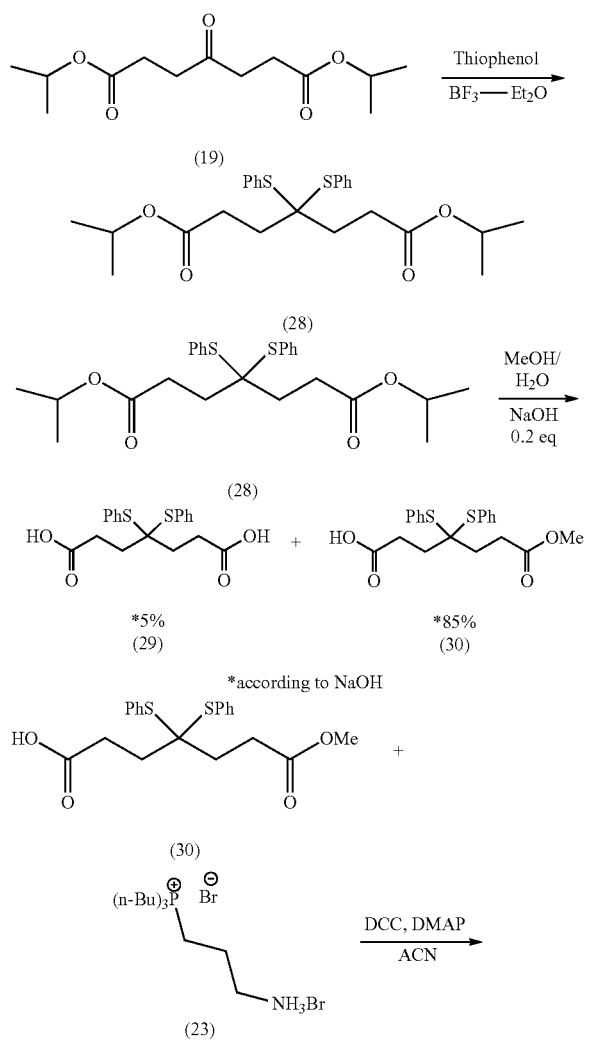

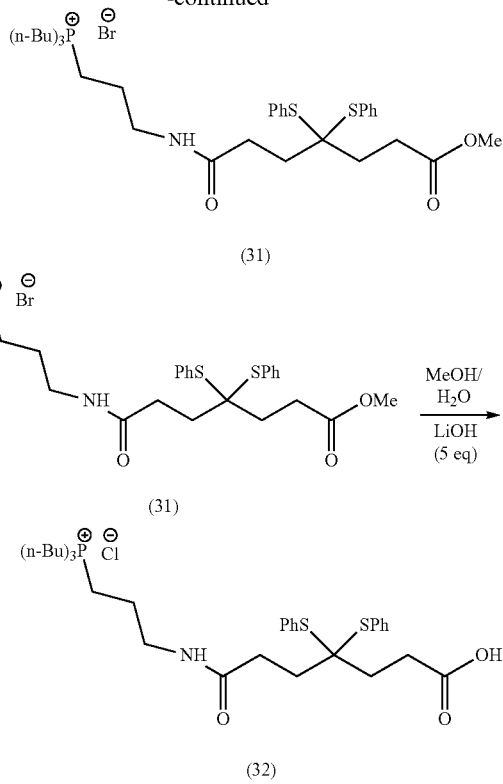

diisopropyl 4,4-bis(phenylthio)heptanedioate (28)

compound (19) (4.69 g, 18.1 mmol) was solvated in 36.3 mL of DCM (0.5 M) followed by 4.83 mL, 2.6 eq of thiophenol (5.203 g, 47.2 mmol). This mixture was cooled down to 0° C. in an ice bath then treated, drop-wise, with stirring 5.75 mL of boron trifluoride etherate (BF$_3$.O(Et)$_2$) (6.44 g, 45.4 mmol). This mixture was stirred and allowed to slowly warm up to room temperature over night. After 10 hours, the mixture was cooled to 0° C. and concentrated NaHCO$_3$ was added carefully to the solution quenching the Boron trifluoride followed by DCM to dilute. The mixture was extracted ×3 with saturated sodium bicarbonate, dried with MgSO$_4$ concentrated to dryness. The compound was purified from excess thiopenol by column chromatography (0→20% Hexanes:ethylacetate) yielding quantitative conversion.

$^1$H NMR (400 MHz, CHLOROFORM-d) δ ppm 1.21 (d, J=6.64 Hz, 12H) 1.78-2.03 (m, 4H) 2.58-2.84 (m, 4H) 4.96 (dt, J=12.60, 6.40 Hz, 2H) 7.30-7.45 (m, 6H) 7.62 (d, J=6.64 Hz, 4H)

$^{13}$C NMR (101 MHz, CHLOROFORM-d) δ ppm 21.82 (s, 1C) 30.20 (s, 1C) 32.87 (s, 1C) 67.80 (s, 1C) 128.80 (s, 1C) 129.38 (s, 1C) 130.55 (s, 1C) 136.83 (s, 1C) 172.42 (s, 1C) C$_{25}$H$_{32}$O$_4$S$_2$ low resolution ESI-MS calculated: 460.17, found: 483.23.

4,4-bis(phenylthio)heptanedioic acid (29) and 7-isopropoxy-7-oxo-4, 4-bis(phenylthio)heptanoic acid (30)

Compound 28 (6.43 g, 14.0 mmol) was solvated in methanol:water 4:1 200 ml and cooled to 0° C. in an ice bath. 0.2 eq of NaOH (0.11 g, 2.8 mmol) was solvated in 10 mL of H₂O and added drop-wise to the above solution. This mixture was allowed to react for 12 h then was concentrated to remove a significant amount of methanol, then 1M HCL was added followed by ethyl acetate and extracted ×2 with 1M HCL. The organic layer was dried with MgSO₄, concentrated to dryness yielding a very complex mixture of compounds. After purifying each spot by column chromatography (0→30% Hexanes:ethylacetate with 1% AcOH) it was determined that not all the methanol was removed and neither was all the HCL, as no brine wash was done at the end and significant transesterification of the isopropyl ester to the methyl ester was observed. The monoester product (30) during this scale-up was completely converted to the methyl ester product in 85% yield.

(29)

$^1$H NMR (400 MHz, DMSO-d₆) δ ppm 1.45-2.01 (m, 4H) 2.50-2.64 (m, 4H) 7.35-7.49 (m, 6H) 7.52-7.65 (m, 4H) 12.19 (s, 2H)

$^{13}$C NMR (101 MHz, DMSO-d₆) δ ppm 29.62 (s, 1C) 32.78 (s, 1C) 38.81 (s, 1C) 68.19 (s, 1C) 129.54 (s, 1C) 130.05 (s, 1C) 130.44 (s, 1C) 136.77 (s, 1C) 174.01 (s, 1C) 178.31 (s, 1C) C₁₉H₂₀O₄S₂ low resolution ESI-MS calculated: 376.08, found: 399.21.

(30)

$^1$H NMR (400 MHz, CHLOROFORM-d) δ ppm 1.82-2.04 (m, 4H) 2.64-2.84 (m, 4H) 3.65 (s, 3H) 7.28-7.45 (m, 6H) 7.54-7.67 (m, 4H)

$^{13}$C NMR (101 MHz, CHLOROFORM-d) δ ppm 29.61 (s, 1C) 29.70 (s, 1C) 32.65 (s, 1C) 32.93 (s, 1C) 51.86 (s, 1C) 66.90 (s, 1C) 128.96 (s, 1C) 129.54 (s, 1C) 130.30 (s, 1C) 136.75 (s, 1C) 173.46 (s, 1C) 179.34 (s, 1C) 183.06 (s, 1C)

C₂₀H₂₂O₄S₂ low resolution ESI-MS calculated: 390.1, found: 413.12.

tributyl(3-(7-methoxy-7-oxo-4,4-bis(phenylthio) heptanamido)propyl) phosphonium bromide (31)

Compound (30) (0.5 g, 1.28 mmol) 1.5 eq of DCC (0.396 g, 1.92 mmol) were solvated in 5 mL of ACN. Phosphonium tag (23) 1.15 eq (0.62 g, 1.47 mmol) was solvated in 2 mL of dry pyridine and added directly to the above solution followed by catalytic amount of DMAP. The reaction was allowed to stir for 6 h until the reaction was complete by MS. The reaction was taken up in ethyl acetate and extracted ×2 with ammonium chloride and once with brine. The organic layer was dried with magnesium sulfate and concentrated to dryness. The mixture was purified by column chromatography to remove excess tag (0→15% MeOH:DCM) and in the process a significant amount of material was lost on the column, yielding 63%, 0.54 g $^1$H NMR (300 MHz, CHLOROFORM-d) δ ppm 0.85-1.05 (m, 9H) 1.36-1.63 (m, 13H) 1.80-2.04 (m, 7H) 2.17-2.35 (m, 6H) 2.58-2.81 (m, 6H) 3.30-3.46 (m, 2H) 3.60 (s, 3H) 7.28-7.40 (m, 6H) 7.59-7.76 (m, 4H) 8.51 (t, J=5.27 Hz, 1H)

$^{13}$C NMR (75 MHz, CHLOROFORM-d) δ ppm 13.44 (s, 1C) 13.46 (s, 1C) 16.92 (s, 1C) 17.57 (s, 1C) 18.59 (s, 1C) 19.22 (s, 1C) 21.27 (s, 1C) 21.33 (s, 1C) 23.63 (s, 1C) 23.69 (s, 1C) 23.88 (s, 1C) 24.08 (s, 1C) 29.66 (s, 1C) 30.95 (s, 1C) 31.33 (s, 1C) 32.82 (s, 1C) 33.40 (s, 1C) 39.16 (s, 1C) 39.36 (s, 1C) 51.62 (s, 1C) 67.92 (s, 1C) 128.75 (s, 1C) 129.14 (s, 1C) 130.82 (s, 1C) 136.91 (s, 1C) 173.24 (s, 1C) 173.57 (s, 1C)

C₃₅H₅₅NO₃PS₂⁺ low resolution ESI-MS calculated: 632.92, found: 632.91.

tributyl(3-(6-carboxy-4,4-bis(phenylthio)hexanamido)propyl)phosphonium chloride (32)

Compound (31) (0.5 g, 0.75 mmol) was solvated in 8 mL of MeOH to which was added 5 eq of NaOH (0.15 g, 3.7 mmol) in 2 mL of water. This mixture was allowed to stir for 3 h until all starting material was consumed. The solution was brought to neutrality by the addition of 1M HCl. This mixture was purified by HCl extraction followed by brine ×3, dried and concentrated. Quantitative recovery.

$^1$H NMR (300 MHz, CHLOROFORM-d) δ ppm 0.98 (t, J=6.59 Hz, 9H) 1.52 (br. s., 13H) 1.88 (d, J=9.67 Hz, 3H) 2.01 (d, J=4.10 Hz, 4H) 2.08-2.25 (m, 7H) 2.49-2.64 (m, 4H) 2.68 (t, J=6.59 Hz, 2H) 3.39 (d, J=4.40 Hz, 2H) 7.12-7.21 (m, 3H) 7.30-7.41 (m, 6H) 7.65-7.79 (m, 4H) 8.00 (br. s., 1H)

C₃₄H₅₃NO₃PS₂⁺ low resolution ESI-MS calculated: 618.32, found: 618.32.

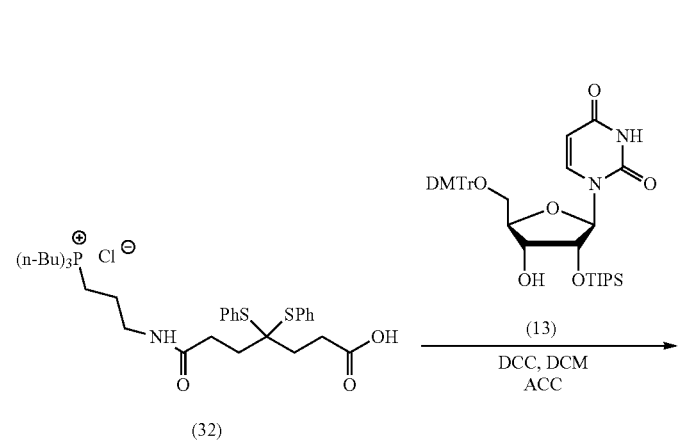

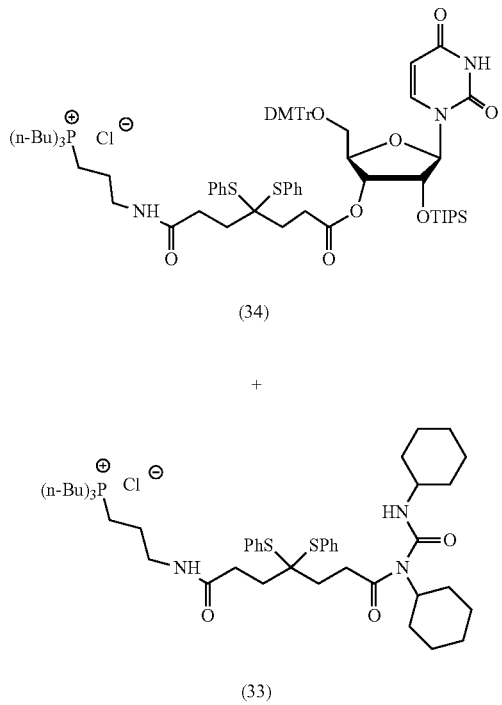

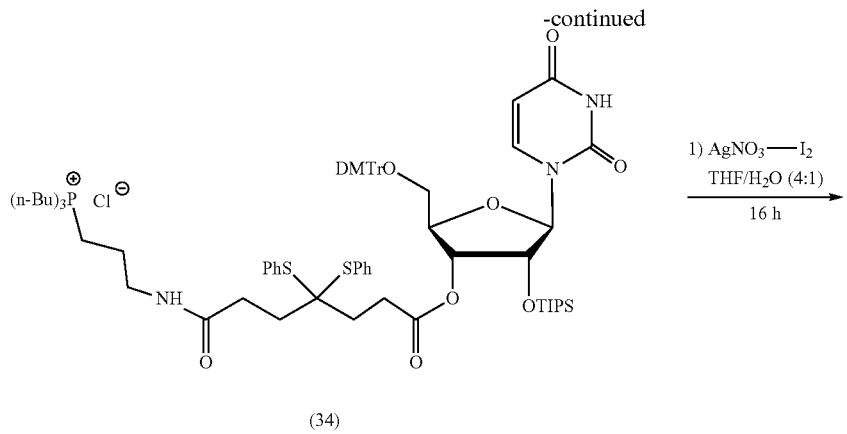

(34)

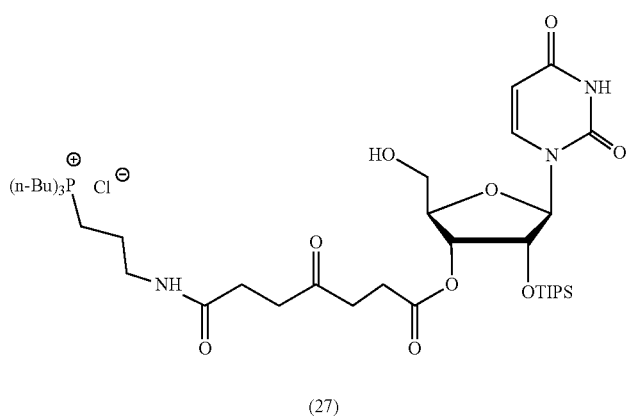

(27)

5'-DMTr-2'-TIPS-3'-[(tributyl(3-(7-oxo-4,4-bis(phenylthio)heptanamido) propyl)phosphonium bromide] uridine (34)

Compound (32) (0.56 g, 0.85 mmol) and 2 eq of DCC (0.35 g, 1.7 mmol) were solvated in 8 mL of ACN. To the above solution 2 eq of nucleoside (13) 1.23 g, 1.7 mmol) was added followed by sub stoichiometric amounts of DMAP. The reaction was allowed to stir for 6 h until all starting material was consumed, monitored by MS. The sample was diluted with ethyl acetate and extracted with ammonium chloride ×2 and once with brine. The organic layer was dried with magnesium sulphate and concentrated to dryness. The mixture was then precipitated in MTBE-Hexanes 50:50 to remove any unreacted DCC then purified by column chromatography (0→10% MeOH-DCM) affording a mixture of compound (34) and (33) as an inseparable mixture in 89% yield.

$^1$H NMR (400 MHz, CHLOROFORM-d) δ ppm 0.81-1.15 (m, 31H) 1.35-1.61 (m, 13H) 1.75-2.06 (m, 7H) 2.12-2.35 (m, 6H) 2.50-2.94 (m, 6H) 3.26-3.52 (m, 4H) 3.77 (s, 6H) 4.19 (d, J=2.34 Hz, 1H) 4.66 (t, J=5.47 Hz, 1H) 5.24 (d, J=8.21 Hz, 2H) 5.35 (dd, J=4.88, 2.54 Hz, 1H) 6.09 (d, J=5.86 Hz, 1H) 6.03-6.16 (m, 1H) 6.81 (dd, J=8.60, 1.56 Hz, 4H) 7.17-7.36 (m, 17H) 7.27-7.28 (m, 1H) 7.59-7.68 (m, 4H) 7.84 (d, J=8.21 Hz, 1H) 8.45 (t, J=5.67 Hz, 1H) 9.36 (br. s., 1H)

$^{13}$C NMR (101 MHz, CHLOROFORM-d) δ ppm 12.03 (s, 1C) 13.44 (s, 1C) 17.60 (s, 1C) 17.77 (s, 1C) 18.56 (s, 1C) 19.03 (s, 1C) 23.52 (s, 1C) 23.57 (s, 1C) 23.83 (s, 1C) 23.97 (s, 1C) 55.20 (s, 1C) 67.53 (s, 1C) 76.95 (s, 1C) 77.26 (s, 1C) 77.48 (s, 1C) 77.59 (s, 1C) 87.45 (s, 1C) 113.25 (s, 1C) 113.28 (s, 1C) 127.21 (s, 1C) 128.00 (s, 1C) 128.83 (s, 1C) 129.25 (s, 1C) 129.95 (s, 1C) 130.08 (s, 1C) 130.44 (s, 1C) 130.58 (s, 1C) 134.71 (s, 1C) 134.93 (s, 1C) 136.74 (s, 1C) 136.82 (s, 1C) 144.05 (s, 1C) 150.77 (s, 1C) 158.64 (s, 1C) 158.67 (s, 1C) 163.38 (s, 1C) 172.16 (s, 1C) 172.94 (s, 1C)

$C_{73}H_{101}N_3O_{10}PS_2Si^+$ low resolution ESI-MS calculated: 1302.64, found: 1302.45 (DCC failure product: $C_{47}H_{75}N_3O_3PS_2+$ resolution ESI-MS calculated: 824.50, found: 824.32).

2'-TIPS-3'-[(tributyl(3-(7-oxy-4,7-dioxoheptanamido)propyl)phosphonium chloride] uridine (27)

Compound (34) (0.51 g, 0.38 mmol) was solvated in 3.8 ml of THF:water 8:2 mixture to which 1.5 eq of silver nitrate was added (96 mg, 0.57 mmol). A cloudy white ppt was formed. Molecular iodine was then added (48 mg, 0.38 mmol). This mixture was allowed to stir for 16 h until all starting material was consumed. The sample was then filtered from precipitated silver iodine over Celite© and washed with ACN. The sample was then condensed, resuspended in DCM and precipitated in MTBE yielding pure compound (27) in 91% yield.

See previous synthesis of (27) for NMR data.

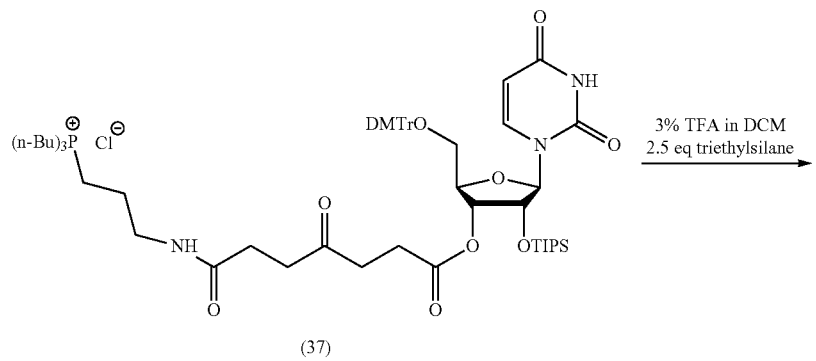

(37)

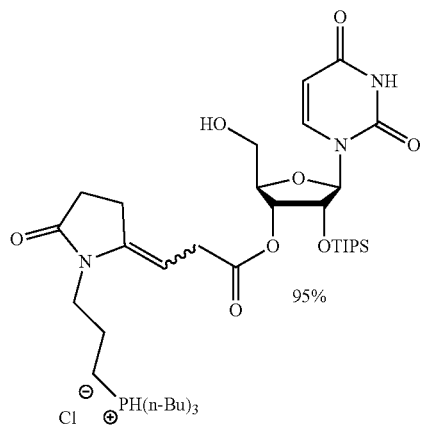

(38)

Compound (37) (0.12 g, 0.105 mmol) was solvated/ reacted directly with 10 mL of a 3% TFA solution in DCM followed by 2.5 eq of triethylsilane to quench the trityl cation. This reaction was allowed to stir for 10 min before 4 mL of methanol was added to further quench the trityl cation. This was followed by 20 mL of toluene then the mixture was concentrated to dryness, taken up in DCM and precipitated in MTBE yielding compound (38) in 95% yield (62 mg, 0.1 mmol)

$^1$H NMR (300 MHz, CHLOROFORM-d) δ ppm 0.78-1.14 (m, 43H) 1.47 (br. s., 18H) 1.66-1.94 (m, 3H) 1.97-2.86 (m, 20H) 2.99-3.23 (m, 1H) 3.34 (br. s., 1H) 3.52-4.01 (m, 3H) 4.16 (br. s., 1H) 4.60-4.80 (m, 1H) 4.93 (br. s., 1H) 5.04-5.24 (m, 1H) 5.72 (br. s., 2H) 7.70 (d, J=7.91 Hz, 1H) 7.96-8.28 (m, 2H) 9.20 (br. s., 1H)

$^{13}$C NMR (75 MHz, CHLOROFORM-d) δ ppm 12.01 (s, 1C) 12.03 (s, 1C) 12.42 (s, 1C) 13.24 (s, 1C) 16.69 (s, 1C) 17.58 (s, 1C) 17.68 (s, 1C) 17.70 (s, 1C) 18.06 (s, 1C) 18.14 (s, 1C) 18.69 (s, 1C) 18.78 (s, 1C) 21.32 (s, 1C) 23.27 (s, 1C) 23.33 (s, 1C) 23.71 (s, 1C) 23.91 (s, 1C) 26.89 (s, 1C) 28.18 (s, 1C) 28.44 (s, 1C) 29.49 (s, 1C) 32.14 (s, 1C) 36.84 (s, 1C) 37.34 (s, 1C) 61.24 (s, 1C) 73.45 (s, 1C) 73.66 (s, 1C) 74.04 (s, 1C) 83.52 (s, 1C) 88.78 (s, 1C) 89.46 (s, 1C) 92.69 (s, 1C) 102.60 (s, 1C) 114.66 (s, 1C) 118.55 (s, 1C) 125.79 (s, 1C) 127.98 (s, 1C) 128.61 (s, 1C) 133.49 (s, 1C) 133.90 (s, 1C) 141.68 (s, 1C) 141.79 (s, 1C) 150.96 (s, 1C) 163.71 (s, 1C) 163.83 (s, 1C) 170.93 (s, 1C) 171.95 (s, 1C) 172.99 (s, 1C) 176.18 (s, 1C) 207.81 (s, 1C)

$C_{40}H_{71}N_3O_8PSi+$ low resolution ESI-MS calculated: 780.47, found: 780.58.

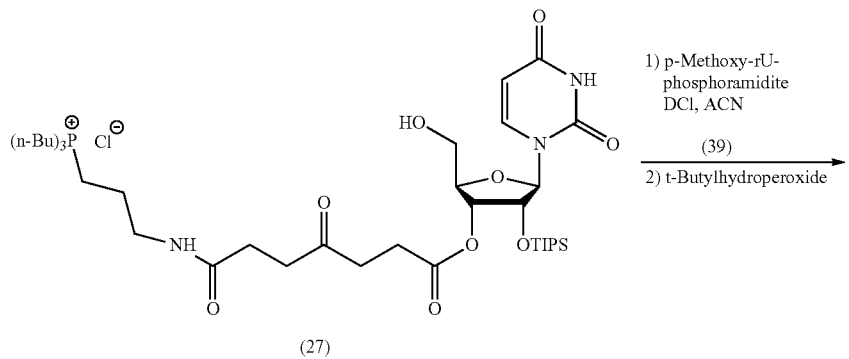

(27)

-continued
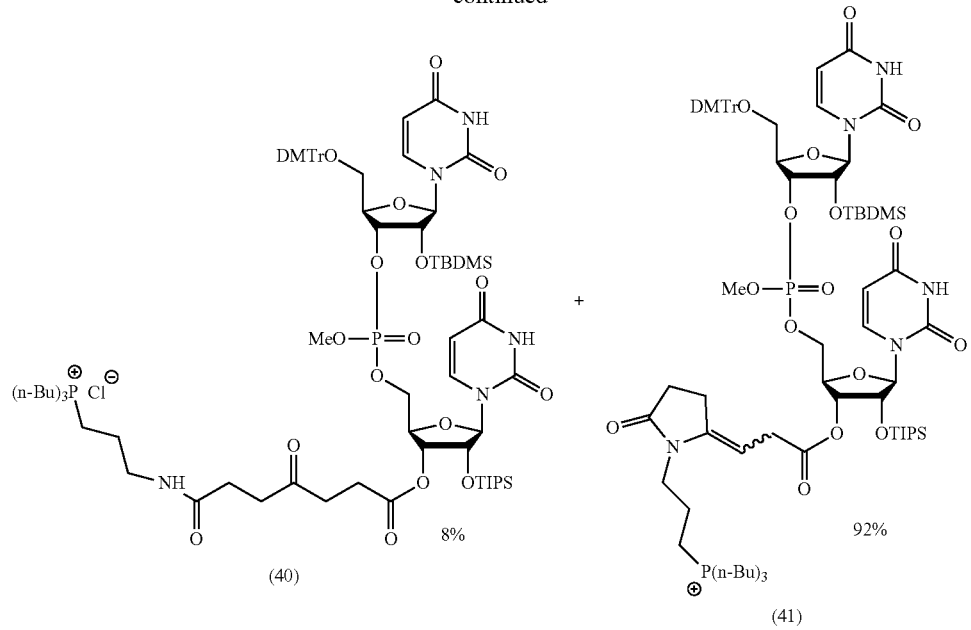
Compound 41 and 42 Mixture
¹H NMR (300 MHz, CHLOROFORM-d) δ ppm 0.07-0.16 (m, 8H) 0.83-1.05 (m, 62H) 1.09-1.28 (m, 9H) 1.33 (d, J=6.15 Hz, 18H) 1.47 (br. s., 20H) 1.91 (br. s., 4H) 2.14 (br. s., 11H) 2.21-2.38 (m, 6H) 2.52 (br. s., 2H) 2.64 (br. s., 2H) 3.14 (br. s., 1H) 3.21 (s, 1H) 3.27-3.41 (m, 4H) 3.48 (d, J=7.91 Hz, 3H) 3.66 (s, 3H) 3.62 (s, 3H) 3.78 (d, J=5.57 Hz, 12H) 3.89 (s, 2H) 4.17-4.35 (m, 4H) 4.50 (br. s., 3H) 4.89 (br. s., 1H) 5.13-5.24 (m, 2H) 5.92-6.03 (m, 2H) 6.77-6.87 (m, 6H) 7.13-7.36 (m, 26H) 7.51 (d, J=7.91 Hz, 1H) 7.69-7.74 (m, 2H) 7.80-7.88 (m, 2H)
³¹P NMR (81 MHz, CHLOROFORM-d) δ ppm −0.91 (s, 1P) −0.36 (s, 1P) 33.91 (s, 1P) 33.96 (s, 1P)
$C_{77}H_{116}N_5O_{18}P_2Si_2+$ low resolution ESI-MS calculated: 1516.73, found: 1516.62.
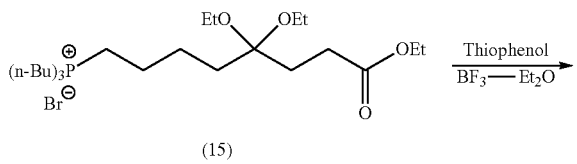
(15)
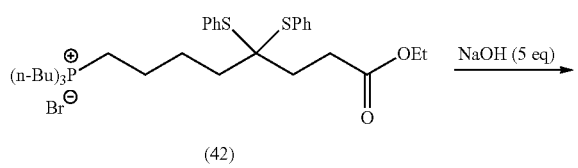
(42)
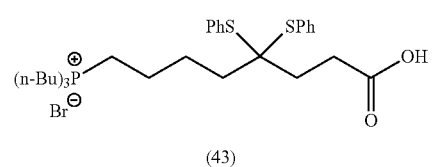
(43)

-continued
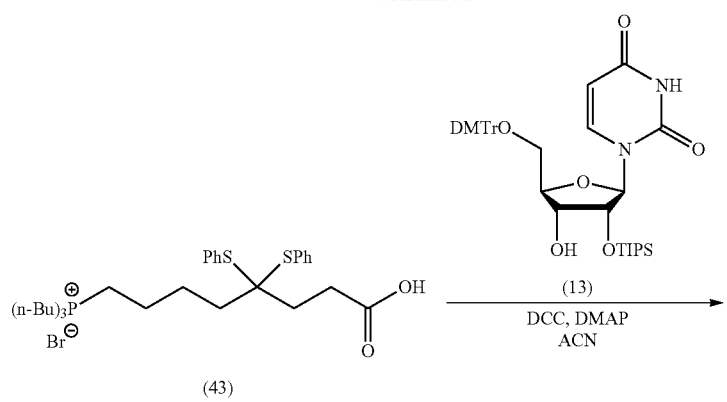
(43) + (13) →[DCC, DMAP, ACN]
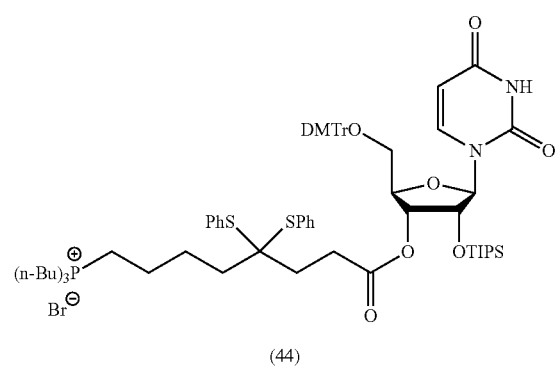
(44)
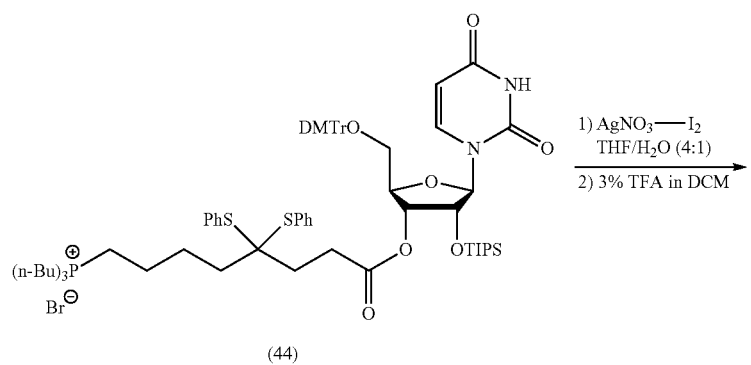
(44) →[1) AgNO₃—I₂ THF/H₂O (4:1)][2) 3% TFA in DCM]
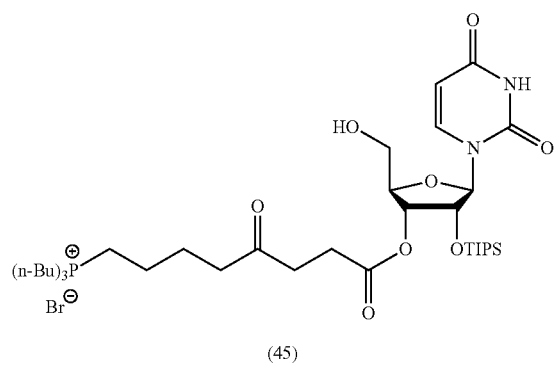
(45)

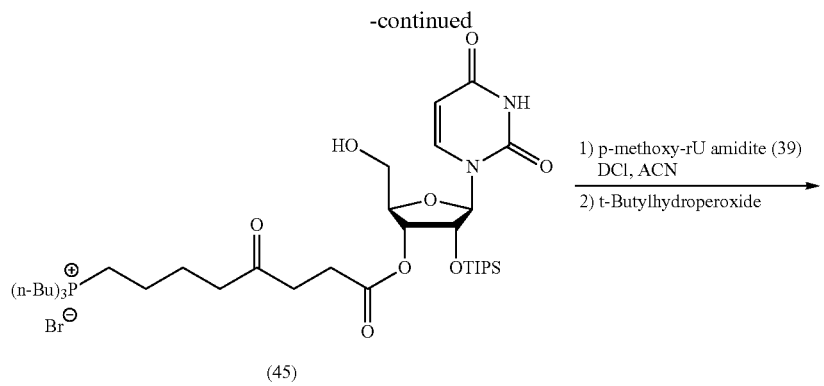

(45)

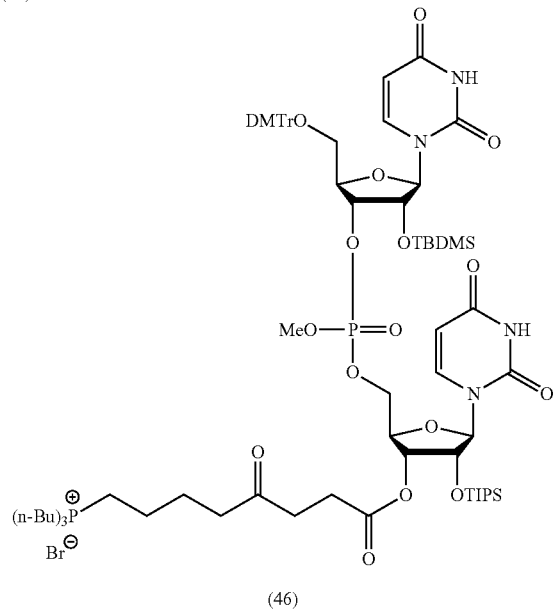

(46)

tributyl (8-ethoxy-8-oxo-5, 5-bis(phenylthio)octyl) phosphonium bromide (42)

Compound (15) (0.82 g, 1.51 mmol) and 3 eq of thiophenol (0.38 mL, 3.0 mmol) were solvated with 6 mL of DCM and cooled to 0° C. in an ice bath. Boron trifluoride etherate (0.46 mL, 4.53 mmol) was then added drop-wise over 10 min. The mixture was allowed to stir at 0° C. for 30 min then allowed to slowly warm up to room temperature for 4 h. The mixture was then cooled to 0° C. again and quenched with saturated sodium bicarbonate and extracted ×3 with DCM. The organic layers were combined, dried, and concentrated to dryness. The mixture was then purified by chromatography (0→5% DCM-MeOH) affording pure (42) in good yield, 93%.

$^1$H NMR (400 MHz, CHLOROFORM-d) δ ppm 0.96 (t, J=7.03 Hz, 9H) 1.19-1.28 (m, 3H) 1.33-1.60 (m, 17H) 1.73-1.85 (m, 2H) 1.87-1.98 (m, 2H) 2.26-2.38 (m, 2H) 2.39-2.52 (m, 7H) 2.63-2.75 (m, 2H) 4.09 (q, J=7.29 Hz, 2H) 7.24-7.28 (m, 2H) 7.30-7.42 (m, 5H) 7.63 (dd, J=7.42, 1.95 Hz, 3H)

$^{13}$C NMR (101 MHz, CHLOROFORM-d) δ ppm 13.44 (s, 1C) 14.10 (s, 1C) 18.59 (s, 1C) 19.06 (s, 1C) 23.68 (s, 1C) 23.73 (s, 1C) 23.79 (s, 1C) 23.94 (s, 1C) 29.77 (s, 1C) 32.86 (s, 1C) 36.85 (s, 1C) 60.46 (s, 1C) 67.75 (s, 1C) 128.77 (s, 1C) 129.04 (s, 1C) 129.23 (s, 1C) 130.77 (s, 1C) 136.42 (s, 1C) 172.75 (s, 1C)

tributyl(7-carboxy-5,5-bis(phenylthio)heptyl)phosphonium bromide (43)

Compound (42) (0.75 g, 1.2 mmol) was solvated with 5 mL of a 4:1 mixture of methanol:water and added to that 5 eq of NaOH (0.24 g, 6 mmol) and was allowed to stir for 2 hours. The reaction was quenched with saturated sodium bicarbonate, then concentrated to remove the methanol. The mixture was then take up in ethyl acetate and extracted with 1M HCl once and three times with brine. The organic layer was dried with magnesium sulfate and condensed to dryness producing compound (43) in near quantitative yield.

$^1$H NMR (400 MHz, CHLOROFORM-d) δ ppm 0.85-1.05 (m, 9H) 1.19-1.42 (m, 4H) 1.45 (br. s., 11H) 1.58 (br. s., 2H) 1.75 (br. s., 2H) 1.94 (t, J=7.23 Hz, 2H) 2.02 (d, J=1.17 Hz, 1H) 2.11-2.27 (m, 8H) 2.75 (t, J=7.42 Hz, 2H) 7.18-7.37 (m, 7H) 7.65 (d, J=7.82 Hz, 4H)

$^{13}$C NMR (75 MHz, CHLOROFORM-d) δ ppm 13.41 (s, 1C) 18.19 (s, 1C) 18.82 (s, 1C) 23.44 (s, 1C) 23.50 (s, 1C) 23.74 (s, 1C) 23.93 (s, 1C) 68.37 (s, 1C) 76.81 (s, 1C) 77.24 (s, 1C) 77.66 (s, 1C) 128.77 (s, 1C) 129.15 (s, 1C) 131.08 (s, 1C) 136.38 (s, 1C) 174.83 (s, 1C)

5'-DMTr-2'-TIPS-3'-[tributyl(7-oxy-5,5-bis(phenylthio)heptyl) phosphonium bromide] uridine (44)

Compound (43) (0.59 g, 0.99 mmol) and 1.5 eq of DCC (0.30 g, 1.48 mmol) were solvated in 9.5 mL of ACN. To the above solution 1.5 eq of nucleoside (13) (1.03 g, 1.48 mmol) was added followed by sub stoichiometric amounts of DMAP. The reaction was allowed to stir for 6 h until all starting material was consumed, monitored by MS. The sample was diluted with ethyl acetate and extracted with ammonium chloride ×2 and once with brine. The organic layer was dried with magnesium sulphate and concentrated to dryness. The mixture was then precipitated in MTBE-Hexanes 50:50 to remove any unreacted DCC then purified by column chromatography (0→10% MeOH-DCM) affording compound (44) in 83% yield (1.05 g, 0.82 mmol)

$^1$H NMR (400 MHz, CHLOROFORM-d) δ ppm 0.94-1.18 (m, 39H) 1.32-1.60 (m, 23H) 1.64-1.72 (m, 3H) 1.74-1.84 (m, 3H) 1.90-2.17 (m, 15H) 2.76-2.84 (m, 2H) 3.42-3.51 (m, 3H) 3.79 (d, J=0.78 Hz, 7H) 4.10-4.15 (m, 2H) 4.67-4.71 (m, 1H) 5.26-5.30 (m, 1H) 5.40 (dd, J=5.08, 2.74 Hz, 1H) 6.10 (d, J=6.25 Hz, 1H) 6.81-6.85 (m, 5H) 7.21-7.38 (m, 23H) 7.60-7.68 (m, 5H) 7.88 (d, J=8.21 Hz, 1H) 8.61 (s, 1H)

$^{13}$C NMR (75 MHz, CHLOROFORM-d) δ ppm 12.13 (s, 1C) 13.38 (s, 1C) 17.68 (s, 1C) 17.85 (s, 1C) 18.01 (s, 1C) 18.64 (s, 1C) 23.45 (s, 1C) 23.52 (s, 1C) 23.76 (s, 1C) 23.96 (s, 1C) 25.02 (s, 1C) 25.65 (s, 1C) 33.86 (s, 1C) 55.27 (s, 1C) 67.41 (s, 1C) 76.69 (s, 1C) 77.11 (s, 1C) 77.53 (s, 1C) 87.57 (s, 1C) 113.33 (s, 1C) 113.36 (s, 1C) 128.05 (s, 1C) 129.00 (s, 1C) 129.43 (s, 1C) 130.02 (s, 1C) 130.15 (s, 1C) 130.71 (s, 1C) 130.74 (s, 1C) 134.75 (s, 1C) 134.93 (s, 1C) 136.52 (s, 1C) 144.09 (s, 1C) 150.66 (s, 1C) 158.74 (s, 1C) 158.78 (s, 1C) 163.29 (s, 1C) 172.20 (s, 1C)

$^{31}$P NMR (81 MHz, CHLOROFORM-d) δ ppm 32.73 (s, 1P)

2'-TIPS-3'-[tributyl(7-oxy-5,5-bis(phenylthio)heptyl) phosphonium bromide] uridine (45)

Compound (44) (0.76 g, 0.59 mmol) was solvated in 8 ml of THF:water 8:2 mixture to which 1.5 eq of silver nitrate was added (150 mg, 0.89 mmol). A cloudy white ppt was formed. Molecular iodine was then added (75 mg, 0.59 mmol). This mixture was allowed to stir for 16 h until all starting material was consumed. The sample was then filtered from precipitated silver iodine over Celite© and washed with ACN. The sample was then condensed, resuspended in DCM and precipitated in MTBE yielding pure compound (45) in 70% yield 0.326 g.

$^1$H NMR (500 MHz, CHLOROFORM-d) δ ppm 0.91-1.10 (m, 11H) 1.44-1.57 (m, 5H) 1.63 (dd, J=15.90, 8.07 Hz, 1H) 1.78 (dd, J=14.06, 6.97 Hz, 1H) 2.29-2.40 (m, 3H) 2.41-2.53 (m, 1H) 2.56-2.85 (m, 3H) 3.76-3.92 (m, 1H) 3.98 (s, 1H) 4.11-4.19 (m, 1H) 4.70-4.78 (m, 1H) 5.18 (dd, J=4.89, 3.42 Hz, 1H) 5.75 (d, J=8.07 Hz, 1H) 5.81 (d, J=5.62 Hz, 1H) 8.00 (d, J=8.31 Hz, 1H) 8.67 (br. s., 1H)

$^{13}$C NMR (126 MHz, CHLOROFORM-d) δ ppm 11.93 (s, 1C) 11.96 (s, 1C) 11.98 (s, 1C) 13.37 (s, 1C) 17.50 (s, 1C) 17.52 (s, 1C) 17.54 (s, 1C) 17.57 (s, 1C) 17.58 (s, 1C) 17.60 (s, 1C) 17.62 (s, 1C) 17.65 (s, 1C) 17.66 (s, 1C) 17.67 (s, 1C) 17.69 (s, 1C) 17.71 (s, 1C) 17.72 (s, 1C) 17.78 (s, 1C) 17.80 (s, 1C) 18.59 (s, 1C) 18.77 (s, 1C) 18.97 (s, 1C) 19.15 (s, 1C) 20.80 (s, 1C) 20.84 (s, 1C) 23.54 (s, 1C) 23.57 (s, 1C) 23.77 (s, 1C) 23.88 (s, 1C) 24.35 (s, 1C) 24.47 (s, 1C) 28.00 (s, 1C) 30.88 (s, 1C) 36.93 (s, 1C) 41.11 (s, 1C) 61.25 (s, 1C) 73.72 (s, 1C) 73.96 (s, 1C) 83.72 (s, 1C) 88.91 (s, 1C) 102.72 (s, 1C) 141.92 (s, 1C) 150.83 (s, 1C) 163.77 (s, 1C) 171.98 (s, 1C) 208.11 (s, 1C)

$^{31}$P NMR (81 MHz, CHLOROFORM-d) δ ppm 33.08 (s, 1P)

[5'-DMTr-2'TBDMS-uridine]-[3'-p(OMe)-5']-[2'-TIPS-3'-(tributyl(7-oxy-,5-bis (phenylthio)heptyl) phosphonium bromide)-uridine (46)

Compound (45) (0.326 g, 0.42 mmol) was solvated in 4.2 mL of dry ACN. To this mixture was added 1.5 eq of phosphoramidite (39) (0.52 g, 0.63 mmol) and 1.6 eq of DCI (82 mg, 0.69 mmol). This mixture was stirred for 6 h at room temperature at which point an MS showed complete consumption of starting material. 0.5 mL of tert-butanol was then added to the mixture to react with excess phosphoramidite and make it more soluble in the MTBE mixture. The mixture was then precipitated into MTBE:hexanes 50:50 to remove the excess amidite and butanol. The solid precipitate was solvated in DCM and treated with 0.5 mL of tert-buty hydroperoxide in decane (5M) to oxidize the internucleotide phosphate. The mixture was then precipitated into MTBE to remove the excess peroxide, decane, DCI, and residual amidite that might remain. This afforded pure (46) in 96% yield.

$^1$H NMR (300 MHz, CHLOROFORM-d) δ ppm −0.05-0.20 (m, 7H) 0.86 (s, 15H) 0.89-1.02 (m, 35H) 1.10-1.29 (m, 8H) 1.35 (d, J=6.15 Hz, 16H) 1.48 (br. s., 16H) 1.74 (br. s., 2H) 2.19 (br. s., 10H) 2.60 (d, J=14.07 Hz, 4H) 2.66-2.77 (m, 1H) 3.20 (s, 1H) 3.27-3.41 (m, 3H) 3.46 (br. s., 2H) 3.52-3.71 (m, 2H) 3.71-3.80 (m, 7H) 3.89 (s, 1H) 4.05 (br. s., 1H) 4.13 (br. s., 1H) 4.43-4.56 (m, 2H) 5.06-5.22 (m, 2H) 5.60-5.77 (m, 1H) 5.82-6.05 (m, 2H) 6.76-6.87 (m, 5H) 7.17-7.38 (m, 16H) 7.41-7.58 (m, 2H) 7.72-7.98 (m, 2H)

$^{31}$P NMR (81 MHz, CHLOROFORM-d) δ ppm −1.07 (s, 1P) −0.30 (s, 1P) 33.31 (s, 1P) 33.35 (s, 1P)

$C_{75}H_{115}N_4O_{18}P_2Si_2$+ low resolution ESI-MS calculated: 1477.72, found: 1477.62.

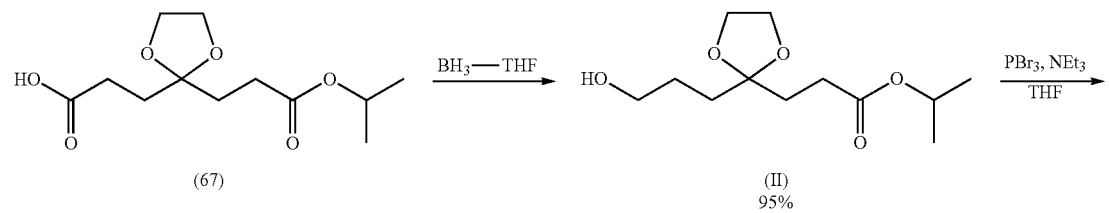

(67)   (II) 95%

-continued
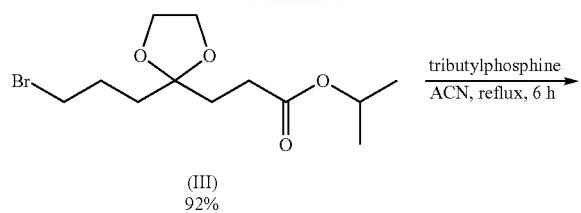
(III)
92%
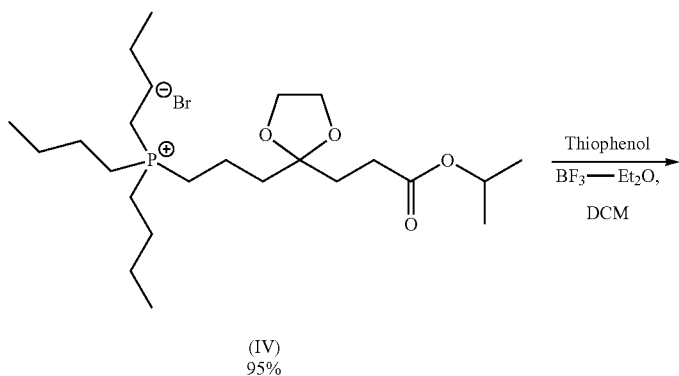
(IV)
95%
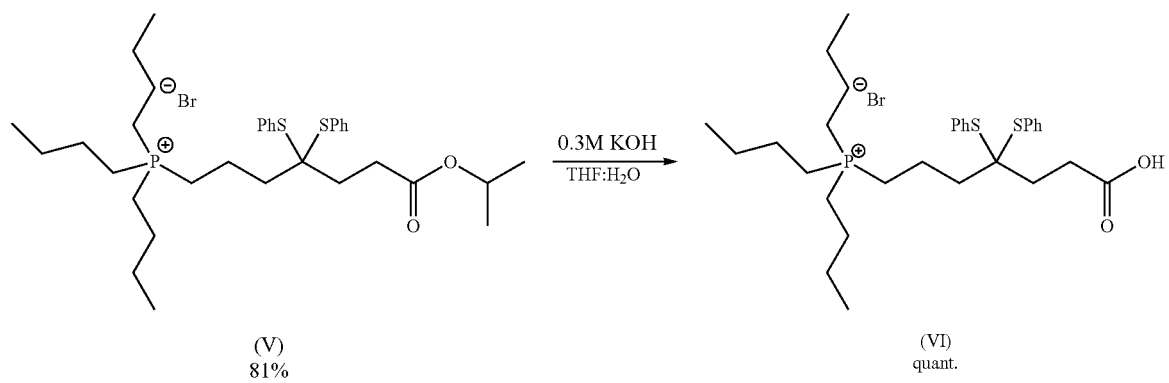
(V)
81%
(VI)
quant.
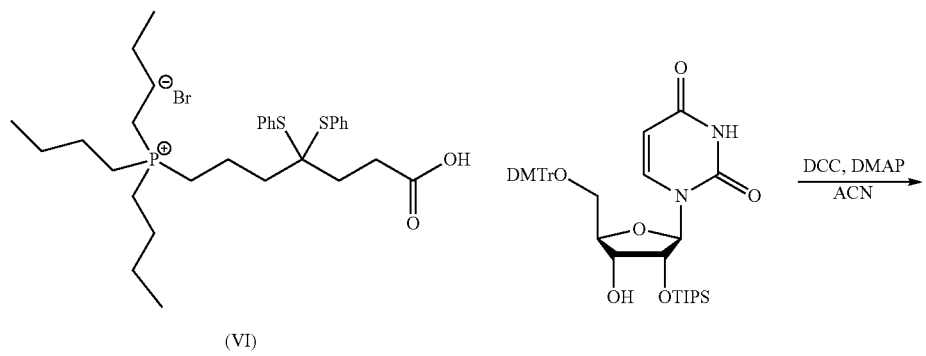
(VI)

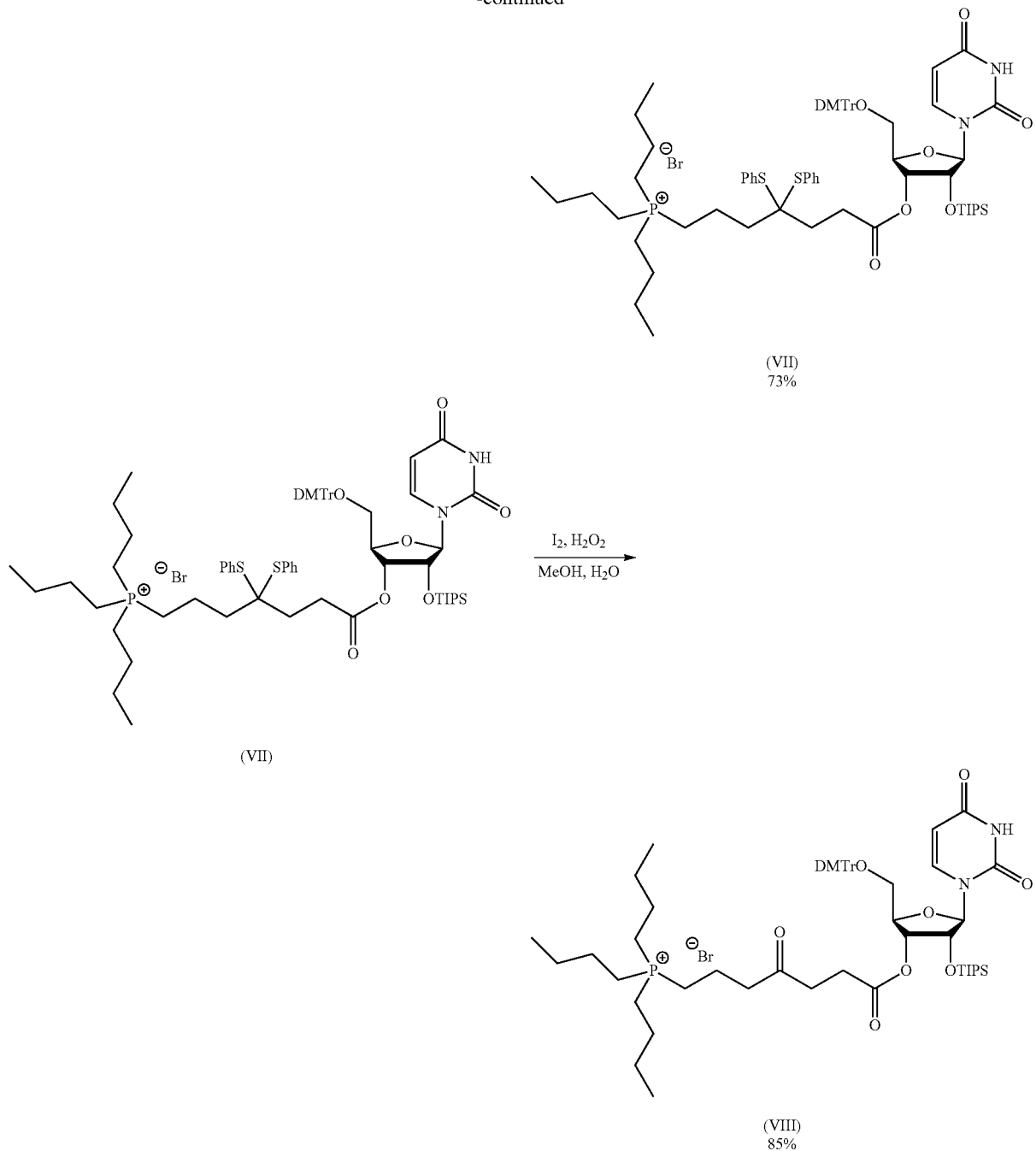

(VII)
73%

(VII)

I$_2$, H$_2$O$_2$
———————→
MeOH, H$_2$O (VIII)
85%

Isopropyl 3-(2-(3-hydroxypropyl)-1, 3-dioxolan-2-yl)propanoate, (II)

Compound (67) (0.334 g, 1.35 mmol) was dissolved in 13.5 mL making a 0.1M solution. This mixture was cooled to 0° C. and borane, and 1M in THF (1.75 mL. 1.75 mmol) was added drop wise. Once the vigorous release of hydrogen subsided, the ice bath was removed and the reaction was allowed to stir for 2 hours until the reaction was complete as shown by TLC. The mixture was quenched by first cooling the solution back down to 0° C. and adding methanol slowly until the release of hydrogen subsided. The crude reaction mixture was then concentrated to dryness, taken up in methanol once more and concentrated again to ensure removal of trimethyl borate. The mixture was purified by column chromatography 100% hexanes to 50:50 hexanes: ethyl acetate yielding pure primary hydroxyl 95%, 0.315 g.

$^1$H NMR (500 MHz, CHLOROFORM-d) δ ppm 1.11 (d, J=6.11 Hz, 6H) 1.46-1.68 (m, 6H) 1.82-1.94 (m, 3H) 2.17-2.32 (m, 3H) 3.43-3.61 (m, 2H) 3.84 (s, 4H) 4.88 (dt, J=12.53, 6.33 Hz, 1H)

$^{13}$C NMR (126 MHz, CHLOROFORM-d) δ ppm 21.67 (s, 1C) 26.85 (s, 1C) 29.14 (s, 1C) 29.69 (s, 1C) 31.90 (s, 1C) 33.68 (s, 1C) 62.46 (s, 1C) 64.91 (s, 1C) 67.52 (s, 1C) 110.69 (s, 1C) 173.07 (s, 1C)

Isopropyl 3-(2-(3-bromopropyl)-1, 3-dioxolan-2-yl) propanoate (III)

Compound (II) (0.32 g, 1.58 mmol) was dissolved in 10 mL of DCM and 2 mL of triethylamine and cooled to 0° in an ice bath. To this solution $PBr_3$ (0.225 mL, 2.37 mmol) was added drop wise over 10 min and allowed to stir for 1 h at zero degrees until the reaction was complete by TLC. The reaction was quenched with saturated sodium bicarbonate diluted with ethyl acetate and extracted with brine twice. The organic layer was dried, concentrated and purified by a short silica plug with a 70:30 Hexanes:ethyl acetate yielding 0.45 g, 1.455 mmol of compound (III).

$^1$H NMR (500 MHz, CHLOROFORM-d) d=5.01-4.87 (m, 1H), 3.97-3.82 (m, 4H), 3.36 (t, J=6.7 Hz, 2H), 2.33-2.20 (m, 2H), 1.96-1.82 (m, 4H), 1.73-1.64 (m, 2H), 1.16 (d, J=6.4 Hz, 6H)

$^{13}$C NMR (126 MHz, CHLOROFORM-d) δ ppm 21.75 (s, 1C) 27.20 (s, 1C) 29.12 (s, 1C) 32.11 (s, 1C) 33.85 (s, 1C) 35.69 (s, 1C) 64.95-65.08 (s, 1C) 67.47 (s, 1C) 110.26 (s, 1C) 172.81 (s, 1C)

Tributyl(3-(2-(3-isopropoxy-3-oxopropyl)-1,3-dioxolan-2-yl)propyl)phosphonium bromide (IV)

Compound (III) (0.33 g, 1.06 mmol) was dissolved with 4 mL of ACN. To this mixture tributylphosphine (0.53 ml, 2.12 mmol) was added directly and heated to 80° C. This was allowed to stir for 6 h. The mixture was concentrated and diluted with acetone then triturated into 250 mL of hexanes. The precipitate was filtered and the hexanes discarded. This process was repeated once more and the resulting goo was pure ionically tagged compound (IV) in near quantitative yield, 0.54 g, 1.05 mmol.

$^1$H NMR (CHLOROFORM-d, 200 MHz): 5=4.91 (quin, J=6.3 Hz, 1H), 3.97-3.82 (s, 4H), 2.56-2.72 (m, 2H), 2.23-2.55 (m, 10H), 1.66-1.99 (m, 6H), 1.35-1.61 (m, 16H), 1.08-1.26 (m, 7H), 0.80-1.02 ppm (m, 12H)

$^{31}$P NMR (81 MHz, CHLOROFORM-d) δ ppm 32.96 (s, 82 P)

Tributyl(7-isopropoxy-7-oxo-4,4-bis(phenylthio) heptyl)phosphonium bromide (V)

Compound (IV) (0.156 g, 0.30 mmol) was dissolved in 8 mL of dry DCM with 5 eq of thiophenol (0.193 mL, 1.52 mmol) followed by 5 eq of boron trifluoride etherate (0.157 mL, 1.52 mmol) and approximately 1 gram of crushed 3 Å molecular sieves. This mixture was stirred for 12 h at which point the reaction was filtered over Celite® to remove the sieves. In the collection flask was 40 mL of saturated sodium bicarbonate. The biphasic mixture was transferred to a seperatory funnel and extracted three times with bicarbonate and once with brine. The organic layer was dried and concentrated; the resulting oil was purified by precipitation in hexanes/MTBE 75:25, resulting in pure compound (V) in 81% recovered yield, 0.162 g, 0.24 mmol.

$^1$H NMR (200 MHz, CHLOROFORM-d) δ ppm 0.80-1.02 (m, 12H) 1.08-1.26 (m, 7H) 1.35-1.61 (m, 16H) 1.66-1.99 (m, 6H) 2.23-2.55 (m, 10H) 2.56-2.72 (m, 2H) 4.91 (quin, J=6.25 Hz, 1H) 7.30-7.43 (m, 5H) 7.52-7.62 (m, 4H)

$^{31}$P NMR (81 MHz, CHLOROFORM-d) δ ppm 33.29 (s, 1P)

Tributyl(6-carboxy-4,4-bis(phenylthio)hexyl)phosphonium bromide (VI)

Compound (V) (0.75 g, 1.19 mmol) was first dissolved in 3 mL of THF and then was treated with 30 mL of 0.2 M solution of KOH in water:THF 50:50. This mixture was allowed to stir vigorously for 1 hour, until the hydrolysis was complete by TLC. The mixture was acidified by the addition of 20 mL of 1M HCl and excess NaCl was added as well. The organic layer was diluted with ethyl acetate and extracted three times with brine, dried and concentrated to dryness. This afforded pure tagged acid, (VI) in quantitative yield.

$^1$H NMR 400 MHz, CHLOROFORM-d) δ ppm 0.82-1.02 (m, 9H) 1.28-1.51 (m, 12H) 1.58 (br. s., 2H) 1.75 (br. s., 2H) 1.94 (t, J=7.23 Hz, 2H) 2.10-2.32 (m, 8H) 2.75 (t, J=7.42 Hz, 2H) 7.27-7.37 (m, 6H) 7.65 (d, J=7.82 Hz, 4H)

$^{13}$C NMR (75 MHz, CHLOROFORM-d) δ ppm 13.41 (s, 1C) 18.19 (s, 1C) 18.82 (s, 1C) 21.44 (s, 1C) 23.44 (s, 1C) 23.50 (s, 1C) 23.74 (s, 1C) 23.93 (s, 1C) 30.10 (s, 1C) 32.76 (s, 1C) 36.32 (s, 1C) 68.37 (s, 1C) 128.76 (s, 1C) 129.14 (s, 1C) 131.08 (s, 1C) 136.38 (s, 1C) 174.83 (s, 1C)

$^{31}$P NMR (81 MHz, CHLOROFORM-d) δ ppm 32.89 (s, 1P) 5'-DMTr-2'-TIPS-3'-[tributyl(7-oxy-4,4-bis(phenylthio) hexyl) phosphonium bromide] uridine (VII) Compound (VI) (0.294 g, 0.49 mmol) and 1.5 equivalents of DCC (0.14 g, 0.76 mmol) were dissolved in 9.5 mL of ACN. To the above solution 1.5 eq of nucleoside (13) (0.54 g, 0.76 mmol) was added followed by sub stoichiometric amounts of DMAP. The reaction was allowed to stir for 6 h until all starting material was consumed, monitored by MS. The sample was diluted with ethyl acetate and extracted with ammonium chloride ×2 and once with brine. The organic layer was dried with magnesium sulphate and concentrated to dryness. The mixture was then precipitated in MTBE-Hexanes 50:50 to remove any unreacted DCC then purified by column chromatography (0.2 mL 10% MeOH-DCM) affording compound (VII) in 82% yield (0.48 g, 0.40 mmol).

$^1$H NMR (400 MHz, CHLOROFORM-d) δ ppm 0.94-1.18 (m, 39H) 1.32-1.60 (m, 21H) 1.64-1.72 (m, 3H) 1.74-1.84 (m, 3H) 1.90-2.17 (m, 15H) 2.76-2.84 (m, 2H) 3.42-3.51 (m, 3H) 3.79 (d, J=0.78 Hz, 7H) 4.10-4.15 (m, 2H) 4.67-4.71 (m, 1H) 5.26-5.30 (m, 1H) 5.40 (dd, J=5.08, 2.74 Hz, 1H) 6.10 (d, J=6.25 Hz, 1H) 6.81-6.85 (m, 5H) 7.21-7.38 (m, 23H) 7.60-7.68 (m, 5H) 7.88 (d, J=8.21 Hz, 1H) 8.61 (s, 1H)

$^{13}$C NMR (75 MHz, CHLOROFORM-d) δ ppm 12.13 (s, 1C) 13.38 (s, 1C) 17.68 (s, 1C) 17.85 (s, 1C) 18.01 (s, 1C) 18.64 (s, 1C) 23.45 (s, 1C) 23.52 (s, 1C) 23.76 (s, 1C) 23.96 (s, 1C) 25.02 (s, 1C) 25.65 (s, 1C) 33.86 (s, 1C) 55.27 (s, 1C) 67.41 (s, 1C) 76.69 (s, 1C) 77.11 (s, 1C) 77.53 (s, 1C) 87.57 (s, 1C) 113.33 (s, 1C) 113.36 (s, 1C) 128.05 (s, 1C) 129.00 (s, 1C) 129.43 (s, 1C) 130.02 (s, 1C) 130.15 (s, 1C) 130.71 (s, 1C) 130.74 (s, 1C) 134.75 (s, 1C) 134.93 (s, 1C) 136.52 (s, 1C) 144.09 (s, 1C) 150.66 (s, 1C) 158.74 (s, 1C) 158.78 (s, 1C) 163.29 (s, 1C) 172.20 (s, 1C)

$^{31}$P NMR (81 MHz, CHLOROFORM-d) δ ppm 32.73 (s, 1P) Low resolution MS, m/z calc: 1231.6 found: 1231.5.

2'-TIPS-3'-[tributyl(6-oxy-4-oxohexyl)phosphonium bromide]uridine (VIII)

Compound (VII) (1.44 g, 1.1 mmol) was dissolved in 10 ml of MeOH:water 8:2 mixture to which 20 mol % of molecular iodine (0.06 g, 0.22 mmol) was added. This was shortly followed by 4 equivalents of 30% hydrogen peroxide (0.5 mL, 4.4 mmol). This mixture was allowed to stir for 2 h until all starting material was consumed. This mixture was first diluted with ethyl acetate then quenched by extracting with 10% solution of sodium thiosulfite, then brine three times. Although the compound could be purified by precipitation alone, a column was run to ensure the highest purity.

This provided the deprotected monomer (VIII) in good yield of 85%. This reaction does yield higher results if no column chromatography is used. 1.03 g.

$^1$H NMR (500 MHz, CHLOROFORM-d) δ ppm 0.91-1.10 (m, 11H) 1.44-1.57 (m, 5H) 1.63 (dd, J=15.90, 8.07 Hz, 1H) 1.78 (dd, J=14.06, 6.97 Hz, 1H) 2.29-2.40 (m, 3H) 2.41-2.53 (m, 1H) 2.56-2.85 (m, 3H) 3.76-3.92 (m, 1H) 3.98 (s, 1H) 4.11-4.19 (m, 1H) 4.70-4.78 (m, 1H) 5.18 (dd, J=4.89, 3.42 Hz, 1H) 5.75 (d, J=8.07 Hz, 1H) 5.81 (d, J=5.62 Hz, 1H) 8.00 (d, J=8.31 Hz, 1H) 8.67 (br. s., 1H)

$^{13}$C NMR (126 MHz, CHLOROFORM-d) δ ppm 11.93 (s, 1C) 11.96 (s, 1C) 11.98 (s, 1C) 13.37 (s, 1C) 17.50 (s, 1C) 17.52 (s, 1C) 17.54 (s, 1C) 17.57 (s, 1C) 17.58 (s, 1C) 17.60 (s, 1C) 17.62 (s, 1C) 17.65 (s, 1C) 17.66 (s, 1C) 17.67 (s, 1C) 17.69 (s, 1C) 17.71 (s, 1C) 17.72 (s, 1C) 17.78 (s, 1C) 17.80 (s, 1C) 18.59 (s, 1C) 18.77 (s, 1C) 18.97 (s, 1C) 19.15 (s, 1C) 20.80 (s, 1C) 20.84 (s, 1C) 23.54 (s, 1C) 23.57 (s, 1C) 23.77 (s, 1C) 23.88 (s, 1C) 24.35 (s, 1C) 24.47 (s, 1C) 28.00 (s, 1C) 30.88 (s, 1C) 36.93 (s, 1C) 41.11 (s, 1C) 61.25 (s, 1C) 73.72 (s, 1C) 73.96 (s, 1C) 83.72 (s, 1C) 88.91 (s, 1C) 102.72 (s, 1C) 141.92 (s, 1C) 150.83 (s, 1C) 163.77 (s, 1C) 171.98 (s, 1C) 208.11 (s, 1C)

$^{31}$P NMR (81 MHz, CHLOROFORM-d) δ ppm 33.08 (s, 1P) Low resolution MS, m/z calc: 1029.6 found: 1029.5.

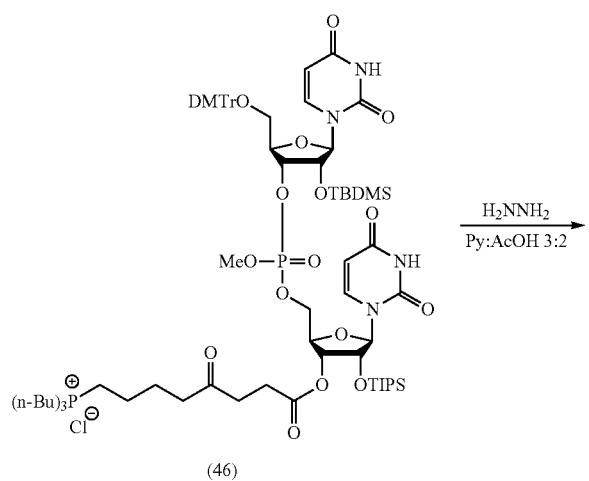

(46)

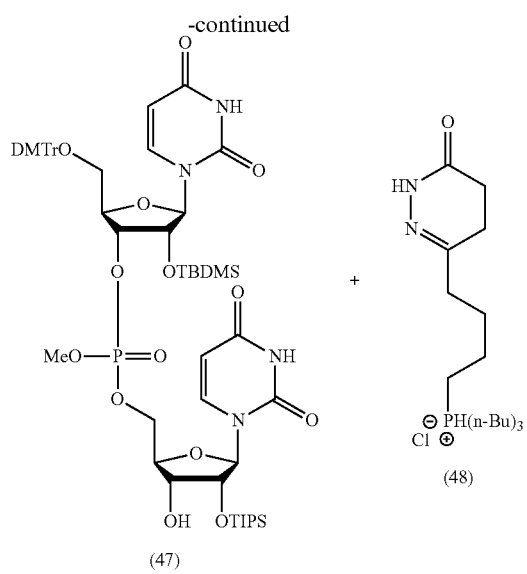

Compound (46) (0.12 g, 0.08 mmol) was solvated in minimal amounts of ACN, approximately 1 ml, then treated with 10 eq of a 0.5 M hydrazine hydrate solution in pyridine:acetic acid (3:2) (40 mg, 0.8 mmol) and allowed to stir for 15 min. The reaction progress was monitored by MS to confirm consumption of starting material. At this point 10 eq of 2,4-pentanedione was added to the solution to quench any excess hydrazine (80 mg, 0.8 mmol. The reaction was then diluted with ethyl acetate and extracted with first a saturated ammonium chloride solution then ×2 with a 5% solution ammonium chloride, then once with brine. The organic layer was dried and concentrated. The mixture was then taken up in minimal amounts of DCM and precipitated in a 75/25 mixture of MTBE/hexanes mixture. The oily precipitate was filtered off and the ether layer was concentrated to dryness. The crude concentrate was then purified by column chromatography (0-75% ethyl acetate: hexanes) yielding isomerically pure (47) in 84% yield, 76 mg.

$^1$H NMR (300 MHz, CHLOROFORM-d) δ ppm 0.09-0.15 (m, 6H) 0.87-1.20 (m, 40H) 1.94-2.00 (m, 1H) 2.10-2.20 (m, 2H) 3.44 (br. s., 3H) 3.67-3.79 (m, 12H) 4.04-4.23 (m, 5H) 4.28-4.35 (m, 2H) 4.38-4.48 (m, 2H) 4.81-4.90 (m, 1H) 5.38 (d, J=8.21 Hz, 1H) 5.64 (d, J=8.20 Hz, 1H) 5.81-5.91 (m, 2H) 6.90 (d, J=7.91 Hz, 5H) 7.24-7.37 (m, 9H) 7.41-7.52 (m, 4H) 7.71 (dd, J=8.20, 2.64 Hz, 1H) 9.62 (br. s., 1H)

$^{31}$P NMR (81 MHz, CHLOROFORM-d) δ ppm 0.58 (s, 1P) 0.83 (s, 1P).

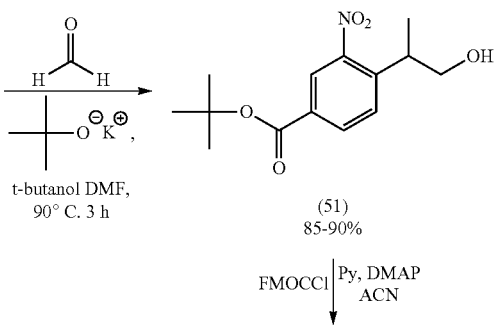

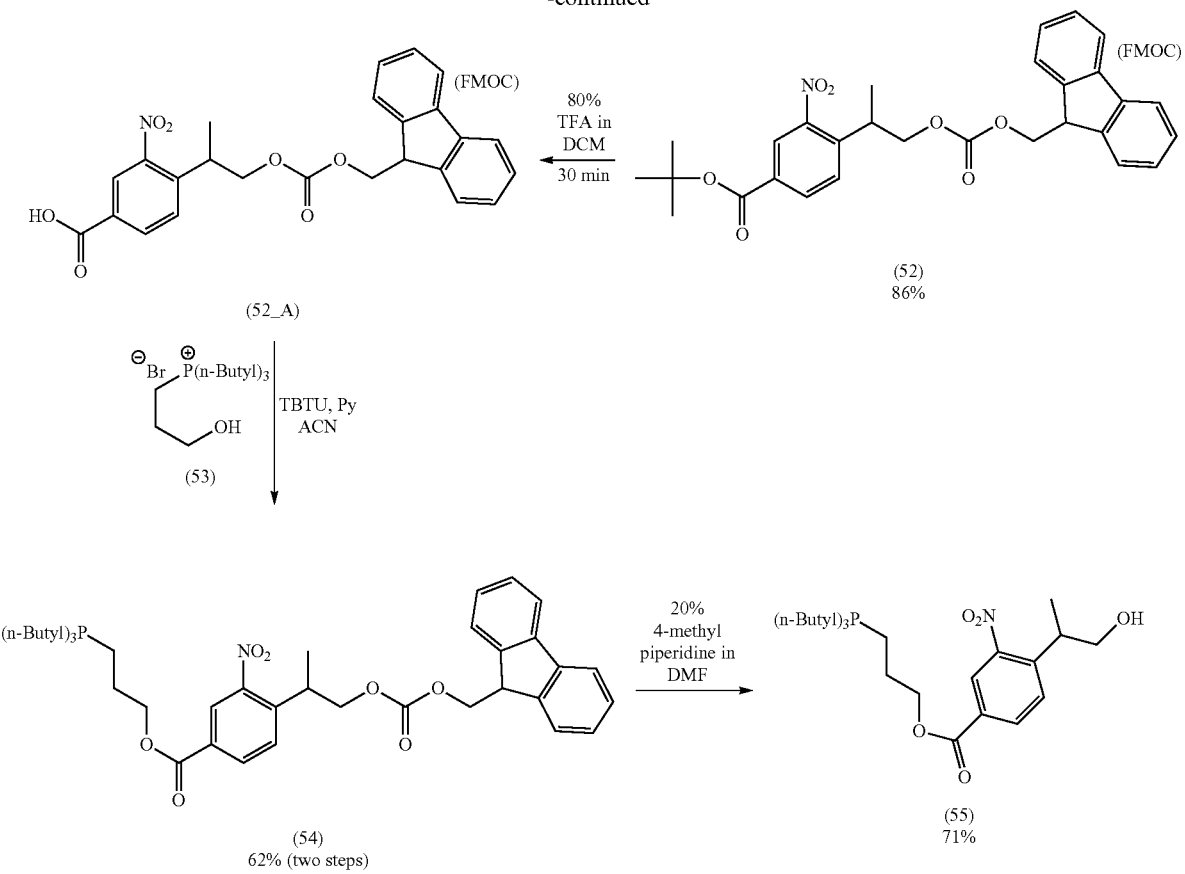

3-Nitro-4-ethyl-benzoic acid (49_A)

Fuming nitric acid (90%) (150 ml) was cooled with stirring to −10° C. and 4-ethyl benzoic acid (49) (30 g, 0.2 moles; Sigma-Aldrich) was added slowly over 30 min directly into the sitting solution (1.33 mmol/ml of (49) to fuming nitric acid). The mixture was then allowed to stir for 30 min after addition was complete. The mixture was then poured over approximately 600 g of crushed ice to quench the reaction. The product formed a white ppt which can be filtered over a sintered glass funnel. The excess ice melted by washing the product with water. The sample was then re-crystallized from ethyl acetate/hexanes. Two rounds of crystallization were preformed. Yield: 37.2 g (95%).

$^1$H NMR (500 MHz, CHLOROFORM-d) δ ppm 1.33 (t, J=7.58 Hz, 3H) 2.99 (q, J=7.58 Hz, 2H) 7.52 (d, J=8.07 Hz, 1H) 8.23 (dd, J=8.07, 1.71 Hz, 1H) 8.58 (d, J=1.71 Hz, 1H) $^{13}$C NMR (126 MHz, CHLOROFORM-d) δ ppm 14.62 (s, 1C) 26.38 (s, 1C) 126.37 (s, 1C) 128.29 (s, 1C) 131.67 (s, 1C) 133.87 (s, 1C) 144.85 (s, 1C) 149.36 (s, 1C) 170.40 (s, 1C) $C_9H_9NO_4Na^{1+}$ low resolution ESI-MS calculated: 195.05, found: 218.2.

tert-Butyl 3-nitro-4-ethyl-benzoate (50)

Compound (49_A) (19.65 g 0.10 moles) was solvated in 500 ml of THF (0.2 M) followed by 1.15 eq (10.14 g, 0.15 moles) of diisopropylcarbodimide. This mixture was allowed to stir for 5 min followed by 1.5 eq of tert-butanol (17.9 mL) and catalytic amounts of 4-(dimethylamino)-pyridine. The mixture was allowed to stir for 60 h before the reaction was complete. The reaction was diluted with diethyl ether and filtered to remove the diisopropylurea (DIU) and condensed to dryness. The mixture was solvated in ethyl acetate and extracted with 5% NaHCO₃. The product was separated from (74) by column chromatography (solvent system: hexanes:DCM 100:0→0:100). Yield of (50): 15.1 g (60%);

(50)

$^1$H NMR (300 MHz, CHLOROFORM-d) δ ppm 1.26 (t, J=7.47 Hz, 3H) 1.57 (s, 11H) 2.91 (q, J=7.33 Hz, 2H) 7.40 (d, J=7.91 Hz, 1H) 8.08 (dd, J=7.91, 1.47 Hz, 1H) 8.38 (d, J=1.47 Hz, 1H) $^{13}$C NMR (75 MHz, CHLOROFORM-d) δ ppm 14.70 (s, 1C) 26.18 (s, 1C) 28.05 (s, 1C) 76.64 (s, 1C) 77.06 (s, 1C) 77.49 (s, 1C) 82.13 (s, 1C) 125.42 (s, 1C) 131.12 (s, 1C) 131.18 (s, 1C) 133.23 (s, 1C) 143.00 (s, 1C) 149.12 (s, 1C) 163.56 (s, 1C) $C_{13}H_{17}NO_4Na^{1+}$ low resolution ESI-MS calculated: 251.11, found: 274.32.

(DCC Failure Product)

$^1$H NMR (300 MHz, CHLOROFORM-d) δ ppm 0.94 (d, J=6.45 Hz, 6H) 1.26 (t, J=7.47 Hz, 3H) 1.39 (d, J=6.74 Hz, 6H) 2.91 (q, J=7.33 Hz, 2H) 3.80 (dq, J=13.88, 6.70 Hz, 1H) 4.44 (quin, J=6.74 Hz, 1H) 6.49 (d, J=7.91 Hz, 1H) 7.40 (d, J=8.20 Hz, 1H) 7.67 (dd, J=7.91, 1.76 Hz, 1H) 8.02 (d, J=1.76 Hz, 1H) $^{13}$C NMR (75 MHz, CHLOROFORM-d) δ ppm 14.80 (s, 1C) 20.75 (s, 1C) 22.04 (s, 1C) 26.12 (s, 1C) 42.96 (s, 1C) 49.54 (s, 1C) 76.63 (s, 1C) 77.05 (s, 1C) 77.48 (s, 1C) 123.13 (s, 1C) 130.76 (s, 1C) 131.52 (s, 1C) 135.78 (s, 1C) 141.49 (s, 1C) 148.95 (s, 1C) 153.60 (s, 1C) 168.67 (s, 1C) $C_{16}H_{23}N_3O_4Na^{1+}$ low resolution ESI-MS calculated: 321.16, found: 344.23.

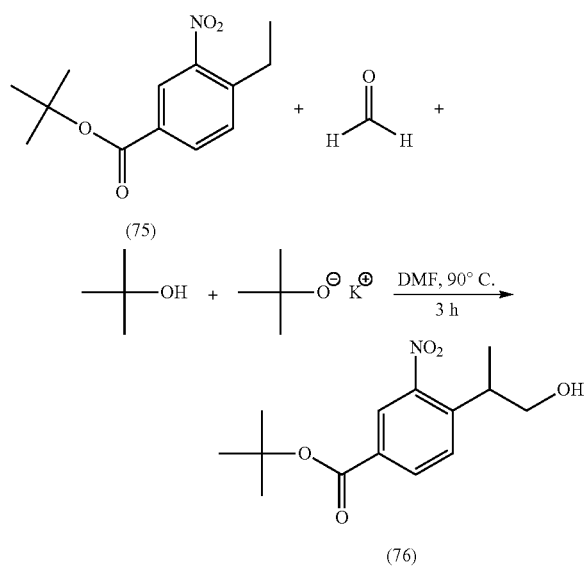

tert-Butyl 4-(1-hydroxypropan-2-yl)-3-nitrobenzoate (51)

Compound (750) (10.5 g, 41.7 mmol) was solvated in 19 mL of DMF (2.2M) to which 1.5 eq (1.88 g) of paraformaldehyde was added followed by a solution of potassium tert-butoxide (0.12 eq, 0.56 g) in tert-butanol (5.7 mL). This mixture was allowed to stir at room temperature for 10 min before being brought up 90° C. for 3 h. The mixture was then acidified to neutrality by the addition of a 1M HCl monitored a by a pH meter. This mixture was then diluted with sat. NaCl and ethyl acetate (×2). Compound (51) was purified by column chromatography in DCM:ethyl acetate 100:0→90:10. Yield: 9.4 g (85%).

$^1$H NMR (400 MHz, ACETONITRILE-$d_3$) δ ppm 1.41 (d, J=7.03 Hz, 3H) 3.80 (sxt, J=6.88 Hz, 1H) 4.49-4.67 (m, 2H) 7.40 (d, J=7.91 Hz, 1H) 8.08 (dd, J=7.91, 1.47 Hz, 1H) 8.38 (d, J=1.47 Hz, 1H)
$^{13}$C NMR (75 MHz, CHLOROFORM-d) δ ppm 17.35 (s, 1C) 27.96 (s, 1C) 36.57 (s, 1C) 67.01 (s, 1C) 82.27 (s, 1C) 124.77 (s, 1C) 128.50 (s, 1C) 131.04 (s, 1C) 131.06 (s, 1C) 132.81 (s, 1C) 142.62 (s, 1C) 150.41 (s, 1C) 163.58 (s, 1C) $C_{14}H_{19}NO_5Na^{1+}$ low resolution ESI-MS calculated: 281.12, found: 304.02.

tert-Butyl 4-(1-(F-moc)propan-2-yl)-3-nitrobenzoate (52)

Compound (51) (5.38 g, 20.2 mmol) was co-evaporated with pyridine (×3) and solvated in 97 mL of ACN (0.2M) and 2 eq of pyridine (3.13 mL, 38.7 mmol). Fmoc-Cl (5.0 g, 19.33 mmol) was added directly to solution and was allowed to stir for 16 h in the dark, covered with aluminum foil. The reaction went to completion by TLC. The solution was extracted (×3) with 5% ammonium chloride and once with brine and purified by column chromatography Hex/EtAc 100:0→75:25. Isolated yield: 8.19 g (86%).

$^1$H NMR (500 MHz, ACETONITRILE-$d_3$) δ ppm 1.30 (d, J=7.09 Hz, 3H) 1.60 (s, 9H) 3.65 (sxt, J=6.94 Hz, 1H) 4.19 (t, J=6.24 Hz, 1H) 4.23-4.34 (m, 2H) 4.39-4.53 (m, 2H) 7.27-7.34 (m, 2H) 7.41 (t, J=7.46 Hz, 2H) 7.53 (d, J=7.34 Hz, 2H) 7.62 (d, J=8.31 Hz, 1H) 7.80 (d, J=7.58 Hz, 2H) 8.13 (dd, J=8.19, 1.59 Hz, 1H) 8.28 (d, J=1.71 Hz, 1H) $^{13}$C NMR (126 MHz, ACETONITRILE-$d_3$) δ ppm −0.10 (s, 1C) 0.06 (s, 1C) 0.23 (s, 1C) 0.40 (s, 1C) 0.56 (s, 1C) 0.73 (s, 1C) 0.89 (s, 1C) 16.83 (s, 1C) 27.30 (s, 1C) 27.32 (s, 1C) 33.47 (s, 1C) 46.64 (s, 1C) 68.89 (s, 1C) 70.90 (s, 1C) 82.13 (s, 1C) 117.34 (s, 1C) 120.06 (s, 1C) 124.56 (s, 1C) 124.87 (s, 1C) 124.90 (s, 1C) 127.17 (s, 1C) 127.18 (s, 1C) 127.81 (s, 1C) 127.83 (s, 1C) 128.87 (s, 1C) 131.72 (s, 1C) 132.75 (s, 1C) 141.03 (s, 1C) 141.17 (s, 1C) 143.50 (s, 1C) 143.55 (s, 1C) 150.42 (s, 1C) 154.54 (s, 1C) 163.26 (s, 1C) $C_{29}H_{29}NO_7Na^{1+}$ low resolution ESI-MS calculated: 503.19, found: 526.41.

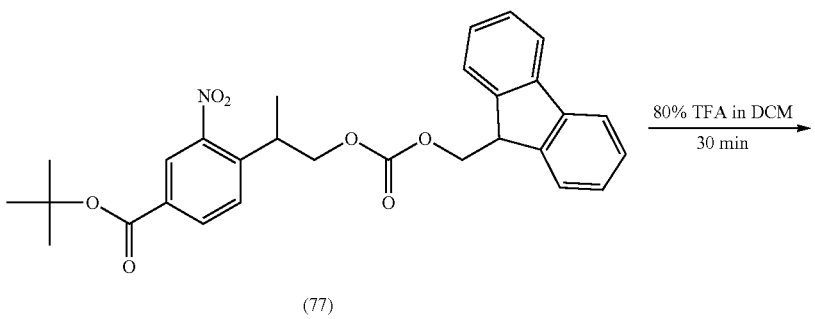

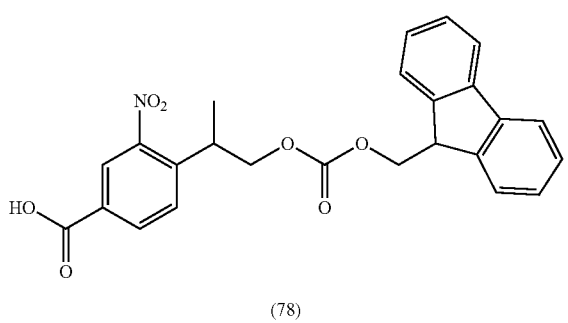

4-(1-(Fmoc)propan-2-yl)-3-nitrobenzoic acid (52_A)

Compound (52) (8.9 g, 17.7 mmol) was directly solvated in a solution of 80% TFA in DCM (50 mL) and allowed to stir for 30 min, until all starting material had been consumed. The sample was then evaporated to dryness on the rotovap and purified by column chromatography, Hex/EtAc 100:0→60:40. Isolated yield: 6.09 g (77%).

$^1$H NMR (500 MHz, CHLOROFORM-d) δ ppm 1.43 (d, J=6.85 Hz, 3H) 3.86 (sxt, J=6.80 Hz, 1H) 4.32-4.46 (m, 4H) 7.28-7.36 (m, 2H) 7.41 (t, J=7.58 Hz, 2H) 7.57 (dd, J=6.97, 4.52 Hz, 2H) 7.65 (d, J=8.07 Hz, 1H) 7.76 (d, J=7.34 Hz, 2H) 8.29 (dd, J=8.07, 1.71 Hz, 1H) 8.53 (d, J=1.71 Hz, 1H) 11.69 (br. s., 1H) $^{13}$C NMR (126 MHz, CHLOROFORM-d) δ ppm 17.58 (s, 1C) 33.71 (s, 1C) 46.62 (s, 1C) 70.08 (s, 1C) 71.14 (s, 1C) 76.80 (s, 1C) 77.05 (s, 1C) 77.31 (s, 1C) 120.06 (s, 1C) 125.10 (s, 1C) 125.11 (s, 1C) 126.16 (s, 1C) 127.16 (s, 1C) 127.17 (s, 1C) 127.91 (s, 1C) 127.93 (s, 1C) 128.87 (s, 1C) 129.00 (s, 1C) 133.71 (s, 1C) 141.26 (s, 1C) 141.27 (s, 1C) 142.82 (s, 1C) 143.14 (s, 1C) 143.20 (s, 1C) 150.39 (s, 1C) 155.00 (s, 1C) 169.79 (s, 1C) $C_{25}H_{20}NO_{71}$ low resolution ESI-MS calculated: 447.13, found: 446.0.

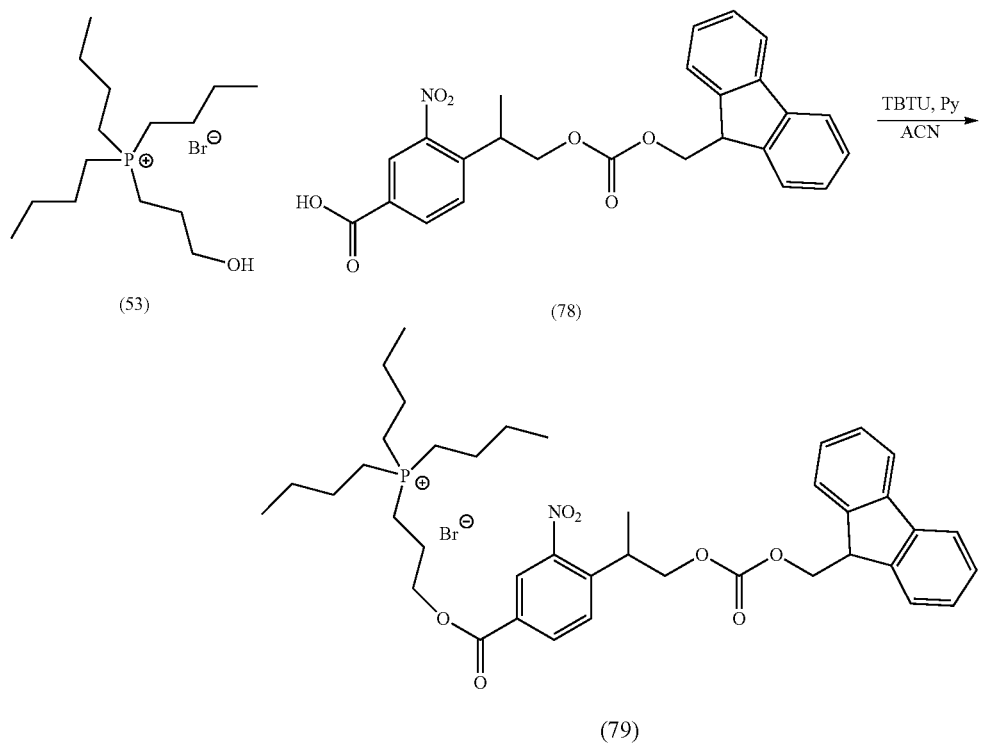

Phosphonium tag 4-(1-(Fmoc)propan-2-yl)-3-nitrobenzoate (54)

Compound (52_A) (3.726 g, 8.33 mmol) was solvated in half the solvent (ACN:Py, 28 mL:1.25 mL) to which was added a solution of the phosphonium tag (53) (3.86 g, 9.16 mmol) in the other half of the solvent, followed directly by TBTU (4.0 g, 12.5 mmol). The solution was allowed to stir overnight and by morning the reaction was complete (12 h), and was concentrated to half solvent volume then extracted with ethyl acetate and 5% NaHCO$_3$ (×3) and once with brine. The organic layer was dried with MgSO$_4$ and condensed to dryness. The compound was then precipitated in 500 mL of MTBE to remove the excess pyridine and TBTU byproduct. The precipitated white goo was filtered and collected over Celite© then purified by column chromatography, DCM:MeOH 100:0→92:8. Isolated yield of (54): 5.52 g (86%).

$^1$H NMR (300 MHz, CHLOROFORM-d) δ ppm 0.81-0.99 (m, 8H) 1.35 (d, J=7.03 Hz, 3H) 1.38-1.61 (m, 11H) 1.99-2.38 (m, 8H) 2.66 (br. s., 2H) 3.54-3.83 (m, 3H) 4.10-4.41 (m, 5H) 7.21-7.44 (m, 4H) 7.57 (dd, J=10.11, 8.06 Hz, 3H) 7.72 (d, J=7.33 Hz, 2H) 8.55 (d, J=1.76 Hz, 1H) 8.70 (dd, J=8.20, 1.76 Hz, 1H)

$^{13}$C NMR (75 MHz, CHLOROFORM-d) δ ppm 13.35 (s, 1C) 17.68 (s, 1C) 18.59 (s, 1C) 19.22 (s, 1C) 23.55 (s, 1C) 23.62 (s, 1C) 23.81 (s, 1C) 24.01 (s, 1C) 33.40 (s, 1C) 46.62 (s, 1C) 69.91 (s, 1C) 71.36 (s, 1C) 76.67 (s, 1C) 77.09 (s, 1C) 77.52 (s, 1C) 119.96 (s, 1C) 124.31 (s, 1C) 125.21 (s, 1C) 127.18 (s, 1C) 127.83 (s, 1C) 128.61 (s, 1C) 131.93 (s, 1C) 133.41 (s, 1C) 139.59 (s, 1C) 141.19 (s, 1C) 143.27 (s, 1C) 143.33 (s, 1C) 150.18 (s, 1C) 154.87 (s, 1C) 165.19 (s, 1C) $^{31}$P NMR (81 MHz, CHLOROFORM-d) δ ppm 35.07 (s, 1P) $C_{40}H_{53}NO_7P^{1+}$ low resolution ESI-MS calculated: 690.30, found: 690.35.
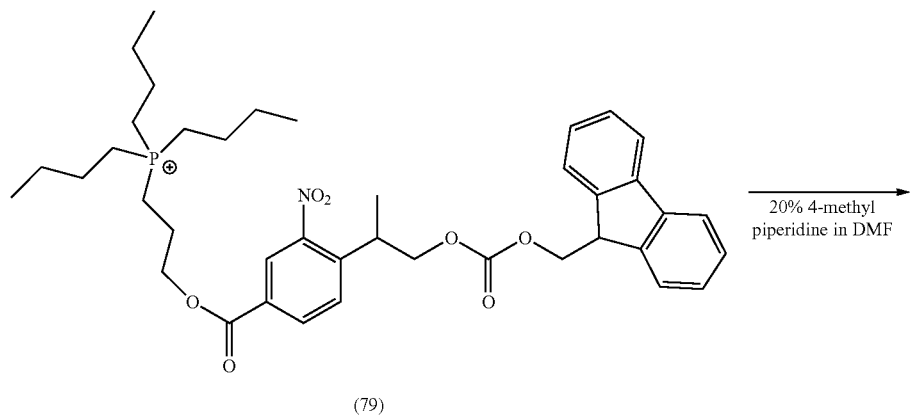
(79)
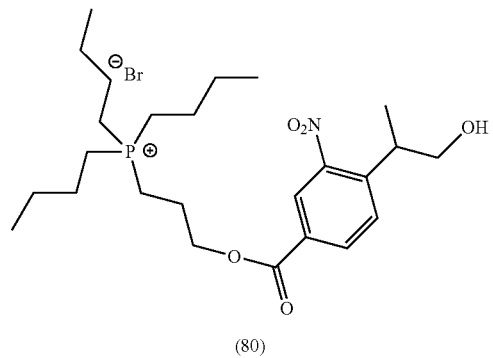
(80)

Phosphonium tag 4-(1-hydroxypropan-2-yl)-3-nitrobenzoate (55)

To compound (54) (6.408 g, 9.29 mmol) was added a 20% solution of 4-methylpiperidine in DMF (20 ml). After 2 h the reaction was complete by TLC and the solution was evaporated to dryness, then taken up in DCM and precipitated in 500 ml of MTBE to yield 3.09 g of (55) (71%).

$^1$H NMR (400 MHz, CHLOROFORM-d) δ ppm 0.91 (t, J=7.03 Hz, 11H) 1.26 (d, J=7.03 Hz, 3H) 1.38-1.59 (m, 13H) 1.98 (d, J=7.03 Hz, 2H) 2.11-2.28 (m, 7H) 2.36-2.51 (m, 2H) 3.40-3.59 (m, 3H) 3.64-3.82 (m, 2H) 7.51 (d, J=8.21 Hz, 1H) 8.22 (d, J=8.21 Hz, 1H) 8.26 (s, 1H) $C_{25}H_{43}NO_5P^{1+}$ low resolution ESI-MS calculated: 468.28, found: 468.28.

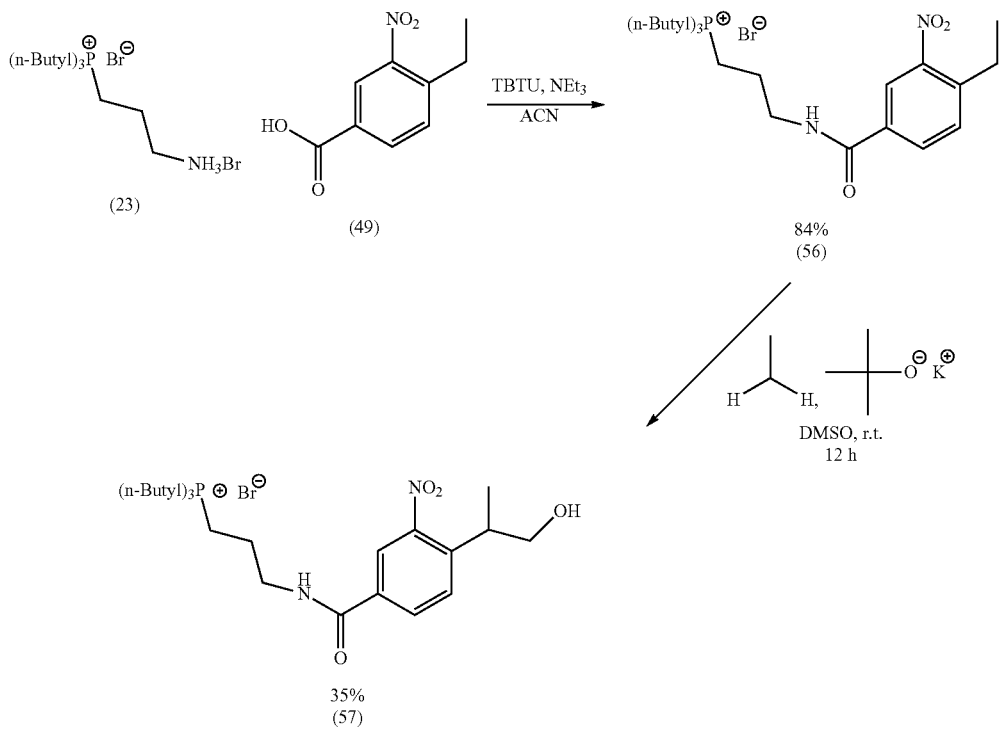

Tributyl(3-(4-ethyl-3-nitrobenzamido)propyl)phosphonium bromide (56)

To a solution of 3-nitro-4-ethyl-benzoic acid (49) (3.15 g, 16.1 mmol) and diisopropylethylamine (4 eq, 11.25 ml) in ACN (30 mL) was added compound (23) (1.3 eq, 20.9 mmol) and TBTU (1.3 eq, 6.74 g, 20.9 mmol). This mixture was allowed to stir for 12 h. The dark brown solution was concentrated to a viscous oil, and taken up in DCM and precipitated in 500 ml of MTBE. The solid was collected and re-purified by silica gel column chromatography (DCM: MeOH, 100:0→85:15) eluting as very dark yellow oil. Isolated yield: 7.07 g (84%).

$^1$H NMR (500 MHz, CHLOROFORM-d) δ ppm 0.90 (t, J=6.97 Hz, 9H) 1.24 (t, J=7.46 Hz, 3H) 1.35-1.56 (m, 12H) 1.96 (d, J=8.07 Hz, 2H) 2.05-2.19 (m, 7H) 2.25-2.38 (m, 2H) 2.78 (s, 2H) 2.87 (q, J=7.34 Hz, 2H) 3.60 (q, J=5.79 Hz, 2H) 7.40 (d, J=8.07 Hz, 1H) 7.78 (t, J=5.50 Hz, 1H) 8.07 (d, J=8.07 Hz, 1H) 8.37 (s, 1H) $^{13}$C NMR (126 MHz, CHLOROFORM-d) δ ppm 13.21 (s, 1C) 14.61 (s, 1C) 18.17 (s, 1C) 18.56 (s, 1C) 23.33 (s, 1C) 23.37 (s, 1C) 23.76 (s, 1C) 23.88 (s, 1C) 25.97 (s, 1C) 38.57 (s, 1C) 76.77 (s, 1C) 77.02 (s, 1C) 77.28 (s, 1C) 123.82 (s, 1C) 131.09 (s, 1C) 131.47 (s, 1C) 132.89 (s, 1C) 141.77 (s, 1C) 149.21 (s, 1C) 165.48 (s, 1C) $C_{24}H_{42}N_2O_3P^{1+}$ low resolution ESI-MS calculated: 437.29, found: 437.30.

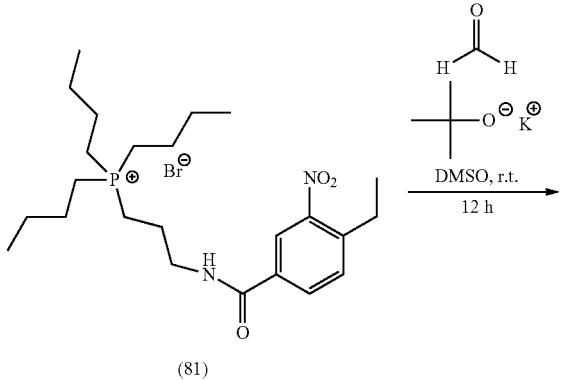

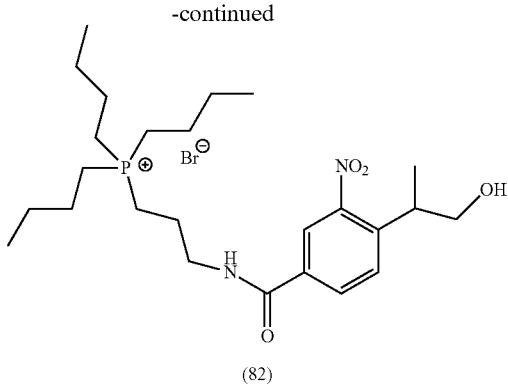

(82)

Tributyl(3-(4-(1-hydroxypropan-2-yl)-3-nitrobenzamido)propyl) phosphonium bromide (57)

To a solution of compound (56) (3.56 g, 6.89 mmol) dry DMSO (13.8 mL), was added para-formaldehyde (2.1 eq, 0.43 g, 14.4 mmol). This mixture was sonicated for 20 min until all of para-formaldehyde dissolved. The resulting mixture was treated with 1.5 eq of potassium tert-butoxide (1.16 g, 10.3 mmol). The reaction turned a dark purple immediately. The reaction was allowed to stir for 12 h at room temperature. The reaction was monitored by MS, showing the disappearance of the starting material. The reaction was treated with 1M HCl in MeOH to bring to neutrality at which point the reaction was precipitated in diethyl ether, and then in DCM. This last precipitation step separated the product from unreacted para-formaldehyde. The product was purified by reverse phase chromatography, using 100 mM TEAA buffer in water (pH 7):ACN 80:20→20:80. Isolated yield: 1.3 g (35%).

$^1$H NMR (400 MHz, CHLOROFORM-d) δ ppm 0.84-0.98 (m, 9H) 1.26 (d, J=7.03 Hz, 3H) 1.38-1.59 (m, 11H) 1.98 (d, J=5.86 Hz, 2H) 2.09-2.27 (m, 6H) 2.34-2.50 (m, 2H) 3.39-3.49 (m, 1H) 3.53 (d, J=5.47 Hz, 2H) 3.64-3.81 (m, 2H) 7.51 (d, J=8.21 Hz, 1H) 8.22 (d, J=8.21 Hz, 1H) 8.26 (s, 1H) 8.45 (br. s., 1H)

$^{13}$C NMR (75 MHz, CHLOROFORM-d) δ ppm 13.38 (s, 1C) 17.65 (s, 1C) 18.43 (s, 1C) 19.05 (s, 1C) 23.61 (s, 1C) 23.68 (s, 1C) 23.78 (s, 1C) 23.99 (s, 1C) 36.68 (s, 1C) 50.06 (s, 1C) 66.17 (s, 1C) 76.69 (s, 1C) 77.11 (s, 1C) 77.54 (s, 1C) 124.73 (s, 1C) 128.38 (s, 1C) 129.42 (s, 1C) 133.08 (s, 1C) 144.51 (s, 1C) 150.43 (s, 1C) 164.33 (s, 1C) $^{31}$P NMR (81 MHz, CHLOROFORM-d) δ ppm 35.07 (s, 1P) $C_{25}H_{44}N_2O_4P^{1+}$ low resolution ESI-MS calculated: 467.30, found: 467.31.

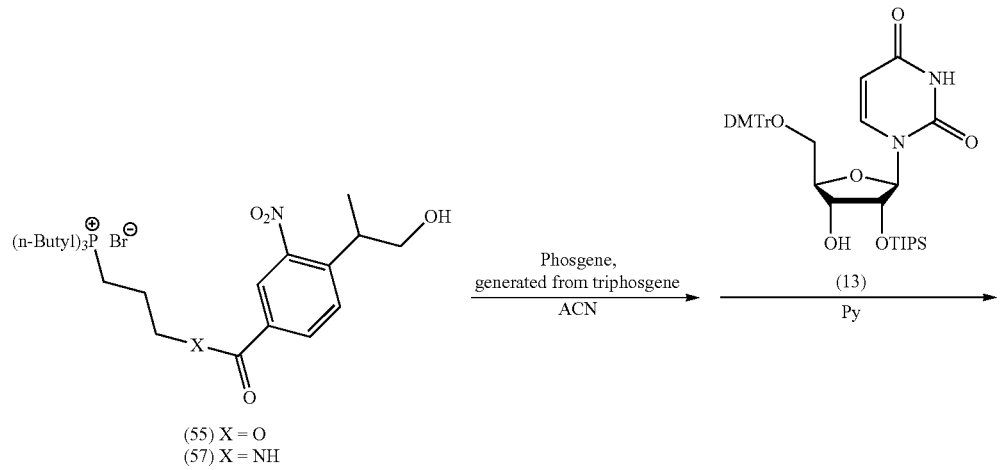

(55) X = O
(57) X = NH

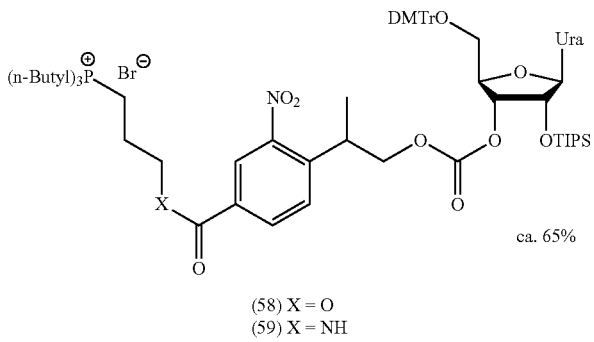

(58) X = O
(59) X = NH

5'-DMTr-2'-TIPS-3'-(tributyl (3-(4-(1-hydroxypropan-2-yl)-3-nitrobenzamido)propyl)phosphonium bromide)-uridine (59)

A two necked flask containing the triphosgene and phenanthridine was connected to a distillation head and condenser. The receiving end of the condenser was attached to an ammonia trap and cooled by a dry ice/acetone bath to condense the phosgene that was produced. The bottom of the ammonia trap was connected to a three necked round bottom flask with a stir bar which was also cooled by a dry ice/acetone bath. All open necks of round bottoms were sealed by fresh septa wrapped with Teflon tape. One neck of the three necked flask was punctured with a 20G needle attached to a tygon tube and two bubblers in series; the first was empty and the second contained mineral oil. Tygon tubing was used to connect the second bubbler to a 9-inch 20G needle that was fully inserted into a saturated solution of sodium hydroxide in methanol. A second needle and tube was inserted into the septa of the methanolic sodium hydroxide, which acted as a vent up into the fume hood. Triphosgene (1.87 g, 6.33 mmol) and cat. phenanthridine were heated to 90° C., at which point the triphosgene melted and solvated the phenanthridine catalyst, promoting the evolution of phosgene gas. After 30 min, all triphosgene was consumed and phosgene had begun condensing in the receiving flask. At this point a balloon of argon was punctured through the septa on the two necked flask, pushing any phosgene gas to the condenser and quenching solution. Once phosgene had stopped condensing, an acetonitrile solution of (57) (1.06 g, 1.9 mmol) was added dropwise to the stirring phosgene, then removed from the dry ice/acetone bath after 10 min. The reaction was stirred for 2 h at room temperature. Next, argon gas was passed over the whole apparatus and also bubbled through the reaction mixture into the methanolic sodium hydroxide to remove and quench the excess phosgene. NOTE: a very low flow from a balloon was used at first to ensure the phosgene was quenched. Once all phosgene was removed, DIPEA (4 mL) was added to the mixture to quench the HCl produced in the reaction with phosgene and compound (57).

A solution of nucleoside (13) (1 eq, 1.35 g, 1.9 mmol) in ACN (3 mL) was added directly to the above mixture, and the resulting solution allowed to stir for 8 h at room temperature. The solution was diluted with ethyl acetate and extracted with sat. NaHCO$_3$ (×3) and once with brine. The mixture was precipitated in 300 mL of MTBE to remove excess nucleoside and DIPEA. The resulting precipitate was then purified by column chromatography (DCM:MeOH 100:0→90:10) to afford 1.32 g of (59) (62% yield).

$^1$H NMR (300 MHz, CHLOROFORM-d) δ ppm 0.82-1.16 (m, 34H) 1.34 (dd, J=6.89, 2.20 Hz, 3H) 1.38-1.63 (m, 15H) 2.05 (br. s., 2H) 2.11-2.31 (m, 12H) 2.67 (br. s., 1H) 3.39-3.53 (m, 1H) 3.57-3.72 (m, 3H) 3.78 (s, 7H) 4.08-4.38 (m, 2H) 4.59-4.69 (m, 1H) 5.16-5.33 (m, 2H) 5.63-5.76 (m, 1H) 6.00 (dd, J=5.27, 2.05 Hz, 1H) 6.81 (dd, J=8.79, 1.47 Hz, 4H) 7.15 (d, J=8.79 Hz, 1H) 7.18-7.41 (m, 10H) 7.56 (d, J=7.91 Hz, 1H) 7.88 (dd, J=8.20, 1.76 Hz, 1H) 8.53 (d, J=7.91 Hz, 1H) 8.67 (t, J=8.94 Hz, 2H) 9.64 (br. s., 1H) $C_{65}H_{92}N_4O_{13}PSi^{1+}$ low resolution ESI-MS calculated: 1195.61, found: 1195.60.

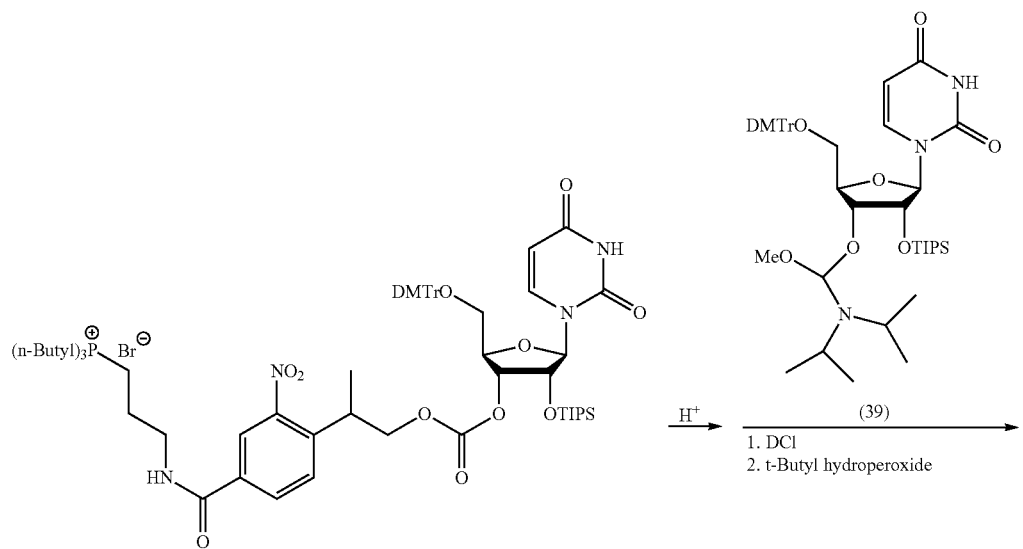

(59)

-continued

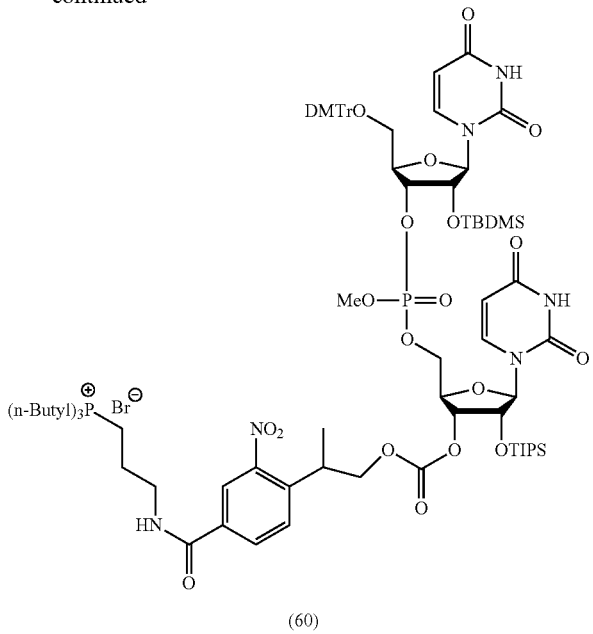

(60)

Compound (59) (316 mg, 0.29 mmol) was treated with 10 mL of 3% TFA in DCM followed by 0.5 mL of triethylsilane. This mixture was allowed to stir for 10 min followed by 5 mL of MeOH to further quench the trityl cation. This mixture was then diluted with 20 mL of toluene and concentrated to near dryness. The mixture was then taken up in acetone and precipitated in MTBE, filtered and solvated in DCM then condensed to dryness. The above process was repeated once more to ensure there was no tritylated material. The mixture was then co-evaporated with toluene to dry. To this mixture, 1.5 eq of DCI was added (52 mg, 0.44 mmol) and 1.5 eq of phosphoramidite (39) (362 mg, 0.44 mmol) was added and finally solvated with 3 mL of ACN.

This mixture was allowed to stir for 4 h until all starting material was consumed as monitored by MS. The mixture was then treated with 1 mL of tert-butanol to react with any excess phosphoramidite. This mixture was directly precipitated in MTBE:hexanes (75:25) to remove all excess reagents. The precipitate was solvated in DCM and treated with 1 mL of tert-butylhydroperoxide in decane and allowed to stir for 20 min until all starting material was oxidised, as monitored by MS. This mixture was then precipitated in MTBE producing compound pure (60) in 91% yield.

$^{31}$P NMR (81 MHz, CHLOROFORM-d) δ ppm −0.93 (s, 1P) −0.90 (s, 1P) −0.36 (s, 1P) −0.31 (s, 1P) 34.20 (s, 1P)

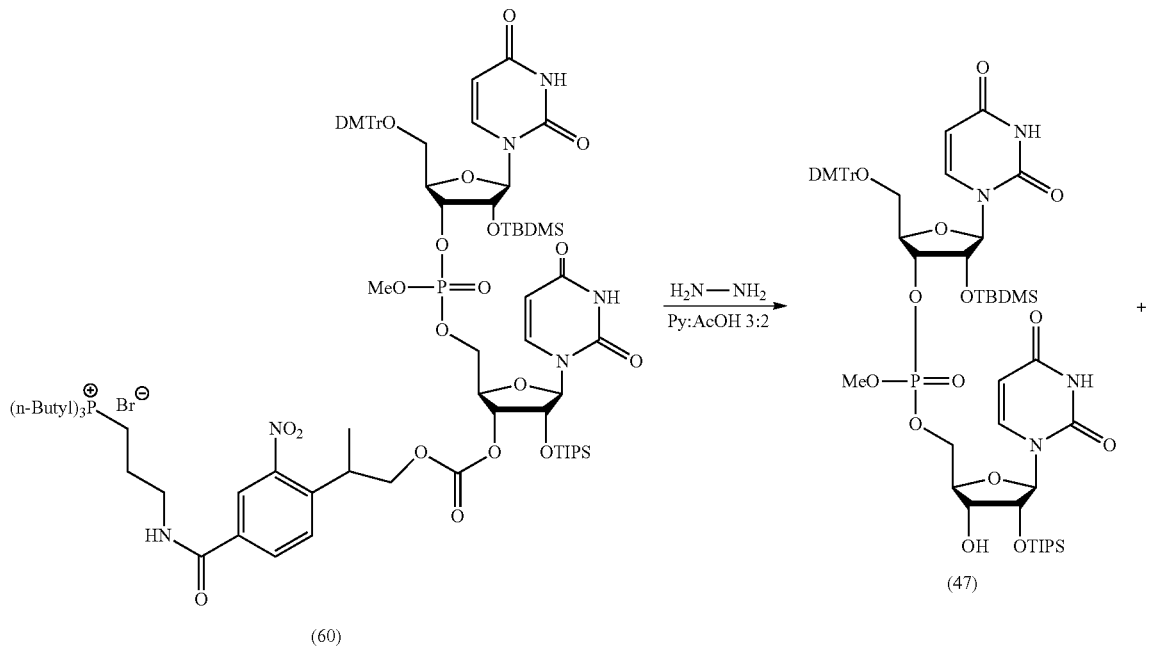

-continued

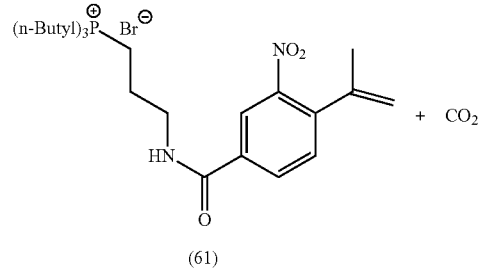

(61)

Compound (60) was treated with UVB for 20 min, solvated in wet ACN producing pure compound (47) in 92% yield after purification by column chromatography (0→75% ethyl aceateLhexanes).

$^1$H NMR (300 MHz, CHLOROFORM-d) δ ppm 0.09-0.15 (m, 6H) 0.87-1.20 (m, 40H) 1.94-2.00 (m, 1H) 2.10-2.20 (m, 2H) 3.44 (br. s., 3H) 3.67-3.79 (m, 12H) 4.04-4.23 (m, 5H) 4.28-4.35 (m, 2H) 4.38-4.48 (m, 2H) 4.81-4.90 (m, 1H) 5.38 (d, J=8.21 Hz, 1H) 5.64 (d, J=8.20 Hz, 1H) 5.81-5.91 (m, 2H) 6.90 (d, J=7.91 Hz, 5H) 7.24-7.37 (m, 9H) 7.41-7.52 (m, 4H) 7.71 (dd, J=8.20, 2.64 Hz, 1H) 9.62 (br. s., 1H)

$^{31}$P NMR (81 MHz, CHLOROFORM-d) δ ppm 0.58 (s, 1P) 0.83 (s, 1P).

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosures as come within known or customary practice within the art to which the disclosure pertains and as may be applied to the essential features herein before set forth, and as follows in the scope of the appended claims.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

All documents and references cited herein are hereby incorporated by reference in their entireties.

What is claimed is:

1. An ionic tag linker comprising a photolabile moiety, an ionic moiety and a linker, wherein the photolabile moiety is a nitrobenzyl derivative, and wherein the ionic tag linker has the structure of formula (P):

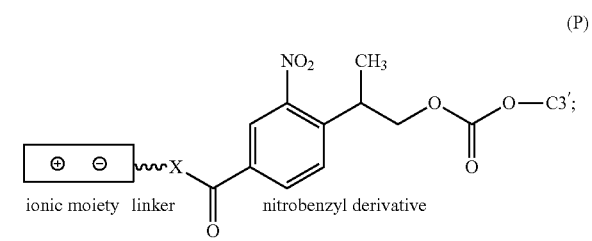

wherein X is N or O, and wherein C3' is the terminal 3'-hydroxyl of an oligoribonucleotide or oligodeoxyribonucleotide.

2. The ionic tag linker of claim 1, wherein the linker is alkyl, glycol or functionalized alkyl.

3. The ionic tag linker of claim 1, wherein the ionic moiety is an imidazolium or phosphonium group; or wherein the ionic moiety comprises a halide; or wherein the ionic moiety comprises Br$^-$, Cl$^-$ or I$^-$.

4. The ionic tag linker of claim 1, wherein the ionic tag linker is orthogonally cleavable from an oligoribonucleotide or oligodeoxyribonucleotide.

* * * * *